(12) United States Patent
Ido et al.

(10) Patent No.: US 9,180,187 B2
(45) Date of Patent: *Nov. 10, 2015

(54) MEDICAMENT FOR TREATING AND/OR PREVENTING CANCER

(75) Inventors: Takayoshi Ido, Kanagawa (JP); Fumiyoshi Okano, Kanagawa (JP); Yoshinori Narita, Kanagawa (JP)

(73) Assignee: TORAY INDUSTRIES, INC., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/576,950

(22) PCT Filed: Feb. 4, 2011

(86) PCT No.: PCT/JP2011/052414
§ 371 (c)(1),
(2), (4) Date: Aug. 3, 2012

(87) PCT Pub. No.: WO2011/096535
PCT Pub. Date: Aug. 11, 2011

(65) Prior Publication Data
US 2012/0294860 A1 Nov. 22, 2012

(30) Foreign Application Priority Data
Feb. 4, 2010 (JP) ................................. 2010-023455

(51) Int. Cl.
*A61K 39/395* (2006.01)

(52) U.S. Cl.
CPC .............................. *A61K 39/39558* (2013.01)

(58) Field of Classification Search
CPC .................. A61K 39/39558; A61K 2300/00; A61K 39/395; C07K 16/30; C07K 16/3015–16/32; C07K 16/28; C07K 15/3015–15/32
See application file for complete search history.

(56) References Cited

U.S. PATENT DOCUMENTS

| | | | |
|---|---|---|---|
| 5,698,396 A | 12/1997 | Pfreundschuh | |
| 6,335,170 B1 | 1/2002 | Orntoft | |
| 6,444,425 B1 | 9/2002 | Reed et al. | |
| 7,449,184 B2 | 11/2008 | Allison et al. | |
| 7,485,302 B2 | 2/2009 | Adams et al. | |
| 7,745,391 B2 | 6/2010 | Mintz et al. | |
| 8,008,431 B2 | 8/2011 | Weinschenk et al. | |
| 8,211,634 B2 | 7/2012 | DePinho et al. | |
| 8,709,418 B2 * | 4/2014 | Okano et al. | 424/130.1 |
| 8,828,398 B2 * | 9/2014 | Kobayashi et al. | 424/155.1 |
| 8,911,740 B2 | 12/2014 | Saito et al. | |
| 2002/0006404 A1 | 1/2002 | Hanna et al. | |
| 2003/0118599 A1 | 6/2003 | Algate et al. | |
| 2003/0190640 A1 | 10/2003 | Faris et al. | |
| 2004/0029114 A1 | 2/2004 | Mack et al. | |
| 2004/0236091 A1 | 11/2004 | Chicz et al. | |
| 2004/0258678 A1 | 12/2004 | Bodary et al. | |
| 2005/0003390 A1 | 1/2005 | Axenovich et al. | |
| 2005/0032113 A1 | 2/2005 | Tanaka et al. | |
| 2005/0244413 A1 * | 11/2005 | Adolf et al. | 424/144.1 |
| 2006/0019256 A1 | 1/2006 | Clarke et al. | |
| 2006/0069054 A1 | 3/2006 | Houghton et al. | |
| 2006/0275305 A1 | 12/2006 | Bryant | |
| 2007/0048301 A1 | 3/2007 | Bodary-Winter et al. | |
| 2007/0154931 A1 | 7/2007 | Radich et al. | |
| 2007/0264253 A1 | 11/2007 | Liu et al. | |
| 2008/0075722 A1 | 3/2008 | DePinho et al. | |
| 2008/0107668 A1 | 5/2008 | Philip et al. | |
| 2010/0029573 A1 | 2/2010 | Weinschenk et al. | |
| 2010/0068724 A1 | 3/2010 | Fung et al. | |
| 2011/0123492 A1 | 5/2011 | Okano et al. | |
| 2011/0136121 A1 | 6/2011 | Okano et al. | |
| 2011/0189700 A1 | 8/2011 | Moses et al. | |
| 2011/0256144 A1 * | 10/2011 | Okano et al. | 424/139.1 |
| 2012/0171699 A1 | 7/2012 | Goodman et al. | |
| 2012/0214975 A1 | 8/2012 | Sandig et al. | |
| 2012/0294860 A1 | 11/2012 | Ido et al. | |
| 2012/0301471 A1 | 11/2012 | Kobayashi et al. | |
| 2012/0301476 A1 | 11/2012 | Okano et al. | |
| 2012/0321641 A1 * | 12/2012 | Okano et al. | 424/158.1 |
| 2013/0045210 A1 | 2/2013 | Kobayashi et al. | |
| 2013/0071398 A1 | 3/2013 | Saito et al. | |

FOREIGN PATENT DOCUMENTS

| | | |
|---|---|---|
| CN | 1678338 A | 10/2005 |
| CN | 1705676 A | 12/2005 |
| CN | 101120252 A | 2/2008 |
| CN | 101189516 A | 5/2008 |
| CN | 102170907 A | 8/2011 |
| EP | 1557172 A1 | 7/2005 |
| EP | 2 325 648 A1 | 5/2011 |

(Continued)

OTHER PUBLICATIONS

Strome et al., The Oncologist, 2007; 12:1084-95.*
Brand et al., Anticancer Res. 2006; 26:463-70.*
Kataja et al., Ann Oncol 2009; 20(sup 4): iv10-14.*
Nelson et al., Ann. Intern Med. 2009; 151:727-737.*
Balmana et al. Ann Oncol 2009; 20(supp 4):iv19-20.*
Jungbluth et al., Int'l J. Cancer, 2001; 92:856-60.*
Bodey et al., In Vivo 2002; 16:583-88.*

(Continued)

*Primary Examiner* — Sheela J Huff
*Assistant Examiner* — Jessica H Roark
(74) *Attorney, Agent, or Firm* — Birch, Stewart, Kolasch & Birch, LLP

(57) ABSTRACT

This invention relates to a medicament for treating and/or preventing a cancer, comprising a combination of an antibody against a cancer antigen CAPRIN-1 protein that is specifically expressed on the surface of the cancer cell, and an antitumor agent, wherein the antibody and the antitumor agent are combined together or separately, and to a use of the medicament.

9 Claims, 10 Drawing Sheets

(56) References Cited

FOREIGN PATENT DOCUMENTS

| | | |
|---|---|---|
| EP | 2322221 A1 | 5/2011 |
| EP | 2 532 367 A1 | 12/2012 |
| EP | 2 532 743 A1 | 12/2012 |
| EP | 2 832 365 A1 | 2/2015 |
| EP | 2 832 366 A1 | 2/2015 |
| JP | 2002-540790 A | 12/2002 |
| JP | 2003-528587 A | 9/2003 |
| JP | 2006-316040 A | 11/2006 |
| JP | 2013-502205 A | 1/2013 |
| JP | 2013-505028 A | 2/2013 |
| RU | 2234942 C2 | 2/2003 |
| RU | 2306952 C2 | 9/2007 |
| RU | 2006 137 060 A | 4/2008 |
| RU | 2006137060 A | 4/2008 |
| WO | WO 00/04149 A2 | 1/2000 |
| WO | WO 00/60077 A2 | 10/2000 |
| WO | WO 01/32910 A2 | 5/2001 |
| WO | WO 01/72295 A2 | 10/2001 |
| WO | WO 02/078524 A2 | 10/2002 |
| WO | WO 02/083070 A2 | 10/2002 |
| WO | WO 02/092001 A2 | 11/2002 |
| WO | WO 2004/076682 A2 | 9/2004 |
| WO | WO 2004/097051 A2 | 11/2004 |
| WO | WO 2005/007830 A2 | 1/2005 |
| WO | WO 2005/100998 A2 | 10/2005 |
| WO | WO 2005/116051 A2 | 12/2005 |
| WO | WO 2005/116076 A2 | 12/2005 |
| WO | WO 2006/002378 A2 | 1/2006 |
| WO | WO 2007/150577 A2 | 12/2007 |
| WO | WO 2008/031041 A2 | 3/2008 |
| WO | WO 2008/059252 A2 | 5/2008 |
| WO | WO 2008/073162 A2 | 6/2008 |
| WO | WO 2008/088583 A2 | 7/2008 |
| WO | WO 2009/113742 A1 | 9/2009 |
| WO | WO 2010/016525 A1 | 2/2010 |
| WO | WO 2010/016526 A1 | 2/2010 |
| WO | WO 2010/016527 A1 | 2/2010 |
| WO | WO 2011/096517 A1 | 8/2011 |
| WO | WO 2011/096528 A1 | 8/2011 |
| WO | WO 2011/096533 A1 | 8/2011 |
| WO | WO 2011/096534 A1 | 8/2011 |
| WO | WO 2011/096535 A1 | 8/2011 |
| WO | WO 2013/018885 A1 | 2/2013 |
| WO | WO 2013/018886 A1 | 2/2013 |
| WO | WO 2013/018894 A1 | 2/2013 |
| WO | WO 2013/147169 A1 | 10/2013 |
| WO | WO 2013/147176 A1 | 10/2013 |

OTHER PUBLICATIONS

Punt et al., Lancet, 2002; 360(9334):671-77.*
Pegram et al., J. Nat'l Cancer Inst. 2004; 96(10):739-49.*
Comtesse et al., Clin. Exp. Immunol. 2000; 121:430-36.*
Jäger et al., Cancer Res. 2001; 61:2055-61.*
Gong et al. Biomed Pharmacother 2013; 67:629-36.*
Sabile et al., Biochim Biophys Acta. Aug. 2013;1832(8):1173-82.*
Qiu et al. Oncotarget, Feb. 10, 2015;6(4):2148-63.*
Chinese Office Action dated Mar. 29, 2013 for Chinese Application No. 200980139037.
Lu et al., "Targeting serum antibody for cancer diagnosis: a focus on colorectal cancer," Oncologic, Endocrine & Metabolic, Expert Opinion on Therapeutic Targets, vol. 11, No. 2, Feb. 2007, pp. 235-244.
NCBI Reference Sequence, caprin-1 [Bos taurus], Feb. 23, 2013, Accession No. NP001069530, XP615677, 1 page.
NCBI Reference Sequence, caprin-1 [Gallus gallus], Feb. 22, 2013, Accession No. NP001026536, XP423820, 1 page.
NCBI Reference Sequence, caprin-1 isoform 1 [Homo sapiens], Mar. 17, 2013, Accession No. NP005889, 3 pages.
NCBI Reference Sequence, caprin-1 isoform 2 [Homo sapiens], Mar. 3, 2013, Accession No. NP976240, 3 pages.
NCBI Reference Sequence, caprin-1 isoform a [Mus musculus], Mar. 23, 2013, Accession No. NP058019, 3 pages.
NCBI Reference Sequence, caprin-1 isoform b [Mus musculus], Mar. 23, 2013, Accession No. NP001104760, 3 pages.
NCBI Reference Sequence, caprin-1 isoform c [Mus musculus], Mar. 23, 2013, Accession No. NP001104761,4 pages.
NCBI Reference Sequence, Predicted: caprin-1 [Equus caballus], Jun. 27, 2011, Accession No. XP001492799, 1 page.
NCBI Reference Sequence, Predicted: caprin-1 isoform 2 [Canis lupus familiaris], Dec. 2, 2011, Accession No. XP858109, 1 page.
Scanlan et al., "Cancer-related Serological Recognition of Human Colon Cancer: Identification of Potential Diagnostic and Immunotherapeutic Targets," Cancer Research, vol. 62, Jul. 15, 2002, pp. 4041-4047.
GeneCards, "Cell Cycle Associated Protein 1—Biological research products for CAPRIN 1", updated Mar. 19, 2013, 10 pages.
Karauzum et al., "Caprin 1 is Frequently Overexpressed in Human Lymphomas," American Society of Human Genetics, Cancer Genetics, Program No. 1190W, Oct. 12, 2011, Abstract only.
United States Office Action, dated Jul. 1, 2013, for U.S. Appl. No. 13/577,212.
United States Office Action, dated Jul. 16, 2013, for U.S. Appl. No. 13/057,709.
Ellis et al., Identification and Characterization of a Novel Protein (p137) Which Transcytoses Bidirectionally in Caco-2 Cells, The Journal of Biological Chemistry, vol. 270, No. 35, pp. 20717-20723, Sep. 1995.
Grill et al., "Activation/Division of Lymphocytes Results in Increased Levels of Cytoplasmic Activation/Proliferation-Associated Protein-1: Prototype of a New Family of Proteins", The Journal of Immunology, vol. 172, pp. 2389-2400, 2004.
International Search Report for PCT/JP2011/052414 dated Mar. 8, 2011.
Katsafanas et al., "Vaccinia Virus Intermediate Stage Transcription Is Complemented by Ras-GTPase-activating Protein SH3 Domain-binding Protein (G3BP) and Cytoplasmic . . . ", The Journal of Biological Chemistry, vol. 279, No. 50, pp. 52210-52217, Dec. 2004.
Kolobova et al., "Microtubule-dependent association of AKA350A and CCAR1 with RNA stress granules", Experimental Cell Research, vol. 315, pp. 542-555, 2009.
Solomon et al., "Distinct Structural Features of Caprin-1 Mediate Its Interaction with G3BP-1 and Its Induction of Phoshorylation of Eukaryotic . . . ", Molecular and Cellular Biology, vol. 27, No. 6, pp. 2324-2342, Mar. 2007.
Wang et al., "Absence of Caprin-1 Results in Defects in Cellular Proliferation", The Journal of Immunology, vol. 175, pp. 4274-4282, 2005.
Akiyoshi, "Cancer Vaccine Therapy Using Peptides Derived from Tumor-rejection Antigens," Jpn. J. Cancer Chemother., vol. 24, No. 5, Mar. 1997, pp. 511-519, with English Abstract (p. 519).
Bodey et al., "Failure of Cancer Vaccines: The Significant Limitations of this Approach to Immunotherapy," Anticancer Research, vol. 20, 2000, pp. 2665-2676.
Brass et al., "Translation initiation factor eIF-4gamma is encoded by an amplified gene and induces an immune response in squamous cell lung carcinoma," Human Molecular Genetics, vol. 6, No. 1, 1997, pp. 33-39.
Chamberlain et al., "Innovations and strategies for the development of anticancer vaccines," Expert Opinion on Pharmacotherapy, vol. 1, No. 4, 2000, pp. 603-614.
Güre et al., "Human Lung Cancer Antigens Recognized by Autologous Antibodies: Definition of a Novel cDNA Derived from the Tumor Suppressor Gene Locus on Chromosome 3p21.3," Cancer Research, vol. 58, Mar. 1, 1998, pp. 1034-1041.
Gure et al., "SSX: A Multigene Family with Several Members Transcribed in Normal Testis and Human Cancer," Int. J. Cancer, vol. 72, 1997, pp. 965-971.
Hugo Gene Nomenclature Committee, Gene Symbol Report, CAPRIN1, Approved Name: Cell Cycle Associated Protein 1, HGNC ID: HGNC:6743, Nov. 3, 2012, 2 pages.
Itoh et al., "HUB1 is an autoantigen frequently eliciting humoral immune response in patients with adult T cell leukemia," Int. J. Oncol., vol. 14, 1999, pp. 703-708 (Abstract only provided).
Jang et al., "Antihypertensive Angiotensin I-Converting Enzyme Inhibitory Activity and Antioxidant Activity of Vitis hybrid-Vitis coignetiae Red Wine Made with Saccharomyces cerevisiae," Mycobiology, vol. 39, No. 2, 2011, pp. 137-139.

(56) References Cited

OTHER PUBLICATIONS

Kaddar et al., "Two new miR-16 targets: caprin-1 and HMGA1, proteins implicated in cell proliferation," Biology of the Cell, vol. 101, No. 9, 2009, pp. 511-524.
Kajiji et al., "Six Monoclonal Antibodies to Human Pancreatic Cancer Antigens," Cancer Research, vol. 47, Mar. 1, 1987, pp. 1367-1376.
Katsafanas et al., "Colocalization of Transcription and Translation within Cytoplasmic Poxvirus Factories Coordinates Viral Expression and Subjugates Host Functions," Cell Host & Microbe, vol. 2, Oct. 2007, pp. 221-228.
Lu et al., "Identification of an immunological signature of tumor rejection in the neu transgenic mouse," 2007 AACR Annual Meeting, Proceedings Abstract No. 4131, Apr. 14-18, 2007 (Presentation conducted on Apr. 17, 2007) (Abstract only provided).
Müller-Pillasch et al., "Identification of a new tumour-associated antigen TM4SF5 and its expression in human cancer," Gene, vol. 208, 1998, pp. 25-30.
Rauch et al., "SEREX, Proteomex, AMIDA, and beyond: Serological screening technologies for target identification," Proteomics Clin. Appl., vol. 2, 2008, pp. 355-371.
Sahin et al., "Human neoplasms elicit multiple specific immune responses in the autologous host," Proc. Natl. Acad. Sci. USA, vol. 92, Dec. 1995, pp. 11810-11813.
Scanlan et al., "Characterization of Human Colon Cancer Antigens Recognized by Autologous Antibodies," Int. J. Cancer, vol. 76, 1998, pp. 652-658.
Türeci et al., "The SSX-2 Gene, Which Is Involved in the t(X; 18) Translocation of Synovial Sarcomas, Codes for the Human Tumor Antigen HOM-MEL-40," Cancer Research, vol. 56, Oct. 15, 1996, pp. 4766-4772.
Van Der Bruggen et al., "A Gene Encoding an Antigen Recognized by Cytolytic T Lymphocytes on a Human Melanoma," Science, vol. 254, No. 5038, Dec. 13, 1991, pp. 1643-1647 (Also published in J. Immunol., vol. 178, 2007, pp. 2617-2621).
Yanai et al., "Dlk-1, a cell surface antigen on foetal hepatic stem/progenitor cells, is expressed in hepatocellular, colon, pancreas and breast carcinomas at a high frequency," The Journal of Biochemistry, vol. 148, No. 1, 2010 (Publ. online Mar. 30, 2010), pp. 85-92.
Evans et al., "Vaccine therapy for cancer-fact or fiction?", Q. J. Med, vol. 92, 1999, pp. 299-307.
Extended European Search Report, dated Aug. 13, 2013, for European Application No. 11739882.6.
Harlow et al., "Antibodies A Laboratory Manual", Cold Spring Harbor Laboratory, Chapter 3, 1988, pp. 23-24.
Munodzana et al., "Conformational Dependence of *Anaplasma marginale* Major Surface Protein 5 Surface-Exposed B-Cell Epitopes", Infection and Immunity, vol. 66, No. 6, Jun. 1998, pp. 2619-2624.
Okano et al., "Identification of a novel target for antibody therapy of breast cancer", Cancer Research, vol. 72, Issue 8, Supplemental 1, Apr. 15, 2012, Abstract 519, 2 pages, XP-002700046.
Polyak et al., "Alanine-170 and proline-172 are critical determinants for extracellular CD20 epitopes; heterogeneity in the fine specificity of CD20 monoclonal antibodies is defined by additional requirements imposed by both amino acid sequence . . . ", Blood, vol. 99, No. 9, May 1, 2002, pp. 3256-3262.
United States Office Action, dated Oct. 15, 2013, for U.S. Appl. No. 13/576,969.
United States Office Action, dated Oct. 21, 2013, for U.S. Appl. No. 13/577,212.
R & D Systems, "IHC Products & Protocol Guide," printed Jan. 9, 2014, pp. 1-112.
US Office Action of U.S. Appl. No. 13/057,515 dated Jan. 16, 2014.
Extended European Search Report, dated Nov. 6, 2013, for European Application No. 11739876.8.
US Office Action, dated Nov. 15, 2013, for U.S. Appl. No. 13/577,028.
English translation of China Office Action for Appl. No. 201180016730.5 dated May 9, 2013.
English translation of Russian Notice of Allowance for Appl. No. 2011108260/10 dated Jun. 4, 2013.
GenBank Accession No. AAU93399, Sep. 22, 2005.
GenBank Accession No. BAF96513, Jan. 5, 2008.
GenBank Accession No. NM_001031365, Sep. 25, 2007.
GenBank Accession No. NM_001076062, Feb. 9, 2008.
GenBank Accession No. NM_001111289, Feb. 11, 2008.
GenBank Accession No. NM_001111290, Feb. 11, 2008.
GenBank Accession No. NM_001111291, Feb. 10, 2008.
GenBank Accession No. NM_001111292, Feb. 11, 2008.
GenBank Accession No. NM_016739, Feb. 10, 2008.
GenBank Accession No. NM_05898, Feb. 11, 2008.
GenBank Accession No. NM_203364, Feb. 10, 2008.
GenBank Accession No. Q14444, Jun. 10, 2008.
GenBank Accession No. Q1LZB6, Jun. 10, 2008.
GenBank Accession No. XM_853016, Aug. 30, 2005.
Patent Examination Report No. 1 issued Oct. 14, 2014, in Australian Patent Application No. 2009278387.
GenBank Accession No. NM_005898, Feb. 11, 2008.
Bodey et al., "MAGE-1, a Cancer/Testis-Antigen, Expression in Childhood Astrocytomas as an Indicator of Tumor Progression," in vivo (2002) vol. 16, pp. 583-588.
Comtesse et al., "Probing the human natural autoantibody repertoire using an immunoscreening approach," Clin. Exp. Immunol. (2000), vol. 121, pp. 430-436.
International Search Report issued Nov. 18, 2014, in PCT International Application No. PCT/JP2014/071094.
Jager at al., "Identification of a Tissue-specific Putative Transcription Factor in Breast Tissue by Serological Screening of a Breast Cancer Library," Cancer Research (Mar. 1, 2001), vol. 61, pp. 2055-2061.
Jungbluth at al., "Immunohistochemical Analysis of NY-ESO-1 Antigen Expression in Normal and Malignant Human Tissues," Int. J. Cancer (2001), vol. 92, pp. 856-860.
Kohler et al., "Tumor antigen analysis in neuroblastoma by serological interrogation at bioinformatic data," Cancer Science (Nov. 2010), vol. 101, No. 11, pp. 2316-2324.
Nakamura et al. "Gene Expression Profile of Metastatic Human Pancreatic Cancer Cells Depends on the Organ Microenvironment," Cancer Research (Jan. 1, 2007), vol. 67, No. 1, pp. 139-148.
Non-Final Office Action issued Nov. 6, 2014, in U.S. Appl. No. 13/576,950.
Pegram et al., "Rational Combinations of Trastuzumab with Chemotherapeutic Drugs Used in the Treatment of Breast Cancer," Journal of the National Cancer Institute (May 19, 2004), vol. 96, No. 10, pp. 739-749.
Punt et al., "Edrecolomab alone or in combination with fluorouracil and folinic acid in the adjuvant treatment of stage III colon cancer: a randomised study," Lancet (Aug. 31, 2002), vol. 360, No. 9334, pp. 671-677.
Buchsbaum et al., "Treatment of Pancreatic Cancer Xenografts with Erbitux (IMC-C225) Anti-EGFR Antibody, Gemcitabine, and Radiation," Int. J. Radiation Oncology Biol. Phys. (2002), vol. 54, No. 4, pp. 1180-1193.
Chames et al., "Therapeutic Antibodies for the Treatment of Pancreatic Cancer," The Scientific World Journal (Jan. 1, 2010), vol. 10, pp. 1107-1120.
Eccleston et al., "Pancreatic Tumor Marker Anti-Mucin Antibody CAM 17.1 Reacts with a Sialyl Blood Group Antigen, Probably I, Which is Expressed throughout the Human Gastrointestinal Tract," Digestion (1998), vol. 59, pp. 665-670.
Esteva et al., "Chemotheraphy of Metastatic Breast Cancer: What to Expect in 2001 and Beyond," The Oncologist (2001), vol. 6, pp. 133-146.
Extended European Search Report issued Feb. 2, 2015, in European Patent Application No. 12819473.5.
Extended European Search Report issued Jan. 29, 2015, in European Patent Application No. 12819899.1.
Houghton, P. J. and J. A. Houghton, "Evaluation of Single-Agent Therapy in Human Colorectal Tumour Xenografts," Br. J. Cancer (1978), vol. 37, pp. 833-840.

(56) References Cited

OTHER PUBLICATIONS

De Pascalis et al., "Grafting of "Abbreviated" Complementarity-Determining Regions Containing Specificity-Determining Residues Essential for Ligand Contact to Engineer a Less Immunogenic Humanized Monoclonal Antibody," J. Immunol. (2002), vol. 169, pp. 3076-3084.

Extended European Search Report issued Mar. 2, 2015, in European Patent Application No. 12819759.7.

Office Action issued Jan. 28, 2015, in Russian Patent Application No. 2012137502, with partial English translation.

Riechmann et al., "Reshaping human antibodies for therapy," Nature (Mar. 24, 1988), vol. 332, pp. 323-327.

Vajdos et al,. "Comprehensive Functional Maps of the Antigen-binding Site of an Anti-ErbB2 Antibody Obtained with Shotgun Scanning Mutagenesis," J. Mol. Biol. (2002), vol. 320, pp. 415-428.

Extended European Search Report issued Mar. 18, 2015, in European Patent Application No. 12820225.6.

Extended European Search Report issued Mar. 23, 2015, in European Patent Application No. 12820596.0.

Non-Final Office Action issued Apr. 14, 2015, in U.S. Appl. No. 14/236,793.

* cited by examiner

MEDICAMENT FOR TREATING AND/OR PREVENTING CANCER

TECHNICAL FIELD

The present invention relates to a medicament for treating and/or preventing a cancer, characterized by combining an antibody or a fragment thereof having immunological reactivity with a CAPRIN-1 protein, with an antitumor agent, and to the use of the same.

BACKGROUND ART

Cancer is the leading cause of death. Current therapies for cancer comprise combinations of principal surgical therapy with radiation therapy and chemotherapy. Furthermore, the current therapies comprise applying a similar therapy to all patients having the same type and the same stage of a cancer. At least 40% of the patients fail a primary therapy and thus are subjected to a series of further therapies. If the patients again fail the therapies, cancer metastasis takes place, finally resulting in an increased possibility of death. Thus, the current radiation therapy and the chemotherapy are unable to compatible with various types of cancers or individual cancer patients, and the surgical therapy itself is also currently insufficient for complete cure of cancers in almost all cases.

Various antibody drugs targeting antigen proteins on cancer cells for treatment of cancers have appeared throughout the world as a technique for overcoming the above-described problems of cancer therapies. Specific examples are as follows. It has been demonstrated that HERCEPTIN (registered trademark) comprising as an active ingredient a monoclonal antibody specifically binding to Her2, the sales of which were approved in 1998 as a therapeutic agent for patients with metastatic breast cancer, has such a clinical effect that HERCEPTIN can decrease the number of death of recurrent and metastatic breast cancer patients among Her2-overexpressing metastatic breast cancer patients. It has also been demonstrated that HERCEPTIN does not cause any severe side effects other than cardiac toxicity compared with conventional chemotherapeutics. As another noteworthy feature, the therapeutic effects of a combined use of HERCEPTIN with chemotherapeutics against breast cancer have been demonstrated (Patent Literatures 1-3). However, most antigenic proteins on cancer cells to be targeted by antibody drugs such as Her2 are also expressed in normal cells, so that not only cancer cells but also normal cells expressing antigens are also cytotoxically impaired by administration of antibodies. The resulting side effects may cause for concern.

Cytoplasmic- and proliferation-associated protein 1 (CAPRIN-1) is expressed when normal cells at the resting phase are activated or undergo cell division, and it is an intracellular protein known to form intracellular stress granules with RNA within cells, so as to be involved in mRNA transport and translational regulation. Meanwhile, many other names that represent CAPRIN-1 exist, such as GPI-anchored membrane protein 1 or membrane component surface marker 1 protein (M11S1), as if such proteins had been known to be cell membrane proteins. These names originated from a report that the gene sequence of CAPRIN-1 is a membrane protein having a GPI-binding region and expressed in colorectal cancer cells (Non-patent Literature 1). However, the gene sequence of CAPRIN-1 provided in this report was later revealed to be wrong. The following has recently been reported; i.e., deletion of a single nucleotide in the gene sequence of CAPRIN-1 registered at GenBank or the like causes a frame shift, so that 80 amino acids are lost from the C-terminus, resulting in generation of an artifact (74 amino acids) which corresponds to the GPI-binding portion in the previous report, and additionally, another error is also present 5' of the gene sequence, so that 53 amino acids were lost from the N-terminus (Non-patent Literature 2). It has been also recently reported that the protein encoded by the gene sequence of CAPRIN-1 registered at GenBank or the like is not a cell membrane protein (Non-patent Literature 2).

In addition, on the basis of the report of Non-patent Literature 1 that CAPRIN-1 is a cell membrane protein, Patent Literatures 4 and 5 describe that CAPRIN-1 (as a cell membrane protein) under the name of M11S1 can be used as a target of an antibody medicine in cancer therapy, although working examples do not describe treatment using an antibody against the protein. However, as reported in Non-patent Literature 2, it has been commonly believed from the time of the filing of Patent Literature 4 to date that CAPRIN-1 is not expressed on the surface of a cell. The contents of Patent Literatures 4 and 5 based only on incorrect information that CAPRIN-1 is a cell membrane protein should not clearly be understood as common general knowledge for persons skilled in the art.

PRIOR ART LITERATURE

Patent Literature

Patent Literature 1 Japanese Patent Publication (Kokai) No. 2006-316040A
Patent Literature 2 U.S. Pat. No. 7,485,302
Patent Literature 3 U.S. Pat. No. 7,449,184
Patent Literature 4 U.S. Patent Publication No. 2008/0075722
Patent Literature 5 International Publication WO2005/100998

Non-Patent Literature

Non-patent Literature 1 J. Biol. Chem., 270: 20717-20723, 1995
Non-patent Literature 2 J. Immunol., 172: 2389-2400, 2004

SUMMARY OF THE INVENTION

Problem to be Solved by the Invention

Objects of the present invention are to identify a cancer antigen protein specifically expressed on the surface of a cancer cell, to combine an antibody targeting the cancer antigen protein with an antitumor agent, and thus to provide use as a medicament for treating and/or preventing a cancer.

Means for Solving the Problem

As a result of intensive studies, the present inventors have now obtained a cDNA encoding a protein that binds to an antibody existing in sera from dogs with breast cancer by the SEREX method using both cDNA libraries prepared from dog testis tissues and sera of dogs with breast cancer. The present inventors have now further prepared CAPRIN-1 proteins having the even-numbered amino acid sequences of SEQ ID NOS: 2 to 30 and antibodies against such CAPRIN-1 proteins based on the obtained dog gene and the corresponding human, cattle, horse, mouse, and chicken homologous genes. Thus, the present inventors have now found that: CAPRIN-1 proteins are specifically expressed in the cells of cancers, such as breast cancer, brain tumor, leukemia, lymphoma, lung cancer, uterine cervix cancer, bladder cancer, esophageal cancer, colorectal cancer, gastric cancer, and renal cancer cells; and that a portion of the CAPRIN-1 protein is specifically expressed on the surface of each cancer cell. The present inventors have thus now found that an antibody or antibodies against the portion of CAPRIN-1 expressed on the surface of each cancer cell are combined with a specific antitumor agent, so that significant cancer therapeutic effects can be obtained. On the basis of these findings, the present invention as described below was completed.

The term "cancer" as used herein is used interchangeably with tumor or carcinoma.

The present invention has the following characteristics.

(1) A medicament for treating and/or preventing a cancer, comprising a combination of an antibody or a fragment thereof having immunological reactivity with a CAPRIN-1 protein and one or two or more types of antitumor agents, wherein the antibody or fragment and the antitumor agent or antitumor agents are combined together or separately.

(2) The medicament according to (1) above, wherein the antibody or a fragment thereof having immunological reactivity with the above CAPRIN-1 protein is an antibody or a fragment thereof, which binds specifically to the extracellular region of a CAPRIN-1 protein existing on the surface of a cancer cell.

(3) The medicament according to (1) or (2) above, wherein the antibody or a fragment thereof having immunological reactivity with the above CAPRIN-1 protein is an antibody or a fragment thereof, which binds specifically to a polypeptide having the amino acid sequence represented by SEQ ID NO: 37 in the extracellular region of the CAPRIN-1 protein existing on the surface of a cancer cell, or an amino acid sequence having 80% or more sequence identity with the amino acid sequence represented by SEQ ID NO: 37.

(4) The medicament according to any one of (1) to (3) above, wherein the above CAPRIN-1 protein is from a human.

(5) The medicament according to any one of (1) to (4) above, wherein the above antitumor agent is any of antitumor agents as described herein.

(6) The medicament according to (5) above, wherein the antitumor agent is selected from the group consisting of cyclophosphamide, paclitaxel, docetaxel, vinorelbine, and pharmaceutically acceptable salts and derivatives thereof.

(7) The medicament according to any one of (1) to (6) above, wherein the cancer is breast cancer, brain tumor, leukemia, lymphoma, lung cancer, mastocytoma, renal cancer, uterine cervix cancer, bladder cancer, esophageal cancer, gastric cancer, or colorectal cancer.

(8) The medicament according to any one of (1) to (7) above, wherein the antibody is a monoclonal antibody, a polyclonal antibody, or a recombinant antibody.

(9) The medicament according to any one of (1) to (8) above, wherein the antibody is a human antibody, a humanized antibody, a chimeric antibody, a single chain antibody, or a bispecific antibody.

(10) A method for treating and/or preventing a cancer, comprising administering the medicament of any one of (1) to (9) above to a subject suspected of having a cancer.

(11) The method according to (10) above, comprising administering to a subject the antibody or a fragment thereof and an antitumor agent, which are contained in the above medicament, simultaneously or separately.

This description includes all or part of the contents as disclosed in the description and/or drawings of Japanese Patent Application No. 2010-023455, from which the present application claims the priority.

Advantageous Effect of the Invention

According to the present invention, surprising synergistic effects of massive cancer reduction and regression can be obtained without detection of significant side effects.

MODE FOR CARRYING OUT THE INVENTION

Figure 1:
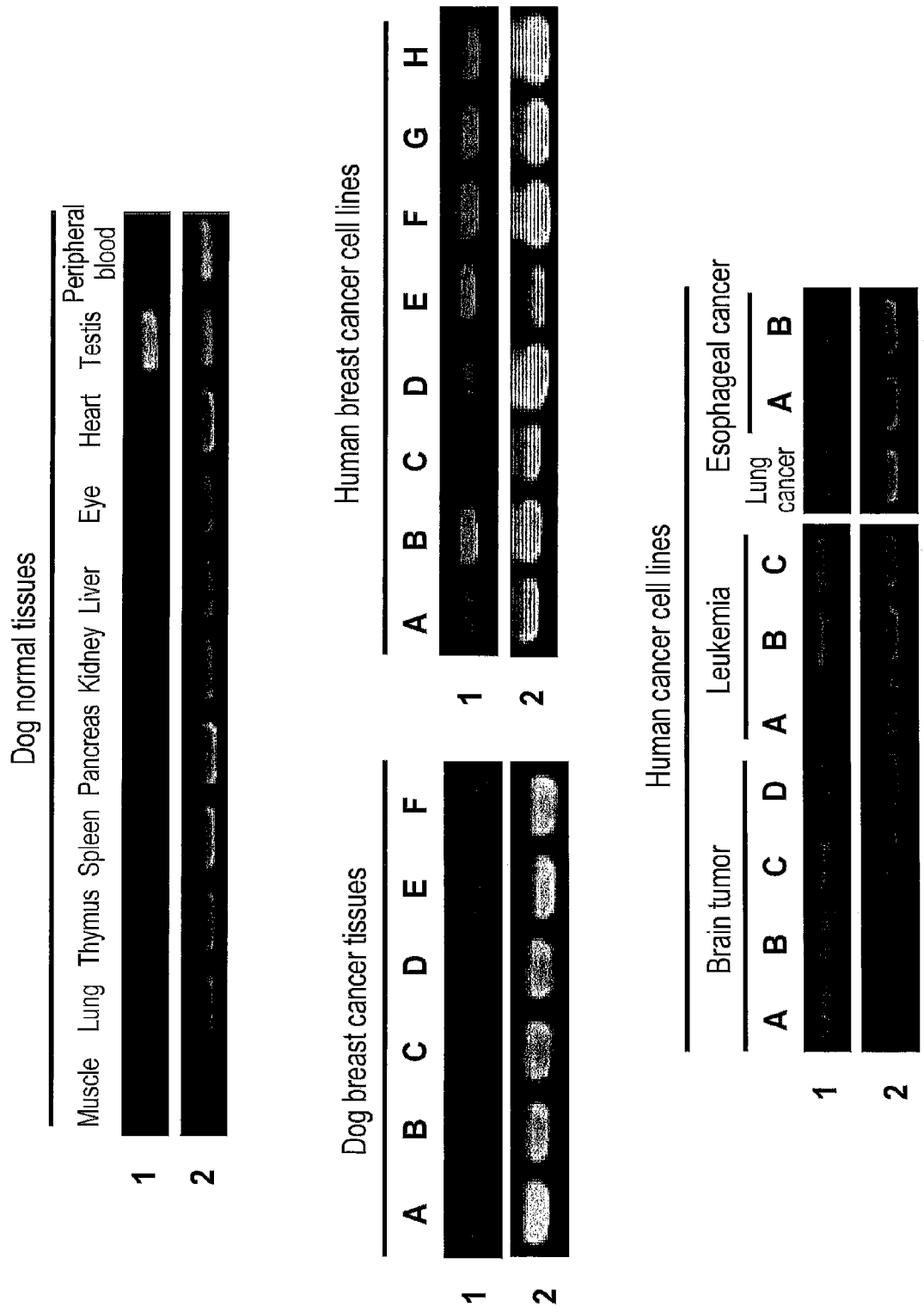
FIG. 1 shows the expression patterns of genes encoding CAPRIN-1 proteins in normal tissues and tumor cell lines. Reference No. 1 indicates the expression patterns of genes encoding CAPRIN-1 proteins and Reference No. 2 indicates the expression patterns of GAPDH genes.
Figure 2:
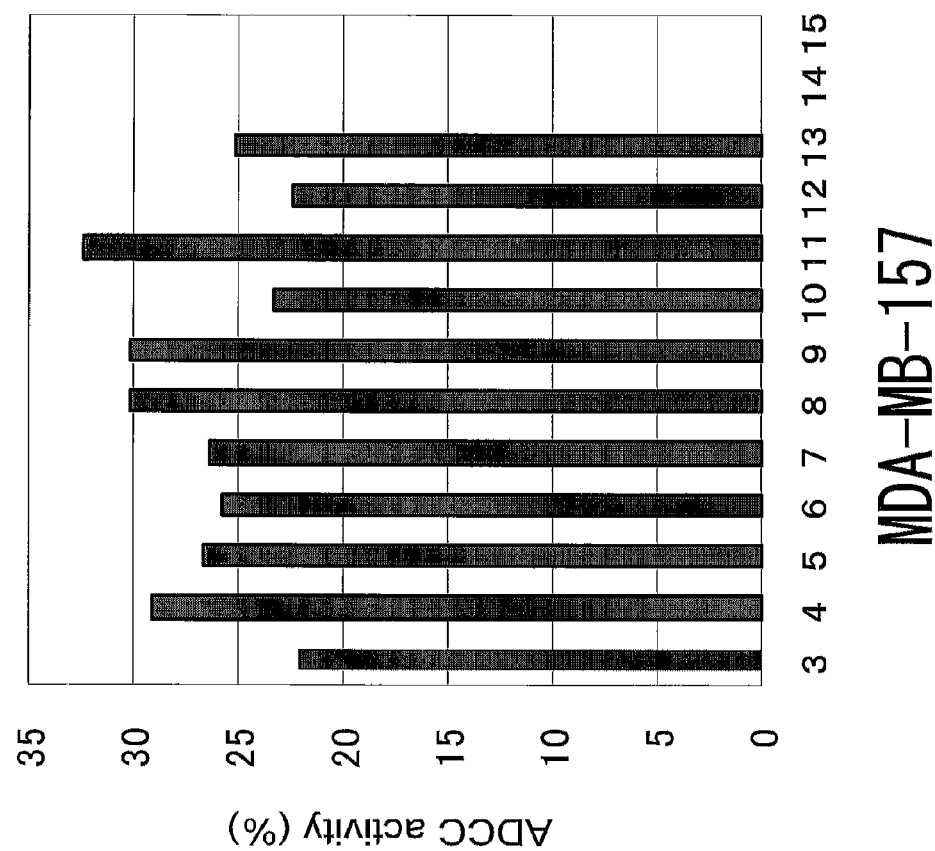
FIG. 2 shows cytotoxicity exhibited by anti-CAPRIN-1 monoclonal antibodies (#1 to #11) that are reactive with the cell surface of the MDA-MB-157 breast cancer cell line which expresses CAPRIN-1. Reference No. 3 indicates a cytotoxic activity exhibited when the anti-CAPRIN-1 monoclonal antibody #1 was added. Reference No. 4 indicates a cytotoxic activity exhibited when the anti-CAPRIN-1 monoclonal antibody #2 was added. Reference No. 5 indicates a cytotoxic activity exhibited when the anti-CAPRIN-1 monoclonal antibody #5 was added. Reference No. 6 indicates a cytotoxic activity exhibited when the anti-CAPRIN-1 monoclonal antibody #4 was added. Reference No. 7 indicates a cytotoxic activity exhibited when the anti-CAPRIN-1 monoclonal antibody #5 was added. Reference No. 8 indicates a cytotoxic activity exhibited when the anti-CAPRIN-1 monoclonal antibody #6 was added. Reference No. 9 indicates a cytotoxic activity exhibited when the anti-CAPRIN-1 monoclonal antibody #7 was added. Reference No. 10 indicates a cytotoxic activity exhibited when the anti-CAPRIN-1 monoclonal antibody #8 was added. Reference No. 11 indicates a cytotoxic activity exhibited when the anti-CAPRIN-1 monoclonal antibody #9 was added. Reference No. 12 indicates a cytotoxic activity exhibited when the anti-CAPRIN-1 monoclonal antibody #10 was added. Reference No. 13 indicates a cytotoxic activity exhibited when the anti-CAPRIN-1 monoclonal antibody #11 was added. Reference No. 14 indicates a cytotoxic activity exhibited when a monoclonal antibody that is reactive with a CAPRIN-1 protein itself but not reactive with the surface of the cancer cell was added. Reference No. 15 indicates a cytotoxic activity exhibited when PBS was added instead of the antibodies.
Figure 3:
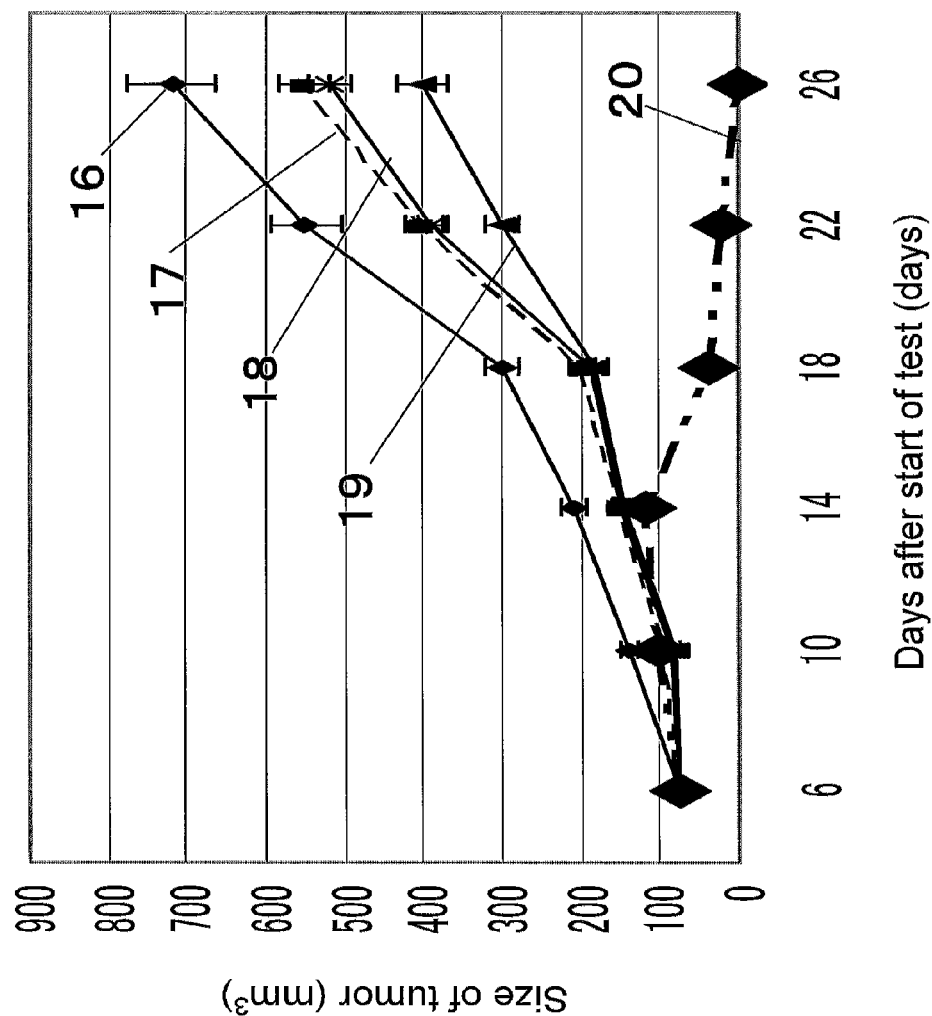
FIG. 3 shows the anti-tumor effect obtained when cyclophosphamide, an antitumor agent, was used in combination with an anti-CAPRIN-1 monoclonal antibody reactive with the surface of cancer cells in nude mice, into which the breast cancer cell line MCF-7 expressing CAPRIN-1 has been transplanted. Reference No. 16 indicates the tumor size of the mouse when PBS was added instead of the antibody. Reference No. 17 indicates the tumor size of the mouse when cyclophosphamide was administered. Reference No. 18 indicates the tumor size of the mouse when the anti-CAPRIN-1 monoclonal antibody #2 was administered. Reference No. 19 indicates the tumor size of the mouse when cyclophosphamide and anti-Her2 antibody were administered. Reference No. 20 indicates the tumor size of the mouse when cyclophosphamide and the anti-CAPRIN-1 monoclonal antibody #2 were administered.
Figure 4:
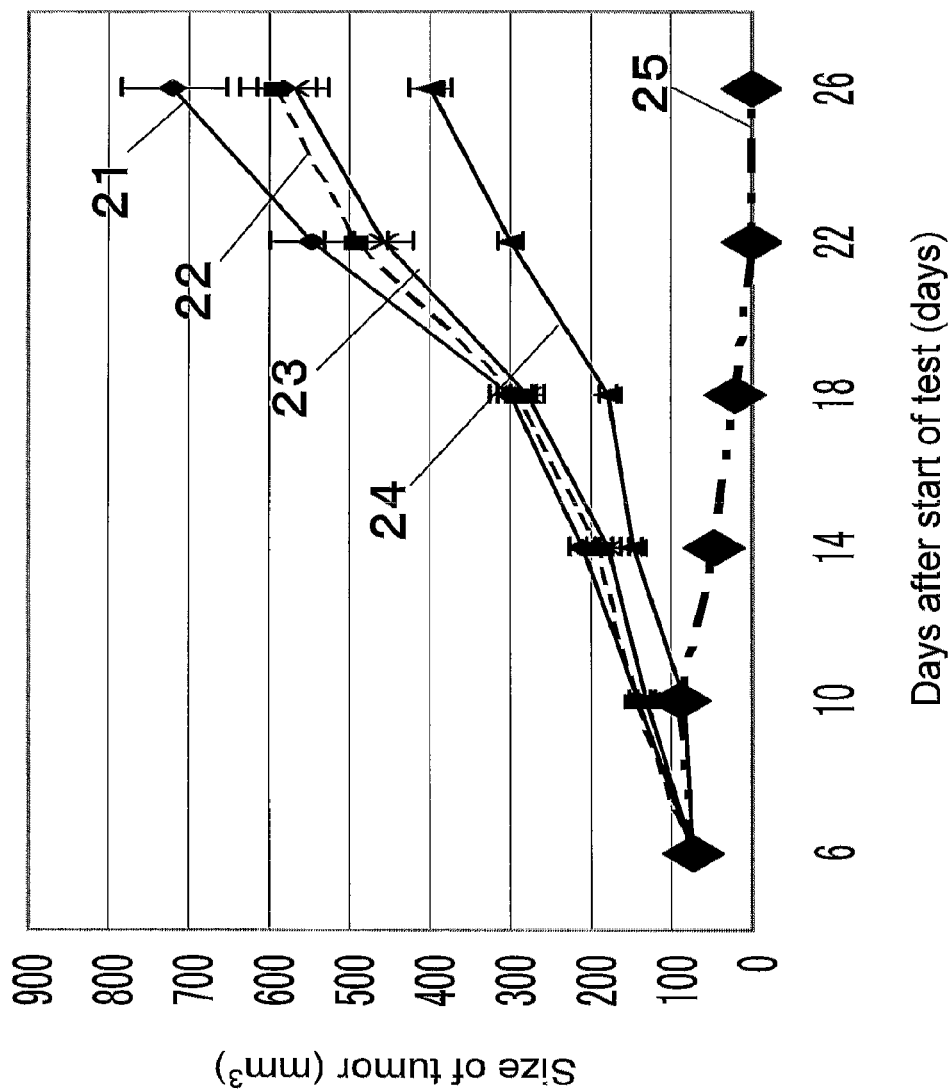
FIG. 4 shows the anti-tumor effect obtained when paclitaxel, an antitumor agent, was used in combination with an anti-CAPRIN-1 monoclonal antibody that is reactive with the surface of cancer cells in nude mice into which the breast cancer cell line MCF-7 expressing CAPRIN-1 has been transplanted. Reference No. 21 indicates the tumor size of the mouse when PBS was administered instead of the antibody. Reference No. 22 indicates the tumor size of the mouse when paclitaxel was administered. Reference No. 23 indicates the tumor size of the mouse when the anti-CAPRIN-1 monoclonal antibody #2 was administered. Reference No. 24 indicates the tumor size of the mouse when paclitaxel and anti-Her2 antibody were administered. Reference No. 25 indicates the tumor size of the mouse when paclitaxel and the anti-CAPRIN-1 monoclonal antibody #2 were administered.
Figure 5:
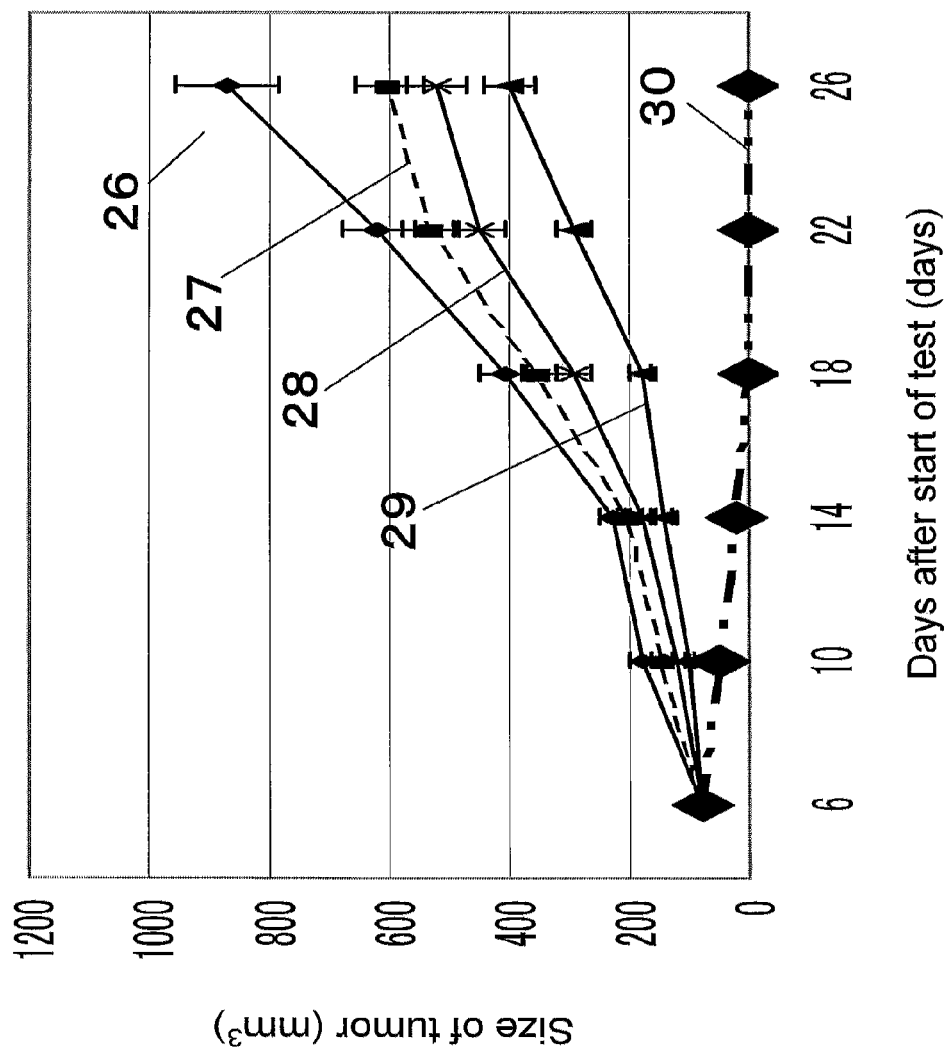
FIG. 5 shows the anti-tumor effect obtained when docetaxel, an antitumor agent, was used in combination with an anti-CAPRIN-1 monoclonal antibody reactive with the surface of cancer cells in nude mice, into which the breast cancer cell line MCF-7 expressing CAPRIN-1 has been transplanted. Reference No. 26 indicates the tumor size of the mouse when PBS was administered instead of the antibody. Reference No. 27 indicates the tumor size of the mouse when docetaxel was administered. Reference No. 28 indicates the tumor size of the mouse when the anti-CAPRIN-1 monoclonal antibody #2 was administered. Reference No. 29 indicates the tumor size of the mouse when docetaxel and anti-Her2 antibody were administered. Reference No. 30 indicates the tumor size of the mouse when docetaxel and the anti-CAPRIN-1 monoclonal antibody #2 were administered.
Figure 6:
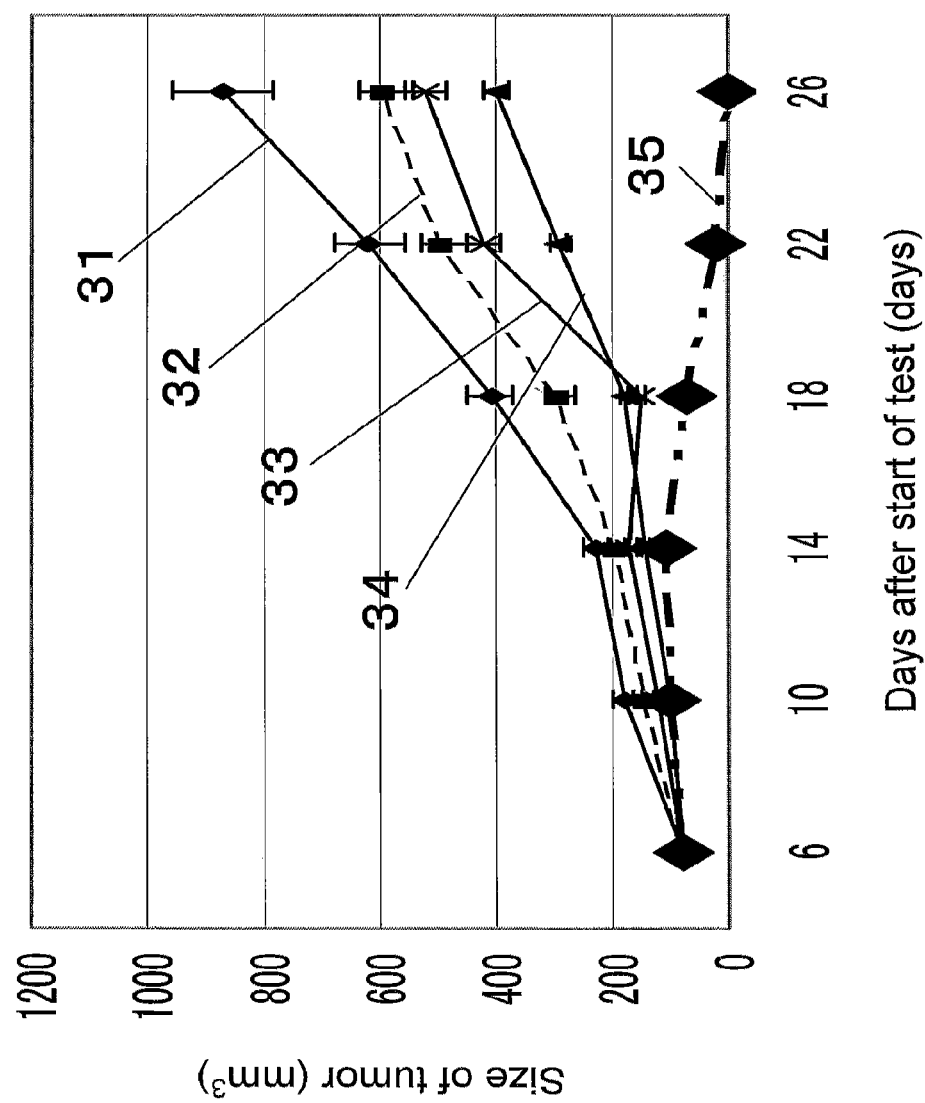
FIG. 6 shows the anti-tumor effect obtained when vinorelbine, an antitumor agent, was used in combination with an anti-CAPRIN-1 monoclonal antibody reactive with the surface of cancer cells in nude mice, into which the breast cancer cell line MCF-7 expressing CAPRIN-1 has been transplanted. Reference No. 31 indicates the tumor size of the mouse when PBS was added instead of an antibody. Reference No. 32 indicates the tumor size of the mouse when vinorelbine was administered. Reference No. 33 indicates the tumor size of the mouse when the anti-CAPRIN-1 monoclonal antibody #2 was administered. Reference No. 34 indicates the tumor size of the mouse when vinorelbine and anti-Her2 antibody were administered. Reference No. 35 indicates the tumor size of the mouse when vinorelbine and the anti-CAPRIN-1 monoclonal antibody #2 were administered.
Figure 7:
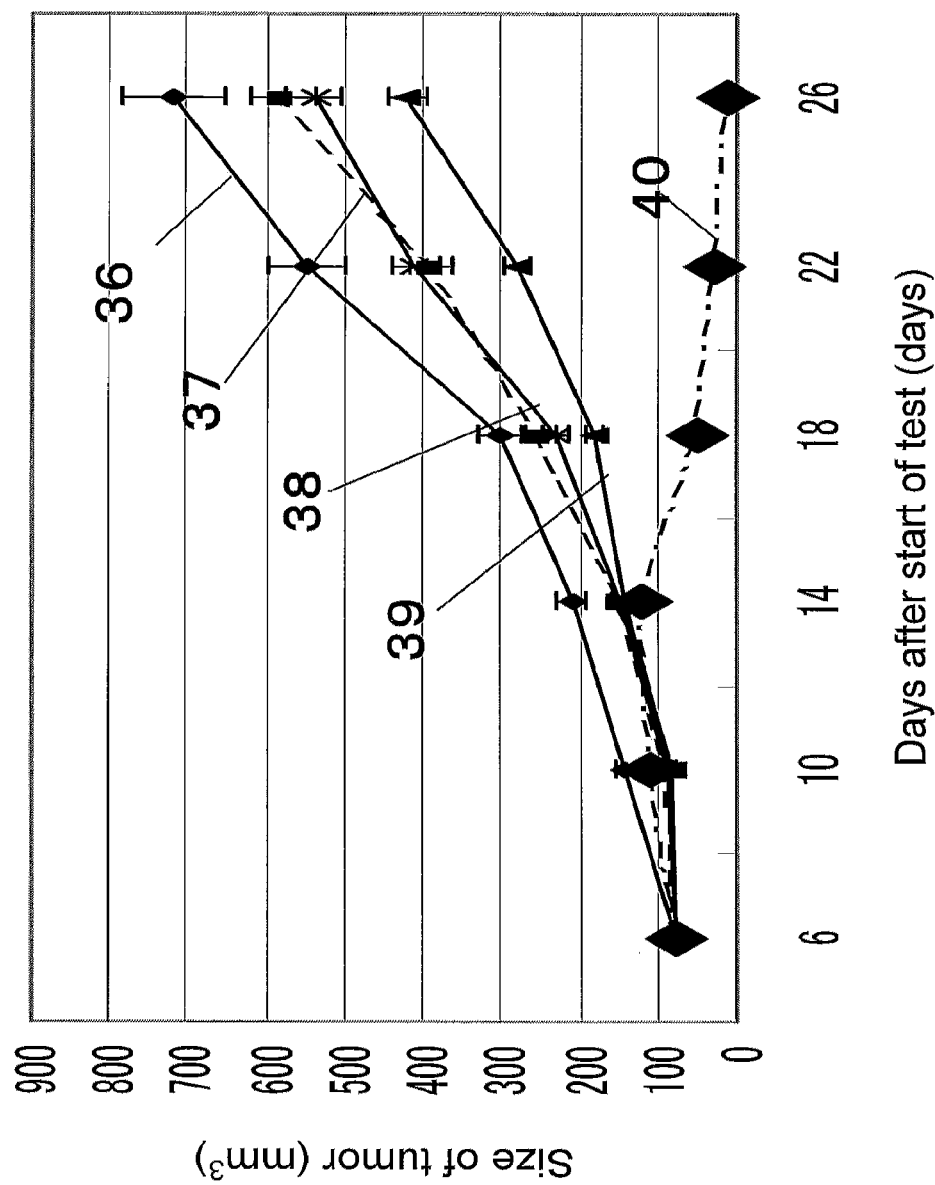
FIG. 7 shows the anti-tumor effect obtained when cyclophosphamide, an antitumor agent, was used in combination with an anti-CAPRIN-1 monoclonal antibody reactive with the surface of cancer cells in nude mice, into which the breast cancer cell line MCF-7 expressing CAPRIN-1 has been transplanted. Reference No. 36 indicates the tumor size the mouse when PBS was administered instead of an antibody. Reference No. 37 indicates the tumor size the mouse when cyclophosphamide was administered. Reference No. 38 indicates the tumor size the mouse when the anti-CAPRIN-1 monoclonal antibody #9 was administered. Reference No. 39 indicates the tumor size the mouse when cyclophosphamide and anti-Her2 antibody were administered. Reference No. 40 indicates the tumor size the mouse when cyclophosphamide and the anti-CAPRIN-1 monoclonal antibody #9 were administered.
Figure 8:
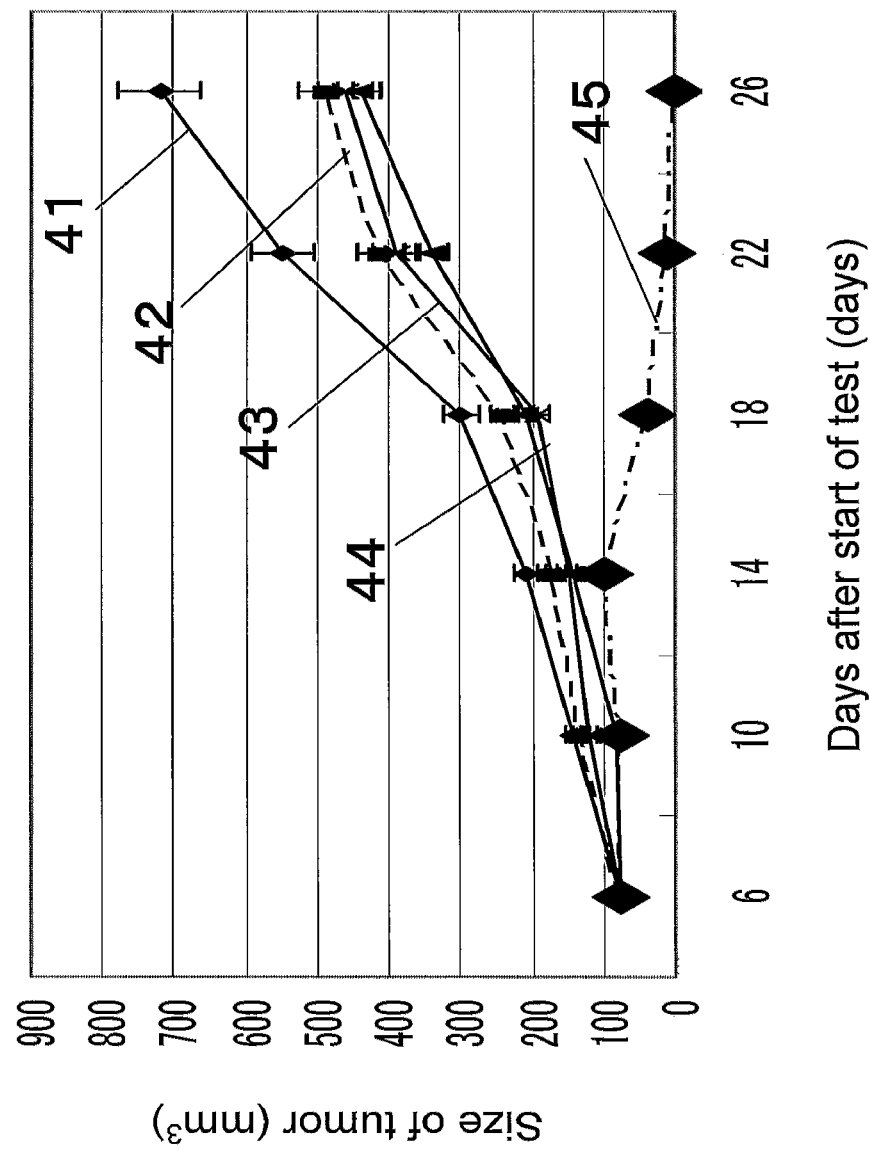
FIG. 8 shows the anti-tumor effect obtained when paclitaxel, an antitumor agent, was used in combination with an anti-CAPRIN-1 monoclonal antibody reactive with the surface of cancer cells in nude mice, into which the breast cancer cell line MCF-7 expressing CAPRIN-1 has been transplanted. Reference No. 41 indicates the tumor size of the mouse when PBS was administered instead of an antibody. Reference No. 42 indicates the tumor size of the mouse when paclitaxel was administered. Reference No. 43 indicates the tumor size of the mouse when the anti-CAPRIN-1 monoclonal antibody #9 was administered. Reference No. 44 indicates the tumor size of the mouse when paclitaxel and anti-Her2 antibody were administered. Reference No. 45 indicates the tumor size of the mouse when paclitaxel and the anti-CAPRIN-1 monoclonal antibody #9 were administered.
Figure 9:
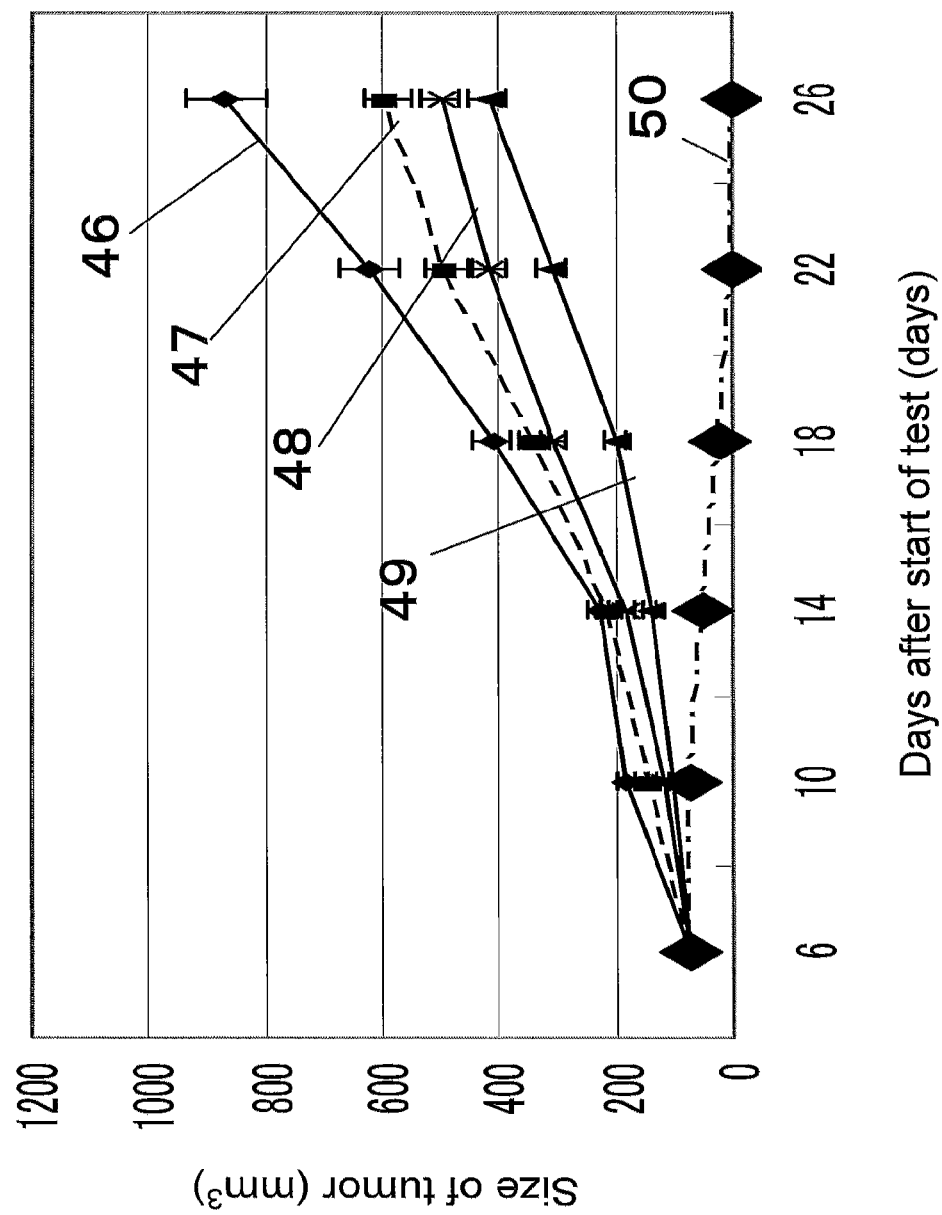
FIG. 9 shows the anti-tumor effect obtained when docetaxel, an antitumor agent, was used in combination with an anti-CAPRIN-1 monoclonal antibody reactive with the surface of cancer cells in nude mice, into which the breast cancer cell line MCF-7 expressing CAPRIN-1 has been transplanted. Reference No. 46 indicates the tumor size of the mouse when PBS was administered instead of the antibody. Reference No. 47 indicates the tumor size of the mouse when docetaxel was administered. Reference No. 48 indicates the tumor size of the mouse when the anti-CAPRIN-1 monoclonal antibody #9 was administered. Reference No. 49 indicates the tumor size of the mouse when docetaxel and anti-Her2 antibody were administered. Reference No. 50 indicates the tumor size of the mouse when docetaxel and the anti-CAPRIN-1 monoclonal antibody #9 were administered.
Figure 10:
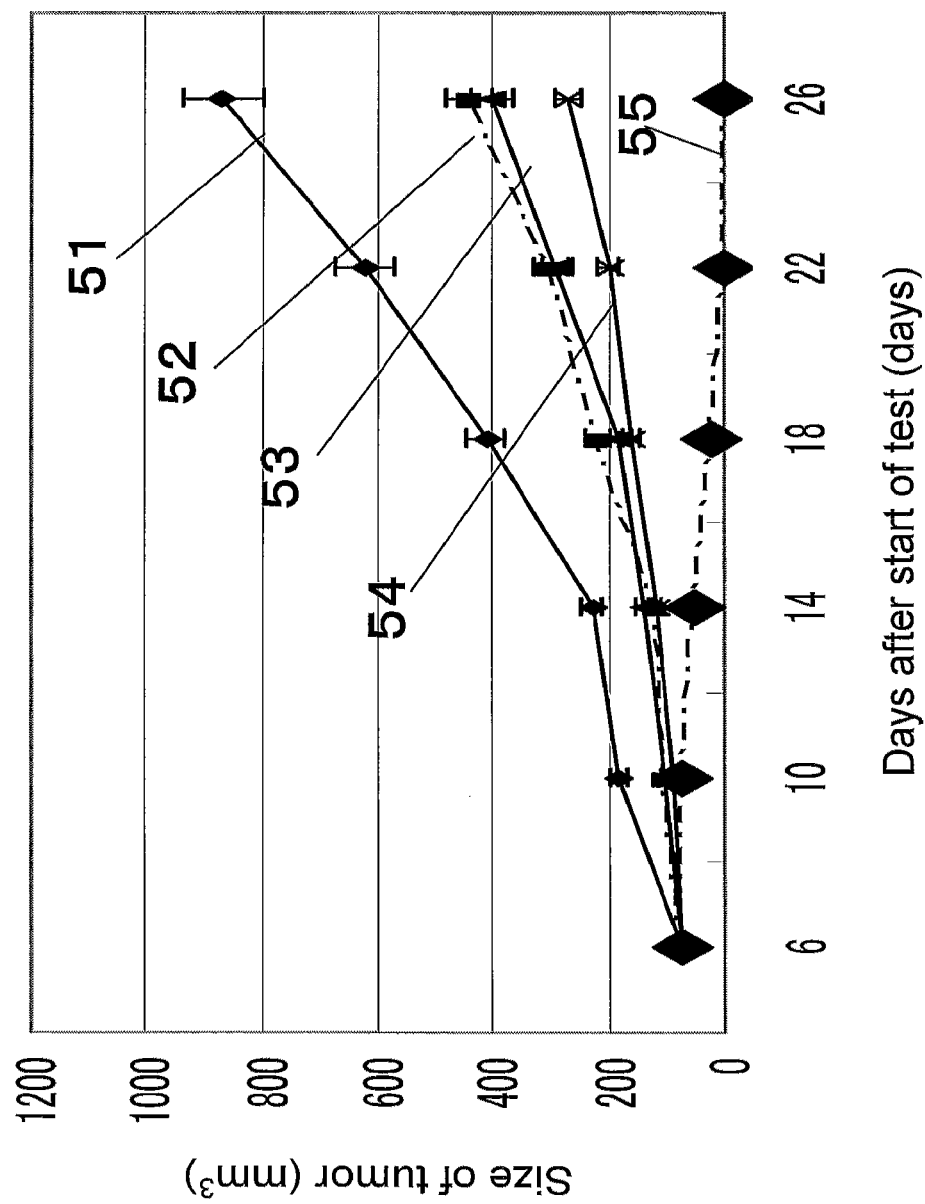
FIG. 10 shows the anti-tumor effect obtained when vinorelbine, an antitumor agent, was used in combination with an anti-CAPRIN-1 monoclonal antibody reactive with the surface of cancer cells in nude mice, into which the MCF-7 breast cancer cell line MCF-7 expressing CAPRIN-1 has been transplanted. Reference No. 51 indicates the tumor size of the mouse when PBS was administered instead of the antibody. Reference No. 52 indicates the tumor size of the mouse when vinorelbine was administered. Reference No. 53 indicates the tumor size of the mouse when the anti-CAPRIN-1 monoclonal antibody #9 was administered. Reference No. 54 indicates the tumor size of the mouse when vinorelbine and anti-Her2 antibody were administered. Reference No. 55 indicates the tumor size of the mouse when vinorelbine and the anti-CAPRIN-1 monoclonal antibody #9 were administered.

The anti-tumor activity of an antibody against a polypeptide represented by any of the even-numbered sequences of SEQ ID NOS: 2 to 30 used in the present invention can be evaluated by examining in vivo suppression of tumor growth in animals with cancer, or, examining whether or not the antibody exhibits cytotoxicity via immunocytes or complements to tumor cells expressing the polypeptide in vitro, as described later.

In the context, the nucleotide sequences of polynucleotides encoding proteins comprising the even-numbered amino acid sequences (i.e., SEQ ID NOS: 2, 4, 6, . . . , 28, 30) of SEQ ID NOS: 2 to 30 are represented by the odd-numbered sequences (i.e., SEQ ID NOS: 1, 3, 5, . . . , 27, 29) of SEQ ID NOS: 1 to 29.

The amino acid sequences that are represented by SEQ ID NOS: 6, 8, 10, 12, and 14 in the Sequence Listing disclosed herein are the amino acid sequences of CAPRIN-1 isolated as polypeptides, which bind to antibodies specifically existing in serum from a dog with cancer, through the SEREX method using a cDNA library from dog testis tissue and the serum of a dog with breast cancer. The amino acid sequences represented by SEQ ID NOS: 2 and 4 are the amino acid sequences of CAPRIN-1 isolated as human homologues. The amino acid sequence represented by SEQ ID NO: 16 is the amino acid sequence of CAPRIN-1 isolated as a cattle homologue. The amino acid sequence represented by SEQ ID NO: 18 is the amino acid sequence of CAPRIN-1 isolated as a horse homologue. The amino acid sequences represented by SEQ ID NOS: 20 to 28 are the amino acid sequences of CAPRIN-1 isolated as mouse homologues. The amino acid sequence represented by SEQ ID NO: 30 is the amino acid sequence of CAPRIN-1 isolated as a chicken homologue (see Example 1 described later). CAPRIN-1 is known to be expressed when normal cells in the resting phase are activated or give rise to cell division.

It was known that CAPRIN-1 is not expressed on the surface of cells; however, the inventors' study has now revealed that a portion of the CAPRIN-1 protein is expressed on the surface of various cancer cells. In the present invention, antibodies which bind to the CAPRIN-1 protein portion to be expressed on the surface of cancer cells are preferably used. An example of a partial peptide of the CAPRIN-1 protein, which is expressed on the surface of cancer cells, is a polypeptide consisting of a sequence of 7 or more continuous amino acid residues within the region of amino acid residue Nos. (aa) 50-98 or 233-305 in the amino acid sequences represented by even-numbered sequences of SEQ ID NOS: 2 to 30 in the sequence listing excluding SEQ ID NOS: 6 and 18. Specific examples include the amino acid sequence represented by SEQ ID NO: 37 and an amino acid sequence having 80% or more, preferably 85% or more, more preferably 90% or more, and further preferably 95% or more sequence identity with the amino acid sequence. Examples of an antibody to be used in the present invention include all antibodies (specifically) binding to these peptides (or (specifically) recognizing these peptides or having immunological reactivity with these peptides) and exhibiting anti-tumor activity.

The above-described anti-CAPRIN-1 antibody used in the present invention may be any type of antibody as long as it can exhibit anti-tumor activity. Examples of such antibodies include monoclonal antibodies, polyclonal antibodies, recombinant antibodies, such as synthetic antibodies, multi-specific antibodies, humanized antibodies, chimeric antibodies, and single chain antibodies (scFv), human antibodies, and fragments thereof, such as Fab, F(ab')$_2$, and Fv. These antibodies and fragments thereof can be prepared by methods known by persons skilled in the art. In the present invention, antibodies capable of specifically binding to a CAPRIN-1 protein are desired. Preferably, they are monoclonal antibodies. Polyclonal antibodies may also be used as long as homogenous antibodies can be stably produced. Also, when a subject is a human, human antibodies or humanized antibodies are desired in order to avoid or suppress rejection.

The term "specifically binding to CAPRIN-1 protein" as used herein refers to specifically bind to a CAPRIN-1 protein, but does not substantially bind to proteins other than the CAPRIN-1 protein.

The anti-tumor activity of an antibody that can be used in the present invention can be evaluated as described below by examining in vivo the suppression of the tumor growth in animals with cancer, or, by examining whether or not it exhibits in vitro an activity of cytotoxicity, which is mediated by immunocytes or complements, to tumor cells expressing the polypeptide.

Furthermore, examples of the subject for cancer treatment and/or prevention in the present invention include mammals, such as humans, pet animals, domestic animals, and animals for competition. A preferable subject is a human.

Preparation of antigens and antibodies, medicaments, and the like relating to the present invention are described below.
<Preparation of Antigens for Antibody Preparation>

Proteins or fragments thereof to be used as sensitizing antigens for obtaining anti-CAPRIN-1 antibodies used in the present invention may be derived from any animal species without particular limitation, such as humans, dogs, cattle, horses, mice, rats, and chickens. However, proteins or fragments thereof are preferably selected in consideration of compatibility with parent cells used for cell fusion. In general, mammal-derived proteins are preferred and, in particular, human-derived protein is preferred. For example, when CAPRIN-1 is human CAPRIN-1, the human CAPRIN-1 protein, a partial peptide thereof, or cells expressing human CAPRIN-1 can be used.

The nucleotide sequences and the amino acid sequences of human CAPRIN-1 and homologues thereof can be obtained by accessing GenBank (NCBI, U.S.A.) and using an algorithm such as BLAST or FASTA (Karlin and Altschul, Proc. Natl. Acad. Sci. U.S.A., 90: 5873-5877, 1993; Altschul et al., Nucleic Acids Res. 25: 3389-3402, 1997).

In the present invention, on the basis of the nucleotide sequence (SEQ ID NO: 1 or 3) or the amino acid sequence (SEQ ID NO: 2 or 4) of human CAPRIN-1, a target nucleic acid or a target protein comprises a sequence having 70% to 100%, preferably 80% to 100%, more preferably 90% to 100%, even more preferably 95% to 100% (e.g., 97% to 100%, 98% to 100%, 99% to 100%, or 99.5% to 100%) sequence identity with the nucleotide sequence or the amino acid sequence of the ORF or the mature portion of human CAPRIN-1. As use herein, the term "% sequence identity" refers to a percentage (%) of identical amino acids (or nucleotides) relative to the total number of amino acids (or nucleotides), when two sequences are aligned to achieve the highest similarity with or without introduction of gaps.

The length of a fragment of CAPRIN-1 protein ranges from the amino acid length of an epitope (antigenic determinant), which is the minimum unit recognized by an antibody, to a length less than the full length of the protein. The term "epitope" refers to a polypeptide fragment having antigenicity or immunogenicity in mammals, preferably in humans, and the minimum unit of the epitope consists of about 7 to 12 (continuous) amino acids, for example 8 to 11 (continuous) amino acids. Examples of a partial sequence of CAPRIN-1 protein specifically binding to an antibody include a partial sequence comprising at least about 7 to 12 amino acids in the amino acid sequence represented by SEQ ID NO: 37 or an amino acid sequence having 80% or more, preferably 85% or more, more preferably 90% or more, further preferably 95% or more sequence identity with the amino acid sequence of SEQ ID NO: 37.

The polypeptides comprising the above-mentioned human CAPRIN-1 protein or partial peptides of the protein, can be synthesized by a chemical synthesis method, such as the Fmoc method (fluorenylmethyloxycarbonyl method) or the tBoc method (t-butyloxycarbonyl method) (Edited by The Japanese Biochemical Society, Seikagaku Jikken Koza (Biochemical Experimental Lecture Series) 1, Protein Chemistry IV, Chemical Modification and Peptide Synthesis, TOKYO KAGAKU DOZIN (Japan), 1981). Alternatively, the above-mentioned polypeptides may also be synthesized by conventional methods using various commercially available peptide synthesizers. Furthermore, with the use of known genetic engineering techniques (e.g., Sambrook et al., Molecular Cloning, $2^{nd}$ Edition, Current Protocols in Molecular Biology (1989), Cold Spring Harbor Laboratory Press, Ausubel et al., Short Protocols in Molecular Biology, $3^{rd}$ Edition, A compendium of Methods from Current Protocols in Molecular Biology (1995), John Wiley & Sons), a polynucleotide encoding the above polypeptide is prepared and then incorporated into an expression vector, which is subsequently introduced into a host cell in order to produce a polypeptide of interest in the host cell, and then recover it.

The polynucleotides encoding the above polypeptides can be easily prepared by known genetic engineering techniques or conventional techniques using a commercially available nucleic acid synthesizer. For example, DNA comprising the nucleotide sequence of SEQ ID NO: 1 can be prepared by PCR using a human chromosomal DNA or cDNA library, as a template, and a pair of primers designed to be able to amplify the nucleotide sequence represented by SEQ ID NO: 1. PCR conditions can be appropriately determined. For example, PCR conditions comprise conducting 30 cycles of the reaction cycle of: denaturation at 94° C. for 30 seconds; annealing at 55° C. for 30 seconds to 1 minute; and extension at 72° C. for 2 minutes, using a thermostable DNA polymerase (e.g., Taq polymerase or the like) and PCR buffer containing $Mg^{2+}$, followed by reacting at 72° C. for 7 minutes. However, the PCR conditions are not limited to the above example. PCR techniques, conditions, and the like are described in Ausubel et al., Short Protocols in Molecular Biology, $3^{rd}$ Edition, A compendium of Methods from Current Protocols in Molecular Biology (1995), John Wiley & Sons (particularly Chapter 15).

Also, on the basis of the nucleotide sequence and amino acid sequence information represented by SEQ ID NOS: 1 to 30 in the Sequence Listing described herein, appropriate probes or primers are prepared, and then a cDNA library of a human or the like is screened using them, so that desired DNA can be isolated. A cDNA library is preferably constructed from cells, organs or tissues, which express proteins having even-numbered sequences of SEQ ID NOS: 2 to 30 Examples of such cells or tissues include cells or tissues derived from testis, and cancers or tumors, such as leukemia, breast cancer, lymphoma, brain tumor, lung cancer, colorectal cancer, and the like. Procedures such as the preparation of probes or primers, construction of a cDNA library, screening of a cDNA library, and cloning of target genes are known by a person skilled in the art and can be carried out by the methods described in Sambrook et al., Molecular Cloning, $2^{nd}$ Edition, Current Protocols in Molecular Biology (1989), Ausbel et al., (above), and the like. DNA encoding a human CAPRIN-1 protein or a partial peptide thereof can be obtained from the thus obtained DNA.

The host cells may be any cells, as long as they can express the above-mentioned polypeptide. Examples of prokaryotic cells include, but are not limited to, *Escherichia coli* and the like. Examples of eukaryotic cells include, but are not limited to, mammalian cells, such as monkey kidney cells (COS1) and Chinese hamster ovary cells (CHO), human fetal kidney cell line (HEK293), fetal mouse skin cell line (NIH3T3), yeast cells such as budding yeast and fission yeast, silkworm cells, and Xenopus oocyte.

When prokaryotic cells are used as host cells, an expression vector used herein contains an origin replicable within prokaryotic cells, a promoter, a ribosome-binding site, a multiple cloning site, a terminator, a drug resistance gene, an auxotrophic complementary gene, and the like. Examples of *Escherichia coli* expression vector include a pUC-based vector, pBluescript II, a pET expression system, and a pGEX expression system. DNA encoding the above polypeptide is incorporated into such an expression vector, prokaryotic host cells are transformed with the vector, the thus obtained transformed cells are cultured, and thus the polypeptide encoded by the DNA can be expressed in prokaryotic host cells. At this time, the polypeptide can also be expressed as a fusion protein with another protein.

When eukaryotic cells are used as host cells, an expression vector used herein is an expression vector for eukaryotic cells, which contains a promoter, a splicing region, a poly(A) addition site, and the like. Examples of such an expression vector include pKA1, pCDM8, pSVK3, pMSG, pSVL, pBK-CMV, pBK-RSV, EBV vector, pRS, pcDNA3, and pYES2. In a manner similar to the above, DNA encoding the above polypeptide is incorporated into such an expression vector, eukaryotic host cells are transformed with the vector, the thus obtained transformed cells are cultured, and thus the polypeptide encoded by the DNA can be expressed in eukaryotic host cells. When pIND/V5-His, pFLAG-CMV-2, pEGFP-N1, pEGFP-C1, or the like is used as an expression vector, the above polypeptide can be expressed as a fusion protein to which a tag from among various tags such as a His tag (e.g., $(His)_6$-$(His)_{10}$), a FLAG tag, a myc tag, an HA tag, and GFP has been added.

For introduction of an expression vector into host cells, a known method can be employed, such as electroporation, a calcium phosphate method, a liposome method, a DEAE dextran method, microinjection, viral infection, lipofection, and binding to a cell membrane-permeable peptide.

The polypeptide of interest can be isolated and purified from host cells by a combination of known separation procedures. Examples of such procedures include, but are not limited to, treatment with a denaturing agent such as urea or a surfactant, ultrasonication, enzymatic digestion, salting-out or solvent fractionation and precipitation, dialysis, centrifugation, ultrafiltration, gel filtration, SDS-PAGE, isoelectric focusing, ion exchange chromatography, hydrophobic chromatography, affinity chromatography, and reverse phase chromatography.

<Antibody Structure>

An antibody is a heteromultimeric glycoprotein that generally contains at least two heavy chains and two light chains Antibodies other than IgM, an antibody are an about 150-kDa heterotetramer glycoprotein composed of two identical light (L) chains and two identical heavy (H) chains. Typically, each light chain is connected to a heavy chain via one disulfide covalent bond, however, the number of disulfide bonds between heavy chains of various immunoglobulin isotypes is varied. Each heavy chain or each light chain also has an intrachain disulfide bond. Each heavy chain has a variable domain (VH region) on one end followed by several constant regions. Each light chain has a variable domain (VL region) and has one constant region on an end opposite to the other end. The constant region of a light chain is aligned with the first constant region of a heavy chain, and a light chain variable domain is aligned with a heavy chain variable domain. A specific region of an antibody variable domain exhibits specific variability that is referred to as a complementarity determining region (CDR), so that it imparts binding specificity to the antibody. A portion of a variable region, which is relatively conserved, is referred to as a framework region (FR). Complete heavy chain and light chain variable domains separately contain four FRs ligated via three CDRs. The three CDRs in a heavy chain are referred to as CDRH1, CDRH2, and CDRH3 in this order from the N-terminus. Similarly, in the case of a light chain, CDRLs are referred to as CDRL1, CDRL2, and CDRL3. CDRH3 is most important for the binding specificity of an antibody to an antigen. Also, the CDRs of each chain are retained together in a state of being adjacent to each other due to the FR regions, contributing to the formation of the antigen binding site of the antibody in cooperation with CDRs from the other chain. A constant region does not directly contribute to the binding of an antibody to an antigen, but exhibits various effector functions, such as involvement in antibody-dependent cell-mediated cytotoxicity (ADCC), phagocytosis via binding to an Fcγ receptor, the rate of half-life/clearance via a neonate Fc receptor (FcRn), and complement-dependent cytotoxicity (CDC) via a C1q constituent of the complement cascade.

<Preparation of Antibody>

The term "anti-CAPRIN-1 antibody" as used herein refers to an antibody having immunological reactivity with a full-length CAPRIN-1 protein or a fragment thereof.

As used herein, the term "immunological reactivity" refers to the property of in vivo binding of an antibody to a CAPRIN-1 antigen. Through such an in vivo binding, the function of damaging tumor (e.g., death, suppression, or degeneration) is exhibited. Specifically, an antibody used in the present invention may be any type of antibody, as long as it binds to a CAPRIN-1 protein so as to be able to cytotoxically impair a tumor, such as leukemia, lymphoma, breast cancer, brain tumor, lung cancer, esophageal cancer, gastric cancer, renal cancer, or colorectal cancer.

Examples of an antibody include a monoclonal antibody, a polyclonal antibody, a recombinant antibody (e.g., a synthetic antibody, a multispecific antibody, a humanized antibody, a chimeric antibody, or a single chain antibody), a human antibody, and an antibody fragment thereof (e.g., Fab, F(ab')$_2$, or Fv). Also, an antibody may be an immunoglobulin molecule of any class such as IgG, IgE, IgM, IgA, IgD, or IgY, or any subclass such as IgG1, IgG2, IgG3, IgG4, IgA1, or IgA2. Any of these antibodies or fragments thereof has immunological reactivity with a CAPRIN-1 protein existing on the surface of cancer cells and preferably to a polypeptide of the extracellular region thereof (preferably, specifically binds to the protein or the polypeptide) and exhibits a cytotoxic activity against cancer.

The antibody may further be modified by, in addition to glycosylation, acetylation, formylation, amidation, phosphorylation, pegylation (PEG), or the like.

Various antibody preparation examples are as described below.

When the antibody is a monoclonal antibody, for example, the breast cancer cell line SK-BR-3 expressing CAPRIN-1 is administered to a mouse for immunization, the spleen is removed from the mouse, cells are separated, and then the cells and mouse myeloma cells are fused. From among the thus obtained fusion cells (hybridomas), a clone producing an antibody having the effect of suppressing cancer cell proliferation is selected. A hybridoma producing a monoclonal antibody that has the effect of suppressing cancer cell proliferation is isolated, the hybridoma is cultured, and then an antibody is purified from the culture supernatant by general affinity purification, so that the antibody can be prepared.

The hybridoma producing a monoclonal antibody can also be prepared as described below, for example. First, an animal is immunized with a sensitizing antigen according to a known method. A general method is carried out by injecting a sensitizing antigen to a mammal intraperitoneally or subcutaneously. Specifically, a sensitizing antigen is diluted with PBS (Phosphate-Buffered Saline), saline, or the like to an appropriate amount, followed by suspension. The resultant is then mixed with an appropriate amount of a general adjuvant as necessary, such as Freund's complete adjuvant. After emulsification, the solution was administered to a mammal several times every 4 to 21 days. Furthermore, an appropriate carrier can also be used upon immunization with a sensitizing antigen.

A mammal is immunized as described above. After confirmation of a rise in a desired serum antibody level, immunized cells are collected from the mammal and then subjected to cell fusion. Preferable immunized cells are particularly splenocytes.

Mammalian myeloma cells are used as the other parent cells to be fused with the immunized cells. As the myeloma cells, various known cell lines are preferably used, such as P3U1 (P3-X63Ag8U1), P3 (P3x63Ag8.653) (J. Immunol. (1979) 123, 1548-1550), P3x63Ag8U.1 (Current Topics in Microbiology and Immunology (1978) 81, 1-7), NS-1 (Kohler. G. and Milstein, C. Eur. J. Immunol. (1976) 6, 511-519), MPC-11 (Margulies. D. H. et al., Cell (1976) 8, 405-415), SP2/0 (Shulman, M. et al., Nature (1978) 276, 269-270), FO (deSt. Groth, S. F. et al., J. Immunol. Methods (1980) 35, 1-21), 5194 (Trowbridge, I. S. J. Exp. Med. (1978) 148, 313-323), and 8210 (Galfre, G. et al., Nature (1979) 277, 131-133).

Fusion of the immunized cell and the myeloma cell can be carried out according to basically a known method such as Kohler and Milstein's technique (Kohler, G. and Milstein, C. Methods Enzymol. (1981) 73, 3-46), for example.

More specifically, the above cell fusion is carried out, for example, in the presence of a cell fusion accelerator in a usual nutrient culture medium. As this fusion accelerator, polyethylene glycol (PEG), Sendai virus (HVJ), or the like is used. If desired, an auxiliary agent such as dimethylsulfoxide may be added and used in order to enhance fusion efficiency.

The ratio of the immunized cells to the myeloma cells to be used herein can be arbitrarily set. For example, the number of immunized cells that are preferably used is one to ten times the number of myeloma cells. As a culture medium to be used for the above-mentioned cell fusion, an RPMI1640 culture medium suitable for proliferation of the above-mentioned myeloma cell line, an MEM culture medium, and other culture media usually used for culturing this kind of cell can be used. Further, liquid that is supplemental to serum such as fetal bovine serum (FCS) can be used together therewith.

Cell fusion can be performed by thoroughly mixing the predetermined amounts of the above immunized cells and the myeloma cells in the above culture medium, and a PEG solution (for example, having an average molecular weight ranging from about 1000 to 6000) prewarmed at about 37° C. is added usually at a concentration of 30%-60% (w/v) and mixed, thereby forming a culture containing hybridomas of interest. Next, a suitable culture medium is successively added to the thus-obtained culture, which is then centrifuged to remove the supernatant, and this procedure is repeated to remove the cell fusion agent or the like which is not preferable for the growth of hybridomas.

The thus obtained hybridomas are cultured for selection in a usual selection culture medium (e.g., a HAT culture medium containing hypoxanthine, aminopterin and thymidine). Culturing in this HAT culture medium is continued for a sufficient period of time (usually several days to several weeks) so that the cells (non-fused cells) other than the target hybridomas die. Subsequently, screening and single cloning of the hybridoma which produces an antibody of interest are performed using the general limiting dilution method.

The above hybridomas are obtained by an immunizing non-human animal with an antigen. In addition to this method, hybridomas that produce a human antibody having desired activity (e.g., activity of suppressing cell proliferation) can also be obtained by in vitro sensitizing human lymphocytes, such as human lymphocytes that have been infected with the EB virus, with a protein, a protein-expressing cell, or a lysate thereof, followed by fusing of the thus sensitized lymphocytes with human-derived myeloma cells having an ability to permanently divide, such as U266 (registration no. TIB196).

The thus prepared hybridoma that produces a monoclonal antibody of interest can be passaged in a general culture medium and can be stored in liquid nitrogen over a long period of time.

Specifically, a hybridoma can be prepared by immunizing by a general immunization method using, as a sensitizing antigen, a desired antigen or a cell that expresses the desired antigen, fusing the thus obtained immunized cell with a known parent cell by a general cell fusion method, and then screening for a monoclonal antibody-producing cell (i.e., a hybridoma) by a general screening method.

Another example of an antibody that can be used in the present invention is a polyclonal antibody. A polyclonal antibody can be obtained as described below, for example.

A small animal, such as a mouse, a human antibody-producing mouse, or a rabbit, is immunized with a natural CAPRIN-1 protein, a recombinant CAPRIN-1 protein expressed in a microorganism such as Escherichia coli in the form of a fusion protein with GST or the like, or a partial peptide thereof, and then serum is obtained. The serum is purified by ammonium sulfate precipitation, protein A column, protein G column, DEAE ion exchange chromatography, affinity column to which a CAPRIN-1 protein or a synthetic peptide has been coupled, or the like, so that a polyclonal antibody can be prepared. In Examples described later, a rabbit polyclonal antibody against the peptide (represented by SEQ ID NO: 37) of a partial region (in the amino acid sequence of a CAPRIN-1 protein) that is expressed on the surface of cancer cells was prepared and the anti-tumor effect was confirmed.

As a human antibody-producing mouse, a KM mouse (Kirin Pharma/Medarex) and a Xeno mouse (Amgen) are known (e.g., International Patent Publications WO02/43478 and WO02/092812), for example. When such a mouse is immunized with a CAPRIN-1 protein or a fragment thereof, a complete human polyclonal antibody can be obtained from blood. Also, splenocytes are collected from the immunized mouse and then a human-type monoclonal antibody can be prepared by a method for fusion with myeloma cells.

An antigen can be prepared according to a method using animal cells (Japanese Patent Publication (Kohyo) No. 2007-530068) or baculovirus (e.g., International Publication WO98/46777), for example. When an antigen has low immunogenicity, the antigen may be bound to a macromolecule having immunogenicity, such as albumin, and then immunization is carried out.

Furthermore, an antibody gene is cloned from said hybridoma and then incorporated into an appropriate vector. The vector is then introduced into a host, and then the genetically recombined antibody produced using gene recombination techniques can be used (e.g., see Carl, A. K. Borrebaeck, James, W. Larrick, THERAPEUTIC MONOCLONAL ANTIBODIES, Published in the United Kingdom by MACMILLAN PUBLISHERS LTD, 1990). Specifically, the cDNA of a variable region (V region) of an antibody is synthesized from the mRNA of the hybridoma using reverse transcriptase. When DNA encoding the V region of an antibody of interest can be obtained, this DNA is ligated to DNA encoding the constant region (C region) of a desired antibody, and then the resultant fusion product is incorporated into an expression vector. Alternatively, DNA encoding the V region of an antibody may be incorporated into an expression vector containing the DNA for the C region of an antibody. At this time, the DNA can be incorporated into an expression vector so that it is expressed under the control of expression control regions, such as enhancer and promoter. Next, host cells are transformed with the expression vector, so that the antibody can be expressed.

The anti-CAPRIN-1 antibody used in the present invention is preferably a monoclonal antibody. However, the anti-CAPRIN-1 antibody of the present invention may also be a polyclonal antibody, or a recombinant antibody or a genetically-modified antibody (e.g., a chimeric antibody, a humanized antibody, a single chain antibody, or a bispecific antibody), for example.

Examples of the monoclonal antibody include human monoclonal antibodies and non-human animal monoclonal antibodies (e.g., a mouse monoclonal antibody, a rat monoclonal antibody, a rabbit monoclonal antibody, and a chicken monoclonal antibody). The monoclonal antibody can be prepared by culturing a hybridoma obtained by cell fusion of a splenocyte from a non-human mammal (e.g., a mouse or a human antibody-producing mouse) immunized with a CAPRIN-1 protein, with a myeloma cell. In Examples described later, mouse monoclonal antibodies were prepared and the anti-tumor effects were confirmed.

These monoclonal antibodies comprise a heavy chain variable (VH) region comprising the amino acid sequence of SEQ ID NO: 43, 73, 83, 93, 103, 113, or SEQ ID NO: 123 and a light chain variable (VL) region comprising the amino acid sequence of SEQ ID NO: 47, 53, 58, 63, 68, 77, 87, 97, 107, 117, or 127, wherein: the VH region comprises CDR1 represented by the amino acid sequence of SEQ ID NO: 40, 70, 80, 90, 100, 110, or 120, CDR2 represented by the amino acid sequence of SEQ ID NO: 41, 71, 81, 91, 101, 111, or 121, and CDR3 represented by the amino acid sequence of SEQ ID NO: 42, 72, 82, 92, 102, 112, or 122; and the VL region comprises CDR1 represented by the amino acid sequence of SEQ ID NO: 44, 50, 55, 60, 65, 74, 84, 94, 104, 114, or 124, CDR2 represented by the amino acid sequence of SEQ ID NO: 45, 51, 56, 61, 66, 75, 85, 95, 105, 115, or 125, and CDR3 represented by the amino acid sequence of SEQ ID NO: 46, 52, 57, 62, 67, 76, 86, 96, 106, 116, or 126.

The chimeric antibody is prepared by combining sequences from different animals. For example, the chimeric antibody comprises mouse antibody heavy chain and light chain variable regions and human antibody heavy chain and light chain constant regions. Such a chimeric antibody can be prepared by known methods. For example, the chimeric antibody can be obtained by ligating DNA encoding an antibody V region to DNA encoding a human antibody C region, incorporating the resultant ligate into an expression vector, introducing the vector into a host, and then causing the host to produce the antibody.

Examples of the polyclonal antibody include an antibody obtained by immunizing a human antibody-producing animal (e.g., a mouse) with a CAPRIN-1 protein.

The humanized antibody is a modified antibody that is also referred to as a reshaped human antibody. A humanized antibody can be constructed by transplanting CDRs of an antibody from an immunized animal into the complementarity determining regions of a human antibody. General gene recombination techniques therefor are also known.

Specifically, DNA sequences designed to have each of the CDRs of a mouse antibody ligated to each of the framework regions (FRs) of a human antibody are synthesized by the PCR method from several oligonucleotides, which are prepared so as to have overlap portions at their terminal portions, for example. A humanized antibody can be obtained by ligating the thus obtained DNA to DNA encoding the constant region of a human antibody, incorporating the resultant fusion product into an expression vector, introducing the vector into a host, and thus causing the host to produce the gene product (see European Patent Publication EP239400 and International Patent Publication WO96/02576). As the FRs of a human antibody, which is ligated via CDRs, FRs that allow the formation of an antigen-binding site with good complementarity determining regions are selected. If necessary, for the formation of an antigen-binding site having the appropriate complementarity determining regions of a reshaped human antibody, the amino acids of the framework regions of an antibody variable region may be substituted (Sato, K. et al., Cancer Research, 1993, 53: 851-856). Also, the amino acids of FRs may be substituted with those of framework regions from various human antibodies (see International Patent Publication WO99/51743).

As the framework regions (FRs) of a human antibody, which is ligated via CDRs, FRs that allows the formation of an antigen-binding site with good complementarity determining regions are selected. If necessary, for the formation of an antigen-binding site having the appropriate complementarity determining regions of a reshaped human antibody, the amino acids of the framework regions of an antibody variable region may be substituted (Sato K. et al., Cancer Research 1993, 53: 851-856).

After preparation of a chimeric antibody or a humanized antibody, amino acids in a variable region (e.g., FR) or a constant region may be substituted with other amino acids.

Amino acid substitution is a substitution of, for example, less than 15, less than 10, 8 or less, 7 or less, 6 or less, 5 or less, 4 or less, 3 or less, or 2 or less amino acids and is preferably a substitution of 1 to 5 amino acids, and more preferably 1 or 2 amino acids. A substituted antibody should be functionally equivalent to an unsubstituted antibody. Substitution is desirably a substitution of a conservative amino acid(s) between amino acids having analogous properties such as electric charge, side chain, polarity, and aromaticity. Amino acids having analogous properties can be classified into basic amino acids (arginine, lysine, and histidine), acidic amino acids (aspartic acid and glutamic acid), uncharged polar amino acids (glycine, asparagine, glutamine, serine, threonine, cysteine, and tyrosine), nonpolar amino acids (leucine, isoleucine, alanine, valine, proline, phenylalanine, tryptophan, and methionine), branched-chain amino acids (threonine, valine, and isoleucine), and aromatic amino acids (phenylalanine, tyrosine, tryptophan, and histidine), for example.

Antibodies may be chemically modified. Examples of such a modified antibody include antibodies bound to various molecules such as polyethylene glycol (PEG) and antitumor compounds (e.g., antitumor agents as exemplified later). Substances to be bound in the modified antibody product of the present invention are not limited. Such a modified antibody product can be obtained by subjecting the thus obtained antibody to chemical modification. Methods therefor have already been established in the art.

As used herein, the term "functionally equivalent" refers to that a subject antibody has biological or biochemical activity similar to that of the antibody of the present invention, and specifically refers to that a subject antibody has the function of impairing tumor without essentially causing rejection upon its application to a human, for example. An example of such activity includes an activity to suppress cell proliferation or a binding activity.

As a method well known by persons skilled in the art for preparation of a polypeptide functionally equivalent to a polypeptide, a method for introducing a mutation into a polypeptide is known. For example, persons skilled in the art can prepare an antibody functionally equivalent to the antibody of the present invention by appropriately introducing a mutation into the antibody using site-directed mutagenesis (Hashimoto-Gotoh, T. et al., (1995) Gene 152, 271-275; Zoller, M J., and Smith, M. (1983) Methods Enzymol. 100, 468-500; Kramer, W. et al., (1984) Nucleic Acids Res. 12, 9441-9456; Kramer, W. and Fritz, H J., (1987) Methods Enzymol. 154, 350-367; Kunkel, T A., (1985) Proc. Natl. Acad. Sci. U.S.A. 82, 488-492; Kunkel (1988) Methods Enzymol. 85, 2763-2766), for example.

An antibody that recognizes an epitope of a CAPRIN-1 protein to be recognized by the above anti-CAPRIN-1 antibody, i.e. an antibody that specifically hinds to the epitope, can be obtained by methods known by persons skilled in the art. For example, such an antibody can be obtained by a method that involves determining an epitope of a CAPRIN-1 protein recognized by an anti-CAPRIN-1 antibody, by a general method (e.g., epitope mapping) and then preparing an antibody using a polypeptide having an amino acid sequence contained in the epitope as an immunogen, or a method that involves determining an epitope of such an antibody prepared by a general method, and then selecting an antibody having the epitope identical with that of an anti-CAPRIN-1 antibody. As used herein, the term "epitope" refers to, in a mammal and preferably a human, a polypeptide fragment having antigenicity or immunogenicity. The minimum size unit thereof consists of about 7 to 12 amino acids, and preferably 8 to 11 amino acids.

The affinity constant $Ka(k_{on}/k_{off})$ of the antibody to be used in the present invention is preferably at least $10^7 M^{-1}$, at least $10^8 M^{-1}$, at least $5 \times 10^8 M^{-1}$, at least $10^9 M^{-1}$, at least $5 \times 10^9 M^{-1}$, at least $10^{10} M^{-1}$, at least $5 \times 10^{10} M^{-1}$ at least $10^{11} M^{-1}$, at least $5 \times 10^{11} M^{-1}$, at least $10^{12} M^{-1}$, or at least $10^{13} M^{-1}$.

The antibody used in the present invention can be conjugated with an antitumor agent. Conjugation of the antibody with an antitumor agent can be carried out via a spacer having a group reactive with an amino group, a carboxyl group, a hydroxy group, a thiol group or the like (e.g., a succinimidyl succinate group, a formyl group, a 2-pyridyldithio group, a maleimidyl group, an alkoxy carbonyl group, and a hydroxy group).

Examples of an antitumor agent usable in the present invention include the following known antitumor agents as in literatures and the like, such as paclitaxel, doxorubicin, daunorubicin, cyclophosphamide, methotrexate, 5-fluorouracil, thiotepa, busulfan, improsulfan, piposulfan, benzodopa, carboquonc, meturedopa, uredopa, altretamine, triethylenemelamine, triethylenephosphoramide, triethilenethiophosphoramide, trimethylolomelamine, bullatacin, bullatacinone, camptothecin, bryostatin, callystatin, cryptophycinl, cryptophycin8, dolastatin, duocarmycin, eleutherobin, pancratistatin, sarcodictyin, spongistatin, chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard, carmustine, chlorozotocin, fotemustine, lomustine, nimustine, ranimustine, calicheamicin, dynemicin, clodronate, esperamicin, aclacinomycin, actinomycin, authramycin, azaserine, bleomycin, cactinomycin, carabicin, caminomycin, carzinophilin, chromomycin, dactinomycin, detorbicin, 6-diazo-5-oxo-L-norleucine, adriamycin, epirubicin, esorubicin, idarubicin, marcellomycin, mitomycinC, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin, denopterin, pteropterin, trimetrexate, fludarabine, 6-mercaptopurine, thiamiprine, thioguanine, ancitabine, azacitidine, 6-azauridine (azauridine), carmofur, cytarabine, dideoxyuridine, doxifluridine, enocitabine, floxuridine, androgens (e.g., calusterone, dromostanolone propionate, epitiostanol, mepitiostane, and testolactone), aminoglutethimide, mitotane, trilostane, frolinic acid, aceglatone, aldophosphamideglycoside, aminolaevulinic acid, eniluracil, amsacrine, bestrabucil, bisantrene, edatraxate, defofamine, demecolcine, diaziquone, elformithine, elliptinium acetate (elliptinium), epothilone, etoglucid, lenthinan, lonidamine, maytansine, ansamitocine, mitoguazone, mitoxantrone, mopidanmol, nitraerine, pentostatin, phenamet, pirarubicin, losoxantrone, podophyllinic acid, 2-ethyl hydrazide, procarbazine, razoxane, rhizoxin, schizophyllan, spirogermanium, tenuazonic acid, triaziquone, roridine A, anguidine, urethane, vindesine, dacarbazine, mannomustine, mitobronitol, mitolactol, pipobroman, gacytosine, docetaxel, chlorambucil, gemcitabine, 6-thioguanine, mercaptopurine, cisplatin, oxaliplatin, carboplatin, vinblastine, etoposide, ifosfamide, mitoxanthrone, vincristine, vinorelbine, novantrone, teniposide, edatraxate, daunomycin, aminopterin, xeloda, ibandronate, irinotecan, topoisomerase inhibitor, difluoromethylolnitine (DMFO), retinoic acid, capecitabine, and pharmaceutically acceptable (known) salts or (known) derivatives thereof.

Alternatively, a known radio isotope as in literatures and the like, such as $^{211}At$, $^{131}I$, $^{125}I$, $^{90}Y$, $^{186}Re$, $^{188}Re$, $^{153}SM$, $^{212}Bi$, $^{32}P$, $^{175}Lu$, or $^{176}Lu$ can be bound to the antibody used in the present invention. A desired radio isotope is effective for treatment or diagnosis of tumor.

The antibody used in the present invention is an antibody having immunological reactivity with CAPRIN-1, an antibody specifically recognizing CAPRIN-1, or an antibody specifically binding to CAPRIN-1, which exhibits cellular cytotoxic activity against cancers, e.g., the effect of suppressing tumor growth. The antibody should have a structure such that rejection is almost or completely avoided in a subject animal to which the antibody is administered. Examples of such an antibody include, when a subject animal is a human, a human antibody, a humanized antibody, a chimeric antibody (e.g., a human-mouse chimeric antibody), a single chain antibody, and a bispecific antibody. These antibodies are: recombinant antibodies in which heavy chain and light chain variable regions are from a human antibody; recombinant antibodies in which heavy chain and light chain variable regions comprise complementarity determining regions (CDR1, CDR2, and CDR3) from a non-human animal antibody, and, framework regions from a human antibody; or recombinant antibodies in which heavy chain and light chain variable regions are from a non-human animal antibody, and, heavy chain and light chain constant regions are from a human antibody. Preferable antibodies are the former two antibodies.

These recombinant antibodies can be prepared as follows by cloning DNA encoding an anti-human CAPRIN-1 monoclonal antibody (e.g., a human monoclonal antibody, a mouse monoclonal antibody, a rat monoclonal antibody, a rabbit monoclonal antibody, or a chicken monoclonal antibody) from an antibody-producing cell such as a hybridoma, preparing DNA encoding a light chain variable region and a heavy chain variable region of the antibody by an RT-PCR method using it as a template, and then determining the sequence of each variable region of light chain and heavy chain or each sequence of CDR1, CDR2, and CDR3 based on the Kabat EU numbering system (Kabat et al., Sequences of Proteins of Immunological Interest, 5$^{th}$ Ed. Public Health Service, National Institute of Health, Bethesda, Md. (1991)).

Furthermore, DNA encoding each of these variable regions or DNA encoding each CDR is prepared using gene recombination techniques (Sambrook et al., Molecular Cloning: A Laboratory Manual, Cold Spring Harbor Laboratory Press (1989)) or a DNA synthesizer. Here, the above human monoclonal antibody-producing hybridoma can be prepared by immunizing a human antibody-producing animal (e.g., a mouse) with human CAPRIN-1 and then fusing splenocytes excised from the immunized animal to myeloma cells. Alternatively, DNAs encoding a light chain or heavy chain variable region and a constant region from a human antibody are prepared as necessary using gene recombination techniques or a DNA synthesizer.

In the case of humanized antibody, DNA is prepared by substituting a CDR coding sequence in DNA encoding a variable region of light chain or heavy chain derived from a human antibody, with a CDR coding sequence corresponding thereto of an antibody derived from a non-human animal (e.g., a mouse, a rat, or a chicken) and then ligating the DNA thus obtained to DNA encoding a constant region of light chain or heavy chain derived from a human antibody. Thus, DNA encoding humanized antibody can be prepared.

In the case of chimeric antibody, DNA encoding a chimeric antibody can be prepared by ligating DNA encoding a light chain or heavy chain variable region of an antibody from a non-human animal (e.g., a mouse, a rat, and a chicken) to DNA encoding a light chain or heavy chain constant region from a human antibody.

In the case of single chain antibody, this antibody is an antibody prepared by linearly ligating a heavy chain variable region to a light chain variable region via a linker. Thus, DNA encoding a single chain antibody can be prepared by binding DNA encoding a heavy chain variable region, DNA encoding a linker, and DNA encoding a light chain variable region. Herein, a heavy chain variable region and a light chain variable region are both from a human antibody, or, only CDRs are substituted with CDRs of an antibody from a non-human animal (e.g., a mouse, a rat, and a chicken) although the other regions are from a human antibody. Also, a linker comprises 12 to 19 amino acids, such as $(G_4S)_3$ of 15 amino acids (G.-B. Kim et al., Protein Engineering Design and Selection 2007, 20 (9): 425-432).

In the case of bispecific antibody (diabody), this antibody is capable of specifically binding to two different epitopes. For example, DNA encoding a bispecific antibody can be prepared by linking DNA encoding a heavy chain variable region A, DNA encoding a light chain variable region B, DNA encoding a heavy chain variable region B, and DNA encoding a light chain variable region A in this order (here, DNA encoding a light chain variable region B is bound to DNA encoding a heavy chain variable region B via DNA encoding the above linker). Here, a heavy chain variable region and a light chain variable region are both from a human antibody, or, only CDRs are substituted with CDRs of an antibody from a non-human animal (e.g., a mouse, a rat, or a chicken) although the other regions are from a human antibody.

The above-prepared recombinant DNA is incorporated into one or a plurality of appropriate vectors, they are introduced into host cells (e.g., mammalian cells, yeast cells, or insect cells), and then (co)expression is caused, so that a recombinant antibody can be prepared (P. J. Delves., ANTIBODY PRODUCTION ESSENTIAL TECHNIQUES., 1997 WILEY, P. Shepherd and C. Dean., Monoclonal Antibodies., 2000 OXFORD UNIVERSITY PRESS; J. W. Goding., Monoclonal Antibodies: principles and practice., 1993 ACADEMIC PRESS).

Examples of the antibody of the present invention prepared by the above method include the following antibodies (a) to (k):

(a) an antibody comprising CDR1, CDR2, and CDR3 of a heavy chain variable region comprising SEQ ID NOS: 40, 41, and 42 and CDR1, CDR2, and CDR3 of a light chain variable region comprising SEQ ID NOS: 44, 45, and 46 (preferably, an antibody comprising the heavy chain variable region of SEQ ID NO: 43 and the light chain variable region of SEQ ID NO: 47);

(b) an antibody comprising CDR1, CDR2, and CDR3 of a heavy chain variable region comprising SEQ ID NOS: 40, 41, and 42 and CDR1, CDR2, and CDR3 of a light chain variable region comprising SEQ ID NOS: 50, 51, and 52 (preferably, an antibody comprising the heavy chain variable region of SEQ ID NO: 43 and the light chain variable region of SEQ ID NO: 53);

(c) an antibody comprising CDR1, CDR2, and CDR3 of a heavy chain variable region comprising SEQ ID NOS: 40, 41, and 42 and CDR1, CDR2, and CDR3 of a light chain variable region comprising SEQ ID NOS: 55, 56, and 57 (preferably, an antibody comprising the heavy chain variable region of SEQ ID NO: 43 and the light chain variable region of SEQ ID NO: 58);

(d) an antibody comprising CDR1, CDR2, and CDR3 of a heavy chain variable region comprising SEQ ID NOS: 40, 41, and 42 and CDR1, CDR2, and CDR3 of a light chain variable region comprising SEQ ID NOS: 60, 61, and 62 (preferably, an antibody comprising the heavy chain variable region of SEQ ID NO: 43 and the light chain variable region of SEQ ID NO: 63);

(e) an antibody comprising CDR1, CDR2, and CDR3 of a heavy chain variable region comprising SEQ ID NOS: 40, 41, and 42 as CDR1, CDR2, and CDR3 of a heavy chain variable region and CDR1, CDR2, and CDR3 of a light chain variable region comprising SEQ ID NOS: 65, 66, and 67 (preferably, an antibody comprising the heavy chain variable region of SEQ ID NO: 43 and the light chain variable region of SEQ ID NO: 68);

(f) an antibody comprising CDR1, CDR2, and CDR3 of a heavy chain variable region comprising SEQ ID NOS: 70, 71, and 72 and CDR1, CDR2, and CDR3 of a light chain variable region comprising SEQ ID NOS: 74, 75, and 76 (preferably, an antibody comprising the heavy chain variable region of SEQ ID NO: 73 and the light chain variable region of SEQ ID NO: 77);

(g) an antibody comprising CDR1, CDR2, and CDR3 of a heavy chain variable region comprising SEQ ID NOS: 80, 81, and 82 and CDR1, CDR2, and CDR3 of a light chain variable region comprising SEQ ID NOS: 84, 85, and 86 (preferably, an antibody comprising the heavy chain variable region of SEQ ID NO: 83 and the light chain variable region of SEQ ID NO: 87);

(h) an antibody comprising CDR1, CDR2, and CDR3 of a heavy chain variable region comprising SEQ ID NOS: 90, 91, and 92 and CDR1, CDR2, and CDR3 of a light chain variable region comprising SEQ ID NOS: 94, 95, and 96 (for example, an antibody comprising the heavy chain variable region of SEQ ID NO: 93 and the light chain variable region of SEQ ID NO: 97);

(i) an antibody comprising CDR1, CDR2, and CDR3 of a heavy chain variable region comprising SEQ ID NOS: 100, 101, and 102 and CDR1, CDR2, and CDR3 of a light chain variable region comprising SEQ ID NOS: 104, 105, and 106 (for example, an antibody comprising the heavy chain variable region of SEQ ID NO: 103 and the light chain variable region of SEQ ID NO: 107);

(j) an antibody comprising CDR1, CDR2, and CDR3 of a heavy chain variable region comprising SEQ ID NOS: 110, 111, and 112 and CDR1, CDR2, and CDR3 of a light chain variable region comprising SEQ ID NOS: 114, 115, and 116 (for example, an antibody comprising the heavy chain variable region of SEQ ID NO: 113 and the light chain variable region of SEQ ID NO: 117); and (k) an antibody comprising CDR1, CDR2, and CDR3 of a heavy chain variable region comprising SEQ ID NOS: 120, 121, and 122 and CDR1, CDR2, and CDR3 of a light chain variable region comprising SEQ TD NOS: 124, 125, and 126 (for example, an antibody comprising the heavy chain variable region of SEQ ID NO: 123 and the light chain variable region of SEQ ID NO: 127).

Here, the amino acid sequences represented by SEQ ID NOS: 40, 41, and 42, SEQ ID NOS: 70, 71, and 72, SEQ ID NO: 80, 81, and 82, SEQ ID NO: 90, 91, and 92, SEQ ID NO: 100, 101, and 102, SEQ ID NO: 110, 111, and 112, or SEQ ID NO: 120, 121, and 122 are CDR1, CDR2, and CDR3, respectively, of a mouse antibody heavy chain variable region. The amino acid sequences represented by SEQ ID NO: 44, 45, and 46, SEQ ID NO: 50, 51, and 52, SEQ ID NO: 55, 56, and 57, SEQ ID NO: 60, 61, and 62, SEQ ID NO: 65, 66, and 67, SEQ ID NO: 74, 75, and 76, SEQ ID NO: 84, 85, and 86, SEQ ID NO: 94, 95, and 96, SEQ ID NO: 104, 105, and 106, SEQ ID NO: 114, 115, and 116, or SEQ ID NO: 124, 125, and 126 are CDR1, CDR2, and CDR3, respectively, of a mouse antibody light chain variable region. Also, the humanized antibody, the chimeric antibody, the single chain antibody, or the bispecific antibody of the present invention is the following antibody (exemplified as "antibody (a)"), for example:

(i) an antibody wherein the heavy chain variable region comprises the amino acid sequences of SEQ ID NOS: 40, 41, and 42 and the amino acid sequences of framework regions from a human antibody, and, the light chain variable region comprises the amino acid sequences of SEQ ID NOS: 44, 45, and 46 and the amino acid sequences of framework regions from a human antibody (e.g., the antibody wherein the heavy chain variable region comprises the amino acid sequence of SEQ ID NO: 43, and, the light chain variable region comprises the amino acid sequence of SEQ ID NO: 47).

(ii) an antibody wherein the heavy chain variable region comprises the amino acid sequences of SEQ ID NOS: 40, 41, and 42 and the amino acid sequences of framework regions from a human antibody, and, the heavy chain constant region comprises an amino acid sequence from a human antibody, and, the light chain variable region comprises the amino acid sequences of SEQ ID NOS: 44, 45, and 46 and the amino acid sequences of framework regions from a human antibody, and the light chain constant region comprises an amino acid sequence from a human antibody (e.g., the antibody wherein the heavy chain variable region comprises the amino acid sequence of SEQ ID NO: 43, and, the heavy chain constant region comprises an amino acid sequence from a human antibody, as well as, the light chain variable region comprises the amino acid sequence of SEQ ID NO: 47, and, the light chain constant region comprises an amino acid sequence from a human antibody).

In this context, the sequences of human antibody heavy chain and light chain constant regions and variable regions can be obtained from NCBI (e.g., U.S.A.: GenBank, UniGene), for example. For example, the sequence of registration no. J00228 can be referred to as a human IgG1 heavy chain constant region, the sequence of registration no. J00230 can be referred to as a human IgG2 heavy chain constant region, the sequence of registration no. X03604 can be referred to as a human IgG3 heavy chain constant region, the sequence of registration no. K01316 can be referred to as a human IgG4 heavy chain constant region, the sequences of registration no. V00557, X64135, X64133, and the like can be referred to as human light chain κ constant regions, and the sequences of registration nos. X64132, X64134, and the like can be referred to as human light chain λ constant regions.

The above antibodies preferably have cellular cytotoxic activity and thus can exhibit anti-tumor effects.

Also, the specific sequences of heavy chain and light chain variable regions or CDRs in the above antibodies are given simply for illustrative purposes, and thus are clearly not limited to such specific sequences. A hybridoma capable of producing another human antibody or non-human animal antibody (e.g., a mouse antibody) against human CAPRIN-1 is prepared, a monoclonal antibody that is produced by the hybridoma is collected, and then whether or not it is a target antibody is determined by immunological binding property with human CAPRIN-1 and cellular cytotoxic activity as indicators. After identification of a hybridoma producing the target monoclonal antibody in this manner, DNA encoding heavy chain and light chain variable regions of the target antibody is prepared from the hybridoma as described above, sequencing is carried out, and then the DNA is used for preparation of another antibody.

Furthermore, regarding the above antibody of the present invention, the sequence of each of the above antibodies (i) to (iv), particularly the sequence of the framework region and/or the sequence of the constant region of each of the antibodies may have a substitution, a deletion, or an addition of one or several (preferably, 1 or 2) amino acids, as long as it has specificity for specific recognition of CAPRIN-1. Here the term "several" refers to 2 to 5, and preferably 2 or 3.

Antibodies used in the present invention can also be produced by gene recombination techniques using DNA encoding the above antibody of the present invention, or, DNA encoding the above antibody heavy chain or light chain, or, DNA encoding the above antibody heavy chain or light chain variable region. Examples of such DNA include, in the case of antibody (a), DNA encoding a heavy chain variable region comprising the nucleotide sequences encoding the amino acid sequences of SEQ ID NOS: 40, 41, and 42 and DNA encoding a light chain variable region comprising the nucleotide sequences encoding the amino acid sequences of SEQ ID NOS: 44, 45, and 46.

Complementarity determining regions (CDRs) encoded by the sequences of DNA are regions for determining the specificity of an antibody. Thus, sequences encoding regions in an antibody other than CDRs (specifically, a constant region and a framework region) may be from other antibodies. Here, examples of such "other antibodies" include antibodies from non-human organisms, and are preferably from a human in view of reduction of side effects. Thus, in the case of the above DNA, regions encoding each framework region and each contact region of heavy chains and light chains preferably comprise nucleotide sequences encoding corresponding amino acid sequences from a human antibody.

Further alternative examples of DNA encoding the antibody used in the present invention include, in the case of antibody (a), DNA encoding a heavy chain variable region comprising the nucleotide sequence encoding the amino acid sequence of SEQ ID NO: 43 and DNA encoding a light chain variable region comprising the nucleotide sequence encoding the amino acid sequence of SEQ ID NO: 47. Here, an example of the nucleotide sequence encoding the amino acid sequence of SEQ ID NO: 43 is the nucleotide sequence of SEQ ID NO: 48. Also, an example of the nucleotide sequence encoding the amino acid sequence of SEQ ID NO: 47 is the nucleotide sequence of SEQ ID NO: 49. In these DNAs, regions encoding each constant region of heavy chains and light chains preferably comprise nucleotide sequences encoding the corresponding amino acid sequences from a human antibody.

The DNA of the present invention can be obtained by the above methods or the following method, for example. First, total RNA is prepared from a hybridoma relating to the antibody of the present invention using a commercially available RNA extraction kit, and then cDNA is synthesized with reverse transcriptase using random primers, and the like. Subsequently, cDNA encoding an antibody is amplified by a PCR method using as primers the oligonucleotides of sequences conserved in each variable region of known mouse antibody heavy chain and light chain genes. The sequence encoding a constant region can be obtained by amplifying a known sequence by a PCR method. The nucleotide sequence of DNA can be determined by a conventional method such as insertion of it into a plasmid or a phage for sequencing.

Examples of DNA relating to the above antibodies (a) to (k) are as follows.

(i) As DNA encoding a polypeptide that comprises the amino acid sequence of SEQ ID NO: 43, 73, 83, 93, 103, 113, 123, 133, 143, or 153, DNA comprising the nucleotide sequence of SEQ ID NO: 48, 78, 88, 98, 108, 118, or 128.

(ii) As DNA encoding a polypeptide that comprises the amino acid sequence of SEQ ID NO: 47, 53, 58, 63, 68, 77, 87, 97, 107, 117, 127, 137, 147, or 157, DNA comprising the nucleotide sequence of SEQ ID NO: 49, 54, 59, 64, 69, 79, 89, 99, 109, 119, or 129.

The anti-CAPRIN-1 antibodies used in the present invention are considered to exhibit the anti-tumor effect against CAPRIN-1-expressing cancer cells through the following mechanism:
the effector-cell-antibody-dependent cytotoxicity (ADCC) of CAPRIN-1-expressing cells; and the complement-dependent cytotoxicity (CDC) of CAPRIN-1-expressing cells.

Therefore, the activity of an anti-CAPRIN-1 antibody to be used in the present invention can be evaluated by measuring ex vivo the above ADCC activity or CDC activity against CAPRIN-1 protein-expressing cancer cells, as specifically described in Examples below.

ADCC activity can be measured using a commercially available kit for measuring cytotoxic activity such as a Cytotoxicity Detection Kit (Roche). According to the method, ADCC activity can be measured by procedures comprising reacting a target cancer cell with an anti-CAPRIN-1 antibody on ice, culturing the cell with an effector cell (e.g., PBMC) for 4 hours, and then measuring the enzyme activity of lactate dehydrogenase (LDH) or Cr51 radioactivity released in the medium in the culture supernatant. Also, CDC activity can be measured by procedures comprising reacting a target cancer cell with an anti-CAPRIN-1 antibody on ice, culturing the cell with a solution containing complements (e.g., serum) for 4 hours, and then measuring enzyme activity or radioactivity similar to the above in the culture supernatant.

An anti-CAPRIN-1 antibody used in the present invention binds to a CAPRIN-1 protein on a cancer cell and exhibits anti-tumor effects due to the above activity, and thus it is useful for treating or preventing cancer. Specifically, the present invention provides a pharmaceutical composition for treating and/or preventing cancer, which comprises an anti-CAPRIN-1 antibody as an active ingredient. When the anti-CAPRIN-1 antibody is used for administration thereof to a human body (antibody therapy), it is preferably human antibody or humanized antibody in order to decrease immunogenicity.

In addition, the higher the binding affinity between an anti-CAPRIN-1 antibody and a CAPRIN-1 protein on the cancer cell surfaces, the stronger the anti-tumor activity of the anti-CAPRIN-1 antibody that can be obtained. Therefore, when an anti-CAPRIN-1 antibody having high binding affinity with a CAPRIN-1 protein can be acquired, stronger antitumor effects can be expected and such antibody's application as a pharmaceutical composition for the purpose of cancer treatment and/or prevention becomes possible. Such high binding affinity is desirably as follows. As described above, binding constant (affinity constant) Ka ($k_{on}/k_{off}$) is preferably at least $10^7$ $M^{-1}$, at least $10^8$ $M^{-1}$, at least $5 \times 10^8$ $M^{-1}$, at least $10^9$ $M^{-1}$, at least $5 \times 10^9$ $M^{-1}$, at least $10^{10}$ $M^{-1}$, at least $5 \times 10^{10}$ $M^{-1}$, at least $10^{11}$ $M^{-1}$, at least $5 \times 10^{11}$ $M^{-1}$, at least $10^{12}$ $M^{-1}$, or, at least $10^{13}$ $M^{-1}$.

<Binding to Antigen-Expressing Cell>

The capacity of an antibody to bind to a CAPRIN-1 protein can be determined by binding assay using ELISA, a Western blot method, immuno-fluorescence and flow cytometric analysis, or the like as described in Examples.

<Immunohistochemical Staining>

An antibody that recognizes a CAPRIN-1 protein can be tested for reactivity with CAPRIN-1 by a method known by persons skilled in the art on the basis of immunohistochemistry using paraformaldehyde- or acetone-fixed frozen sections or paraformaldehyde-fixed paraffin-embedded tissue sections (prepared from tissue samples obtained from a patient during surgery, or tissue samples obtained from an animal having heterotransplant tissue inoculated with a cell system expressing CAPRIN-1, naturally or after transfection).

An antibody reactive with CAPRIN-1 can be stained by various methods for immunohistochemical staining. For example, a horseradish peroxidase-conjugated goat anti-mouse antibody or goat anti-rabbit antibody is caused to undergo reaction, a target antibody can be visualized.

<Antitumor Agent>

The present invention is characterized by combining an anti-CAPRIN-1 antibody with an antitumor agent as exemplified above. An anti-CAPRIN-1 antibody and an antitumor agent each having antitumor activity are administered in combination to a cancer patient, so that synergistically significant anti-tumor effect, specifically the effect of causing almost complete tumor regression in a cancer-bearing animal model, can be obtained as described in Examples. Such special antitumor effect is observed when an anti-CAPRIN-1 antibody and an antitumor agent are used in combination, even when tumor growth gradually increases over time. This effect is completely extraordinary.

In the present invention, examples of an antitumor agent to be used in combination with an anti-CAPRIN-1 antibody include all chemotherapeutics that are used, were used, or will be used for treating various types of cancers or tumors. Examples of such an antitumor agent include an antimetabolic drug, an antibiotic anticancer agent, a plant alkaloid-based anticancer agent, a topoisomerase inhibitor, and an antitumor alkylating agent. For example, all antitumor agents (as exemplified above) known in literatures and the like are included herein. Examples thereof include, but are not limited to, antitumor agents that are used in Examples described below, such as anticancer agents (e.g., cyclophosphamide, paclitaxel, docetaxel, and vinorelbine), the significant antitumor effects of which have been confirmed. Therefore, in the present invention, one or two or more drugs selected from cyclophosphamide, paclitaxel, docetaxel, vinorelbine, and pharmacologically acceptable salts or derivatives thereof can be used as antitumor agents.

<Medicament for Treating and/or Preventing Cancer>

A target of the pharmaceutical composition for treating and/or preventing cancer of the present invention is not particularly limited, as long as it is cancer (cell) expressing a CAPRIN-1 gene.

The term "tumor" and "cancer" as used herein refers to malignant neoplasm and is used interchangeably.

The medicament of the present invention is characterized by comprising a combination of an antibody or a fragment thereof having immunological reactivity with a CAPRIN-1 protein and one or two or more types of antitumor agents, wherein the antibody or fragment and the antitumor agents are combined together or separately. Specifically, when these active ingredients are combined together, the above antibody or a fragment thereof and the above antitumor agent(s) can be mixed together in a carrier (or an excipient) to be formulated in the form of a pharmaceutical composition. On the other hand, when these active ingredients are separately combined, a pharmaceutical composition containing the above antibody or a fragment thereof as an active ingredient and a pharmaceutical composition containing the above antitumor agent(s) as an active ingredient are separately formulated so that a medicament can be produced in the form of a pharmaceutical kit. Such a pharmaceutical composition and pharmaceutical kit are more specifically described below.

Cancer to be subjected to the present invention is cancer expressing genes encoding CAPRIN-1 proteins having amino acid sequences of even-numbered SEQ ID NOS: 2 to 30. Examples of such cancer include preferably breast cancer, brain tumor, leukemia, lung cancer, lymphoma, mastocytoma, renal cancer, uterine cervix cancer, bladder cancer, esophageal cancer, gastric cancer, and colorectal cancer.

Examples of such specific cancer include, but are not limited to, breast adenocarcinoma, composite type breast adenocarcinoma, mammary gland malignant mixed tumor, intraductal papillary adenocarcinoma, lung adenocarcinoma, squamous cell carcinoma, small cell carcinoma, large cell carcinoma, glioma that is neural epithelial tissue tumor, ependymoma, neurocytoma, fetal neuroectodermal tumor, schwannoma, neurofibroma, meningioma, chronic lymphocytic leukemia, lymphoma, gastrointestinal lymphoma, digestive lymphoma, small-cell to medium-cell lymphoma, cancer of cecum, ascending colon cancer, descending colon cancer, transverse colon cancer, sigmoid colon cancer, and rectal cancer.

Moreover, preferable subjects are mammals including primates, pet animals, domestic animals, animals for competition, and the like and are particularly preferably humans, dogs, and cats.

<Pharmaceutical Composition>

The active ingredients contained in the medicament for treating and/or preventing a cancer of the present invention, i.e. the above antibody or a fragment thereof and the above antitumor agent, can be formulated by a method known by persons skilled in the art in the from of a pharmaceutical composition prepared by mixing them or in the form of individual pharmaceutical compositions thereof.

For example, the pharmaceutical composition can be used parenterally in the form of an injection preparation such as an aseptic solution prepared with water or a pharmacologically acceptable solution other than water or a suspension. For example, it can be formulated by mixing in a unit dosage form required by generally accepted pharmaceutical practice in appropriate combination with a pharmacologically acceptable carrier or medium, specifically, sterile water or saline, vegetable oil, an emulsifier, a suspension, a surfactant, a stabilizer, a flavoring compound, an excipient, a vehicle, an antiseptic, a binder, and the like. Also, the pharmaceutical composition of the present invention can contain a pharmacologically acceptable salt. As a pharmacologically acceptable salt, for example, inorganic acid such as hydrochloric acid or phosphoric acid, or organic acid such as acetic acid, tartaric acid, or mandelic acid can be used. Furthermore, a salt formed with a free carboxyl group can be used. For example, such a salt can also be induced from an inorganic base such as sodium, potassium, ammonium, calcium, hydroxide of iron (I), or the like, or an organic base such as isopropylamine, trimethylamine, 2-ethyl aminoethanol, histidine, or procaine.

An aseptic composition for injection can be prescribed according to general pharmaceutical practice using a vehicle such as distilled water for injection.

Examples of an aqueous solution for injection include saline, an isotonic solution containing dextrose or other adjuvants, such as D-sorbitol, D-mannose, D-mannitol, and sodium chloride. These examples may be used in combination with an appropriate solubilizing agent such as alcohol, specifically ethanol and polyalcohol (e.g., propylene glycol and polyethylene glycol), and nonionic surfactant (e.g., polysorbate 80™ and HCO-60).

Examples of an oily fluid include sesame oil and soybean oil, which can be used in combination with a solubilizing agent such as benzyl benzoate or benzyl alcohol. Also, a buffering agent such as phosphate buffer or sodium acetate buffer, a soothing agent such as procaine hydrochloride, a stabilizer such as benzyl alcohol or phenol, and an antioxidant may be combined therewith. An appropriate amplus is generally filled with the thus prepared injection solution.

Administration is oral or perenteral administration. Examples of perenteral administration include injection, transnasal administration, pulmonary administration, and transdermal administration. Examples of injection include intravenous injection, intramuscular injection, intraperitoneal injection, and subcutaneous injection, so that systemic or local administration is possible. Also, in the case of perenteral administration, infusion administration that is gradually or slowly performed taking much time is possible. Administration methods can be appropriately selected depending on a patient's age, body weight, sex, symptom, and the like. The pharmaceutical composition comprising an antibody is preferably parenteraly administered. On the other hand, in the case of a pharmaceutical composition comprising an antitumor agent, either oral administration or parenteral administration is selected depending on types of antitumor agents and indications.

In the case of the pharmaceutical composition for treating and/or preventing a cancer of the present invention, the dosage of the above antibody can be selected from the range between 0.0001 mg and 1000 mg per kg body weight, for example. Alternatively, for example, the dosage can be selected from the range between 0.001 mg/body of a patient and 100000 mg/body of a patient; however, the dosage range is not always limited to these numerical values. Furthermore, the dosage of the above antitumor agent can be selected from the range between 1 and 1000 mg/body of a patient and preferably between 10 and 500 mg/body of a patient, for example; however, the dosage range is not always limited to these numerical values. In addition, the dosage and administration method are varied depending on a patient's body weight, age, sex, symptom, and the like, but can be appropriately selected by persons skilled in the art.

<Administration Method>

Cancer treatment and/or prevention using the agent for treating and/or preventing a cancer of the present invention involve various forms in addition to administration of the agent as the above pharmaceutical composition. For example, the active ingredients of the agent for treating and/or preventing a cancer of the present invention can be administered simultaneously or can be separately administered in order. In a specific example, the active ingredients can be administered at intervals of up to about 3 weeks, that is, during about 3 weeks after administration of the first active ingredient, the second active ingredient can be administered. At this time, this administration may be performed subsequent to surgical treatment, or surgical treatment may also be performed between the administration of the first agent and the administration of the second agent. Also, the agent for treating and/or preventing a cancer of the present invention may be administered according to a plurality of administration cycles. For example, when the simultaneous administration of the active ingredients of the agent for treating and/or preventing a cancer of the present invention is performed, the pharmaceutical composition comprising both active ingredients is administered with a cycle of about 2 days to about 3 weeks. Subsequently, where needed, the therapeutic cycle may also be repeated according to the physician's judgment. Similarly, when the formulation for administering the active ingredients in order is planned, the administration periods of the individual agents are adjusted to be the same period. An interval between cycles may vary from 0 to 2 months. The dosage of each active ingredient of the agent for treating and/or preventing a cancer of the present invention can be set similarly to the dosage used for administration of each active ingredient of the pharmaceutical composition.

<Pharmaceutical Kit>

The medicament for treating and/or preventing a cancer of the present invention may be in the form of a pharmaceutical kit. The term "pharmaceutical kit" as used herein refers to, in a method for treating or preventing a cancer, a package for using the above anti-CAPRIN-1 antibody or a fragment thereof and the above antitumor agent that are active ingredients in the form of individual pharmaceutical compositions. The package includes instructions for administration of each active ingredient. Each active ingredient of the above pharmaceutical composition for treating and/or preventing a cancer, which is contained in a pharmaceutical kit can be in the form of a pharmaceutical composition that has been formulated as described above so that active ingredients can be administered together or separately. Also, a pharmaceutical kit contains the amounts of active ingredients sufficient for a single dose or multiple doses so that each active ingredient can be administered according to the above administration method.

Based on the content described specifically above, the present invention further provides a method for treating and/or preventing a cancer, comprising administering the above medicament of the present invention to a subject suspected of having cancer (including a subject with cancer). In an embodiment, an antibody or a fragment thereof and an antitumor agent, which are contained in the above medicament, are administered simultaneously or separately to the above subject.

EXAMPLES

The present invention is described more specifically based on Examples, but the scope of the present invention is not limited by these specific examples.

Example 1

Identification of Novel Cancer Antigen Protein by SEREX Method (1) Preparation of cDNA Library Total RNA was extracted from a testis tissue of a healthy dog by an acid guanidium-phenol-chloroform method. PolyA RNA was purified according to protocols attached to an Oligotex-dT30 mRNA purification Kit (Takara Shuzo Co., Ltd.) using the kit.

A dog testis cDNA phage library was synthesized using the thus obtained mRNA (5 μg). For preparation of the cDNA phage library, a cDNA synthesis kit, a ZAP-cDNA synthesis kit, and a ZAP-cDNA gigapack III gold cloning kit (STRATAGENE) were used and the library was prepared according to protocols attached to the kit. The size of the thus prepared cDNA phage library was $7.73 \times 10^5$ pfu/ml.

(2) Screening of cDNA Library Using Serum

Immunoscreening was carried out using the above-prepared dog testis cDNA phage library. Specifically, host *Escherichia coli* (XL1-Blue MRF') was infected with the phage so that 2210 clones were present on a φ90×15 mm NZY agarose plate. Cells were cultured at 42° C. for 3 to 4 hours, so as to cause plaque formation. The plate was covered with a nitrocellulose membrane (Hybond C Extra: GE HealthCare Bio-Sciences) impregnated with IPTG (isopropyl-β-D-thiogalactoside) at 37° C. for 4 hours. Proteins were induced, expressed, and then transferred to the membrane. Subsequently, the membrane was recovered, immersed, and shaken in TBS (10 mM Tris-HCl, 150 mM NaCl pH 7.5) containing 0.5% powdered skim milk at 4° C. overnight, so that nonspecific reaction was suppressed. The filter was caused to react with 500-fold diluted sera of dogs with cancer at room temperature for 2 to 3 hours.

As the above sera from dogs with cancer, sera collected from dogs with breast cancer were used. The sera were stored at −80° C. and then subjected to pretreatment immediately before use. Pretreatment for sera was performed by the following method. Specifically, host *Escherichia coli* (XL1-Blure MRF') was infected with λ ZAP Express phage into which no foreign gene had been inserted, and then cultured on NZY plate medium at 37° C. overnight. Subsequently, a 0.2 M NaHCO$_3$ buffer (pH 8.3) containing 0.5 M NaCl was added to the plate and the plate was left to stand at 4° C. for 15 hours. The supernatants were collected as *Escherichia coli*/phage extracts. Next, the collected *Escherichia coli*/phage extract was passed through a NHS-column (GE HealthCare Bio-Sciences), so as to immobilize the *Escherichia coli* phage-derived protein. The serum of a dog with cancer was passed through the column to which the protein had been immobilized for reaction, thereby removing *Escherichia coli* and antibodies adsorbed to the phage from the serum. Each serum fraction that had passed through the column was diluted 500-fold with TBS containing 0.5% powdered skim milk, and the resultant was used as an immunoscreening material.

A membrane, to which the thus treated serum and the fusion protein had been blotted, was washed 4 times with TBS-T (0.05% Tween20/TBS). The membrane was reacted with goat anti-dog IgG (Goat anti Dog IgG-h+l HRP conjugated: BETHYL Laboratories) diluted 5000-fold as a secondary antibody with TBS containing 0.5% powdered skim milk at room temperature for 1 hour. Detection was carried out by enzyme color reaction using an NBT/BCIP reaction solution (Roche). Colonies corresponding to the color reaction positive site were collected from the φ90×15 mm NZY agarose plate, and then dissolved in 500 μl of SM buffer (100 mM NaCl, 10 mM MgClSO$_4$, 50 mM Tris-HCl, 0.01% gelatin, pH 7.5). Until unification of color reaction positive colonies, secondary screening and tertiary screening were repeated by a method similar to the above. Thus, 30940 phage clones that had reacted with serum IgG were screened so that 5 positive clones were isolated.

(3) Homology Search for Isolated Antigen Gene

A procedure for conversion of phage vectors to plasmid vectors was performed for the 5 positive clones isolated by the above method for the purpose of subjecting the clones to nucleotide sequence analysis. Specifically, 200 μl of a solution of host *Escherichia coli* (XL1-Blue MRF') prepared to give an absorbance OD$_{600}$ of 1.0, 250 μl of a purified phage solution, and 1 μl of ExAssist helper phage (STRATAGENE) were mixed and allowed to react at 37° C. for 15 minutes. After that, 3 ml of LB medium was added, cells were cultured at 37° C. for 2.5 to 3 hours, and then the resultant was immediately put in water bath at 70° C. for incubation for 20 minutes. Centrifugation was carried out at 4° C., 1000×g for 15 minutes, and then the supernatant was collected as a phagemid solution. Subsequently, 200 μl of a solution prepared from phagemid host *Escherichia coli* SOLR to give an absorbance OD$_{600}$ of 1.0 and 10 μl of the purified phage solution were mixed, followed by 15 minutes of reaction at 37° C. 50 μl of the resultant was plated on LB agar medium containing ampicillin (at final concentration of 50 μg/ml) and then cultured overnight at 37° C. A single colony of transformed SOLR was collected and then cultured on LB medium containing ampicillin (at final concentration of 50 μg/ml) at 37° C. After culture, plasmid DNA carrying an insert of interest was purified using a QIAGEN plasmid Miniprep Kit (QIAGEN).

The purified plasmid was subjected to the analysis of the entire sequence of the insert by the primer walking method using the T3 primer of SEQ ID NO: 31 and the T7 primer of SEQ ID NO: 32. The gene sequences of SEQ ID NOS: 5, 7, 9, 11, and 13 were obtained by the sequence analysis. With the use of the nucleotide sequences of the genes and the amino acid sequences thereof (SEQ ID NOS: 6, 8, 10, 12, and 14), homology search program BLAST search (www.ncbi.nlm.nih.gov/BLAST/) was conducted for searching homology with known genes. As a result, it was revealed that all the five obtained genes were genes encoding CAPRIN-1. The sequence identities among the five genes were 100% at the nucleotide sequence level and 99% at the amino acid sequence level in the regions to be translated into proteins. The sequence identities of these genes and the human homologue-encoding gene were 94% at the nucleotide sequence level and 98% at the amino acid sequence level in the regions to be translated into proteins. The nucleotide sequences of the human homologues are represented by SEQ ID NOS: 1 and 3 and the amino acid sequences of the same are represented by SEQ ID NOS: 2 and 4. Also, the sequence identities of the obtained dog genes and the cattle homologue-encoding gene were 94% at the nucleotide sequence level and 97% at the amino acid sequence level in the regions to be translated into proteins. The nucleotide sequence of the cattle homologue is represented by SEQ ID NO: 15 and the amino acid sequence of the same is represented by SEQ ID NO: 16. In addition, the sequence identities of the human homologue-encoding genes and the cattle homologue-encoding gene were 94% at the nucleotide sequence level and 93% to 97% at the amino acid sequence level in the regions to be translated into proteins. Also, the sequence identities of the obtained dog genes and the horse homologue-encoding gene were 93% at the nucleotide sequence level and 97% at the amino acid sequence level in the regions to be translated into proteins. The nucleotide sequence of the horse homologue is represented by SEQ ID NO: 17 and the amino acid sequence of the same is represented by SEQ ID NO: 18. In addition, the sequence identities of the human homologue-encoding genes and the horse homologue-encoding gene were 93% at the nucleotide sequence level and 96% at the amino acid sequence level in the regions to be translated into proteins. Also, the sequence identities of the obtained dog genes and the mouse homologue-encoding genes were 87% to 89% at the nucleotide sequence level and 95% to 97% at the amino acid sequence level in the regions to be translated into proteins. The nucleotide sequences of the mouse homologues are represented by SEQ ID NOS: 19, 21, 23, 25, and 27 and the amino acid sequences of the same are represented by SEQ ID NOS: 20, 22, 24, 26, and 28. In addition, the sequence identities of the human homologue-encoding genes and the mouse homologue-encoding genes were 89% to 91% at the nucleotide sequence level and were 95% to 96% at the amino acid sequence level in the regions to be translated into proteins. Also, the sequence identities of the obtained dog genes and the chicken homologue-encoding gene were 82% at the nucleotide sequence level and 87% at the amino acid sequence level in the regions to be translated into proteins. The nucleotide sequence of the chicken homologue is represented by SEQ ID NO: 29 and the amino acid sequence of the same is represented by SEQ ID NO: 30. In addition, the sequence identities of the human homologue-encoding genes and the chicken homologue-encoding gene were 81% to 82% at the nucleotide sequence level and 86% at the amino acid sequence level in the regions to be translated into proteins.

(4) Gene Expression Analysis in Each Tissue

The expression of genes obtained by the above method was examined in dog and human normal tissues and various cell lines by an RT-PCR method. Reverse transcription reaction was performed as follows. Specifically, total RNA was extracted from 5 mg of each tissue or 5 to $10 \times 10^6$ cells of the cell line using a TRIZOL reagent (Invitrogen) according to the accompanying protocols. cDNA was synthesized with the total RNA using a Superscript First-Strand Synthesis System for RT-PCR (Invitrogen) according to the accompanying protocols. PCR was performed as follows using primers of SEQ ID NOS: 33 and 34 specific to the obtained genes. Specifically, reagents and an accompanying buffer were added to 0.25 μl of the sample prepared by the reverse transcription reaction to a total volume of 25 μl, so that the resultant contained the above primers of 2 μM each, dNTPs of 0.2 mM each, and 0.65 U ExTaq polymerase (Takara Shuzo Co., Ltd.). PCR was carried out by repeating a cycle of 94° C. for 30 seconds, 60° C. for 30 seconds, and 72° C. for 30 seconds 30 times using a Thermal Cycler (BIO RAD). The above gene-specific primers are capable of amplifying the region ranging from nucleotides 206 to 632 in the nucleotide sequence of SEQ ID NO: 5 (dog CAPRIN-1 gene) and the region ranging from nucleotides 698 to 1124 in the nucleotide sequence of SEQ ID NO: 1 (human CAPRIN-1 gene). As a control for comparison, GAPDH-specific primers of SEQ ID NOS: 35 and 36 were also used concurrently. As a result, as shown in FIG. 1, strong expression was observed in testis among normal dog tissues, while expression was observed in dog breast cancer and adenocarcinoma tissues. Moreover, the observation of the expression of the human homologues from the obtained genes was also carried out. As a result, similarly to the case of the dog CAPRIN-1 gene, expression could be observed in only testis among normal tissues. However, in the case of cancer cells, expression was detected in many types of cancer cell lines, including breast cancer, brain tumor, leukemia, lung cancer, and esophageal cancer cell lines. Expression was observed particularly in many breast cancer cell lines. It was confirmed by the results that the expression of CAPRIN-1 is not observed in normal tissues other than testis, while CAPRIN-1 was expressed in many cancer cells and particularly in breast cancer cell lines.

In FIG. 1, reference number 1 on each vertical axis indicates the expression patterns of genes identified above and reference number 2 indicates the expression patterns of the GAPDH gene as a control.

(5) Immunohistochemical Staining (5)-1 CAPRIN-1 Expression in Mouse and Dog Normal Tissues Mice (Balb/c, female) and dogs (beagles, female) were exsanguinated under ether anesthesia and ketamine/isoflurane anesthesia. After laparotomy, each organ (stomach, liver, eyeball, thymus gland, muscle, bone marrow, uterus, small intestine, esophagus, heart, kidney, salivary gland, large intestine, mammary gland, brain, lung, skin, adrenal gland, ovary, pancreas, spleen, and bladder) was transferred to a 10-cm dish containing PBS. Each organ was cut open in PBS and then subjected to perfusion fixation overnight in 0.1 M phosphate buffer (pH 7.4) containing 4% paraformaldehyde (PFA). The perfusion solution was discarded, the tissue surface of each organ was rinsed with PBS, a PBS solution containing 10% sucrose was added to a 50-ml centrifuge tube, each tissue was added to the tube, and then the tube was shaken using a rotor at 4° C. for 2 hours. The solution was replaced by a PBS solution containing 20% sucrose, and then left to stand at 4° C. until the tissue sank. The solution was replaced by a PBS solution containing 30% sucrose and then left to stand at 4° C. until the tissue sank. The tissue was removed and then needed portions were excised with a surgical scalpel. Next, an OCT compound (Tissue Tek) was added to the tissue so that it was thoroughly applied to the tissue surface, and then the tissue was placed in a cryomold. The cryomold was placed on dry ice for quick freezing. Thereafter, the tissue was sliced to 10 μm to 20 μm using a cryostat (LEICA). Slices were air-dried on slide glasses using a hair dryer for 30 minutes, to prepare the sliced tissue mounted on a slide glass. Next, each sample was placed in a staining bottle filled with PBS-T (saline containing 0.05% Tween20) and then subjected to replacement with PBS-T being repeated three times every 5 minutes. Excess water around the sections was removed with Kimwipes, and then the sections were circled using a DAKOPEN (DAKO). As blocking solutions, an MOM mouse Ig blocking reagent (VECTASTAIN) and a PBS-T solution containing 10% FBS were overlaid on mouse tissue and dog tissue, respectively, and then left to stand in a moist chamber at room temperature for 1 hour. Next, a solution of the anti-CAPRIN-1 monoclonal antibody (monoclonal antibody #6; prepared in Example 3) of 10 μg/ml adjusted with a blocking solution, which reacts with cancer cell surfaces and comprises the heavy chain variable region of SEQ ID NO: 73 and the light chain variable region of SEQ ID NO: 77, was placed on and then left to stand overnight in a moist chamber at 4° C. 10 minutes of washing with PBS-T was performed three times, and then an MOM biotin-labeled anti-IgG antibody (VECTASTAIN) diluted 250-fold with the blocking solution was placed and then left to stand at room temperature for 1 hour in a moist chamber. After ten (10) minutes of washing with PBS-T was performed three times, an avidin-biotin ABC reagent (VECTASTAIN) was placed on, and then the sample was left to stand in a moist chamber at room temperature for 5 minutes. After 10 minutes of washing with PBS-T was performed 3 times, a DAB color-development solution (DAB 10 mg+30% $H_2O_2$ 10 μl/0.05 M Tris-HCl (pH 7.6) 50 ml) was placed on, and then the sample was left to stand in a moist chamber at room temperature for 30 minutes. After rinsing with distilled water, a hematoxylin reagent (DAKO) was placed on, the sample was left to stand at room temperature for 1 minute, and then rinsed with distilled water. The slide glass was immersed in 70%, 80%, 90%, 95%, and then 100% ethanol solutions in such order for 1 minute each and then left to stand overnight in xylene. The slide glass was removed, sealed in Glycergel Mounting Medium (DAKO), and then observed. As a result, the expression of CAPRIN-1 was slightly observed within cells of each tissue of salivary gland, kidney, colon, and stomach, but the expression of the same was not observed on cell surfaces. Furthermore, no expression was observed in tissues from other organs. In addition, similar results were obtained in the case of using the anti-CAPRIN-1 monoclonal antibody (monoclonal antibody #9) comprising the heavy chain variable region of SEQ ID NO: 103 and the light chain variable region of SEQ ID NO: 107.

(5)-2 CAPRIN-1 Expression in Dog Breast Cancer Tissue

Frozen section slides were prepared by a method similar to the above using 108 frozen breast cancer tissue specimens of dogs pathologically diagnosed as having malignant breast cancer, and immunohistochemical staining was performed using the monoclonal antibody #6 prepared in Example 3. As a result, the expression of CAPRIN-1 was observed in 100 out of 108 specimens (92.5%) and CAPRIN-1 was strongly expressed on the surfaces of cancer cells with a particularly high grade of atypism. In addition, similar results were obtained in the case of using the monoclonal antibody #9 prepared in Example 3.

(5)-3 CAPRIN-1 Expression in Human Breast Cancer Tissue

Immunohistochemical staining was performed using 188 breast cancer tissue specimens on a paraffin-embedded human breast cancer tissue array (BIOMAX). After 3 hours of treatment of the human breast cancer tissue array at 60° C., the array was placed in a staining bottle filled with xylene, followed by xylene replacement being repeated three times every 5 minutes. Next, a similar procedure was performed with ethanol and PBS-T instead of xylene. The human breast cancer tissue array was placed in a staining bottle filled with 10 mM citrate buffer (pH 6.0) containing 0.05% Tween20. After 5 minutes of treatment at 125° C., the array was left to stand at room temperature for 40 minutes or more. Excess water around the sections was removed with Kimwipes, the sections were circled with a DAKOPEN, and Peroxidase Block (DAKO) was added dropwise in appropriate amounts. After left to stand at room temperature for 5 minutes, the array was placed in a staining bottle filled with PBS-T, followed by PBS-T replacement being repeated three times every 5 minutes. As a blocking solution, a PBS-T solution containing 10% FBS was placed on the array, and then the array was left to stand in a moist chamber at room temperature for 1 hour. Next, a solution of the monoclonal antibody #6 (prepared in Example 4) of 10 μg/ml adjusted with a PBS-T solution containing 5% FBS, which reacts with cancer cell surfaces, was placed on, and the array was left to stand overnight in a moist chamber at 4° C. After ten (10) minutes of washing with PBS-T was performed 3 times, Peroxidase Labeled Polymer Conjugated (DAKO) was added dropwise in appropriate amounts and then the array was left to stand in a moist chamber at room temperature for 30 minutes. After ten (10) minutes of washing with PBS-T was performed 3 times, a DAB coloring solution (DAKO) was placed on and then it was left to stand at room temperature for about 10 minutes. The coloring solution was discarded, 10 minutes of washing with PBS-T was performed 3 times, and then it was rinsed with distilled water. The array was immersed in 70%, 80%, 90%, 95%, and then 100% ethanol solutions in such order for 1 minute each, and then left to stand in xylene overnight. The slide glass was removed, sealed in Glycergel Mounting Medium (DAKO), and then observed. As a result, the strong expression of CAPRIN-1 was observed in 138 out of a total of 188 breast cancer tissue specimens (73%). In addition, similar results were obtained in the case of using the monoclonal antibody #2 or #9 prepared in Example 3.

(5)-4 CAPRIN-1 Expression in Human Malignant Brain Tumor

Immunohistochemical staining was performed according to a method similar to that used in (5)-3 above with 247 malignant brain tumor tissue specimens on a paraffin-embedded human malignant brain tumor tissue array (BIOMAX), using the monoclonal antibody #6 prepared in Example 3. As a result, the strong expression of CAPRIN-1 was observed in 227 out of a total of 247 malignant brain tumor tissue specimens (92%). In addition, similar results were obtained in the case of using the monoclonal antibody #2 or #9 prepared in Example 3.

(5)-5 CAPRIN-1 Expression in Human Breast Cancer Metastasized Lymph Node

Immunohistochemical staining was performed according to a method similar to that in (5)-3 above with 150 breast cancer metastasized lymph node tissue specimens on a paraffin-embedded human breast cancer metastasized lymph node tissue array (BIOMAX), using the monoclonal antibody #6 prepared in Example 3. As a result, the strong expression of CAPRIN-1 was observed in 136 out of a total of 150 breast cancer metastasized lymph node tissue specimens (90%). Specifically, it was revealed that CAPRIN-1 was strongly expressed also in cancer tissues that had metastasized from breast cancer. In addition, similar results were obtained in the case of using the monoclonal antibody #2 or #9 prepared in Example 3.

(5)-6 CAPRIN-1 Expression in Various Human Cancer Tissues

Immunohistochemical staining was performed according to a method similar to the above with specimens on various paraffin-embedded human cancer tissue arrays (BIOMAX), using the monoclonal antibody #6 prepared in Example 3. As a result, the strong expression of CAPRIN-1 was observed in esophageal cancer, colon cancer, rectal cancer, lung cancer, renal cancer, bladder cancer, and uterine cervix cancer. In addition, similar results were obtained in the case of using the monoclonal antibody #2 or #9.

Example 2

Preparation of Novel Human Cancer Antigen Protein (1) Preparation of Recombinant Protein Based on the gene of SEQ ID NO: 1, a recombinant protein from the human homologous gene was prepared by the following method. PCR was performed in a total volume of 50 μl with 1 μl of cDNA (the expression of which had been confirmed by an RT-PCR method for the cDNA used herein from among breast cancer tissue- or cell-derived cDNAs), two types of primer (SEQ ID NOS: 38 and 39 comprising Sac I and Xho I restriction enzyme cleavage sequences) of 0.4 μM each, 0.2 mM dNTP, and 1.25 U PrimeSTAR HS polymerase (Takara Shuzo Co., Ltd.), prepared by adding the reagents and an accompanying buffer. PCR was preformed by repeating a cycle of 98° C. for 10 seconds and 68° C. for 2.5 minutes 30 times using a Thermal Cycler (BIO RAD). The above two primers are capable of amplifying a region encoding the entire amino acid sequence of SEQ ID NO: 2. After PCR, the thus amplified DNA was subjected to electrophoresis on 1% agarose gel, and then an about 2.1 kbp DNA fragment was purified using a QIAquick Gel Extraction Kit (QIAGEN).

The thus purified DNA fragment was ligated to a cloning vector PCR-Blunt (Invitrogen). After transformation of *Escherichia coli* with it, plasmid was collected. It was verified by sequencing that the thus amplified gene fragment has the sequence of interest. The plasmid having a matched sequence with the sequence of interest was treated with Sac I and Xho I restriction enzymes and then purified with a QIAquick Gel Extraction Kit. The gene sequence of interest was inserted into an *Escherichia coli* expression vector pET30a (Novagen) treated with Sac I and Xho I restriction enzymes. A His-tag fused recombinant protein can be produced using the vector. The plasmid was transformed into *Escherichia coli* for recombinant expression, BL21(DE3), and then expression was induced with 1 mM IPTG, so that the protein of interest was expressed in *Escherichia coli*.

(2) Purification of Recombinant Protein

The above-obtained recombinant *Escherichia coli* expressing the gene of SEQ ID NO: 1 was cultured in LB medium containing 30 µg/ml kanamycin at 37° C. until absorbance at 600 nm reached around 0.7, isopropyl-β-D-1-thiogalactopyranoside was added at a final concentration of 1 mM, and then cells were cultured at 37° C. for 4 hours. Subsequently, centrifugation was performed at 4800 rpm for 10 minutes and then cells were collected. The resulting cell pellet was suspended in phosphate buffered saline and centrifuged at 4800 rpm for 10 minutes, and then cells were washed.

The cells were suspended in phosphate buffered saline and then disrupted by ultrasonication on ice. The resulting lysate of the ultrasonicated *Escherichia coli* was subjected to centrifugation at 6000 rpm for 20 minutes, and then the resulting supernatant was regarded as a soluble fraction and the precipitate was regarded as an insoluble fraction.

The soluble fraction was added to a nickel chelate column adjusted according to a conventional method (carrier: Chelating Sepharose™ Fast Flow (GE HealthCare); column capacity of 5 ml; and equilibration buffer: 50 mM hydrochloride buffer (pH 8.0)). Unadsorbed fractions were washed off with 50 mM hydrochloride buffer (pH 8.0) in an amount 10 times the column capacity and 20 mM phosphate buffer (pH 8.0) containing 20 mM imidazole. Immediately after washing, 6 beds were eluted with 20 mM phosphate buffer (pH 8.0) containing 100 mM imidazole. The elution of the protein of interest was confirmed by Coomassie staining on the elution fraction with 20 mM phosphate buffer (pH 8.0) containing 100 mM imidazole, and then the elution fraction was added to a strong anion exchange column (carrier: Q Sepharose™ Fast Flow (GE HealthCare); column capacity of 5 ml; and 20 mM phosphate buffer (pH 8.0) as an equilibration buffer). An unadsorbed fraction was washed off with 20 mM phosphate buffer (pH 7.0) in an amount 10 times the column capacity and 20 mM phosphate buffer (pH 7.0) containing 200 mM sodium chloride. Immediately after washing, 5 beds were eluted with 20 mM phosphate buffer (pH 7.0) containing 400 mM sodium chloride, and thus the purified fraction of the protein having the amino acid sequence represented by SEQ ID NO: 2 was obtained.

200 µl of each purified sample obtained by the above method was dispensed into 1 ml of reaction buffer (20 mM Tris-Hcl, 50 mM, NaCl, 2 mM CaCl$_2$, pH 7.4), followed by addition of 2 µl of enterokinase (Novagen). After that, the resultant was left to stand overnight at room temperature for reaction so that His-tag was cleaved off, and then purification was performed using an Enterokinase Cleavage Capture Kit (Novagen) according to the accompanying protocols. Next, 1.2 ml of the purified sample obtained by the above method was subjected to the buffer replacement with physiological phosphate buffer (Nissui Pharmaceutical Co., Ltd.) using an ultrafiltration NANOSEP 10K OMEGA (PALL). Further, sterile filtration was performed using HT Tuffryn Acrodisc 0.22 µm (PALL) and then the resultant was used for the following experiment.

Example 3 Preparation of mouse monoclonal antibody against CAPRIN-1 100 µg of the antigen protein (human CAPRIN-1) represented by SEQ ID NO: 2 prepared in Example 2 was mixed with an equivalent amount of MPL+ TDM adjuvant (Sigma), and then this was used as an antigen solution per one mouse. The antigen solution was intraperitoneally administered to 6-week-old Balb/c mice (Japan SLC Inc.), and then the administration was performed 3 times every week (24 times of administration in total), and thus immunization was completed. Each spleen was excised on day 3 after the final immunization, and sandwiched between two sterilized slide glasses and then crushed. The resultant was washed with PBS(-) (Nissui) and then centrifuged at 1500 rpm for 10 minutes to remove the supernatant. This procedure was repeated 3 times, so that splenocytes were obtained. The thus obtained splenocytes and mouse myeloma cells SP2/0 (purchased from ATCC) were mixed at a ratio of 10:1. A PEG solution prepared by mixing 200 µl of RPMI1640 medium containing 10% FBS heated at 37° C. and 800 µl of PEG1500 (Boehringer) was added to the mixture, left to stand for 5 minutes for cell fusion, and then subjected to centrifugation at 1700 rpm for 5 minutes. After removal of the supernatant, cells were suspended in 150 ml of RPMI1640 medium containing 15% FBS, supplemented with a HAT solution (Gibco) (2% equivalent) (HAT selective medium), and then the cell suspension was seeded on fifteen 96-well plates (Nunc) at 100 µl per well. Cells were cultured under conditions of 7 days, at 37° C., in the presence of 5% CO$_2$, so that hybridomas prepared by fusion of splenocytes and myeloma cells were obtained.

Hybridomas were selected using as a marker the binding affinity of the antibody produced by the prepared hybridomas to the CAPRIN-1 protein. The CAPRIN-1 protein solution (1 µg/ml) prepared in Example 1 was added to a 96-well plate at 100 µl per well and then left to stand at 4° C. for 18 hours. Each well was washed 3 times with PBS-T, 400 µl of a 0.5% Bovine Serum Albumin (BSA) solution (Sigma) was added per well, and then the plate was left to stand at room temperature for 3 hours. The solution was removed, and then the wells were washed three times with 400 µl of PBS-T per well. The culture supernatant of the above-obtained hybridomas was added at 100 µl per well, and then left to stand at room temperature for 2 hours. After washing each well three times with PBS-T, the HRP-labeled anti-mouse IgG (H+L) antibody (Invitrogen) diluted 5000-fold with PBS was added at 100 µl per well and the resultant was then left to stand at room temperature for 1 hour. After washing the wells three times with PBS-T, 100 µl of a TMB substrate solution (Thermo) was added per well and then left to stand for 15 to 30 minutes for color development reaction. After color development, 100 µl of 1N sulfuric acid was added per well to stop the reaction, and then absorbances at 450 nm and 595 nm were measured using an absorption spectrometer. As a result, several hybridomas producing antibodies with high absorbance values were selected.

The thus selected hybridomas were added to a 96-well plate at 0.5 cells per well and then cultured. After 1 week, hybridomas that had formed single colonies in wells were observed. These cells in the wells were further cultured, and then hybridomas were selected using as a marker the binding affinity of antibodies produced by the cloned hybridomas to the CAPRIN-1 protein. The CAPRIN-1 protein solution (1 μg/ml) prepared in Example 1 was added to a 96-well plate at 100 μl per well, and then left to stand at 4° C. for 18 hours. Each well was washed with PBS-T three times, 400 μl of a 0.5% BSA solution was added per well, and then the resultant was left to stand at room temperature for 3 hours. The solution was removed, and then the wells were washed three times with 400 μl of PBS-T per well. 100 μl of each culture supernatant of the above-obtained hybridomas was added per well, and then the plate was left to stand at room temperature for 2 hours. After washing each well three times with PBS-T, 100 μl of an HRP-labeled anti-mouse IgG (H+L) antibody (Invitrogen) diluted 5000-fold with PBS was added per well and then left to stand at room temperature for 1 hour. After washing the wells three times with PBS-T, 100 μl of a TMB substrate solution (Thermo) was added per well, and then left to stand for 15 to 30 minutes for color development reaction. After color development, 100 μl of 1N sulfuric acid was added per well to stop the reaction and then absorbances at 450 nm and 595 nm were measured using an absorption spectrometer. As a result, 150 hybridoma cell lines producing monoclonal antibodies reactive with the CAPRIN-1 protein were obtained.

Next, of those monoclonal antibodies, antibodies reactive to the cell surface of breast cancer cells expressing CAPRIN-1 were selected. Specifically, $10^6$ cells of the human breast cancer cell line MDA-MB-231V were subjected to centrifugation with a 1.5-ml microcentrifuge tube, and 100 μl of the culture supernatant of each of the above hybridomas was added to the tube, and then the tube was left to stand on ice for 1 hour. After washing with PBS, an FITC-labeled goat anti-mouse IgG antibody (Invitrogen) diluted 500-fold with PBS containing 0.1% FBS was added, and then the resultant was left to stand on ice for 1 hour. After washing with PBS, fluorescence intensity was measured using a FACS caliber (Becton, Dickinson and Company). Meanwhile, procedures similar to the above were performed using the serum (of a 6-week-old Balb/c mouse not treated with the antibodies) diluted 500-fold with medium for culturing hybridomas, so that a control sample was prepared. As a result, 11 monoclonal antibodies (#1 to #11) that had exhibited a fluorescence intensity stronger than that of the control, and that is, that reacted with the cell surface of breast cancer cells, were selected.

Example 4

Characterization of Selected Antibody (1) Cloning of Anti-CAPRIN-1 Monoclonal Antibody Variable Region Gene mRNA was extracted from each hybridoma cell line producing each of the 11 mouse monoclonal antibodies selected in Example 3. The genes of the heavy chain variable (VH) and light chain variable (VL) regions of all anti-CAPRIN-1 monoclonal antibodies were obtained by an RT-PCR method using primers specific to a mouse FR1-derived sequence and a mouse FR4-derived sequence. For sequence determination, these genes were cloned into a pCR2.1 vector (Invitrogen). Furthermore, mRNA was extracted from two mouse-derived hybridoma cell lines producing monoclonal antibodies reactive with the surface of CAPRIN-1-expressing breast cancer cells. The genes of the heavy chain variable (VH) region and light chain variable (VL) region of each antibody were obtained by an RT-PCR method using primers specific to the mouse FR1-derived sequence and the mouse FR4-derived sequence. For sequence determination, these genes were cloned into a pCR2.1 vector (Invitrogen).

(1)-1 RT-PCR

After extraction of total RNA from $10^6$ cells of each hybridoma cell line using a High Pure RNA Isolation Kit (Roche), cDNA was synthesized using a PrimeScriptII 1st strand cDNA Synthesis Kit (Takara). These procedures were performed according to protocols attached to each kit.

The gene of the mouse antibody heavy chain variable region and the gene of the mouse antibody light chain variable region were separately amplified by a PCR method according to a conventional method using the thus synthesized cDNA as a template and KOD-Plus-DNA Polymerase (TOYOBO).

To obtain the genes of the mouse antibody VH and VL regions, a primer (SEQ ID NO: 130) specific to the mouse heavy chain FR1 sequence, a primer (SEQ ID NO: 131) specific to the mouse heavy chain FR4 sequence, a primer (SEQ ID NO: 132) specific to the mouse light chain FR1 sequence, a primer (SEQ ID NO: 133) specific to the mouse light chain FR4 sequence were used.

The thus obtained PCR products were each subjected to agarose gel electrophoresis, and DNA bands of the VH region and the VL region were excised. DNA fragments were purified using a QIAquick Gel purification kit (QIAGEN) according to the accompanying protocols. The purified DNA was cloned into a pCR2.1 vector using a TA cloning kit (Invitrogen). The ligated vector was transformed into DH5 competent cells (TOYOBO) according to a conventional method. 10 clones of each transformant were cultured overnight in medium (100 μg/ml ampicillin) at 37° C., and then plasmid DNA was purified using a Qiaspin Miniprep kit (QIAGEN).

(1)-2 Sequence Determination

The gene sequences of the VH region and the VL region in each plasmid obtained above were analyzed with an M13 forward primer (SEQ ID NO: 134) and an M13 reverse primer (SEQ ID NO: 135) on a fluorescence sequencer (DNA sequencer 3130XL; ABI), using a Big Dye Terminator Ver3.1 Cycle Sequencing Kit (ABI) according to the accompanying protocols. As a result, each gene sequence was determined. The sequences were identical among the 10 clones.

The gene sequences of the heavy chain variable regions of the thus obtained monoclonal antibodies are each represented by SEQ ID NOS: 48, 78, 88, 98, 108, 118, and 128, and the amino acid sequences of the heavy chain variable regions are each represented by SEQ ID NOS: 43, 73, 83, 93, 103, 113, and 123. The gene sequences of the light chain variable regions of the same monoclonal antibodies are each represented by SEQ ID NOS: 49, 54, 59, 64, 69, 79, 89, 99, 109, 119, and 129, and the amino acid sequences of the light chain variable regions are each represented by SEQ ID NOS: 47, 53, 58, 63, 68, 77, 87, 97, 107, 117, and 127.

Specifically, the monoclonal antibody #1 comprises the heavy chain variable region of SEQ ID NO: 43 and the light chain variable region of SEQ ID NO: 47, #2 comprises the heavy chain variable region of SEQ ID NO: 43 and the light chain variable region of SEQ ID NO: 53, #3 comprises the heavy chain variable region of SEQ ID NO: 43 and the light chain variable region of SEQ ID NO: 58, #4 comprises the heavy chain variable region of SEQ ID NO: 43 and the light chain variable region of SEQ ID NO: 63, #5 comprises the heavy chain variable region of SEQ ID NO: 43 and the light chain variable region of SEQ ID NO: 68, #6 comprises the heavy chain variable region of SEQ ID NO: 73 and the light chain variable region of SEQ ID NO: 77, #7 comprise the heavy chain variable region of SEQ ID NO: 83 and the light chain variable region of SEQ ID NO: 87, #8 comprises the heavy chain variable region of SEQ ID NO: 93 and the light chain variable region of SEQ ID NO: 97, #9 comprises the heavy chain variable region of SEQ ID NO: 103 and the light chain variable region of SEQ ID NO: 107, #10 comprises the heavy chain variable region of SEQ ID NO: 113 and the light chain variable region of SEQ ID NO: 117, and #11 comprises the heavy chain variable region of SEQ ID NO: 123 and the light chain variable region of SEQ ID NO: 127.

(2) Expression of CAPRIN-1 on the Surface of Various Cancer Cells Using Anti-CAPRIN-1 Antibodies #2 and #9

Next, 7 breast cancer cell lines (MDA-MB-157, T47D, MRK-nu-1, MDA-MB-231V, BT20, SK-BR-3, and MDA-MB-231T) for which CAPRIN-1 gene expression had been observed, and the other 3 breast cancer cell lines (MDA-MB-231C, MCF-7, and ZR75-1), 5 glioma cell lines (T98G, SNB19, U251, U87MG, and U373), 4 renal cancer cell lines (Caki-1, Caki-2, A498, and ACHN), 2 gastric cancer cell lines (MNK28 and MKN45), 5 colorectal cancer cell lines (HT29, LoVo, Caco2, SW480, and HCT116), 3 lung cancer cell lines (A549, QG56, and PC8), 4 leukemia cell lines (AML5, Namalwa, BDCM, RPI1788), one (1) lymphoma cell line (Ramos), one (1) uterine cervix cancer cell line (SW756), one (1) bladder cancer cell line (T24), and one (1) esophageal cancer cell line (KYSE180) were examined for expression of CAPRIN-1 protein on the cell surface of each cell line using the culture supernatants of hybridomas producing #2 and #9 obtained in Example 3. $10^6$ cells of each cell line were centrifuged using a 1.5 ml microcentrifuge tube. Each culture supernatant (100 µl) of hybridomas producing #2 and #9 obtained in Example 3 was added and then left to stand on ice for 1 hour. After washing with PBS, a FITC-labeled goat-anti human IgG (H+L) antibody (SouthernBiotech) diluted 500-fold with PBS containing 0.1% FBS and a FITC-labeled anti-mouse IgG (H+L) antibody (Invitrogen) were added and then the resultant was left to stand on ice for 1 hour. After washing with PBS, fluorescence intensity was measured using a FACS Calibur (Becton, Dickinson and Company). Meanwhile, a procedure similar to the above was performed using a medium for culturing hybridomas, and it was used as a negative control. As a result, cells to which the antibodies #2 and #9 had been added exhibited fluorescence intensity stronger by 20% or more than that of the control. It was revealed by these results that the CAPRIN-1 protein was expressed on the cell membrane surfaces of the above human cancer cell lines. The percentage of enhancement in the above fluorescence intensity was expressed as percentage of increase in mean fluorescence intensity (MFI level) in each type of cell and calculated by the following formula.

Percentage of increase in mean fluorescence intensity (percentage of enhancement in fluorescence intensity)(%)=((MFI level in cells having reacted with anti-human CAPRIN-1 antibody)−(MFI level of the control))/(MFI level of control)×100.

(3) Anti-Tumor Effect of Anti-CAPRIN-1 Antibodies on Cancer Cells (ADCC Activity)

The above-selected anti-CAPRIN-1 monoclonal antibodies #1 to #11 were evaluated for their cytotoxic activities against cancer cells (ADCC activity). Hybridomas producing the monoclonal antibodies #1 to #11 were each cultured using hybridoma SFM medium (Invitrogen). The thus obtained supernatant was purified using Hitrap ProteinA Sepharose FF (GE HealthCare), replaced with PBS(−), and then filtered through 0.22 µm filter (Millipore). The obtained filtrates were used as antibodies for assay. The human breast cancer cell line MDA-MB-157 ($10^6$ cells) was collected in a 50-ml centrifuge tube, to which 100 µCi chromium(Cr)-51 was then added, and incubated at 37° C. for 2 hours. Subsequently, the cells were washed 3 times with RPMI1640 medium containing 10% FBS, and then dispensed into each well of a 96-well V-bottom plate at $10^3$ cells per well. The thus obtained cells are used as target cell. The above purified antibodies (1 µg each) were added to the cells. Separately, mouse lymphocytes separated from the mouse spleen were further added ($2 \times 10^5$ cells) and then cultured under conditions of 37° C. and 5% $CO_2$ for 4 hours. After culture, the amount of chromium(Cr)-51 released from cytotoxically impaired tumor cells in a culture supernatant was measured, so that the ADCC activity of each anti-CAPRIN-1 antibody against cancer cells was calculated. As a result, all the monoclonal antibodies #1 to #11 exhibited 20% or more ADCC activity against MDA-MB-157. Specifically, for example #1 exhibited 22.1% cytotoxic activity, #2 exhibited 29.1% cytotoxic activity, #6 exhibited 30.2% cytotoxic activity, and #9 exhibited 32.4% cytotoxic activity (see FIG. 1). On the other hand, similar procedures were performed using the monoclonal antibodies (which were prepared in Example 2) reactive with the CAPRIN-1 protein itself, but not reactive with the surface of cancer cells, no cytotoxic activity was observed (see FIG. 1). From the above results, it was demonstrated that the thus obtained anti-CAPRIN-1 monoclonal antibodies (#1 to #11) cytotoxically impaired CAPRIN-1-expressing cancer cells by the ADCC activity. Similarly, the anti-CAPRIN-1 antibodies were examined for ADCC activity against other human cancer cell lines including glioma cell lines (T98G and U373), lung cancer cell lines (A549 and QG56), renal cancer cell lines (Caki-1 and ACHN), a uterine cervix cancer cell line (SW756), a bladder cancer cell line (T24), an esophageal cancer cell line (KYSE180), gastric cancer cell lines (MNK28 and MNK45), a colorectal cancer cell line (SW480), a leukemia cell line (AML5), and a lymphoma cell line (Ramos). As a result, all the monoclonal antibodies #1 to #11 exhibited ADCC activities higher than those of isotype controls. Specifically, for example, #9 exhibited 12% or more (1.3% in the case of the isotype control) activity against T98G, #9 exhibited 16% or more (3% in the case of isotype control) against U373, #9 exhibited 24% or more (2.6% in the case of isotype control) activity against A549, #9 exhibited 20% or more (0.2% in the case of isotype control) activity against QG56, #9 exhibited 23% or more (3.0% in the case of isotype control) against Caki-L #9 exhibited 14% or more (1.5% in the case of isotype control) against ACHN, #9 exhibited 16% or more activity (2.5% in the case of isotype control) against SW756, #9 exhibited 18% or more activity (2.1% in the case of isotype control) against T24, #9 exhibited 22% or more activity (3.0% in the case of isotype control) against KYSE180, #9 exhibited 15% or more activity (1.7% in the case of isotype control) against MNK28, #9 exhibited 10% or more activity (2.3% in the case of isotype control) against MNK45, #9 exhibited 17% or more activity (1.3% in the case of isotype control) against SW480, #9 exhibited 10% or more activity (3.0% in the case of isotype control) against AML5, and #9 exhibited 10% or more activity (4.1% in the case of isotype control) against Ramos. It was demonstrated by the above results that the obtained anti-CAPRIN-1 antibodies (#1 to #11) cytotoxically impaired various human cancer cells expressing CAPRIN-1.

(4) Anti-Tumor Effect of Anti-CAPRIN-1 Antibodies on Cancer Cells (CDC Activity)

The above-selected anti-CAPRIN-1 monoclonal antibodies #1 to #11 were evaluated for cytotoxic activity against cancer cells (CDC activity). Blood taken from a rabbit was added to an Eppendorf tube, left to stand at room temperature for 60 minutes, and then centrifuged at 3000 rpm for 5 minutes. Thus, the serum for assay of CDC activity was prepared.

10⁵ cells of MDA-MB-231V, a human breast cancer cell, were collected in a 50-ml centrifuge tube, to which 100 µCi chromium-51 was then added, and incubated at 37° C. for 2 hours. The cells were washed 3 times with RPMI medium containing 10% FBS, suspended in RPMI medium containing the above-prepared rabbit serum at a concentration of 50%, and then dispensed into each well of a 96-well V-bottom plate at $10^3$ cells per well. The monoclonal antibodies #1 to #13 obtained in Example 3 were each added (1 µg each) to the cells, which were then cultured under conditions of 37° C. and 5% $CO_2$ for 4 hours. After culture, the amount of chromium-51 released from cytotoxically impaired tumor cells in a culture supernatant was measured, and the CDC activity of each anti-CAPRIN-1 monoclonal antibody against MDA-MB-231V in a hybridoma supernatant was calculated. As a result, all the monoclonal antibodies #1 to #11 exhibited 30% or more CDC activity. On the other hand, no cytotoxic activity was observed when similar procedures were performed using the monoclonal antibodies (which were prepared in Example 2) reactive with the CAPRIN-1 protein itself, but not reactive with the surface of cancer cells. Therefore, it was revealed that the anti-CAPRIN-1 monoclonal antibodies (#1 to #11) can cytotoxically impair tumor cells expressing CAPRIN-1, as also seen from the results of CDC activity.

Example 5

Identification of a Peptide in a CAPRIN-1 Protein to which Anti-CAPRIN-1 Antibodies Reactive with the Surface of Cancer Cells Bind A partial sequence of a CAPRIN-1 protein to be recognized by the above-obtained anti-CAPRIN-1 monoclonal antibodies #1 to #11 reactive with the surface of cancer cells was identified using each antibody.

First, DTT (Fluka) was added to 100 µl of a recombinant CAPRIN-1 protein solution prepared by dissolving the protein to a concentration of 1 µg/µl in PBS, so that the final concentration was 10 mM, followed by 5 minutes of reaction at 95° C. Disulfide bonds within the CAPRIN-1 protein were reduced, iodacetamide (Wako Pure Chemical Industries, Ltd.) at a final concentration of 20 mM was added, and then the alkylation reaction of a thiol group was performed at 37° C. under light shielding conditions for 30 minutes. The anti-CAPRIN-1 monoclonal antibodies #1 to #11 were each added (50 µg each) to 40 µg of the thus reduced and alkylated CAPRIN-1 protein. Each solution was diluted to a volume of 1 ml with 20 mM phosphate buffer (pH 7.0), followed by reacting at 4° C. overnight while agitating and mixing the solution.

Next, trypsin (Promega) was added to a final concentration of 0.2 µg. After reaction at 37° C. for 1 hour, 2 hours, 4 hours, or 12 hours, each resultant was blocked with PBS containing 1% BSA (Sigma) in advance, and then mixed with protein A-glass beads (GE), which were previously washed with PBS, and 1 mM calcium carbonate in NP-40 buffer (20 mM phosphate buffer (pH 7.4), 5 mM EDTA, 150 mM NaCl, 1% NP-40), followed by 30 minutes of reaction for each solution.

The reaction mixture was washed with 25 mM ammonium carbonate buffer (pH 8.0), and then an antigen-antibody complex was eluted using 100 µl of 0.1% formic acid. The eluate was subjected to LC-MS analysis using Q-TOF Premier (Waters-MicroMass). LC-MS analysis was conducted according to protocols attached to the apparatus.

As a result, the polypeptide of SEQ ID NO: 37 was identified as a partial CAPRIN-1 sequence, which was recognized by any of the anti-CAPRIN-1 monoclonal antibodies #1 to #11.

Example 6

Effect of Antitumor Agents on Expression of CAPRIN-1 on the Surface of Cancer Cells (1) Calculation of 50% Inhibitory Concentration of Antitumor Agents Against Cancer Cell To evaluate the effect of antitumor agents on the expression of CAPRIN-1 on the surface of a cancer cell, the 50% inhibitory concentration of each antitumor agent was calculated using the MCF-7 cancer cell. Using the MCF-7 human breast cancer cell line, 50% inhibitory concentrations of 4 types of antitumor agents that are currently used as remedies for breast cancer (i.e., cyclophosphamide: "Endoxan" (registered trademark, Shionogi & Co., Ltd.), paclitaxel: "Taxol" (registered trademark, Bristol-Myers), docetaxel: "Taxotere" (registered trademark, Sanofi-aventis K.K.), vinorelbine: "Navelbine" (registered trademark, Kyowa Hakko Kirin Co., Ltd.)), were examined. The cell line was prepared to $1 \times 10^5$ cells/ml and then cultured on a 6-well plate under conditions of 37° C. and 5% $CO_2$ for one day. Then, the cell was treated with each antitumor agent at final concentrations of 0.001 µM, 0.01 µM, 0.1 µM, 1.0 µM, and 10 µM, followed by 2-days culture under conditions of 37° C. and 5% $CO_2$. After removal of the culture medium, the cell was washed twice with PBS(−), to which 0.25% Trypsin-EDTA was then added in order to detach the cell from the plate. The thus detached cell was suspended with PBS(−) to a volume of 100 to which 10 µl of 0.4% trypan blue stock solution was then added, and the mixture was measured for counts of living cells using a hemocytometer. The rate of living cells in case that the cell was treated with each antitumor agent (i.e., a chemotherapeutic) was calculated, wherein the number of living cells in case that the cell was not treated with each antitumor agent was designated at 100%. 50% inhibitory concentration was roughly estimated based on the obtained values, and each antitumor agent was prepared to have a concentration around the determined 50% inhibitory concentration, and thereafter procedures similar to the above were further performed in order to calculate a more specific 50% inhibitory concentration.

As an example, the results of examination for cyclophosphamide (an antitumor agent) are described below. MCF-7 cell line was prepared to $1 \times 10^5$ cells/mL, and then cultured on a 6-well plate under conditions of 37° C. and 5% $CO_2$ for one day. Then, the cell was treated with cyclophosphamide at final concentrations of $1 \times 10^{-1}$ µM, $5 \times 10^{-2}$ µM, $2 \times 10^{-2}$ µM, and $1 \times 10^{-2}$ µM, followed by 2-days culture under conditions of 37° C. and 5% $CO_2$. After removal of the culture medium, the cell was washed with PBS(−) twice, to which 0.25% Trypsin-EDTA was added in order to detach the cell from the plate. The detached cell was suspended in PBS(−) to a volume of 100 µl, to which 10 µl of 0.4% trypan blue stock solution was further added. The mixture was measured for counts of living cells using a hemocytometer. As a result, the 50% inhibitory concentration was determined to be $3 \times 10^{-2}$ µM. The IC50 values of respective antitumor agents in each type of cancer cells were calculated by using the same procedures. The results are shown in Table 1.

TABLE 1

50% inhibitory concentration of antitumor agents against MCF-7

| | |
|---|---|
| Cyclophosphamide (μM) | $3 \times 10^{-2}$ |
| Paclitaxel (μM) | $1 \times 10^{-2}$ |
| Docetaxel (μM) | $1 \times 10^{-4}$ |
| Vinorelbine (μM) | $2 \times 10^{-2}$ |

(2) Effect of Antitumor Agents on Expression of CAPRIN-1 Upon Treatment of Cancer Cell with Them The cancer cell line MCF-7 was treated with each antitumor agent at a 50% inhibitory concentration which was calculated in (1) above, and the expression behavior of a CAPRIN-1 protein on the cell surface was examined.

The expression behavior of the CAPRIN-1 protein on the surface of the above-treated MCF-7 human breast cancer cell was examined. The cell was prepared to a concentration of $1 \times 10^5$ cells/ml, and then cultured on a 6-well plate under conditions of 37° C. and 5% $CO_2$ for 1 day. Next, the cell was treated with antitumor agents at the 50% inhibitory concentration calculated in (1) above, or with PBS(−) as a control, and then cultured under conditions of 37° C. and 5% $CO_2$ for 2 days. After removal of the culture medium, the cell was washed with PBS(−) twice and then detached from the plate using a cell scraper. Thereafter, the cell was centrifuged with a 1.5-ml microcentrifuge tube. One (1) μg (5 μl) of the mouse anti-CAPRIN-1 monoclonal antibody #9 was added to the separated cell, which was further suspended in 95 μl of PBS containing 0.1% fetal calf serum and then left to stand on ice for 1 hour. After washing with PBS, the cell was suspended in PBS containing 5 μl of a FITC-labeled goat anti-rabbit IgG antibody (SantaCruz) and 95 μl of 0.1% fetal bovine serum (FBS) and then left to stand on ice for 1 hour. After washing with PBS, fluorescence intensity was measured using a FACS caliber (Becton, Dickinson and Company). Meanwhile, the same procedure as the above was performed using a control antibody instead of the mouse anti-CAPRIN-1 monoclonal antibody, and it was used as a control. As a result, no significant difference in fluorescence intensity was observed regardless of treatment with an antitumor agent. Specifically, the fluorescence intensity obtained in the case of adding the anti-CAPRIN-1 antibody to MCF-7 not treated with any antitumor agent indicated 32% higher enhancement when compared with that in the case of adding the control antibody. On the other hand, when MCF-7 was treated with the antitumor agent using the same procedure, the 32% enhancement in fluorescence intensity was observed, and thus this result was the same as that in the case of no treatment with the antitumor agent. It was revealed by these results that the treatment of breast cancer cells with an antitumor agent has no effect on expression of CAPRIN-1 on the surface of breast cancer cells. Here, the percentage of enhancement in fluorescence intensity was represented by the percentage of increase in mean fluorescence intensity (MFI level) in each cell and calculated by the following formula.

Percentage of increase in mean fluorescence intensity (percentage of enhancement in fluorescence intensity)(%)=((MFI level of cells having reacted with anti-human CAPRIN-1 antibody)−(control MFI level))÷(control MFI level)×100.

Example 7

In Vivo Combination Therapy Using Anti-CAPRIN-1 Antibody and Antitumor Agent (1) With the use of tumor-bearing mice into which the CAPRIN-1-expressing MCF-7 human breast cancer cell line had been transplanted, the anti-tumor effect of the combined use of an anti-CAPRIN-1 monoclonal antibody and antitumor agents was examined. A method for examining the anti-tumor effect using mice into which MCF-7 had been transplanted and the results thereof are as described below. $10^6$ MCF-7 cells (purchased from ATCC) were transplanted subcutaneously to the dorsal region of each of 280 nude mice (Japan SLC Inc.). Mice were grown until each tumor reached a size of about 7 mm in diameter.

Next, as described specifically in the following experimental section 1 and experimental section 2, tumor-bearing mice into which MCF-7 had been transplanted were divided into 5 groups, a group to which only the anti-CAPRIN-1 antibody was administered, a group to which only an antitumor agent (of 4 types) was administered, a group to which an antitumor agent and an anti-Her2 antibody (mouse anti-human ErbB2 monoclonal antibody, isotype: IgG2b (R&D systems, catalog No. MAB11291)) were administered in combination, a group to which an antitumor agent and anti-CAPRIN-1 monoclonal antibody were administered in combination, and a group to which control (PBS(−)) was administered. In addition, mouse PBMC was administered to all the administration groups.

<Experimental Section 1>

(Group to which Only Anti-CAPRIN-1 Antibody was Administered)

The anti-CAPRIN-1 monoclonal antibody #2 was intraperitoneally administered to each of 5 tumor-bearing mice at 5 mg/kg/shot on days 0, 4, 8, 11, 15, and 17 after the start of the experiment. PBMC separated from Balb/c mouse spleen was intravenously administered to each mouse at $1 \times 10^7$ cells/0.2 mL (RPMI1640) on days 0, 8, and 15 after the start of the experiment.

(Group to which Cyclophosphamide was Administered)

Cyclophosphamide was intraperitoneally administered to each of 5 tumor-bearing mice at 80 mg/kg/shot on days 0 and 4 after the start of the experiment. PBMC separated from Balb/c mouse spleen was intravenously administered to each mouse at $1 \times 10^7$ cells/0.2 mL (RPMI1640) on days 0, 8, and 15 after the start of the experiment.

(Group to which Paclitaxel was Administered)

Paclitaxel was intraperitoneally administered to each of 5 tumor-bearing mice at 15 mg/kg/shot on days 0 and 3 after the start of the experiment. PBMC separated from Balb/c mouse spleen was intravenously administered to each mouse at $1 \times 10^7$ cells/0.2 mL (RPMI1640) on days 0, 8, and 15 after the start of the experiment.

(Group to which Docetaxel was Administered)

Docetaxel was intraperitoneally administered to each of 5 tumor-bearing mice at 10 mg/kg/shot on days 0 and 3 after the start of the experiment. PBMC separated from Balb/c mouse spleen was intravenously administered to each mouse at $1 \times 10^7$ cells/0.2 mL (RPMI1640) on days 0, 8, and 15 after the start of the experiment.

(Group to which Vinorelbine was Administered)

Vinorelbine was intraperitoneally administered to each of 5 tumor-bearing mice at 1 mg/kg/shot on day 0 after the start of the experiment. PBMC separated from Balb/c mouse spleen was intravenously administered to each mouse at $1 \times 10^7$ cells/0.2 mL (RPMI1640) on days 0, 8, and 15 after the start of the experiment.

(Group to which Cyclophosphamide and Anti-Her2 Antibody were Administered)

Cyclophosphamide was intraperitoneally administered to each of 5 tumor-bearing mice at 80 mg/kg/shot on days 0 and 4 after the start of the experiment, and at the same time the anti-Her2 antibody was intraperitoneally administered to each mouse at 5 mg/kg/shot on days 0, 4, 8, 11, 15, and 17 after the start of the experiment. PBMC separated from Balb/c mouse spleen was intravenously administered to each mouse at $1\times10^7$ cells/0.2 mL (RPMI1640) on days 0, 8, and 15 after the start of the experiment.

(Group to which Paclitaxel and Anti-Her2 Antibody were Administered)

Paclitaxel was intraperitoneally administered to each of 5 tumor-bearing mice at 15 mg/kg/shot on days 0 and 3 after the start of the experiment, and at the same time, the anti-Her2 antibody was intraperitoneally administered to each mouse at 5 mg/kg/shot on days 0, 4, 8, 11, 15, and 17 after the start of the experiment. PBMC separated from Balb/c mouse spleen was intravenously administered to each mouse at $1\times10^7$ cells/0.2 mL (RPMI1640) on days 0, 8, and 15 after the start of the experiment.

(Group to which Docetaxel and Anti-Her2 Antibody were Administered)

Docetaxel was intraperitoneally administered to each of 5 tumor-bearing mice at 10 mg/kg/shot on days 0 and 3 after the start of the experiment, and at the same time, the anti-Her2 antibody was intraperitoneally administered to each mouse at 5 mg/kg/shot on days 0, 4, 8, 11, 15, and 17 after the start of the experiment. PBMC separated from Balb/c mouse spleen was intravenously administered to each mouse at $1\times10^7$ cells/0.2 mL (RPMI1640) on days 0, 8, and 15 after the start of the experiment.

(Group to which Vinorelbine and Anti-Her2 were Administered)

Vinorelbine was intraperitoneally administered to each of 5 tumor-bearing mice at 1 mg/kg/shot on day 0 after the start of the experiment, and at the same time, the anti-Her2 antibody was intraperitoneally administered to each mouse at 5 mg/kg/shot on days 0, 4, 8, 11, 15, and 17 after the start of the experiment. PBMC separated from Balb/c mouse spleen was intravenously administered to each mouse at $1\times10^7$ cells/0.2 mL (RPMI1640) on days 0, 8, and 15 after the start of the experiment.

(Group to which Cyclophosphamide and Anti-CAPRIN-1 Antibody were Administered)

Cyclophosphamide was intraperitoneally administered to each of 5 tumor-bearing mice at 80 ng/kg/shot on days 0 and 4 after the start of the experiment, and at the same time, the anti-CAPRIN-1 monoclonal antibody #2 was intraperitoneally administered to each mouse at 5 mg/kg/shot on days 0, 4, 8, 11, 15, and 17 after the start of the experiment. PBMC separated from Balb/c mouse spleen was intravenously administered to each mouse at $1\times10^7$ cells/0.2 mL (RPMI1640) on days 0, 8, and 15 after the start of the experiment.

(Group to which Paclitaxel and Anti-CAPRIN-1 Antibody were Administered)

Paclitaxel was intraperitoneally administered to each of 5 tumor-bearing mice at 15 mg/kg/shot on days 0 and 3 after the start of the experiment, and at the same time, the anti-CAPRIN-1 monoclonal antibody #2 was intraperitoneally administered to each mouse at 5 mg/kg/shot on days 0, 4, 8, 11, 15, and 17 after the start of the experiment. PBMC separated from Balb/c mouse spleen was intravenously administered to each mouse at $1\times10^7$ cells/0.2 mL (RPMI1640) on days 0, 8, and 15 after the start of the experiment.

(Group to which Docetaxel and Anti-CAPRIN-1 Antibody were Administered)

Docetaxel was intraperitoneally administered to each of 5 tumor-bearing mice at 10 mg/kg/shot on days 0 and 3 after the start of the experiment, and at the same time, the anti-CAPRIN-1 monoclonal antibody #2 was intraperitoneally administered to each mouse at 5 mg/kg/shot on days 0, 4, 8, 11, 15, and 17 after the start of the experiment. PBMC separated from Balb/c mouse spleen was intravenously administered to each mouse at $1\times10^7$ cells/0.2 mL (RPMI1640) on days 0, 8, and 15 after the start of the experiment.

(Group to which Vinorelbine and Anti-CAPRIN-1 Antibody were Administered)

Vinorelbine was intraperitoneally administered to each of 5 tumor-bearing mice at 1 mg/kg/shot on day 0 after the start of the experiment, and at the same time, the anti-CAPRIN-1 monoclonal antibody #2 was intraperitoneally administered to each mouse at 5 mg/kg/shot on days 0, 4, 8, 11, 15, and 17 after the start of the experiment. PBMC separated from Balb/c mouse spleen was intravenously administered to each mouse at $1\times10^7$ cells/0.2 mL (RPMI1640) on days 0, 8, and 15 after the start of the experiment.

<Experimental Section 2>

Experimental conditions similar to those for the experimental section 1 were used for a group to which only an anti-CAPRIN-1 antibody was administered, a group to which cyclophosphamide and the anti-CAPRIN-1 antibody were administered, a group to which paclitaxel and the anti-CAPRIN-1 antibody were administered, a group to which docetaxel and the anti-CAPRIN-1 antibody were administered, and a group to which vinorelbine and the anti-CAPRIN-1 antibody were administered, except that the anti-CAPRIN-1 monoclonal antibody #9 was administered as the anti-CAPRIN-1 antibody.

Experimental conditions similar to those for the experimental section 1 were used for a group to which cyclophosphamide was administered, a group to which paclitaxel was administered, a group to which docetaxel was administered, a group to which vinorelbine was administered, a group to which cyclophosphamide and an anti-Her2 antibody were administered, a group to which paclitaxel and the anti-Her2 antibody were administered, a group to which docetaxel and the anti-Her2 antibody were administered, and a group to which vinorelbine and the anti-Her2 antibody were administered.

Tumor sizes were measured every day and anti-tumor effect was observed for each administration group of each of the above experimental sections. A group of 5 tumor-bearing mice to which PBS(−) was administered instead of an antibody was used as a control group. In addition, the tumor size was determined by calculating the volume using the formula of major axis×minor axis×minor axis×0.5.

As a result of observation of the anti-tumor effect, in the experimental section 1, the tumor was found to have regressed to about 79% in the group to which each antitumor agent had been administered, about 56% in the group to which only the anti-CAPRIN-1 antibody had been administered, and about 74% in the group to which each antitumor agent and the anti-Her2 antibody had been administered, when the tumor volume in the control group, to which PBS(−) had been administered on day 26 after the start of the experiment, was designated at 100%. On the other hand, in the group to which each antitumor agent and the anti-CAPRIN-1 antibody had been administered, the tumor was found to have regressed to about several tens of % on day 14 and found to have almost completely regressed on and after day 22 (see FIG. 3 to FIG. 6).

Also, in the experimental section 2, the tumor was found to have regressed to about 68% in the group to which each antitumor agent had been administered, about 45% in the group to which only the anti-CAPRIN-1 antibody had been administered, and about 55% in the group to which each antitumor agent and the anti-Her2 antibody had been administered, when the tumor volume in the control group, to which PBS(−) had been administered, on day 26 after the start of the experiment was designated at 100%. On the other hand, in the group to which each antitumor agent and the anti-CAPRIN-1 antibody had been administered, tumors were found to have regressed to several tens of % on day 14 and also found to have almost completely regressed on and after day 22 (see FIG. 7 to FIG. 10).

INDUSTRIAL APPLICABILITY

The antibodies of the present invention are useful for treating and/or preventing cancers.

All publications, patents, and patent applications cited herein are incorporated herein by reference in their entirety.

Sequence Listing Free Text

SEQ ID NO: 31: T3 primer
SEQ ID NO: 32: T7 primer
SEQ ID NOS: 33 and 34: primer
SEQ ID NOS: 35 and 36: GAPDH primer
SEQ ID NOS: 38 and 39: primer
SEQ ID NOS: 130 to 135: primer

The invention claimed is:

1. A method for treating and/or preventing recurrence of a CAPRIN-1 expressing cancer, comprising:
   administering a medicament to a subject suspected of having a cancer,
   wherein the medicament comprises a combination of an antibody or a fragment thereof having immunological reactivity with a CAPRIN-1 protein, and one or two or more types of antitumor agents,
   wherein the antibody or fragment and the antitumor agent or antitumor agents are combined together or separately,
   wherein the antibody or fragment and the antitumor agent are not conjugated together,
   wherein the cancer expresses the CAPRIN-1 protein on the cell surface of the cancer and the antibody or fragment binds specifically to the extracellular region of a CAPRIN-1 protein existing on the surface of a cancer cell.

2. The method according to claim 1, wherein the antibody or a fragment thereof having immunological reactivity with a CAPRIN-1 protein is an antibody or a fragment thereof which binds specifically to a polypeptide consisting of the amino acid sequence of SEQ ID NO: 37 in the extracellular region of the CAPRIN-1 protein existing on the surface of a cancer cell.

3. The method according to claim 1, wherein the CAPRIN-1 protein is from a human.

4. The method according to claim 1, wherein the above antitumor agent is selected from one or more of the group consisting of: paclitaxel, doxorubicin, daunorubicin, cyclophosphamide, methotrexate, 5-fluorouracil, thiotepa, busulfan, improsulfan, piposulfan, benzodopa, carboquone, meturedopa, uredopa, altretamine, triethylenemelamine, triethylenephosphoramide, triethilenethiophosphoramide, trimethylolomelamine, bullatacin, bullatacinone, camptothecin, bryostatin, callystatin, cryptophycinl, cryptophycin8, dolastatin, duocarmycin, eleutherobin, pancratistatin, sarcodictyin, spongistatin, chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard, carmustine, chlorozotocin, fotemustine, lomustine, nimustine, ranimustine, calicheamicin, dynemicin, clodronate, esperamicin, aclacinomycin, actinomycin, authramycin, azaserine, bleomycin, cactinomycin, carabicin, carminomycin, carzinophilin, chromomycin, dactinomycin, detorbicin, 6-diazo-5-oxo-L-norleucine, adriamycin, epirubicin, esorubicin, idarubicin, marcellomycin, mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin, denopterin, pteropterin, trimetrexate, fludarabine, 6-mercaptopurine, thiamiprine, thioguanine, ancitabine, azacitidine, 6-azauridine (azauridine), carmofur, cytarabine, dideoxyuridine, doxifluridine, enocitabine, floxuridine, calusterone, dromostanolone propionate, epitiostanol, mepitiostane, testolactone, aminoglutethimide, mitotane, trilostane, frolinic acid, aceglatone, aldophosphamideglycoside, aminolaevulinic acid, eniluracil, amsacrine, bestrabucil, bisantrene, edatraxate, defofamine, demecolcine, diaziquone, elfornithine, elliptinium acetate (elliptinium), epothilone, etoglucid, lenthinan, lonidamine, maytansine, ansamitocine, mitoguazone, mitoxantrone, mopidanmol, nitraerine, pentostatin, phenamet, pirarubicin, losoxantrone, podophyllinic acid, 2-ethyl hydrazide, procarbazine, razoxane, rhizoxin, schizophyllan, spirogermanium, tenuazonic acid, triaziquone, roridine A, anguidine, urethane, vindesine, dacarbazine, mannomustine, mitobronitol, mitolactol, pipobroman, gacytosine, docetaxel, chlorambucil, gemcitabine, 6-thioguanine, mercaptopurine, cisplatin, oxaliplatin, carboplatin, vinblastine, etoposide, ifosfamide, mitoxanthrone, vincristine, vinorelbine, novantrone, teniposide, edatrexate, daunomycin, aminopterin, xeloda, ibandronate, irinotecan, topoisomerase inhibitor, difluoromethylolnitine (DMFO), retinoic acid, capecitabine, and pharmaceutically acceptable salts and derivatives thereof.

5. The method according to claim 1, wherein the antitumor agent is selected from the group consisting of cyclophosphamide, paclitaxel, docetaxel, vinorelbine, and pharmaceutically acceptable salts and derivatives thereof.

6. The method according to claim 1, wherein the antibody is selected from the group consisting of single chain antibodies (scFv), Fab, F(ab')$_2$, and Fv.

7. The method according to claim 1, wherein the antibody is a human antibody, humanized antibody, chimeric antibody, single chain antibody, or bispecific antibody.

8. The method according to claim 1, wherein the above antitumor agent is one or more androgens.

9. A method for treating and/or preventing recurrence of a CAPRIN-1 expressing cancer, comprising
administering a medicament to a subject suspected of having a cancer,
wherein the medicament comprises a combination of an antibody or a fragment thereof having immunological reactivity with a CAPRIN-1 protein, and one or two or more types of antitumor agents,
wherein the antibody or fragment and the antitumor agent or antitumor agents are combined together or separately,
wherein the antibody or fragment and the antitumor agent are not conjugated together,
wherein the cancer expresses the CAPRIN-1 protein on the cell surface of the cancer, and
wherein the antibody or a fragment thereof having immunological reactivity with a CAPRIN-1 protein is an antibody or a fragment thereof which binds specifically to a polypeptide consisting of the amino acid sequence of SEQ ID NO: 37 in the extracellular region of the CAPRIN-1 protein existing on the surface of a cancer cell.

* * * * *

```
                        SEQUENCE LISTING

<160> NUMBER OF SEQ ID NOS: 135

<210> SEQ ID NO 1
<211> LENGTH: 5562
<212> TYPE: DNA
<213> ORGANISM: Homo sapiens
<220> FEATURE:
<221> NAME/KEY: CDS
<222> LOCATION: (190)..(2319)
<223> OTHER INFORMATION:

<400> SEQUENCE: 1
cagagggctg ctggctggct aagtccctcc cgctcccggc tctcgcctca ctaggagcgg      60
ctctcggtgc agcgggacag ggcgaagcgg cctgcgccca cggagcgcgc gacactgccc     120
ggaagggacc gccaccttg cccctcagc tgcccactcg tgatttccag cggcctccgc      180 gcgcgcacg atg ccc tcg gcc acc agc cac agc ggg agc ggc agc aag tcg    231
           Met Pro Ser Ala Thr Ser His Ser Gly Ser Gly Ser Lys Ser
            1               5                  10 tcc gga ccg cca ccg ccg tcg ggt tcc tcc ggg agt gag gcg gcc gcg      279
Ser Gly Pro Pro Pro Pro Ser Gly Ser Ser Gly Ser Glu Ala Ala Ala
 15              20                  25                  30 gga gcc ggg gcc gcc gcg ccg gct tct cag cac ccc gca acc ggc acc      327
Gly Ala Gly Ala Ala Ala Pro Ala Ser Gln His Pro Ala Thr Gly Thr
                 35                  40                  45 ggc gct gtc cag acc gag gcc atg aag cag att ctc ggg gtg atc gac      375
Gly Ala Val Gln Thr Glu Ala Met Lys Gln Ile Leu Gly Val Ile Asp
             50                  55                  60 aag aaa ctt cgg aac ctg gag aag aaa aag ggt aag ctt gat gat tac      423
Lys Lys Leu Arg Asn Leu Glu Lys Lys Lys Gly Lys Leu Asp Asp Tyr
 65                  70                  75 cag gaa cga atg aac aaa ggg gaa agg ctt aat caa gat cag ctg gat      471
Gln Glu Arg Met Asn Lys Gly Glu Arg Leu Asn Gln Asp Gln Leu Asp
 80                  85                  90 gcc gtt tct aag tac cag gaa gtc aca aat aat ttg gag ttt gca aaa      519
Ala Val Ser Lys Tyr Gln Glu Val Thr Asn Asn Leu Glu Phe Ala Lys
 95                 100                 105                 110 gaa tta cag agg agt ttc atg gca cta agt caa gat att cag aaa aca      567
Glu Leu Gln Arg Ser Phe Met Ala Leu Ser Gln Asp Ile Gln Lys Thr
                115                 120                 125 ata aag aag aca gca cgt cgg gag cag ctt atg aga gaa gaa gct gaa      615
Ile Lys Lys Thr Ala Arg Arg Glu Gln Leu Met Arg Glu Glu Ala Glu
                130                 135                 140 cag aaa cgt tta aaa act gta ctt gag cta cag tat gtt ttg gac aaa      663
Gln Lys Arg Leu Lys Thr Val Leu Glu Leu Gln Tyr Val Leu Asp Lys
            145                 150                 155 ttg gga gat gat gaa gtg cgg act gac ctg aaa caa ggt ttg aat gga      711
Leu Gly Asp Asp Glu Val Arg Thr Asp Leu Lys Gln Gly Leu Asn Gly
        160                 165                 170
```

```
gtg cca ata ttg tcc gaa gag gag ttg tca ttg ttg gat gaa ttc tat      759
Val Pro Ile Leu Ser Glu Glu Glu Leu Ser Leu Leu Asp Glu Phe Tyr
175                 180                 185                 190 aag cta gta gac cct gaa cgg gac atg agc ttg agg ttg aat gaa cag      807
Lys Leu Val Asp Pro Glu Arg Asp Met Ser Leu Arg Leu Asn Glu Gln
            195                 200                 205 tat gaa cat gcc tcc att cac ctg tgg gac ctg ctg gaa ggg aag gaa      855
Tyr Glu His Ala Ser Ile His Leu Trp Asp Leu Leu Glu Gly Lys Glu
                210                 215                 220 aaa cct gta tgt gga acc acc tat aaa gtt cta aag gaa att gtt gag      903
Lys Pro Val Cys Gly Thr Thr Tyr Lys Val Leu Lys Glu Ile Val Glu
225                 230                 235 cgt gtt ttt cag tca aac tac ttt gac agc acc cac aac cac cag aat      951
Arg Val Phe Gln Ser Asn Tyr Phe Asp Ser Thr His Asn His Gln Asn
        240                 245                 250 ggg ctg tgt gag gaa gaa gag gca gcc tca gca cct gca gtt gaa gac      999
Gly Leu Cys Glu Glu Glu Glu Ala Ala Ser Ala Pro Ala Val Glu Asp
255                 260                 265                 270 cag gta cct gaa gct gaa cct gag cca gca gaa gag tac act gag caa     1047
Gln Val Pro Glu Ala Glu Pro Glu Pro Ala Glu Glu Tyr Thr Glu Gln
                275                 280                 285 agt gaa gtt gaa tca aca gag tat gta aat aga cag ttc atg gca gaa     1095
Ser Glu Val Glu Ser Thr Glu Tyr Val Asn Arg Gln Phe Met Ala Glu
                290                 295                 300 aca cag ttc acc agt ggt gaa aag gag cag gta gat gag tgg aca gtt     1143
Thr Gln Phe Thr Ser Gly Glu Lys Glu Gln Val Asp Glu Trp Thr Val
305                 310                 315 gaa acg gtt gag gtg gta aat tca ctc cag cag caa cct cag gct gca     1191
Glu Thr Val Glu Val Val Asn Ser Leu Gln Gln Gln Pro Gln Ala Ala
        320                 325                 330 tcc cct tca gta cca gag ccc cac tct ttg act cca gtg gct cag gca     1239
Ser Pro Ser Val Pro Glu Pro His Ser Leu Thr Pro Val Ala Gln Ala
335                 340                 345                 350 gat ccc ctt gtg aga aga cag cga gta caa gac ctt atg gca caa atg     1287
Asp Pro Leu Val Arg Arg Gln Arg Val Gln Asp Leu Met Ala Gln Met
                355                 360                 365 cag ggt ccc tat aat ttc ata cag gat tca atg ctg gat ttt gaa aat     1335
Gln Gly Pro Tyr Asn Phe Ile Gln Asp Ser Met Leu Asp Phe Glu Asn
                370                 375                 380 cag aca ctt gat cct gcc att gta tct gca cag cct atg aat cca aca     1383
Gln Thr Leu Asp Pro Ala Ile Val Ser Ala Gln Pro Met Asn Pro Thr
            385                 390                 395 caa aac atg gac atg ccc cag ctg gtt tgc cct cca gtt cat tct gaa     1431
Gln Asn Met Asp Met Pro Gln Leu Val Cys Pro Pro Val His Ser Glu
400                 405                 410 tct aga ctt gct cag cct aat caa gtt cct gta caa cca gaa gcg aca     1479
Ser Arg Leu Ala Gln Pro Asn Gln Val Pro Val Gln Pro Glu Ala Thr
415                 420                 425                 430 cag gtt cct ttg gta tca tcc aca agt gag ggg tac aca gca tct caa     1527
Gln Val Pro Leu Val Ser Ser Thr Ser Glu Gly Tyr Thr Ala Ser Gln
                435                 440                 445 ccc ttg tac cag cct tct cat gct aca gag caa cga cca cag aag gaa     1575
Pro Leu Tyr Gln Pro Ser His Ala Thr Glu Gln Arg Pro Gln Lys Glu
                450                 455                 460 cca att gat cag att cag gca aca atc tct tta aat aca gac cag act     1623
Pro Ile Asp Gln Ile Gln Ala Thr Ile Ser Leu Asn Thr Asp Gln Thr
            465                 470                 475 aca gca tca tca tcc ctt cct gct gcg tct cag cct caa gta ttt cag     1671
Thr Ala Ser Ser Ser Leu Pro Ala Ala Ser Gln Pro Gln Val Phe Gln
480                 485                 490
```

-continued

| | | |
|---|---|---|
| gct ggg aca agc aaa cct tta cat agc agt gga atc aat gta aat gca<br>Ala Gly Thr Ser Lys Pro Leu His Ser Ser Gly Ile Asn Val Asn Ala<br>495                            500                      505                   510 | | 1719 |
| gct cca ttc caa tcc atg caa acg gtg ttc aat atg aat gcc cca gtt<br>Ala Pro Phe Gln Ser Met Gln Thr Val Phe Asn Met Asn Ala Pro Val<br>                    515                      520                    525 | | 1767 |
| cct cct gtt aat gaa cca gaa act tta aaa cag caa aat cag tac cag<br>Pro Pro Val Asn Glu Pro Glu Thr Leu Lys Gln Gln Asn Gln Tyr Gln<br>                        530                      535                   540 | | 1815 |
| gcc agt tat aac cag agc ttt tct agt cag cct cac caa gta gaa caa<br>Ala Ser Tyr Asn Gln Ser Phe Ser Ser Gln Pro His Gln Val Glu Gln<br>                545                      550                   555 | | 1863 |
| aca gag ctt cag caa gaa cag ctt caa aca gtg gtt ggc act tac cat<br>Thr Glu Leu Gln Gln Glu Gln Leu Gln Thr Val Val Gly Thr Tyr His<br>     560                      565                      570 | | 1911 |
| ggt tcc cca gac cag tcc cat caa gtg act ggt aac cac cag cag cct<br>Gly Ser Pro Asp Gln Ser His Gln Val Thr Gly Asn His Gln Gln Pro<br>575                            580                      585                   590 | | 1959 |
| cct cag cag aac act gga ttt cca cgt agc aat cag ccc tat tac aat<br>Pro Gln Gln Asn Thr Gly Phe Pro Arg Ser Asn Gln Pro Tyr Tyr Asn<br>                    595                      600                    605 | | 2007 |
| agt cgt ggt gtg tct cgt gga ggc tcc cgt ggt gct aga ggc ttg atg<br>Ser Arg Gly Val Ser Arg Gly Gly Ser Arg Gly Ala Arg Gly Leu Met<br>                        610                      615                   620 | | 2055 |
| aat gga tac cgg ggc cct gcc aat gga ttc aga gga gga tat gat ggt<br>Asn Gly Tyr Arg Gly Pro Ala Asn Gly Phe Arg Gly Gly Tyr Asp Gly<br>              625                      630                   635 | | 2103 |
| tac cgc cct tca ttc tct aac act cca aac agt ggt tat aca cag tct<br>Tyr Arg Pro Ser Phe Ser Asn Thr Pro Asn Ser Gly Tyr Thr Gln Ser<br>     640                      645                      650 | | 2151 |
| cag ttc agt gct ccc cgg gat tac tct ggc tat caa cgg gat gga tat<br>Gln Phe Ser Ala Pro Arg Asp Tyr Ser Gly Tyr Gln Arg Asp Gly Tyr<br>655                            660                      665                   670 | | 2199 |
| cag cag aat ttc aag cga ggc tct ggg cag agt gga cca cgg gga gcc<br>Gln Gln Asn Phe Lys Arg Gly Ser Gly Gln Ser Gly Pro Arg Gly Ala<br>                    675                      680                    685 | | 2247 |
| cca cga ggt cgt gga ggg ccc cca aga ccc aac aga ggg atg ccg caa<br>Pro Arg Gly Arg Gly Gly Pro Pro Arg Pro Asn Arg Gly Met Pro Gln<br>              690                      695                   700 | | 2295 |
| atg aac act cag caa gtg aat taa tctgattcac aggattatgt ttaatcgcca<br>Met Asn Thr Gln Gln Val Asn<br>     705 | | 2349 |
| aaaacacact ggccagtgta ccataatatg ttaccagaag agttattatc tatttgttct | | 2409 |
| cccttcagg aaacttattg taaagggact gttttcatcc cataaagaca ggactacaat | | 2469 |
| tgtcagcttt ctattacctg gatatggaag gaaactattt ttactctgca tgttctgtcc | | 2529 |
| taagcgtcat cttgagcctt gcacatgata ctcagattcc tcacccttgc ttaggagtaa | | 2589 |
| aacaatatac tttacagggt gataataatc tccatagtta tttgaagtgg cttgaaaaag | | 2649 |
| gcaagattga cttttatgac attggataaa atctacaaat cagccctcga gttattcaat | | 2709 |
| gataactgac aaactaaatt atttccctag aaaggaagat gaaaggagtg gagtgtggtt | | 2769 |
| tggcagaaca actgcatttc acagcttttc cagttaaatt ggagcactga acgttcgat | | 2829 |
| gcataccaaa ttatgcatgg gtcctaatca cacatataag gctggctacc agctttgaca | | 2889 |
| cagcactgtt catctggcca aacaactgtg ttaaaaaca catgtaaaat gcttttaac | | 2949 |
| agctgatact gtataagaca aagccaagat gcaaaattag gctttgattg gcactttttg | | 3009 |

```
aaaaatatgc aacaaatatg ggatgtaatc cggatggccg cttctgtact taatgtgaaa    3069
tatttagata cctttttgaa cacttaacag tttctttgag acaatgactt ttgtaaggat    3129
tggtactatc tatcattcct tatgacatgt acattgtctg tcactaatcc ttggatttg    3189 ctgtattgtc acctaaattg gtacaggtac tgatgaaaat ctctagtgga taatcataac    3249
actctcggtc acatgttttt ccttcagctt gaaagctttt ttttaaaagg aaaagatacc    3309
aaatgcctgc tgctaccacc ctttcaatt gctatctttt gaaaggcacc agtatgtgtt    3369
ttagattgat ttccctgttt cagggaaatc acggacagta gtttcagttc tgatggtata    3429
agcaaaacaa ataaaacgtt tataaaagtt gtatcttgaa acactggtgt tcaacagcta    3489
gcagcttatg tgattcaccc catgccacgt tagtgtcaca aattttatgg tttatctcca    3549
gcaacatttc tctagtactt gcacttatta tcttttgtct aatttaacct taactgaatt    3609 ctccgttct cctggaggca tttatattca gtgataattc cttcccttag atgcataggg    3669
agagtctcta aatttgatgg aaatggacac ttgagtagtg acttagcctt atgtactctg    3729
ttggaatttg tgctagcagt ttgagcacta gttctgtgtg cctaggaagt taatgctgct    3789
tattgtctca ttctgacttc atggagaatt aatcccacct ttaagcaaag gctactaagt    3849
taatggtatt ttctgtgcag aaattaaatt ttattttcag catttagccc aggaattctt    3909
ccagtaggtg ctcagctatt taaaaacaaa actattctca aacattcatc attagacaac    3969
tggagttttt gctggttttg taacctacca aaatggatag gctgttgaac attccacatt    4029
caaaagtttt gtagggtggt gggaaatggg ggatcttcaa tgtttattt aaaataaaat    4089 aaaataagtt cttgactttt ctcatgtgtg gttgtggtac atcatattgg aagggttaac    4149
ctgttacttt ggcaaatgag tatttttttg ctagcacctc cccttgcgtg ctttaaatga    4209
catctgcctg ggatgtacca caaccatatg ttacctgtat cttaggggaa tggataaaat    4269
atttgtggtt tactgggtaa tccctagatg atgtatgctt gcagtcctat ataaaactaa    4329
atttgctatc tgtgtagaaa ataatttcat gacatttaca atcaggactg aagtaagttc    4389
ttcacacagt gacctctgaa tcagtttcag agaagggatg ggggagaaaa tgccttctag    4449
gttttgaact tctatgcatt agtgcagatg ttgtgaatgt gtaaaggtgt tcatagtttg    4509
actgtttcta tgtatgtttt ttcaaagaat tgttcctttt tttgaactat aattttttctt    4569 tttttggtta tttaccatc acagtttaaa tgtatatctt ttatgtctct actcagacca    4629
tatttttaaa ggggtgcctc attatggggc agagaacttt tcaataagtc tcattaagat    4689
ctgaatcttg gttctaagca ttctgtataa tatgtgattg cttgtcctag ctgcagaagg    4749
ccttttgttt ggtcaaatgc atattttagc agagtttcaa ggaaatgatt gtcacacatg    4809
tcactgtagc ctcttggtgt agcaagctca catacaaaat acttttgtat atgcataata    4869
taaatcatct catgtggata tgaaacttct tttttaaaac ttaaaaaggt agaatgttat    4929
tgattacctt gattagggca gttttatttc cagatcctaa taattcctaa aaaatatgga    4989
aaagtttttt ttcaatcatt gtaccttgat attaaaacaa atatccttta agtatttcta    5049
atcagttagc ttctacagtt cttttgtctc cttttatatg cagctcttac gtgggagact    5109
tttccactta aaggagacat agaatgtgtg cttattctca gaaggttcat taactgaggt    5169
gatgagttaa caactagttg agcagtcagc ttcctaagtg ttttaggaca tttgttcatt    5229
atattttccg tcatataact agaggaagtg gaatgcagat aagtgccgaa ttcaaaccct    5289 tcatttatg tttaagctcc tgaatctgca ttccacttgg gttgttttta agcattctaa    5349
attttagttg attataagtt agatttcaca gaatcagtat tgcccttgat cttgtccttt    5409
```

```
ttatggagtt aacggggagg aagacccctc aggaaaacga agtaaaattg ttaaggctca    5469
tcttcatacc tttttccatt ttgaatccta caaaaatact gcaaaagact agtgaatgtt    5529
taaaattaca ctagattaaa taatatgaaa gtc                                 5562
```

<210> SEQ ID NO 2
<211> LENGTH: 709
<212> TYPE: PRT
<213> ORGANISM: Homo sapiens

<400> SEQUENCE: 2

```
Met Pro Ser Ala Thr Ser His Ser Gly Ser Gly Ser Lys Ser Gly
1               5                   10                  15

Pro Pro Pro Pro Ser Gly Ser Ser Gly Ser Glu Ala Ala Gly Ala
                20                  25                  30

Gly Ala Ala Ala Pro Ala Ser Gln His Pro Ala Thr Gly Thr Gly Ala
                35                  40                  45

Val Gln Thr Glu Ala Met Lys Gln Ile Leu Gly Val Ile Asp Lys Lys
50                  55                  60

Leu Arg Asn Leu Glu Lys Lys Gly Lys Leu Asp Asp Tyr Gln Glu
65                  70                  75                  80

Arg Met Asn Lys Gly Glu Arg Leu Asn Gln Asp Gln Leu Asp Ala Val
                85                  90                  95

Ser Lys Tyr Gln Glu Val Thr Asn Asn Leu Glu Phe Ala Lys Glu Leu
                100                 105                 110

Gln Arg Ser Phe Met Ala Leu Ser Gln Asp Ile Gln Lys Thr Ile Lys
                115                 120                 125

Lys Thr Ala Arg Arg Glu Gln Leu Met Arg Glu Glu Ala Glu Gln Lys
                130                 135                 140

Arg Leu Lys Thr Val Leu Glu Leu Gln Tyr Val Leu Asp Lys Leu Gly
145                 150                 155                 160

Asp Asp Glu Val Arg Thr Asp Leu Lys Gln Gly Leu Asn Gly Val Pro
                165                 170                 175

Ile Leu Ser Glu Glu Glu Leu Ser Leu Leu Asp Glu Phe Tyr Lys Leu
                180                 185                 190

Val Asp Pro Glu Arg Asp Met Ser Leu Arg Leu Asn Glu Gln Tyr Glu
                195                 200                 205

His Ala Ser Ile His Leu Trp Asp Leu Leu Glu Gly Lys Glu Lys Pro
                210                 215                 220

Val Cys Gly Thr Thr Tyr Lys Val Leu Lys Glu Ile Val Glu Arg Val
225                 230                 235                 240

Phe Gln Ser Asn Tyr Phe Asp Ser Thr His Asn His Gln Asn Gly Leu
                245                 250                 255

Cys Glu Glu Glu Glu Ala Ala Ser Ala Pro Ala Val Glu Asp Gln Val
                260                 265                 270

Pro Glu Ala Glu Pro Glu Pro Ala Glu Glu Tyr Thr Glu Gln Ser Glu
                275                 280                 285

Val Glu Ser Thr Glu Tyr Val Asn Arg Gln Phe Met Ala Glu Thr Gln
                290                 295                 300

Phe Thr Ser Gly Glu Lys Glu Gln Val Asp Glu Trp Thr Val Glu Thr
305                 310                 315                 320

Val Glu Val Val Asn Ser Leu Gln Gln Gln Pro Gln Ala Ala Ser Pro
                325                 330                 335

Ser Val Pro Glu Pro His Ser Leu Thr Pro Val Ala Gln Ala Asp Pro
```

340                 345                 350
Leu Val Arg Arg Gln Arg Val Gln Asp Leu Met Ala Gln Met Gln Gly
                355                 360                 365

Pro Tyr Asn Phe Ile Gln Asp Ser Met Leu Asp Phe Glu Asn Gln Thr
            370                 375                 380

Leu Asp Pro Ala Ile Val Ser Ala Gln Pro Met Asn Pro Thr Gln Asn
385                 390                 395                 400

Met Asp Met Pro Gln Leu Val Cys Pro Pro Val His Ser Glu Ser Arg
                405                 410                 415

Leu Ala Gln Pro Asn Gln Val Pro Val Gln Pro Glu Ala Thr Gln Val
            420                 425                 430

Pro Leu Val Ser Ser Thr Ser Glu Gly Tyr Thr Ala Ser Gln Pro Leu
        435                 440                 445

Tyr Gln Pro Ser His Ala Thr Glu Gln Arg Pro Gln Lys Glu Pro Ile
    450                 455                 460

Asp Gln Ile Gln Ala Thr Ile Ser Leu Asn Thr Asp Gln Thr Thr Ala
465                 470                 475                 480

Ser Ser Ser Leu Pro Ala Ala Ser Gln Pro Gln Val Phe Gln Ala Gly
                485                 490                 495

Thr Ser Lys Pro Leu His Ser Ser Gly Ile Asn Val Asn Ala Ala Pro
            500                 505                 510

Phe Gln Ser Met Gln Thr Val Phe Asn Met Asn Ala Pro Val Pro Pro
        515                 520                 525

Val Asn Glu Pro Glu Thr Leu Lys Gln Gln Asn Gln Tyr Gln Ala Ser
    530                 535                 540

Tyr Asn Gln Ser Phe Ser Ser Gln Pro His Gln Val Glu Gln Thr Glu
545                 550                 555                 560

Leu Gln Gln Glu Gln Leu Gln Thr Val Val Gly Thr Tyr His Gly Ser
                565                 570                 575

Pro Asp Gln Ser His Gln Val Thr Gly Asn His Gln Gln Pro Pro Gln
            580                 585                 590

Gln Asn Thr Gly Phe Pro Arg Ser Asn Gln Pro Tyr Tyr Asn Ser Arg
        595                 600                 605

Gly Val Ser Arg Gly Gly Ser Arg Gly Ala Arg Gly Leu Met Asn Gly
    610                 615                 620

Tyr Arg Gly Pro Ala Asn Gly Phe Arg Gly Gly Tyr Asp Gly Tyr Arg
625                 630                 635                 640

Pro Ser Phe Ser Asn Thr Pro Asn Ser Gly Tyr Thr Gln Ser Gln Phe
                645                 650                 655

Ser Ala Pro Arg Asp Tyr Ser Gly Tyr Gln Arg Asp Gly Tyr Gln Gln
            660                 665                 670

Asn Phe Lys Arg Gly Ser Gly Gln Ser Gly Pro Arg Gly Ala Pro Arg
        675                 680                 685

Gly Arg Gly Gly Pro Pro Arg Pro Asn Arg Gly Met Pro Gln Met Asn
    690                 695                 700

Thr Gln Gln Val Asn
705

<210> SEQ ID NO 3
<211> LENGTH: 3553
<212> TYPE: DNA
<213> ORGANISM: Homo sapiens
<220> FEATURE:
<221> NAME/KEY: CDS
<222> LOCATION: (190)..(2274)

<223> OTHER INFORMATION:

<400> SEQUENCE: 3

```
cagagggctg ctggctggct aagtccctcc cgctcccggc tctcgcctca ctaggagcgg      60
ctctcggtgc agcgggacag ggcgaagcgg cctgcgccca cggagcgcgc gacactgccc     120
ggaagggacc gccacccttg cccctcagc tgcccactcg tgatttccag cggcctccgc     180
```

| | | | | | | | | | | | | | | | | |
|---|---|---|---|---|---|---|---|---|---|---|---|---|---|---|---|---|
| gcgcgcacg | atg | ccc | tcg | gcc | acc | agc | cac | agc | ggg | agc | ggc | agc | aag | tcg | | 231 |
| | Met | Pro | Ser | Ala | Thr | Ser | His | Ser | Gly | Ser | Gly | Ser | Lys | Ser | | |
| | 1 | | | | 5 | | | | | 10 | | | | | | |

| tcc | gga | ccg | cca | ccg | ccg | tcg | ggt | tcc | tcc | ggg | agt | gag | gcg | gcc | gcg | 279 |
|---|---|---|---|---|---|---|---|---|---|---|---|---|---|---|---|---|
| Ser | Gly | Pro | Pro | Pro | Pro | Ser | Gly | Ser | Ser | Gly | Ser | Glu | Ala | Ala | Ala | |
| 15 | | | | 20 | | | | | 25 | | | | | 30 | | |

| gga | gcc | ggg | gcc | gcc | gcg | ccg | gct | tct | cag | cac | ccc | gca | acc | ggc | acc | 327 |
|---|---|---|---|---|---|---|---|---|---|---|---|---|---|---|---|---|
| Gly | Ala | Gly | Ala | Ala | Ala | Pro | Ala | Ser | Gln | His | Pro | Ala | Thr | Gly | Thr | |
| | | | | 35 | | | | | 40 | | | | | 45 | | |

| ggc | gct | gtc | cag | acc | gag | gcc | atg | aag | cag | att | ctc | ggg | gtg | atc | gac | 375 |
|---|---|---|---|---|---|---|---|---|---|---|---|---|---|---|---|---|
| Gly | Ala | Val | Gln | Thr | Glu | Ala | Met | Lys | Gln | Ile | Leu | Gly | Val | Ile | Asp | |
| | | | 50 | | | | | 55 | | | | | 60 | | | |

| aag | aaa | ctt | cgg | aac | ctg | gag | aag | aaa | aag | ggt | aag | ctt | gat | gat | tac | 423 |
|---|---|---|---|---|---|---|---|---|---|---|---|---|---|---|---|---|
| Lys | Lys | Leu | Arg | Asn | Leu | Glu | Lys | Lys | Lys | Gly | Lys | Leu | Asp | Asp | Tyr | |
| | | | 65 | | | | | 70 | | | | | 75 | | | |

| cag | gaa | cga | atg | aac | aaa | ggg | gaa | agg | ctt | aat | caa | gat | cag | ctg | gat | 471 |
|---|---|---|---|---|---|---|---|---|---|---|---|---|---|---|---|---|
| Gln | Glu | Arg | Met | Asn | Lys | Gly | Glu | Arg | Leu | Asn | Gln | Asp | Gln | Leu | Asp | |
| 80 | | | | | 85 | | | | | 90 | | | | | | |

| gcc | gtt | tct | aag | tac | cag | gaa | gtc | aca | aat | aat | ttg | gag | ttt | gca | aaa | 519 |
|---|---|---|---|---|---|---|---|---|---|---|---|---|---|---|---|---|
| Ala | Val | Ser | Lys | Tyr | Gln | Glu | Val | Thr | Asn | Asn | Leu | Glu | Phe | Ala | Lys | |
| 95 | | | | | 100 | | | | | 105 | | | | | 110 | |

| gaa | tta | cag | agg | agt | ttc | atg | gca | cta | agt | caa | gat | att | cag | aaa | aca | 567 |
|---|---|---|---|---|---|---|---|---|---|---|---|---|---|---|---|---|
| Glu | Leu | Gln | Arg | Ser | Phe | Met | Ala | Leu | Ser | Gln | Asp | Ile | Gln | Lys | Thr | |
| | | | | 115 | | | | | 120 | | | | | 125 | | |

| ata | aag | aag | aca | gca | cgt | cgg | gag | cag | ctt | atg | aga | gaa | gaa | gct | gaa | 615 |
|---|---|---|---|---|---|---|---|---|---|---|---|---|---|---|---|---|
| Ile | Lys | Lys | Thr | Ala | Arg | Arg | Glu | Gln | Leu | Met | Arg | Glu | Glu | Ala | Glu | |
| | | | 130 | | | | | 135 | | | | | 140 | | | |

| cag | aaa | cgt | tta | aaa | act | gta | ctt | gag | cta | cag | tat | gtt | ttg | gac | aaa | 663 |
|---|---|---|---|---|---|---|---|---|---|---|---|---|---|---|---|---|
| Gln | Lys | Arg | Leu | Lys | Thr | Val | Leu | Glu | Leu | Gln | Tyr | Val | Leu | Asp | Lys | |
| | | 145 | | | | | 150 | | | | | 155 | | | | |

| ttg | gga | gat | gat | gaa | gtg | cgg | act | gac | ctg | aaa | caa | ggt | ttg | aat | gga | 711 |
|---|---|---|---|---|---|---|---|---|---|---|---|---|---|---|---|---|
| Leu | Gly | Asp | Asp | Glu | Val | Arg | Thr | Asp | Leu | Lys | Gln | Gly | Leu | Asn | Gly | |
| | 160 | | | | | 165 | | | | | 170 | | | | | |

| gtg | cca | ata | ttg | tcc | gaa | gag | gag | ttg | tca | ttg | ttg | gat | gaa | ttc | tat | 759 |
|---|---|---|---|---|---|---|---|---|---|---|---|---|---|---|---|---|
| Val | Pro | Ile | Leu | Ser | Glu | Glu | Glu | Leu | Ser | Leu | Leu | Asp | Glu | Phe | Tyr | |
| 175 | | | | | 180 | | | | | 185 | | | | | 190 | |

| aag | cta | gta | gac | cct | gaa | cgg | gac | atg | agc | ttg | agg | ttg | aat | gaa | cag | 807 |
|---|---|---|---|---|---|---|---|---|---|---|---|---|---|---|---|---|
| Lys | Leu | Val | Asp | Pro | Glu | Arg | Asp | Met | Ser | Leu | Arg | Leu | Asn | Glu | Gln | |
| | | | | 195 | | | | | 200 | | | | | 205 | | |

| tat | gaa | cat | gcc | tcc | att | cac | ctg | tgg | gac | ctg | ctg | gaa | ggg | aag | gaa | 855 |
|---|---|---|---|---|---|---|---|---|---|---|---|---|---|---|---|---|
| Tyr | Glu | His | Ala | Ser | Ile | His | Leu | Trp | Asp | Leu | Leu | Glu | Gly | Lys | Glu | |
| | | | 210 | | | | | 215 | | | | | 220 | | | |

| aaa | cct | gta | tgt | gga | acc | acc | tat | aaa | gtt | cta | aag | gaa | att | gtt | gag | 903 |
|---|---|---|---|---|---|---|---|---|---|---|---|---|---|---|---|---|
| Lys | Pro | Val | Cys | Gly | Thr | Thr | Tyr | Lys | Val | Leu | Lys | Glu | Ile | Val | Glu | |
| | | 225 | | | | | 230 | | | | | 235 | | | | |

| cgt | gtt | ttt | cag | tca | aac | tac | ttt | gac | agc | acc | cac | aac | cac | cag | aat | 951 |
|---|---|---|---|---|---|---|---|---|---|---|---|---|---|---|---|---|
| Arg | Val | Phe | Gln | Ser | Asn | Tyr | Phe | Asp | Ser | Thr | His | Asn | His | Gln | Asn | |
| | 240 | | | | | 245 | | | | | 250 | | | | | |

| ggg | ctg | tgt | gag | gaa | gaa | gag | gca | gcc | tca | gca | cct | gca | gtt | gaa | gac | 999 |
|---|---|---|---|---|---|---|---|---|---|---|---|---|---|---|---|---|
| Gly | Leu | Cys | Glu | Glu | Glu | Glu | Ala | Ala | Ser | Ala | Pro | Ala | Val | Glu | Asp | |
| 255 | | | | | 260 | | | | | 265 | | | | | 270 | |

| cag | gta | cct | gaa | gct | gaa | cct | gag | cca | gca | gaa | gag | tac | act | gag | caa | 1047 |

```
                Gln Val Pro Glu Ala Glu Pro Glu Pro Ala Glu Glu Tyr Thr Glu Gln
                            275                 280                 285 agt gaa gtt gaa tca aca gag tat gta aat aga cag ttc atg gca gaa        1095
Ser Glu Val Glu Ser Thr Glu Tyr Val Asn Arg Gln Phe Met Ala Glu
            290                 295                 300 aca cag ttc acc agt ggt gaa aag gag cag gta gat gag tgg aca gtt        1143
Thr Gln Phe Thr Ser Gly Glu Lys Glu Gln Val Asp Glu Trp Thr Val
        305                 310                 315 gaa acg gtt gag gtg gta aat tca ctc cag cag caa cct cag gct gca        1191
Glu Thr Val Glu Val Val Asn Ser Leu Gln Gln Gln Pro Gln Ala Ala
320                 325                 330 tcc cct tca gta cca gag ccc cac tct ttg act cca gtg gct cag gca        1239
Ser Pro Ser Val Pro Glu Pro His Ser Leu Thr Pro Val Ala Gln Ala
335                 340                 345                 350 gat ccc ctt gtg aga aga cag cga gta caa gac ctt atg gca caa atg        1287
Asp Pro Leu Val Arg Arg Gln Arg Val Gln Asp Leu Met Ala Gln Met
                355                 360                 365 cag ggt ccc tat aat ttc ata cag gat tca atg ctg gat ttt gaa aat        1335
Gln Gly Pro Tyr Asn Phe Ile Gln Asp Ser Met Leu Asp Phe Glu Asn
            370                 375                 380 cag aca ctt gat cct gcc att gta tct gca cag cct atg aat cca aca        1383
Gln Thr Leu Asp Pro Ala Ile Val Ser Ala Gln Pro Met Asn Pro Thr
        385                 390                 395 caa aac atg gac atg ccc cag ctg gtt tgc cct cca gtt cat tct gaa        1431
Gln Asn Met Asp Met Pro Gln Leu Val Cys Pro Pro Val His Ser Glu
400                 405                 410 tct aga ctt gct cag cct aat caa gtt cct gta caa cca gaa gcg aca        1479
Ser Arg Leu Ala Gln Pro Asn Gln Val Pro Val Gln Pro Glu Ala Thr
415                 420                 425                 430 cag gtt cct ttg gta tca tcc aca agt gag ggg tac aca gca tct caa        1527
Gln Val Pro Leu Val Ser Ser Thr Ser Glu Gly Tyr Thr Ala Ser Gln
                435                 440                 445 ccc ttg tac cag cct tct cat gct aca gag caa cga cca cag aag gaa        1575
Pro Leu Tyr Gln Pro Ser His Ala Thr Glu Gln Arg Pro Gln Lys Glu
            450                 455                 460 cca att gat cag att cag gca aca atc tct tta aat aca gac cag act        1623
Pro Ile Asp Gln Ile Gln Ala Thr Ile Ser Leu Asn Thr Asp Gln Thr
        465                 470                 475 aca gca tca tca tcc ctt cct gct gcg tct cag cct caa gta ttt cag        1671
Thr Ala Ser Ser Ser Leu Pro Ala Ala Ser Gln Pro Gln Val Phe Gln
480                 485                 490 gct ggg aca agc aaa cct tta cat agc agt gga atc aat gta aat gca        1719
Ala Gly Thr Ser Lys Pro Leu His Ser Ser Gly Ile Asn Val Asn Ala
495                 500                 505                 510 gct cca ttc caa tcc atg caa acg gtg ttc aat atg aat gcc cca gtt        1767
Ala Pro Phe Gln Ser Met Gln Thr Val Phe Asn Met Asn Ala Pro Val
                515                 520                 525 cct cct gtt aat gaa cca gaa act tta aaa cag caa aat cag tac cag        1815
Pro Pro Val Asn Glu Pro Glu Thr Leu Lys Gln Gln Asn Gln Tyr Gln
            530                 535                 540 gcc agt tat aac cag agc ttt tct agt cag cct cac caa gta gaa caa        1863
Ala Ser Tyr Asn Gln Ser Phe Ser Ser Gln Pro His Gln Val Glu Gln
        545                 550                 555 aca gag ctt cag caa gaa cag ctt caa aca gtg gtt ggc act tac cat        1911
Thr Glu Leu Gln Gln Glu Gln Leu Gln Thr Val Val Gly Thr Tyr His
560                 565                 570 ggt tcc cca gac cag tcc cat caa gtg act ggt aac cac cag cag cct        1959
Gly Ser Pro Asp Gln Ser His Gln Val Thr Gly Asn His Gln Gln Pro
575                 580                 585                 590
```

| | | |
|---|---|---|
| cct cag cag aac act gga ttt cca cgt agc aat cag ccc tat tac aat<br>Pro Gln Gln Asn Thr Gly Phe Pro Arg Ser Asn Gln Pro Tyr Tyr Asn<br>595 600 605 | | 2007 |
| agt cgt ggt gtg tct cgt gga ggc tcc cgt ggt gct aga ggc ttg atg<br>Ser Arg Gly Val Ser Arg Gly Gly Ser Arg Gly Ala Arg Gly Leu Met<br>610 615 620 | | 2055 |
| aat gga tac cgg ggc cct gcc aat gga ttc aga gga gga tat gat ggt<br>Asn Gly Tyr Arg Gly Pro Ala Asn Gly Phe Arg Gly Gly Tyr Asp Gly<br>625 630 635 | | 2103 |
| tac cgc cct tca ttc tct aac act cca aac agt ggt tat aca cag tct<br>Tyr Arg Pro Ser Phe Ser Asn Thr Pro Asn Ser Gly Tyr Thr Gln Ser<br>640 645 650 | | 2151 |
| cag ttc agt gct ccc cgg gat tac tct ggc tat caa cgg gat gga tat<br>Gln Phe Ser Ala Pro Arg Asp Tyr Ser Gly Tyr Gln Arg Asp Gly Tyr<br>655 660 665 670 | | 2199 |
| cag cag aat ttc aag cga ggc tct ggg cag agt gga cca cgg gga gcc<br>Gln Gln Asn Phe Lys Arg Gly Ser Gly Gln Ser Gly Pro Arg Gly Ala<br>675 680 685 | | 2247 |
| cca cga ggt aat att ttg tgg tgg tga tcctagctcc taagtggagc<br>Pro Arg Gly Asn Ile Leu Trp Trp<br>690 | | 2294 |
| ttctgttctg gccttggaag agctgttaat agtctgcatg ttaggaatac atttatcctt | | 2354 |
| tccagacttg ttgctaggga ttaaatgaaa tgctctgttt ctaaaactta atcttggacc | | 2414 |
| caaattttaa ttttgaatg atttaatttt ccctgttact atataaactg tcttgaaaac | | 2474 |
| tagaacatat tctcttctca gaaaaagtgt ttttccaact gaaaattatt tttcaggtcc | | 2534 |
| taaaacctgc taaatgtttt taggaagtac ttactgaaac atttttgtaa gacattttg | | 2594 |
| gaatgagatt gaacatttat ataaatttat tattcctctt tcattttttt gaaacatgcc | | 2654 |
| tattatattt tagggccaga cacccttta tggccggata agccatagtt aacatttaga | | 2714 |
| gaaccattta gaagtgatag aactaatgga atttgcaatg ccttttggac tctattagt | | 2774 |
| gatataaata tcaagttatt tctgactttt aaacaaaact cccaaattcc taacttattg | | 2834 |
| agctatactt aaaaaaaatt acaggtttag agagttttt gttttctt tactgttgga | | 2894 |
| aaactacttc ccatttggc aggaagttaa cctatttaac aattagagct agcatttcat | | 2954 |
| gtagtctgaa attctaaatg gttctctgat ttgagggagg ttaaacatca acaggtttc | | 3014 |
| ctctattggc cataacatgt ataaaatgt tgttaaggag gaattacaac gtactttgat | | 3074 |
| ttgaatacta gtagaaactg gccaggaaaa aggtacattt ttctaaaaat taatggatca | | 3134 |
| cttgggaatt actgacttga ctagaagtat caaaggatgt ttgcatgtga atgtgggtta | | 3194 |
| tgttctttcc caccttgtag catattcgat gaaagttgag ttaactgata gctaaaaatc | | 3254 |
| tgttttaaca gcatgtaaaa agttatttta tctgttaaaa gtcattatac agttttgaat | | 3314 |
| gttatgtagt ttcttttaa cagtttaggt aataaggtct gttttcattc tggtgctttt | | 3374 |
| attaattttg atagtatgat gttacttact actgaaatgt aagctagagt gtacactaga | | 3434 |
| atgtaagctc catgagagca ggtaccttgt ctgtcttctc tgctgtatct attcccaacg | | 3494 |
| cttgatgatg gtgcctggca catagtaggc actcaataaa tatttgttga atgaatgaa | | 3553 |

<210> SEQ ID NO 4
<211> LENGTH: 694
<212> TYPE: PRT
<213> ORGANISM: Homo sapiens

<400> SEQUENCE: 4

Met Pro Ser Ala Thr Ser His Ser Gly Ser Gly Ser Lys Ser Ser Gly

-continued

```
1               5                   10                  15
Pro Pro Pro Pro Ser Gly Ser Ser Gly Ser Glu Ala Ala Gly Ala
                20                  25                  30
Gly Ala Ala Ala Pro Ala Ser Gln His Pro Ala Thr Gly Thr Gly Ala
                35                  40                  45
Val Gln Thr Glu Ala Met Lys Gln Ile Leu Gly Val Ile Asp Lys Lys
    50                  55                  60
Leu Arg Asn Leu Glu Lys Lys Gly Lys Leu Asp Asp Tyr Gln Glu
65                  70                  75                  80
Arg Met Asn Lys Gly Glu Arg Leu Asn Gln Asp Gln Leu Asp Ala Val
                85                  90                  95
Ser Lys Tyr Gln Glu Val Thr Asn Asn Leu Glu Phe Ala Lys Glu Leu
                100                 105                 110
Gln Arg Ser Phe Met Ala Leu Ser Gln Asp Ile Gln Lys Thr Ile Lys
                115                 120                 125
Lys Thr Ala Arg Arg Glu Gln Leu Met Arg Glu Glu Ala Gly Gln Lys
                130                 135                 140
Arg Leu Lys Thr Val Leu Glu Leu Gln Tyr Val Leu Asp Lys Leu Gly
145                 150                 155                 160
Asp Asp Glu Val Arg Thr Asp Leu Lys Gln Gly Leu Asn Gly Val Pro
                165                 170                 175
Ile Leu Ser Glu Glu Glu Leu Ser Leu Leu Asp Glu Phe Tyr Lys Leu
                180                 185                 190
Val Asp Pro Glu Arg Asp Met Ser Leu Arg Leu Asn Glu Gln Tyr Glu
                195                 200                 205
His Ala Ser Ile His Leu Trp Asp Leu Leu Glu Gly Lys Glu Lys Pro
                210                 215                 220
Val Cys Gly Thr Thr Tyr Lys Val Leu Lys Glu Ile Val Glu Arg Val
225                 230                 235                 240
Phe Gln Ser Asn Tyr Phe Asp Ser Thr His Asn His Gln Asn Gly Leu
                245                 250                 255
Cys Glu Glu Glu Glu Ala Ala Ser Ala Pro Ala Val Glu Asp Gln Val
                260                 265                 270
Pro Glu Ala Glu Pro Glu Pro Ala Glu Tyr Thr Glu Gln Ser Glu
                275                 280                 285
Val Glu Ser Thr Glu Tyr Val Asn Arg Gln Phe Met Ala Glu Thr Gln
                290                 295                 300
Phe Thr Ser Gly Glu Lys Glu Gln Val Asp Glu Trp Thr Val Glu Thr
305                 310                 315                 320
Val Glu Val Val Asn Ser Leu Gln Gln Gln Pro Gln Ala Ala Ser Pro
                325                 330                 335
Ser Val Pro Glu Pro His Ser Leu Thr Pro Val Ala Gln Ala Asp Pro
                340                 345                 350
Leu Val Arg Arg Gln Arg Val Gln Asp Leu Met Ala Gln Met Gln Gly
                355                 360                 365
Pro Tyr Asn Phe Ile Gln Asp Ser Met Leu Asp Phe Glu Asn Gln Thr
                370                 375                 380
Leu Asp Pro Ala Ile Val Ser Ala Gln Pro Met Asn Pro Thr Gln Asn
385                 390                 395                 400
Met Asp Met Pro Gln Leu Val Cys Pro Pro Val His Ser Glu Ser Arg
                405                 410                 415
Leu Ala Gln Pro Asn Gln Val Pro Val Gln Pro Glu Ala Thr Gln Val
                420                 425                 430
```

```
Pro Leu Val Ser Ser Thr Ser Glu Gly Tyr Thr Ala Ser Gln Pro Leu
            435                 440                 445

Tyr Gln Pro Ser His Ala Thr Glu Gln Arg Pro Gln Lys Glu Pro Ile
    450                 455                 460

Asp Gln Ile Gln Ala Thr Ile Ser Leu Asn Thr Asp Gln Thr Thr Ala
465                 470                 475                 480

Ser Ser Ser Leu Pro Ala Ala Ser Gln Pro Gln Val Phe Gln Ala Gly
                485                 490                 495

Thr Ser Lys Pro Leu His Ser Ser Gly Ile Asn Val Asn Ala Ala Pro
            500                 505                 510

Phe Gln Ser Met Gln Thr Val Phe Asn Met Asn Ala Pro Val Pro Pro
            515                 520                 525

Val Asn Glu Pro Glu Thr Leu Lys Gln Gln Asn Gln Tyr Gln Ala Ser
530                 535                 540

Tyr Asn Gln Ser Phe Ser Ser Gln Pro His Gln Val Glu Gln Thr Glu
545                 550                 555                 560

Leu Gln Gln Glu Gln Leu Gln Thr Val Val Gly Thr Tyr His Gly Ser
                565                 570                 575

Pro Asp Gln Ser His Gln Val Thr Gly Asn His Gln Gln Pro Pro Gln
            580                 585                 590

Gln Asn Thr Gly Phe Pro Arg Ser Asn Gln Pro Tyr Tyr Asn Ser Arg
            595                 600                 605

Gly Val Ser Arg Gly Gly Ser Arg Gly Ala Arg Gly Leu Met Asn Gly
            610                 615                 620

Tyr Arg Gly Pro Ala Asn Gly Phe Arg Gly Tyr Asp Gly Tyr Arg
625                 630                 635                 640

Pro Ser Phe Ser Asn Thr Pro Asn Ser Gly Tyr Thr Gln Ser Gln Phe
                645                 650                 655

Ser Ala Pro Arg Asp Tyr Ser Gly Tyr Gln Arg Asp Gly Tyr Gln Gln
            660                 665                 670

Asn Phe Lys Arg Gly Ser Gly Gln Ser Gly Pro Arg Gly Ala Pro Arg
            675                 680                 685

Gly Asn Ile Leu Trp Trp
            690

<210> SEQ ID NO 5
<211> LENGTH: 1605
<212> TYPE: DNA
<213> ORGANISM: Canis familiaris
<220> FEATURE:
<221> NAME/KEY: CDS
<222> LOCATION: (46)..(1392)
<223> OTHER INFORMATION:

<400> SEQUENCE: 5
gtcacaaata acttggagtt tgcaaaagaa ttacagagga gtttc atg gca tta agt      57
                                                 Met Ala Leu Ser
                                                   1 caa gat att cag aaa aca ata aag aag act gca cgt cgg gag cag ctt     105
Gln Asp Ile Gln Lys Thr Ile Lys Lys Thr Ala Arg Arg Glu Gln Leu
  5                  10                  15                  20 atg aga gag gaa gcg gaa caa aaa cgt tta aaa act gta ctt gag ctc     153
Met Arg Glu Glu Ala Glu Gln Lys Arg Leu Lys Thr Val Leu Glu Leu
                 25                  30                  35 cag tat gtt ttg gac aaa ttg gga gat gat gaa gtg aga act gac ctg     201
Gln Tyr Val Leu Asp Lys Leu Gly Asp Asp Glu Val Arg Thr Asp Leu
             40                  45                  50
```

-continued

| | |
|---|---|
| aag caa ggt ttg aat gga gtg cca ata ttg tct gaa gaa gaa ttg tcg<br>Lys Gln Gly Leu Asn Gly Val Pro Ile Leu Ser Glu Glu Glu Leu Ser<br>        55                  60                  65 | 249 |
| ttg ttg gat gaa ttc tac aaa tta gca gac cct gaa cgg gac atg agc<br>Leu Leu Asp Glu Phe Tyr Lys Leu Ala Asp Pro Glu Arg Asp Met Ser<br>70                   75                     80 | 297 |
| ttg agg ttg aat gag cag tat gaa cat gct tcc att cac ctg tgg gac<br>Leu Arg Leu Asn Glu Gln Tyr Glu His Ala Ser Ile His Leu Trp Asp<br>85                   90                    95                    100 | 345 |
| ttg ctg gaa gga aag gaa aag tct gta tgt gga aca acc tat aaa gca<br>Leu Leu Glu Gly Lys Glu Lys Ser Val Cys Gly Thr Thr Tyr Lys Ala<br>                  105                 110                 115 | 393 |
| cta aag gaa att gtt gag cgt gtt ttc cag tca aat tac ttt gac agc<br>Leu Lys Glu Ile Val Glu Arg Val Phe Gln Ser Asn Tyr Phe Asp Ser<br>120                        125                 130 | 441 |
| act cac aac cac cag aat ggg cta tgt gag gaa gaa gag gca gcc tca<br>Thr His Asn His Gln Asn Gly Leu Cys Glu Glu Glu Glu Ala Ala Ser<br>                  135                 140                 145 | 489 |
| gca cct aca gtt gaa gac cag gta gct gaa gct gag cct gag cca gca<br>Ala Pro Thr Val Glu Asp Gln Val Ala Glu Ala Glu Pro Glu Pro Ala<br>150                        155                 160 | 537 |
| gaa gaa tac act gaa caa agt gaa gtt gaa tca aca gag tat gta aat<br>Glu Glu Tyr Thr Glu Gln Ser Glu Val Glu Ser Thr Glu Tyr Val Asn<br>165                      170                 175               180 | 585 |
| aga caa ttt atg gca gaa aca cag ttc agc agt ggt gaa aag gag cag<br>Arg Gln Phe Met Ala Glu Thr Gln Phe Ser Ser Gly Glu Lys Glu Gln<br>                  185                 190                 195 | 633 |
| gta gat gag tgg acg gtc gaa aca gtg gag gtg gtg aat tca ctc cag<br>Val Asp Glu Trp Thr Val Glu Thr Val Glu Val Val Asn Ser Leu Gln<br>200                        205                 210 | 681 |
| cag caa cct cag gct gcg tct cct tca gta cca gag ccc cac tct ttg<br>Gln Gln Pro Gln Ala Ala Ser Pro Ser Val Pro Glu Pro His Ser Leu<br>215                      220                 225 | 729 |
| act ccg gtg gct cag gca gat ccc ctt gtg aga aga cag cga gtc cag<br>Thr Pro Val Ala Gln Ala Asp Pro Leu Val Arg Arg Gln Arg Val Gln<br>                  230                 235                 240 | 777 |
| gac ctt atg gcg cag atg cag ggg cct tat aat ttc ata cag gat tca<br>Asp Leu Met Ala Gln Met Gln Gly Pro Tyr Asn Phe Ile Gln Asp Ser<br>245                      250                 255               260 | 825 |
| atg ctg gat ttt gaa aac cag aca ctc gat cct gcc att gta tct gca<br>Met Leu Asp Phe Glu Asn Gln Thr Leu Asp Pro Ala Ile Val Ser Ala<br>                  265                 270                 275 | 873 |
| cag cct atg aat ccg aca caa aac atg gac atg ccc cag ctg gtt tgc<br>Gln Pro Met Asn Pro Thr Gln Asn Met Asp Met Pro Gln Leu Val Cys<br>280                      285                 290 | 921 |
| cct cca gtt cat tct gaa tct aga ctt gct caa cct aat caa gtt cct<br>Pro Pro Val His Ser Glu Ser Arg Leu Ala Gln Pro Asn Gln Val Pro<br>295                      300                 305 | 969 |
| gta caa cca gaa gct aca cag gtt cct ttg gtt tca tcc aca agt gag<br>Val Gln Pro Glu Ala Thr Gln Val Pro Leu Val Ser Ser Thr Ser Glu<br>310                      315                 320 | 1017 |
| ggg tat aca gca tct caa ccc ttg tac cag cct tct cat gct aca gag<br>Gly Tyr Thr Ala Ser Gln Pro Leu Tyr Gln Pro Ser His Ala Thr Glu<br>325                      330                 335               340 | 1065 |
| caa cga cca caa aag gaa cca att gac cag att cag gca aca atc tct<br>Gln Arg Pro Gln Lys Glu Pro Ile Asp Gln Ile Gln Ala Thr Ile Ser<br>                  345                 350                 355 | 1113 |
| tta aat aca gac cag act aca gcg tca tca tcc ctt ccg gct gct tct<br>Leu Asn Thr Asp Gln Thr Thr Ala Ser Ser Ser Leu Pro Ala Ala Ser | 1161 |

```
              360                 365                 370
cag cct cag gta ttc cag gct ggg aca agc aaa cca tta cat agc agt      1209
Gln Pro Gln Val Phe Gln Ala Gly Thr Ser Lys Pro Leu His Ser Ser
        375                 380                 385 gga atc aat gta aat gca gct cca ttc caa tcc atg caa acg gtg ttc      1257
Gly Ile Asn Val Asn Ala Ala Pro Phe Gln Ser Met Gln Thr Val Phe
390                 395                 400 aat atg aat gcc cca gtt cct cct gtt aat gaa cca gaa act ttg aaa      1305
Asn Met Asn Ala Pro Val Pro Pro Val Asn Glu Pro Glu Thr Leu Lys
405                 410                 415                 420 caa caa aat cag tac cag gcc agt tat aac cag agc ttt tct agt cag      1353
Gln Gln Asn Gln Tyr Gln Ala Ser Tyr Asn Gln Ser Phe Ser Ser Gln
            425                 430                 435 cct cac caa gta gaa caa aca gag gga tgc cgc aaa tga acactcagca       1402
Pro His Gln Val Glu Gln Thr Glu Gly Cys Arg Lys
                440                 445 agtgaattaa tctgattcac aggattatgt ttaaacgcca aaacacact ggccagtgta     1462 ccataatatg ttaccagaag agttattatc tatttgttct cccttcagg aaacttattg     1522 taaagggact gttttcatcc cataaagaca ggactacaat tgtcagcttt atattacctg    1582 gaaaaaaaa aaaaaaaaa aaa                                              1605

<210> SEQ ID NO 6
<211> LENGTH: 448
<212> TYPE: PRT
<213> ORGANISM: Canis familiaris

<400> SEQUENCE: 6

Met Ala Leu Ser Gln Asp Ile Gln Lys Thr Ile Lys Lys Thr Ala Arg
1               5                   10                  15

Arg Glu Gln Leu Met Arg Glu Glu Ala Glu Gln Lys Arg Leu Lys Thr
            20                  25                  30

Val Leu Glu Leu Gln Tyr Val Leu Asp Lys Leu Gly Asp Asp Glu Val
        35                  40                  45

Arg Thr Asp Leu Lys Gln Gly Leu Asn Gly Val Pro Ile Leu Ser Glu
    50                  55                  60

Glu Glu Leu Ser Leu Leu Asp Glu Phe Tyr Lys Leu Ala Asp Pro Glu
65                  70                  75                  80

Arg Asp Met Ser Leu Arg Leu Asn Glu Gln Tyr Glu His Ala Ser Ile
                85                  90                  95

His Leu Trp Asp Leu Leu Glu Gly Lys Glu Lys Ser Val Cys Gly Thr
            100                 105                 110

Thr Tyr Lys Ala Leu Lys Glu Ile Val Glu Arg Val Phe Gln Ser Asn
        115                 120                 125

Tyr Phe Asp Ser Thr His Asn His Gln Asn Gly Leu Cys Glu Glu Glu
    130                 135                 140

Glu Ala Ala Ser Ala Pro Thr Val Glu Asp Gln Val Ala Glu Ala Glu
145                 150                 155                 160

Pro Glu Pro Ala Glu Glu Tyr Thr Glu Gln Ser Glu Val Glu Ser Thr
                165                 170                 175

Glu Tyr Val Asn Arg Gln Phe Met Ala Glu Thr Gln Phe Ser Ser Gly
            180                 185                 190

Glu Lys Glu Gln Val Asp Glu Trp Thr Val Glu Thr Val Glu Val Val
        195                 200                 205

Asn Ser Leu Gln Gln Gln Pro Gln Ala Ala Ser Pro Ser Val Pro Glu
    210                 215                 220
```

Pro His Ser Leu Thr Pro Val Ala Gln Ala Asp Pro Leu Val Arg Arg
225                 230                 235                 240

Gln Arg Val Gln Asp Leu Met Ala Gln Met Gln Gly Pro Tyr Asn Phe
            245                 250                 255

Ile Gln Asp Ser Met Leu Asp Phe Glu Asn Gln Thr Leu Asp Pro Ala
            260                 265                 270

Ile Val Ser Ala Gln Pro Met Asn Pro Thr Gln Asn Met Asp Met Pro
            275                 280                 285

Gln Leu Val Cys Pro Pro Val His Ser Glu Ser Arg Leu Ala Gln Pro
        290                 295                 300

Asn Gln Val Pro Val Gln Pro Glu Ala Thr Gln Val Pro Leu Val Ser
305                 310                 315                 320

Ser Thr Ser Glu Gly Tyr Thr Ala Ser Gln Pro Leu Tyr Gln Pro Ser
                325                 330                 335

His Ala Thr Glu Gln Arg Pro Gln Lys Glu Pro Ile Asp Gln Ile Gln
            340                 345                 350

Ala Thr Ile Ser Leu Asn Thr Asp Gln Thr Thr Ala Ser Ser Ser Leu
            355                 360                 365

Pro Ala Ala Ser Gln Pro Gln Val Phe Gln Ala Gly Thr Ser Lys Pro
370                 375                 380

Leu His Ser Ser Gly Ile Asn Val Asn Ala Ala Pro Phe Gln Ser Met
385                 390                 395                 400

Gln Thr Val Phe Asn Met Asn Ala Pro Val Pro Pro Val Asn Glu Pro
                405                 410                 415

Glu Thr Leu Lys Gln Gln Asn Gln Tyr Gln Ala Ser Tyr Asn Gln Ser
            420                 425                 430

Phe Ser Ser Gln Pro His Gln Val Glu Gln Thr Glu Gly Cys Arg Lys
            435                 440                 445

<210> SEQ ID NO 7
<211> LENGTH: 4154
<212> TYPE: DNA
<213> ORGANISM: Canis familiaris
<220> FEATURE:
<221> NAME/KEY: CDS
<222> LOCATION: (1)..(2154)
<223> OTHER INFORMATION:

<400> SEQUENCE: 7

```
atg ccg tcg gcc acc agc ctc agc gga agc ggc agc aag tcg tcg ggc      48
Met Pro Ser Ala Thr Ser Leu Ser Gly Ser Gly Ser Lys Ser Ser Gly
1               5                   10                  15 ccg ccg ccc ccg tcg ggt tcc tcc ggg agc gag gcg gcg gcg gcg gcg      96
Pro Pro Pro Pro Ser Gly Ser Ser Gly Ser Glu Ala Ala Ala Ala Ala
                20                  25                  30 ggg gcg gcg ggg gcg gcg ggg gcc ggg gcg gct gcg ccc gcc tcc cag     144
Gly Ala Ala Gly Ala Ala Gly Ala Gly Ala Ala Ala Pro Ala Ser Gln
            35                  40                  45 cac ccc gcg acc ggc acc ggc gct gtc cag acc gag gcc atg aag cag     192
His Pro Ala Thr Gly Thr Gly Ala Val Gln Thr Glu Ala Met Lys Gln
        50                  55                  60 atc ctc ggg gtg atc gac aag aaa ctc cgg aac ctg gag aag aaa aag     240
Ile Leu Gly Val Ile Asp Lys Lys Leu Arg Asn Leu Glu Lys Lys Lys
65                  70                  75                  80 ggc aag ctt gat gat tac cag gaa cga atg aac aaa ggg gaa agg ctt     288
Gly Lys Leu Asp Asp Tyr Gln Glu Arg Met Asn Lys Gly Glu Arg Leu
                85                  90                  95
```

| | | |
|---|---|---|
| aat caa gat cag ctg gat gcc gta tct aag tac cag gaa gtc aca aat<br>Asn Gln Asp Gln Leu Asp Ala Val Ser Lys Tyr Gln Glu Val Thr Asn<br>100 105 110 | 336 | |
| aac ttg gag ttt gca aaa gaa tta cag agg agt ttc atg gca tta agt<br>Asn Leu Glu Phe Ala Lys Glu Leu Gln Arg Ser Phe Met Ala Leu Ser<br>115 120 125 | 384 | |
| caa gat att cag aaa aca ata aag aag act gca cgt cgg gag cag ctt<br>Gln Asp Ile Gln Lys Thr Ile Lys Lys Thr Ala Arg Arg Glu Gln Leu<br>130 135 140 | 432 | |
| atg aga gag gaa gcg gaa caa aaa cgt tta aaa act gta ctt gag ctc<br>Met Arg Glu Glu Ala Glu Gln Lys Arg Leu Lys Thr Val Leu Glu Leu<br>145 150 155 160 | 480 | |
| cag tat gtt ttg gac aaa ttg gga gat gat gaa gtg aga act gac ctg<br>Gln Tyr Val Leu Asp Lys Leu Gly Asp Asp Glu Val Arg Thr Asp Leu<br>165 170 175 | 528 | |
| aag caa ggt ttg aat gga gtg cca ata ttg tct gaa gaa gaa ttg tcg<br>Lys Gln Gly Leu Asn Gly Val Pro Ile Leu Ser Glu Glu Glu Leu Ser<br>180 185 190 | 576 | |
| ttg ttg gat gaa ttc tac aaa tta gca gac cct gaa cgg gac atg agc<br>Leu Leu Asp Glu Phe Tyr Lys Leu Ala Asp Pro Glu Arg Asp Met Ser<br>195 200 205 | 624 | |
| ttg agg ttg aat gag cag tat gaa cat gct tcc att cac ctg tgg gac<br>Leu Arg Leu Asn Glu Gln Tyr Glu His Ala Ser Ile His Leu Trp Asp<br>210 215 220 | 672 | |
| ttg ctg gaa gga aag gaa aag tct gta tgt gga aca acc tat aaa gca<br>Leu Leu Glu Gly Lys Glu Lys Ser Val Cys Gly Thr Thr Tyr Lys Ala<br>225 230 235 240 | 720 | |
| cta aag gaa att gtt gag cgt gtt ttc cag tca aat tac ttt gac agc<br>Leu Lys Glu Ile Val Glu Arg Val Phe Gln Ser Asn Tyr Phe Asp Ser<br>245 250 255 | 768 | |
| act cac aac cac cag aat ggg cta tgt gag gaa gaa gag gca gcc tca<br>Thr His Asn His Gln Asn Gly Leu Cys Glu Glu Glu Glu Ala Ala Ser<br>260 265 270 | 816 | |
| gca cct aca gtt gaa gac cag gta gct gaa gct gag cct gag cca gca<br>Ala Pro Thr Val Glu Asp Gln Val Ala Glu Ala Glu Pro Glu Pro Ala<br>275 280 285 | 864 | |
| gaa gaa tac act gaa caa agt gaa gtt gaa tca aca gag tat gta aat<br>Glu Glu Tyr Thr Glu Gln Ser Glu Val Glu Ser Thr Glu Tyr Val Asn<br>290 295 300 | 912 | |
| aga caa ttt atg gca gaa aca cag ttc agc agt ggt gaa aag gag cag<br>Arg Gln Phe Met Ala Glu Thr Gln Phe Ser Ser Gly Glu Lys Glu Gln<br>305 310 315 320 | 960 | |
| gta gat gag tgg acg gtc gaa aca gtg gag gtg gtg aat tca ctc cag<br>Val Asp Glu Trp Thr Val Glu Thr Val Glu Val Val Asn Ser Leu Gln<br>325 330 335 | 1008 | |
| cag caa cct cag gct gcg tct cct tca gta cca gag ccc cac tct ttg<br>Gln Gln Pro Gln Ala Ala Ser Pro Ser Val Pro Glu Pro His Ser Leu<br>340 345 350 | 1056 | |
| act ccg gtg gct cag gca gat ccc ctt gtg aga aga cag cga gtc cag<br>Thr Pro Val Ala Gln Ala Asp Pro Leu Val Arg Arg Gln Arg Val Gln<br>355 360 365 | 1104 | |
| gac ctt atg gcg cag atg cag ggg ccc tat aat ttc ata cag gat tca<br>Asp Leu Met Ala Gln Met Gln Gly Pro Tyr Asn Phe Ile Gln Asp Ser<br>370 375 380 | 1152 | |
| atg ctg gat ttt gaa aac cag aca ctc gat cct gcc att gta tct gca<br>Met Leu Asp Phe Glu Asn Gln Thr Leu Asp Pro Ala Ile Val Ser Ala<br>385 390 395 400 | 1200 | |
| cag cct atg aat ccg aca caa aac atg gac atg ccc cag ctg gtt tgc<br>Gln Pro Met Asn Pro Thr Gln Asn Met Asp Met Pro Gln Leu Val Cys<br>405 410 415 | 1248 | |

```
cct cca gtt cat tct gaa tct aga ctt gct caa cct aat caa gtt cct    1296
Pro Pro Val His Ser Glu Ser Arg Leu Ala Gln Pro Asn Gln Val Pro
            420                 425                 430 gta caa cca gaa gct aca cag gtt cct ttg gtt tca tcc aca agt gag    1344
Val Gln Pro Glu Ala Thr Gln Val Pro Leu Val Ser Ser Thr Ser Glu
        435                 440                 445 ggg tat aca gca tct caa ccc ttg tac cag cct tct cat gct aca gag    1392
Gly Tyr Thr Ala Ser Gln Pro Leu Tyr Gln Pro Ser His Ala Thr Glu
    450                 455                 460 caa cga cca caa aag gaa cca att gac cag att cag gca aca atc tct    1440
Gln Arg Pro Gln Lys Glu Pro Ile Asp Gln Ile Gln Ala Thr Ile Ser
465                 470                 475                 480 tta aat aca gac cag act aca gcg tca tca tcc ctt ccg gct gct tct    1488
Leu Asn Thr Asp Gln Thr Thr Ala Ser Ser Ser Leu Pro Ala Ala Ser
                485                 490                 495 cag cct cag gta ttc cag gct ggg aca agc aaa cca tta cat agc agt    1536
Gln Pro Gln Val Phe Gln Ala Gly Thr Ser Lys Pro Leu His Ser Ser
            500                 505                 510 gga atc aat gta aat gca gct cca ttc caa tcc atg caa acg gtg ttc    1584
Gly Ile Asn Val Asn Ala Ala Pro Phe Gln Ser Met Gln Thr Val Phe
        515                 520                 525 aat atg aat gcc cca gtt cct cct gtt aat gaa cca gaa act ttg aaa    1632
Asn Met Asn Ala Pro Val Pro Pro Val Asn Glu Pro Glu Thr Leu Lys
    530                 535                 540 caa caa aat cag tac cag gcc agt tat aac cag agc ttt tct agt cag    1680
Gln Gln Asn Gln Tyr Gln Ala Ser Tyr Asn Gln Ser Phe Ser Ser Gln
545                 550                 555                 560 cct cac caa gta gaa caa aca gac ctt cag caa gaa cag ctt caa aca    1728
Pro His Gln Val Glu Gln Thr Asp Leu Gln Gln Glu Gln Leu Gln Thr
                565                 570                 575 gtg gtt ggc act tac cat ggt tcc cag gac cag ccc cac caa gtg act    1776
Val Val Gly Thr Tyr His Gly Ser Gln Asp Gln Pro His Gln Val Thr
            580                 585                 590 ggt aac cat cag cag cct ccc cag cag aac act gga ttt cca cgt agc    1824
Gly Asn His Gln Gln Pro Pro Gln Gln Asn Thr Gly Phe Pro Arg Ser
        595                 600                 605 agt cag ccc tat tac aat agt cgt ggt gtg tct cgt ggt ggt tcc cgt    1872
Ser Gln Pro Tyr Tyr Asn Ser Arg Gly Val Ser Arg Gly Gly Ser Arg
    610                 615                 620 ggt gct aga ggc tta atg aat gga tac agg ggc cct gcc aat gga ttc    1920
Gly Ala Arg Gly Leu Met Asn Gly Tyr Arg Gly Pro Ala Asn Gly Phe
625                 630                 635                 640 aga gga gga tat gat ggt tac cgc cct tca ttc tct aac act cca aac    1968
Arg Gly Gly Tyr Asp Gly Tyr Arg Pro Ser Phe Ser Asn Thr Pro Asn
                645                 650                 655 agt ggt tat aca cag tct cag ttc agt gct ccc cgg gac tac tct ggc    2016
Ser Gly Tyr Thr Gln Ser Gln Phe Ser Ala Pro Arg Asp Tyr Ser Gly
            660                 665                 670 tat cag cgg gat gga tat cag cag aat ttc aag cga ggc tct ggg cag    2064
Tyr Gln Arg Asp Gly Tyr Gln Gln Asn Phe Lys Arg Gly Ser Gly Gln
        675                 680                 685 agt gga cca cgg gga gcc cca cga ggt cgt gga ggg ccc cca aga ccc    2112
Ser Gly Pro Arg Gly Ala Pro Arg Gly Arg Gly Gly Pro Pro Arg Pro
    690                 695                 700 aac aga ggg atg ccg caa atg aac act cag caa gtg aat taa             2154
Asn Arg Gly Met Pro Gln Met Asn Thr Gln Gln Val Asn
705                 710                 715 tctgattcac aggattatgt ttaaacgcca aaaacacact ggccagtgta ccataatatg   2214
```

```
ttaccagaag agttattatc tatttgttct cccttttcagg aaacttattg taaagggact    2274
gttttcatcc cataaagaca ggactacaat tgtcagcttt atattacctg gatatggaag    2334
gaaactattt ttattctgca tgttcttcct aagcgtcatc ttgagccttg cacatgatac    2394
tcagattcct caccccttgct taggagtaaa acataataca ctttacaggg tgatatctcc    2454
atagttattt gaagtggctt ggaaaaagca agattaactt ctgacattgg ataaaaatca    2514
acaaatcagc cctagagtta ttcaaatggt aattgacaaa actaaaata tttcccttcg    2574 agaaggagtg gaatgtggtt tggcagaaca actgcatttc acagcttttc cggttaaatt    2634
ggagcactaa acgtttagat gcataccaaa ttatgcatgg gcccttaata taaaaggctg    2694
gctaccagct ttgacacagc actattcatc ctctggccaa acaactgtgg ttaaacaaca    2754
catgtaaatt gcttttttaac agctgatact ataataagac aaagccaaaa tgcaaaaatt    2814
gggctttgat tggcactttt tgaaaaatat gcaacaaata tgggatgtaa tctggatggc    2874
cgcttctgta cttaatgtga agtatttaga taccttttg aacacttaac agtttcttct    2934
gacaatgact tttgtaagga ttggtactat ctatcattcc ttataatgta cattgtctgt    2994
cactaatcct cagatcttgc tgtattgtca cctaaattgg tacaggtact gatgaaaata    3054
tctaatggat aatcataaca ctcttggtca catgttttc ctgcagcctg aaggttttta    3114
aaagaaaaag atatcaaatg cctgctgcta ccacccttttt aaattgctat cttttgaaaa    3174
gcaccagtat gtgttttaga ttgatttccc tattttaggg aaatgacaga cagtagtttc    3234
agttctgatg gtataagcaa aacaaataaa acatgtttat aaaagttgta tcttgaaaca    3294
ctggtgttca acagctagca gcttatgtgg ttcaccccat gcattgttag tgtttcagat    3354
tttatggtta tctccagcag ctgtttctgt agtacttgca tttatctttt gtctaaccct    3414
aatattctca cggaggcatt tatattcaaa gtggtgatcc cttcacttag acgcataggg    3474
agagtcacaa gtttgatgaa gaggacagtg tagtaattta tatgctgttg gaatttgtgc    3534
tagcagtttg agcactagtt ctgtgtgcct atgaacttaa tgctgcttgt catattccac    3594
tttgacttca tggagaatta atcccatcta ctcagcaaag gctatactaa tactaagtta    3654
atggtatttt ctgtgcagaa attgaatttt gttttattag catttagcta aggaattttt    3714
ccagtaggtg ctcagctact aaagaaaaac aaaaacaaga cacaaaacta ttctcaaaca    3774
ttcattgtta gacaactgga gttttttgctg gttttgtaac ctactaaaat ggataggctg    3834
ttgaacattc cacattcaaa gtttttttgt agggtggtgg ggaaggggg gtgtcttcaa    3894 tgtttatttt aaaataaaat aagttcttga cttttctcat gtgtggttgt ggtacatcat    3954
attggaaggg ttatctgttt acttttgcaa atgagtattt ctcttgctag cacctcccgt    4014
tgtgcgcttt aaatgacatc tgcctgggat gtaccacaac catatgttag ctgtattta    4074 tggggaatag ataaaatatt cgtggtttat tgggtaatcc ctagatgtgt atgcttacaa    4134
tcctatatat aaaactaaat                                                 4154
```

<210> SEQ ID NO 8
<211> LENGTH: 717
<212> TYPE: PRT
<213> ORGANISM: Canis familiaris

<400> SEQUENCE: 8

```
Met Pro Ser Ala Thr Ser Leu Ser Gly Ser Gly Ser Lys Ser Ser Gly
1               5                   10                  15

Pro Pro Pro Pro Ser Gly Ser Ser Gly Ser Glu Ala Ala Ala Ala Ala
            20                  25                  30
```

```
Gly Ala Ala Gly Ala Ala Gly Ala Ala Ala Pro Ala Ser Gln
            35                  40                  45

His Pro Ala Thr Gly Thr Gly Ala Val Gln Thr Glu Ala Met Lys Gln
 50                  55                  60

Ile Leu Gly Val Ile Asp Lys Lys Leu Arg Asn Leu Glu Lys Lys Lys
 65                  70                  75                  80

Gly Lys Leu Asp Asp Tyr Gln Glu Arg Met Asn Lys Gly Glu Arg Leu
                 85                  90                  95

Asn Gln Asp Gln Leu Asp Ala Val Ser Lys Tyr Gln Glu Val Thr Asn
            100                 105                 110

Asn Leu Glu Phe Ala Lys Glu Leu Gln Arg Ser Phe Met Ala Leu Ser
            115                 120                 125

Gln Asp Ile Gln Lys Thr Ile Lys Lys Thr Ala Arg Arg Glu Gln Leu
130                 135                 140

Met Arg Glu Glu Ala Glu Gln Lys Arg Leu Lys Thr Val Leu Glu Leu
145                 150                 155                 160

Gln Tyr Val Leu Asp Lys Leu Gly Asp Glu Val Arg Thr Asp Leu
            165                 170                 175

Lys Gln Gly Leu Asn Gly Val Pro Ile Leu Ser Glu Glu Leu Ser
            180                 185                 190

Leu Leu Asp Glu Phe Tyr Lys Leu Ala Asp Pro Glu Arg Asp Met Ser
            195                 200                 205

Leu Arg Leu Asn Glu Gln Tyr Glu His Ala Ser Ile His Leu Trp Asp
            210                 215                 220

Leu Leu Glu Gly Lys Glu Lys Ser Val Cys Gly Thr Thr Tyr Lys Ala
225                 230                 235                 240

Leu Lys Glu Ile Val Glu Arg Val Phe Gln Ser Asn Tyr Phe Asp Ser
                245                 250                 255

Thr His Asn His Gln Asn Gly Leu Cys Glu Glu Glu Ala Ala Ser
            260                 265                 270

Ala Pro Thr Val Glu Asp Gln Val Ala Glu Ala Glu Pro Glu Pro Ala
            275                 280                 285

Glu Glu Tyr Thr Glu Gln Ser Glu Val Glu Ser Thr Glu Tyr Val Asn
290                 295                 300

Arg Gln Phe Met Ala Glu Thr Gln Phe Ser Ser Gly Glu Lys Glu Gln
305                 310                 315                 320

Val Asp Glu Trp Thr Val Glu Thr Val Glu Val Asn Ser Leu Gln
                325                 330                 335

Gln Gln Pro Gln Ala Ala Ser Pro Ser Val Pro Glu Pro His Ser Leu
            340                 345                 350

Thr Pro Val Ala Gln Ala Asp Pro Leu Val Arg Arg Gln Arg Val Gln
            355                 360                 365

Asp Leu Met Ala Gln Met Gln Gly Pro Tyr Asn Phe Ile Gln Asp Ser
            370                 375                 380

Met Leu Asp Phe Glu Asn Gln Thr Leu Asp Pro Ala Ile Val Ser Ala
385                 390                 395                 400

Gln Pro Met Asn Pro Thr Gln Asn Met Asp Met Pro Gln Leu Val Cys
                405                 410                 415

Pro Pro Val His Ser Glu Ser Arg Leu Ala Gln Pro Asn Gln Val Pro
            420                 425                 430

Val Gln Pro Glu Ala Thr Gln Val Pro Leu Val Ser Ser Thr Ser Glu
            435                 440                 445
```

```
Gly Tyr Thr Ala Ser Gln Pro Leu Tyr Gln Pro Ser His Ala Thr Glu
    450                 455                 460
Gln Arg Pro Gln Lys Glu Pro Ile Asp Gln Ile Gln Ala Thr Ile Ser
465                 470                 475                 480
Leu Asn Thr Asp Gln Thr Thr Ala Ser Ser Leu Pro Ala Ala Ser
                485                 490                 495
Gln Pro Gln Val Phe Gln Ala Gly Thr Ser Lys Pro Leu His Ser Ser
                500                 505                 510
Gly Ile Asn Val Asn Ala Ala Pro Phe Gln Ser Met Gln Thr Val Phe
                515                 520                 525
Asn Met Asn Ala Pro Val Pro Pro Val Asn Glu Pro Glu Thr Leu Lys
530                 535                 540
Gln Gln Asn Gln Tyr Gln Ala Ser Tyr Asn Gln Ser Phe Ser Ser Gln
545                 550                 555                 560
Pro His Gln Val Glu Gln Thr Asp Leu Gln Gln Glu Gln Leu Gln Thr
                565                 570                 575
Val Val Gly Thr Tyr His Gly Ser Gln Asp Gln Pro Gln Val Thr
                580                 585                 590
Gly Asn His Gln Gln Pro Pro Gln Gln Asn Thr Gly Phe Pro Arg Ser
            595                 600                 605
Ser Gln Pro Tyr Tyr Asn Ser Arg Gly Val Ser Arg Gly Gly Ser Arg
        610                 615                 620
Gly Ala Arg Gly Leu Met Asn Gly Tyr Arg Gly Pro Ala Asn Gly Phe
625                 630                 635                 640
Arg Gly Gly Tyr Asp Gly Tyr Arg Pro Ser Phe Ser Asn Thr Pro Asn
                645                 650                 655
Ser Gly Tyr Thr Gln Ser Gln Phe Ser Ala Pro Arg Asp Tyr Ser Gly
                660                 665                 670
Tyr Gln Arg Asp Gly Tyr Gln Gln Asn Phe Lys Arg Gly Ser Gly Gln
                675                 680                 685
Ser Gly Pro Arg Gly Ala Pro Arg Gly Arg Gly Pro Pro Arg Pro
            690                 695                 700
Asn Arg Gly Met Pro Gln Met Asn Thr Gln Gln Val Asn
705                 710                 715

<210> SEQ ID NO 9
<211> LENGTH: 4939
<212> TYPE: DNA
<213> ORGANISM: Canis familiaris
<220> FEATURE:
<221> NAME/KEY: CDS
<222> LOCATION: (1)..(2109)
<223> OTHER INFORMATION:

<400> SEQUENCE: 9 atg ccg tcg gcc acc agc ctc agc gga agc ggc agc aag tcg tcg ggc      48
Met Pro Ser Ala Thr Ser Leu Ser Gly Ser Gly Ser Lys Ser Ser Gly
1               5                   10                  15 ccg ccg ccc ccg tcg ggt tcc tcc ggg agc gag gcg gcg gcg gcg gcg      96
Pro Pro Pro Pro Ser Gly Ser Ser Gly Ser Glu Ala Ala Ala Ala Ala
            20                  25                  30 ggg gcg gcg ggg gcg gcg ggg gcc ggg gcg gct gcg ccc gcc tcc cag     144
Gly Ala Ala Gly Ala Ala Gly Ala Gly Ala Ala Pro Ala Ser Gln
        35                  40                  45 cac ccg gcg acc ggc acc ggc gct gtc cag acc gag gcc atg aag cag     192
His Pro Ala Thr Gly Thr Gly Ala Val Gln Thr Glu Ala Met Lys Gln
50                  55                  60
```

-continued

| | | |
|---|---|---|
| atc ctc ggg gtg atc gac aag aaa ctc cgg aac ctg gag aag aaa aag<br>Ile Leu Gly Val Ile Asp Lys Lys Leu Arg Asn Leu Glu Lys Lys Lys<br>65                      70                      75                      80 | 240 |
| ggc aag ctt gat gat tac cag gaa cga atg aac aaa ggg gaa agg ctt<br>Gly Lys Leu Asp Asp Tyr Gln Glu Arg Met Asn Lys Gly Glu Arg Leu<br>                    85                      90                      95 | 288 |
| aat caa gat cag ctg gat gcc gta tct aag tac cag gaa gtc aca aat<br>Asn Gln Asp Gln Leu Asp Ala Val Ser Lys Tyr Gln Glu Val Thr Asn<br>                          100                    105                    110 | 336 |
| aac ttg gag ttt gca aaa gaa tta cag agg agt ttc atg gca tta agt<br>Asn Leu Glu Phe Ala Lys Glu Leu Gln Arg Ser Phe Met Ala Leu Ser<br>            115                    120                    125 | 384 |
| caa gat att cag aaa aca ata aag aag act gca cgt cgg gag cag ctt<br>Gln Asp Ile Gln Lys Thr Ile Lys Lys Thr Ala Arg Arg Glu Gln Leu<br>130                      135                    140 | 432 |
| atg aga gag gaa gcg gaa caa aaa cgt tta aaa act gta ctt gag ctc<br>Met Arg Glu Glu Ala Glu Gln Lys Arg Leu Lys Thr Val Leu Glu Leu<br>145                      150                    155                    160 | 480 |
| cag tat gtt ttg gac aaa ttg gga gat gat gaa gtg aga act gac ctg<br>Gln Tyr Val Leu Asp Lys Leu Gly Asp Asp Glu Val Arg Thr Asp Leu<br>                    165                    170                    175 | 528 |
| aag caa ggt ttg aat gga gtg cca ata ttg tct gaa gaa gaa ttg tcg<br>Lys Gln Gly Leu Asn Gly Val Pro Ile Leu Ser Glu Glu Glu Leu Ser<br>            180                    185                    190 | 576 |
| ttg ttg gat gaa ttc tac aaa tta gca gac cct gaa cgg gac atg agc<br>Leu Leu Asp Glu Phe Tyr Lys Leu Ala Asp Pro Glu Arg Asp Met Ser<br>            195                    200                    205 | 624 |
| ttg agg ttg aat gag cag tat gaa cat gct tcc att cac ctg tgg gac<br>Leu Arg Leu Asn Glu Gln Tyr Glu His Ala Ser Ile His Leu Trp Asp<br>210                      215                    220 | 672 |
| ttg ctg gaa gga aag gaa aag tct gta tgt gga aca acc tat aaa gca<br>Leu Leu Glu Gly Lys Glu Lys Ser Val Cys Gly Thr Thr Tyr Lys Ala<br>225                      230                    235                    240 | 720 |
| cta aag gaa att gtt gag cgt gtt ttc cag tca aat tac ttt gac agc<br>Leu Lys Glu Ile Val Glu Arg Val Phe Gln Ser Asn Tyr Phe Asp Ser<br>                    245                    250                    255 | 768 |
| act cac aac cac cag aat ggg cta tgt gag gaa gaa gag gca gcc tca<br>Thr His Asn His Gln Asn Gly Leu Cys Glu Glu Glu Glu Ala Ala Ser<br>            260                    265                    270 | 816 |
| gca cct aca gtt gaa gac cag gta gct gaa gct gag cct gag cca gca<br>Ala Pro Thr Val Glu Asp Gln Val Ala Glu Ala Glu Pro Glu Pro Ala<br>            275                    280                    285 | 864 |
| gaa gaa tac act gaa caa agt gaa gtt gaa tca aca gag tat gta aat<br>Glu Glu Tyr Thr Glu Gln Ser Glu Val Glu Ser Thr Glu Tyr Val Asn<br>290                      295                    300 | 912 |
| aga caa ttt atg gca gaa aca cag ttc agc agt ggt gaa aag gag cag<br>Arg Gln Phe Met Ala Glu Thr Gln Phe Ser Ser Gly Glu Lys Glu Gln<br>305                      310                    315                    320 | 960 |
| gta gat gag tgg acg gtc gaa aca gtg gag gtg gtg aat tca ctc cag<br>Val Asp Glu Trp Thr Val Glu Thr Val Glu Val Val Asn Ser Leu Gln<br>                    325                    330                    335 | 1008 |
| cag caa cct cag gct gcg tct cct tca gta cca gag ccc cac tct ttg<br>Gln Gln Pro Gln Ala Ala Ser Pro Ser Val Pro Glu Pro His Ser Leu<br>            340                    345                    350 | 1056 |
| act ccg gtg gct cag gca gat ccc ctt gtg aga aga cag cga gtc cag<br>Thr Pro Val Ala Gln Ala Asp Pro Leu Val Arg Arg Gln Arg Val Gln<br>            355                    360                    365 | 1104 |
| gac ctt atg gcg cag atg cag ggg ccc tat aat ttc ata cag gat tca<br>Asp Leu Met Ala Gln Met Gln Gly Pro Tyr Asn Phe Ile Gln Asp Ser<br>            370                    375                    380 | 1152 |

```
atg ctg gat ttt gaa aac cag aca ctc gat cct gcc att gta tct gca   1200
Met Leu Asp Phe Glu Asn Gln Thr Leu Asp Pro Ala Ile Val Ser Ala
385                 390                 395                 400 cag cct atg aat ccg aca caa aac atg gac atg ccc cag ctg gtt tgc   1248
Gln Pro Met Asn Pro Thr Gln Asn Met Asp Met Pro Gln Leu Val Cys
                405                 410                 415 cct cca gtt cat tct gaa tct aga ctt gct caa cct aat caa gtt cct   1296
Pro Pro Val His Ser Glu Ser Arg Leu Ala Gln Pro Asn Gln Val Pro
            420                 425                 430 gta caa cca gaa gct aca cag gtt cct ttg gtt tca tcc aca agt gag   1344
Val Gln Pro Glu Ala Thr Gln Val Pro Leu Val Ser Ser Thr Ser Glu
        435                 440                 445 ggg tat aca gca tct caa ccc ttg tac cag cct tct cat gct aca gag   1392
Gly Tyr Thr Ala Ser Gln Pro Leu Tyr Gln Pro Ser His Ala Thr Glu
    450                 455                 460 caa cga cca caa aag gaa cca att gac cag att cag gca aca atc tct   1440
Gln Arg Pro Gln Lys Glu Pro Ile Asp Gln Ile Gln Ala Thr Ile Ser
465                 470                 475                 480 tta aat aca gac cag act aca gcg tca tca tcc ctt ccg gct gct tct   1488
Leu Asn Thr Asp Gln Thr Thr Ala Ser Ser Ser Leu Pro Ala Ala Ser
                485                 490                 495 cag cct cag gta ttc cag gct ggg aca agc aaa cca tta cat agc agt   1536
Gln Pro Gln Val Phe Gln Ala Gly Thr Ser Lys Pro Leu His Ser Ser
            500                 505                 510 gga atc aat gta aat gca gct cca ttc caa tcc atg caa acg gtg ttc   1584
Gly Ile Asn Val Asn Ala Ala Pro Phe Gln Ser Met Gln Thr Val Phe
        515                 520                 525 aat atg aat gcc cca gtt cct cct gtt aat gaa cca gaa act ttg aaa   1632
Asn Met Asn Ala Pro Val Pro Pro Val Asn Glu Pro Glu Thr Leu Lys
    530                 535                 540 caa caa aat cag tac cag gcc agt tat aac cag agc ttt tct agt cag   1680
Gln Gln Asn Gln Tyr Gln Ala Ser Tyr Asn Gln Ser Phe Ser Ser Gln
545                 550                 555                 560 cct cac caa gta gaa caa aca gac ctt cag caa gaa cag ctt caa aca   1728
Pro His Gln Val Glu Gln Thr Asp Leu Gln Gln Glu Gln Leu Gln Thr
                565                 570                 575 gtg gtt ggc act tac cat ggt tcc cag gac cag ccc cac caa gtg act   1776
Val Val Gly Thr Tyr His Gly Ser Gln Asp Gln Pro His Gln Val Thr
            580                 585                 590 ggt aac cat cag cag cct ccc cag cag aac act gga ttt cca cgt agc   1824
Gly Asn His Gln Gln Pro Pro Gln Gln Asn Thr Gly Phe Pro Arg Ser
        595                 600                 605 agt cag ccc tat tac aat agt cgt ggt gtg tct cgt ggt ggt tcc cgt   1872
Ser Gln Pro Tyr Tyr Asn Ser Arg Gly Val Ser Arg Gly Gly Ser Arg
    610                 615                 620 ggt gct aga ggc tta atg aat gga tac agg ggc cct gcc aat gga ttc   1920
Gly Ala Arg Gly Leu Met Asn Gly Tyr Arg Gly Pro Ala Asn Gly Phe
625                 630                 635                 640 aga gga gga tat gat ggt tac cgc cct tca ttc tct aac act cca aac   1968
Arg Gly Gly Tyr Asp Gly Tyr Arg Pro Ser Phe Ser Asn Thr Pro Asn
                645                 650                 655 agt ggt tat aca cag tct cag ttc agt gct ccc cgg gac tac tct ggc   2016
Ser Gly Tyr Thr Gln Ser Gln Phe Ser Ala Pro Arg Asp Tyr Ser Gly
            660                 665                 670 tat cag cgg gat gga tat cag cag aat ttc aag cga ggc tct ggg cag   2064
Tyr Gln Arg Asp Gly Tyr Gln Gln Asn Phe Lys Arg Gly Ser Gly Gln
        675                 680                 685 agt gga cca cgg gga gcc cca cga ggt aat att ttg tgg tgg tga        2109
Ser Gly Pro Arg Gly Ala Pro Arg Gly Asn Ile Leu Trp Trp
```

```
                                                    -continued
        690           695           700
tcctagctcc taagtggagc ttctgttctg gccttggaag agctgttcca tagtctgcat   2169
gtaggttaca tgttaggaat acatttatca ttaccagact tgttgctagg gattaaatga   2229
aatgctctgt ttctaaaact tctcttgaac ccaaatttaa ttttttgaat gactttccct   2289
gttactatat aaattgtctt gaaaactaga acatttctcc tcctcagaaa aagtgttttt   2349
ccaactgcaa attattttc aggtcctaaa acctgctaaa tgttttagg aagtacttac    2409 tgaaacattt ttgtaagaca ttttggaat gagattgaac atttatataa atttattatt    2469
attcctcttt cattttgaa catgcatatt atattagg gtcagaaatc ctttaatggc     2529
caaataagcc atagttacat ttagagaacc atttagaagt gatagaacta actgaaattt   2589
caatgccttt ggatcattaa tagcgatata aatttcaaat tgtttctgac ttttaaataa   2649
aacatccaaa atcctaacta acttcctgaa ctatatttaa aaattacagg tttaaggagt   2709
ttctggtttt ttttctctta ccataggaaa actgttccct gtttggccag gaagtcaacc   2769
tgtgtaataa ttagaagtag catttcatat gatctgaagt tctaaatggt tctctgattt   2829
aagggaagtt aaattgaata ggtttcctct agttattggc cataacatgt ataaaatgta   2889
tattaaggag gaatacaaag tactttgatt tcaatgctag tagaaactgg ccagcaaaaa   2949
ggtgcatttt attttaaat taatggatca cttgggaatt actgacttga agtatcaaag    3009
gatatttgca tgtgaatgtg ggttatgttc tttctcacct tgtagcatat tctatgaaag   3069
ttgagttgac tggtagctaa aaatctgttt taacagcatg taaaaagtta tttatctgt    3129 tacaagtcat tatacaattt tgaatgttat gtagtttctt tttaacagtt taggtaacaa   3189
ggtctgtttt tcattctggt gcttttatta attttgatag tatgatgtta cttactactg   3249
aaatgtaagc tagagtgtac actagaatgt aagctccatg agagcaggta ccttgtctgt   3309
cttcactgct gtatctattt ccaacgcctg atgacagtgc ctgacacata gtaggcactc   3369
aataaatact tgttgaatga atgaatgaat gagtactggt ggaatactcc attagctcta   3429
ctcttctttt agctagagaa catgagcaaa tttgcgcatg acaacttcca ggacaggtga   3489
acactgaaga attgacctct taaacctaat aatgtggtga caagctgccc acatgcttct   3549
tgacttcaga tgaaaatctg cttgaaggca aagcaaataa tatttgaaag aaaaaccaaa   3609
tgccattttt gtcttctagg tcgtggaggg cccccaagac ccaacagagg gatgccgcaa   3669
atgaacactc agcaagtgaa ttaatctgat tcacaggatt atgtttaaac gccaaaaaca   3729
cactggccag tgtaccataa tatgttacca gaagagttat tatctatttg ttctcccttt   3789
caggaaactt attgtaaagg gactgttttc atcccataaa gacaggacta caattgtcag   3849
ctttatatta cctggatatg gaaggaaact atttttattc tgcatgttct tcctaagcgt   3909
catcttgagc cttgcacatg atactcagat tcctcaccct tgcttaggag taaaacataa   3969
tacactttac agggtgatat ctccatagtt atttgaagtg gcttgaaaa agcaagatta    4029 acttctgaca ttggataaaa atcaacaaat cagccctaga gttattcaaa tggtaattga   4089
caaaaactaa atatttccc ttcgagaagg agtggaatgt ggtttggcag aacaactgca    4149
tttcacagct tttccggtta aattggagca ctaaacgttt agatgcatac caaattatgc   4209
atgggccctt aatataaaag gctggctacc agctttgaca cagcactatt catcctctgg   4269
ccaaacaact gtggttaaac aacacatgta aattgctttt taacagctga tactataata   4329
agacaaagcc aaaatgcaaa aattgggctt tgattggcac tttttgaaaa atatgcaaca   4389
aatatgggat gtaatctgga tggccgcttc tgtacttaat gtgaagtatt tagataccct   4449
```

```
tttgaacact taacagtttc ttctgacaat gacttttgta aggattggta ctatctatca    4509
ttccttataa tgtacattgt ctgtcactaa tcctcagatc ttgctgtatt gtcacctaaa    4569
ttggtacagg tactgatgaa aatatctaat ggataatcat aacactcttg gtcacatgtt    4629
tttcctgcag cctgaaggtt tttaaaagaa aaagatatca aatgcctgct gctaccaccc    4689
ttttaaattg ctatcttttg aaaagcacca gtatgtgttt tagattgatt tccctatttt    4749
agggaaatga cagacagtag tttcagttct gatggtataa gcaaaacaaa taaaacatgt    4809
ttataaaagt tgtatcttga aacactggtg ttcaacagct agcagcttat gtggttcacc    4869
ccatgcattg ttagtgtttc agattttatg gttatctcca gcagctgttt ctgtagtact    4929
tgcatttatc                                                          4939
```

<210> SEQ ID NO 10
<211> LENGTH: 702
<212> TYPE: PRT
<213> ORGANISM: Canis familiaris

<400> SEQUENCE: 10

Met Pro Ser Ala Thr Ser Leu Ser Gly Ser Gly Ser Lys Ser Ser Gly
1               5                   10                  15

Pro Pro Pro Pro Ser Gly Ser Ser Gly Ser Glu Ala Ala Ala Ala Ala
                20                  25                  30

Gly Ala Ala Gly Ala Ala Gly Ala Ala Gly Ala Ala Ala Pro Ala Ser Gln
            35                  40                  45

His Pro Ala Thr Gly Thr Gly Ala Val Gln Thr Glu Ala Met Lys Gln
        50                  55                  60

Ile Leu Gly Val Ile Asp Lys Lys Leu Arg Asn Leu Glu Lys Lys Lys
65                  70                  75                  80

Gly Lys Leu Asp Asp Tyr Gln Glu Arg Met Asn Lys Gly Glu Arg Leu
                85                  90                  95

Asn Gln Asp Gln Leu Asp Ala Val Ser Lys Tyr Gln Glu Val Thr Asn
            100                 105                 110

Asn Leu Glu Phe Ala Lys Glu Leu Gln Arg Ser Phe Met Ala Leu Ser
        115                 120                 125

Gln Asp Ile Gln Lys Thr Ile Lys Lys Thr Ala Arg Arg Glu Gln Leu
    130                 135                 140

Met Arg Glu Glu Ala Glu Gln Lys Arg Leu Lys Thr Val Leu Glu Leu
145                 150                 155                 160

Gln Tyr Val Leu Asp Lys Leu Gly Asp Asp Glu Val Arg Thr Asp Leu
                165                 170                 175

Lys Gln Gly Leu Asn Gly Val Pro Ile Leu Ser Glu Glu Leu Ser
            180                 185                 190

Leu Leu Asp Glu Phe Tyr Lys Leu Ala Asp Pro Glu Arg Asp Met Ser
        195                 200                 205

Leu Arg Leu Asn Glu Gln Tyr Glu His Ala Ser Ile His Leu Trp Asp
    210                 215                 220

Leu Leu Glu Gly Lys Glu Lys Ser Val Cys Gly Thr Thr Tyr Lys Ala
225                 230                 235                 240

Leu Lys Glu Ile Val Glu Arg Val Phe Gln Ser Asn Tyr Phe Asp Ser
                245                 250                 255

Thr His Asn His Gln Asn Gly Leu Cys Glu Glu Glu Ala Ala Ser
            260                 265                 270

Ala Pro Thr Val Glu Asp Gln Val Ala Glu Ala Glu Pro Glu Pro Ala

```
            275                 280                 285
Glu Glu Tyr Thr Glu Gln Ser Glu Val Glu Ser Thr Glu Tyr Val Asn
            290                 295                 300
Arg Gln Phe Met Ala Glu Thr Gln Phe Ser Ser Gly Glu Lys Glu Gln
305                 310                 315                 320
Val Asp Glu Trp Thr Val Thr Val Glu Val Asn Ser Leu Gln
                    325                 330                 335
Gln Gln Pro Gln Ala Ala Ser Pro Ser Val Pro Glu Pro His Ser Leu
            340                 345                 350
Thr Pro Val Ala Gln Ala Asp Pro Leu Val Arg Arg Gln Arg Val Gln
            355                 360                 365
Asp Leu Met Ala Gln Met Gln Gly Pro Tyr Asn Phe Ile Gln Asp Ser
            370                 375                 380
Met Leu Asp Phe Glu Asn Gln Thr Leu Asp Pro Ala Ile Val Ser Ala
385                 390                 395                 400
Gln Pro Met Asn Pro Thr Gln Asn Met Asp Met Pro Gln Leu Val Cys
                    405                 410                 415
Pro Pro Val His Ser Glu Ser Arg Leu Ala Gln Pro Asn Gln Val Pro
                    420                 425                 430
Val Gln Pro Glu Ala Thr Gln Val Pro Leu Val Ser Ser Thr Ser Glu
            435                 440                 445
Gly Tyr Thr Ala Ser Gln Pro Leu Tyr Gln Pro Ser His Ala Thr Glu
            450                 455                 460
Gln Arg Pro Gln Lys Glu Pro Ile Asp Gln Ile Gln Ala Thr Ile Ser
465                 470                 475                 480
Leu Asn Thr Asp Gln Thr Thr Ala Ser Ser Ser Leu Pro Ala Ala Ser
                    485                 490                 495
Gln Pro Gln Val Phe Gln Ala Gly Thr Ser Lys Pro Leu His Ser Ser
            500                 505                 510
Gly Ile Asn Val Asn Ala Ala Pro Phe Gln Ser Met Gln Thr Val Phe
            515                 520                 525
Asn Met Asn Ala Pro Val Pro Pro Val Asn Glu Pro Glu Thr Leu Lys
            530                 535                 540
Gln Gln Asn Gln Tyr Gln Ala Ser Tyr Asn Gln Ser Phe Ser Ser Gln
545                 550                 555                 560
Pro His Gln Val Glu Gln Thr Asp Leu Gln Gln Glu Gln Leu Gln Thr
                    565                 570                 575
Val Val Gly Thr Tyr His Gly Ser Gln Asp Gln Pro His Gln Val Thr
            580                 585                 590
Gly Asn His Gln Gln Pro Pro Gln Gln Asn Thr Gly Phe Pro Arg Ser
            595                 600                 605
Ser Gln Pro Tyr Tyr Asn Ser Arg Gly Val Ser Arg Gly Gly Ser Arg
            610                 615                 620
Gly Ala Arg Gly Leu Met Asn Gly Tyr Arg Gly Pro Ala Asn Gly Phe
625                 630                 635                 640
Arg Gly Gly Tyr Asp Gly Tyr Arg Pro Ser Phe Ser Asn Thr Pro Asn
                    645                 650                 655
Ser Gly Tyr Thr Gln Ser Gln Phe Ser Ala Pro Arg Asp Tyr Ser Gly
                    660                 665                 670
Tyr Gln Arg Asp Gly Tyr Gln Gln Asn Phe Lys Arg Gly Ser Gly Gln
            675                 680                 685
Ser Gly Pro Arg Gly Ala Pro Arg Gly Asn Ile Leu Trp Trp
            690                 695                 700
```

-continued

<210> SEQ ID NO 11
<211> LENGTH: 3306
<212> TYPE: DNA
<213> ORGANISM: Canis familiaris
<220> FEATURE:
<221> NAME/KEY: CDS
<222> LOCATION: (1)..(2040)
<223> OTHER INFORMATION:

<400> SEQUENCE: 11

| atg | ccg | tcg | gcc | acc | agc | ctc | agc | gga | agc | ggc | agc | aag | tcg | tcg | ggc | 48 |
| Met | Pro | Ser | Ala | Thr | Ser | Leu | Ser | Gly | Ser | Gly | Ser | Lys | Ser | Ser | Gly | |
| 1   |     |     |     | 5   |     |     |     |     | 10  |     |     |     |     | 15  |     | |

| ccg | ccg | ccc | ccg | tcg | ggt | tcc | tcc | ggg | agc | gag | gcg | gcg | gcg | gcg | gcg | 96 |
| Pro | Pro | Pro | Pro | Ser | Gly | Ser | Ser | Gly | Ser | Glu | Ala | Ala | Ala | Ala | Ala | |
|     |     |     | 20  |     |     |     |     | 25  |     |     |     |     | 30  |     |     | |

| ggg | gcg | gcg | ggg | gcg | gcg | ggg | gcc | ggg | gcg | gct | gcg | ccc | gcc | tcc | cag | 144 |
| Gly | Ala | Ala | Gly | Ala | Ala | Gly | Ala | Gly | Ala | Ala | Ala | Pro | Ala | Ser | Gln | |
|     |     | 35  |     |     |     |     | 40  |     |     |     |     | 45  |     |     |     | |

| cac | ccc | gcg | acc | ggc | acc | ggc | gct | gtc | cag | acc | gag | gcc | atg | aag | cag | 192 |
| His | Pro | Ala | Thr | Gly | Thr | Gly | Ala | Val | Gln | Thr | Glu | Ala | Met | Lys | Gln | |
| 50  |     |     |     |     | 55  |     |     |     |     | 60  |     |     |     |     |     | |

| atc | ctc | ggg | gtg | atc | gac | aag | aaa | ctc | cgg | aac | ctg | gag | aag | aaa | aag | 240 |
| Ile | Leu | Gly | Val | Ile | Asp | Lys | Lys | Leu | Arg | Asn | Leu | Glu | Lys | Lys | Lys | |
| 65  |     |     |     |     | 70  |     |     |     |     | 75  |     |     |     |     | 80  | |

| ggc | aag | ctt | gat | gat | tac | cag | gaa | cga | atg | aac | aaa | ggg | gaa | agg | ctt | 288 |
| Gly | Lys | Leu | Asp | Asp | Tyr | Gln | Glu | Arg | Met | Asn | Lys | Gly | Glu | Arg | Leu | |
|     |     |     |     | 85  |     |     |     |     | 90  |     |     |     |     | 95  |     | |

| aat | caa | gat | cag | ctg | gat | gcc | gta | tct | aag | tac | cag | gaa | gtc | aca | aat | 336 |
| Asn | Gln | Asp | Gln | Leu | Asp | Ala | Val | Ser | Lys | Tyr | Gln | Glu | Val | Thr | Asn | |
|     |     |     | 100 |     |     |     |     | 105 |     |     |     |     | 110 |     |     | |

| aac | ttg | gag | ttt | gca | aaa | gaa | tta | cag | agg | agt | ttc | atg | gca | tta | agt | 384 |
| Asn | Leu | Glu | Phe | Ala | Lys | Glu | Leu | Gln | Arg | Ser | Phe | Met | Ala | Leu | Ser | |
|     |     | 115 |     |     |     |     | 120 |     |     |     |     | 125 |     |     |     | |

| caa | gat | att | cag | aaa | aca | ata | aag | aag | act | gca | cgt | cgg | gag | cag | ctt | 432 |
| Gln | Asp | Ile | Gln | Lys | Thr | Ile | Lys | Lys | Thr | Ala | Arg | Arg | Glu | Gln | Leu | |
| 130 |     |     |     |     | 135 |     |     |     |     | 140 |     |     |     |     |     | |

| atg | aga | gag | gaa | gcg | gaa | caa | aaa | cgt | tta | aaa | act | gta | ctt | gag | ctc | 480 |
| Met | Arg | Glu | Glu | Ala | Glu | Gln | Lys | Arg | Leu | Lys | Thr | Val | Leu | Glu | Leu | |
| 145 |     |     |     |     | 150 |     |     |     |     | 155 |     |     |     |     | 160 | |

| cag | tat | gtt | ttg | gac | aaa | ttg | gga | gat | gat | gaa | gtg | aga | act | gac | ctg | 528 |
| Gln | Tyr | Val | Leu | Asp | Lys | Leu | Gly | Asp | Asp | Glu | Val | Arg | Thr | Asp | Leu | |
|     |     |     |     | 165 |     |     |     |     | 170 |     |     |     |     | 175 |     | |

| aag | caa | ggt | ttg | aat | gga | gtg | cca | ata | ttg | tct | gaa | gaa | gaa | ttg | tcg | 576 |
| Lys | Gln | Gly | Leu | Asn | Gly | Val | Pro | Ile | Leu | Ser | Glu | Glu | Glu | Leu | Ser | |
|     |     |     | 180 |     |     |     |     | 185 |     |     |     |     | 190 |     |     | |

| ttg | ttg | gat | gaa | ttc | tac | aaa | tta | gca | gac | cct | gaa | cgg | gac | atg | agc | 624 |
| Leu | Leu | Asp | Glu | Phe | Tyr | Lys | Leu | Ala | Asp | Pro | Glu | Arg | Asp | Met | Ser | |
|     |     |     |     | 195 |     |     |     |     | 200 |     |     |     |     | 205 |     | |

| ttg | agg | ttg | aat | gag | cag | tat | gaa | cat | gct | tcc | att | cac | ctg | tgg | gac | 672 |
| Leu | Arg | Leu | Asn | Glu | Gln | Tyr | Glu | His | Ala | Ser | Ile | His | Leu | Trp | Asp | |
|     | 210 |     |     |     |     | 215 |     |     |     |     | 220 |     |     |     |     | |

| ttg | ctg | gaa | gga | aag | gaa | aag | tct | gta | tgt | gga | aca | acc | tat | aaa | gca | 720 |
| Leu | Leu | Glu | Gly | Lys | Glu | Lys | Ser | Val | Cys | Gly | Thr | Thr | Tyr | Lys | Ala | |
| 225 |     |     |     |     | 230 |     |     |     |     | 235 |     |     |     |     | 240 | |

| cta | aag | gaa | att | gtt | gag | cgt | gtt | ttc | cag | tca | aat | tac | ttt | gac | agc | 768 |
| Leu | Lys | Glu | Ile | Val | Glu | Arg | Val | Phe | Gln | Ser | Asn | Tyr | Phe | Asp | Ser | |
|     |     |     |     | 245 |     |     |     |     | 250 |     |     |     |     | 255 |     | |

| act | cac | aac | cac | cag | aat | ggg | cta | tgt | gag | gaa | gaa | gag | gca | gcc | tca | 816 |
| Thr | His | Asn | His | Gln | Asn | Gly | Leu | Cys | Glu | Glu | Glu | Glu | Ala | Ala | Ser | |

-continued

```
              260                 265                 270
gca cct aca gtt gaa gac cag gta gct gaa gct gag cct gag cca gca      864
Ala Pro Thr Val Glu Asp Gln Val Ala Glu Ala Glu Pro Glu Pro Ala
    275                 280                 285 gaa gaa tac act gaa caa agt gaa gtt gaa tca aca gag tat gta aat      912
Glu Glu Tyr Thr Glu Gln Ser Glu Val Glu Ser Thr Glu Tyr Val Asn
290                 295                 300 aga caa ttt atg gca gaa aca cag ttc agc agt ggt gaa aag gag cag      960
Arg Gln Phe Met Ala Glu Thr Gln Phe Ser Ser Gly Glu Lys Glu Gln
305                 310                 315                 320 gta gat gag tgg acg gtc gaa aca gtg gag gtg gtg aat tca ctc cag     1008
Val Asp Glu Trp Thr Val Glu Thr Val Glu Val Val Asn Ser Leu Gln
                325                 330                 335 cag caa cct cag gct gcg tct cct tca gta cca gag ccc cac tct ttg     1056
Gln Gln Pro Gln Ala Ala Ser Pro Ser Val Pro Glu Pro His Ser Leu
            340                 345                 350 act ccg gtg gct cag gca gat ccc ctt gtg aga aga cag cga gtc cag     1104
Thr Pro Val Ala Gln Ala Asp Pro Leu Val Arg Arg Gln Arg Val Gln
        355                 360                 365 gac ctt atg gcg cag atg cag ggg ccc tat aat ttc ata cag gat tca     1152
Asp Leu Met Ala Gln Met Gln Gly Pro Tyr Asn Phe Ile Gln Asp Ser
370                 375                 380 atg ctg gat ttt gaa aac cag aca ctc gat cct gcc att gta tct gca     1200
Met Leu Asp Phe Glu Asn Gln Thr Leu Asp Pro Ala Ile Val Ser Ala
385                 390                 395                 400 cag cct atg aat ccg aca caa aac atg gac atg ccc cag ctg gtt tgc     1248
Gln Pro Met Asn Pro Thr Gln Asn Met Asp Met Pro Gln Leu Val Cys
                405                 410                 415 cct cca gtt cat tct gaa tct aga ctt gct caa cct aat caa gtt cct     1296
Pro Pro Val His Ser Glu Ser Arg Leu Ala Gln Pro Asn Gln Val Pro
            420                 425                 430 gta caa cca gaa gct aca cag gtt cct ttg gtt tca tcc aca agt gag     1344
Val Gln Pro Glu Ala Thr Gln Val Pro Leu Val Ser Ser Thr Ser Glu
        435                 440                 445 ggg tat aca gca tct caa ccc ttg tac cag cct tct cat gct aca gag     1392
Gly Tyr Thr Ala Ser Gln Pro Leu Tyr Gln Pro Ser His Ala Thr Glu
450                 455                 460 caa cga cca caa aag gaa cca att gac cag att cag gca aca atc tct     1440
Gln Arg Pro Gln Lys Glu Pro Ile Asp Gln Ile Gln Ala Thr Ile Ser
465                 470                 475                 480 tta aat aca gac cag act aca gcg tca tca tcc ctt ccg gct gct tct     1488
Leu Asn Thr Asp Gln Thr Thr Ala Ser Ser Ser Leu Pro Ala Ala Ser
                485                 490                 495 cag cct cag gta ttc cag gct ggg aca agc aaa cca tta cat agc agt     1536
Gln Pro Gln Val Phe Gln Ala Gly Thr Ser Lys Pro Leu His Ser Ser
            500                 505                 510 gga atc aat gta aat gca gct cca ttc caa tcc atg caa acg gtg ttc     1584
Gly Ile Asn Val Asn Ala Ala Pro Phe Gln Ser Met Gln Thr Val Phe
        515                 520                 525 aat atg aat gcc cca gtt cct cct gtt aat gaa cca gaa act ttg aaa     1632
Asn Met Asn Ala Pro Val Pro Pro Val Asn Glu Pro Glu Thr Leu Lys
530                 535                 540 caa caa aat cag tac cag gcc agt tat aac cag agc ttt tct agt cag     1680
Gln Gln Asn Gln Tyr Gln Ala Ser Tyr Asn Gln Ser Phe Ser Ser Gln
545                 550                 555                 560 cct cac caa gta gaa caa aca gac ctt cag caa gaa cag ctt caa aca     1728
Pro His Gln Val Glu Gln Thr Asp Leu Gln Gln Glu Gln Leu Gln Thr
                565                 570                 575 gtg gtt ggc act tac cat ggt tcc cag gac cag ccc cac caa gtg act     1776
```

```
                Val Val Gly Thr Tyr His Gly Ser Gln Asp Gln Pro His Gln Val Thr
                            580                 585                 590 gtt aac cat cag cag cct ccc cag cag aac act gga ttt cca cgt agc              1824
Gly Asn His Gln Gln Pro Pro Gln Gln Asn Thr Gly Phe Pro Arg Ser
            595                 600                 605 agt cag ccc tat tac aat agt cgt ggt gtg tct cgt ggt ggt tcc cgt              1872
Ser Gln Pro Tyr Tyr Asn Ser Arg Gly Val Ser Arg Gly Gly Ser Arg
            610                 615                 620 ggt gct aga ggc tta atg aat gga tac agg ggc cct gcc aat gga ttc              1920
Gly Ala Arg Gly Leu Met Asn Gly Tyr Arg Gly Pro Ala Asn Gly Phe
625                 630                 635                 640 aga gga gga tat gat ggt tac cgc cct tca ttc tct aac act cca aac              1968
Arg Gly Gly Tyr Asp Gly Tyr Arg Pro Ser Phe Ser Asn Thr Pro Asn
                645                 650                 655 agt ggt tat aca cag tct cag ttc agt gct ccc cgg gac tac tct ggc              2016
Ser Gly Tyr Thr Gln Ser Gln Phe Ser Ala Pro Arg Asp Tyr Ser Gly
            660                 665                 670 tat cag cgg gga tgc cgc aaa tga acactcagca agtgaattaa tctgattcac             2070
Tyr Gln Arg Gly Cys Arg Lys
            675 aggattatgt ttaaacgcca aaaacacact ggccagtgta ccataatatg ttaccagaag            2130 agttattatc tatttgttct cccttttcagg aaacttattg taaagggact gttttcatcc           2190 cataaagaca ggactacaat tgtcagcttt atattacctg gatatggaag gaaactattt            2250 ttattctgca tgttcttcct aagcgtcatc ttgagccttg cacatgatac tcagattcct            2310 caccccttgct taggagtaaa acataataca ctttacaggg tgatatctcc atagttattt           2370 gaagtggctt ggaaaaagca agattaactt ctgacattgg ataaaaatca acaaatcagc            2430 cctagagtta ttcaaatggt aattgacaaa aactaaaata tttcccttcg agaaggagtg            2490 gaatgtggtt tggcagaaca actgcatttc acagcttttc cggttaaatt ggagcactaa            2550 acgtttagat gcataccaaa ttatgcatgg gcccttaata taaaaggctg gctaccagct            2610 ttgacacagc actattcatc ctctggccaa acaactgtgg ttaaacaaca catgtaaatt            2670 gcttttaac agctgatact ataataagac aaagccaaaa tgcaaaaatt gggctttgat             2730 tggcactttt tgaaaaatat gcaacaaata tgggatgtaa tctggatggc cgcttctgta            2790 cttaatgtga agtatttaga tacctttttg aacacttaac agtttcttct gacaatgact            2850 tttgtaagga ttggtactat ctatcattcc ttataatgta cattgtctgt cactaatcct            2910 cagatcttgc tgtattgtca cctaaattgg tacaggtact gatgaaaata tctaatggat            2970 aatcataaca ctcttggtca catgttttc ctgcagcctg aaggttttta aagaaaaag              3030 atatcaaatg cctgctgcta ccacccttt aaattgctat cttttgaaaa gcaccagtat             3090 gtgttttaga ttgatttccc tattttaggg aaatgacaga cagtagtttc agttctgatg            3150 gtataagcaa acaaataaa acatgtttat aaaagttgta tcttgaaaca ctggtgttca             3210 acagctagca gctatgtgg ttcaccccat gcattgttag tgtttcagat tttatggtta             3270 tctccagcag ctgtttctgt agtacttgca tttatc                                      3306
```

<210> SEQ ID NO 12
<211> LENGTH: 679
<212> TYPE: PRT
<213> ORGANISM: Canis familiaris

<400> SEQUENCE: 12

Met Pro Ser Ala Thr Ser Leu Ser Gly Ser Gly Ser Lys Ser Ser Gly
1               5                   10                  15

-continued

```
Pro Pro Pro Pro Ser Gly Ser Ser Gly Ser Glu Ala Ala Ala Ala
         20              25              30

Gly Ala Ala Gly Ala Ala Gly Ala Ala Ala Pro Ala Ser Gln
     35              40              45

His Pro Ala Thr Gly Thr Gly Ala Val Gln Thr Glu Ala Met Lys Gln
 50              55              60

Ile Leu Gly Val Ile Asp Lys Lys Leu Arg Asn Leu Glu Lys Lys Lys
 65              70              75              80

Gly Lys Leu Asp Asp Tyr Gln Glu Arg Met Asn Lys Gly Glu Arg Leu
             85              90              95

Asn Gln Asp Gln Leu Asp Ala Val Ser Lys Tyr Gln Glu Val Thr Asn
         100             105             110

Asn Leu Glu Phe Ala Lys Glu Leu Gln Arg Ser Phe Met Ala Leu Ser
         115             120             125

Gln Asp Ile Gln Lys Thr Ile Lys Lys Thr Ala Arg Arg Glu Gln Leu
     130             135             140

Met Arg Glu Glu Ala Glu Gln Lys Arg Leu Lys Thr Val Leu Glu Leu
145             150             155             160

Gln Tyr Val Leu Asp Lys Leu Gly Asp Asp Glu Val Arg Thr Asp Leu
                 165             170             175

Lys Gln Gly Leu Asn Gly Val Pro Ile Leu Ser Glu Glu Leu Ser
         180             185             190

Leu Leu Asp Glu Phe Tyr Lys Leu Ala Asp Pro Glu Arg Asp Met Ser
     195             200             205

Leu Arg Leu Asn Glu Gln Tyr Glu His Ala Ser Ile His Leu Trp Asp
 210             215             220

Leu Leu Glu Gly Lys Glu Lys Ser Val Cys Gly Thr Thr Tyr Lys Ala
225             230             235             240

Leu Lys Glu Ile Val Glu Arg Val Phe Gln Ser Asn Tyr Phe Asp Ser
                 245             250             255

Thr His Asn His Gln Asn Gly Leu Cys Glu Glu Glu Ala Ala Ser
         260             265             270

Ala Pro Thr Val Glu Asp Gln Val Ala Glu Ala Glu Pro Glu Pro Ala
     275             280             285

Glu Glu Tyr Thr Glu Gln Ser Glu Val Glu Ser Thr Glu Tyr Val Asn
290             295             300

Arg Gln Phe Met Ala Glu Thr Gln Phe Ser Ser Gly Glu Lys Glu Gln
305             310             315             320

Val Asp Glu Trp Thr Val Thr Val Glu Val Asn Ser Leu Gln
                 325             330             335

Gln Gln Pro Gln Ala Ala Ser Pro Ser Val Pro Glu Pro His Ser Leu
         340             345             350

Thr Pro Val Ala Gln Ala Asp Pro Leu Val Arg Arg Gln Arg Val Gln
     355             360             365

Asp Leu Met Ala Gln Met Gln Gly Pro Tyr Asn Phe Ile Gln Asp Ser
     370             375             380

Met Leu Asp Phe Glu Asn Gln Thr Leu Asp Pro Ala Ile Val Ser Ala
385             390             395             400

Gln Pro Met Asn Pro Thr Gln Asn Met Asp Met Pro Gln Leu Val Cys
                 405             410             415

Pro Pro Val His Ser Glu Ser Arg Leu Ala Gln Pro Asn Gln Val Pro
         420             425             430
```

```
Val Gln Pro Glu Ala Thr Gln Val Pro Leu Val Ser Thr Ser Glu
        435                 440                 445

Gly Tyr Thr Ala Ser Gln Pro Leu Tyr Gln Pro Ser His Ala Thr Glu
    450                 455                 460

Gln Arg Pro Gln Lys Glu Pro Ile Asp Gln Ile Gln Ala Thr Ile Ser
465                 470                 475                 480

Leu Asn Thr Asp Gln Thr Thr Ala Ser Ser Leu Pro Ala Ala Ser
                485                 490                 495

Gln Pro Gln Val Phe Gln Ala Gly Thr Ser Lys Pro Leu His Ser Ser
                500                 505                 510

Gly Ile Asn Val Asn Ala Ala Pro Phe Gln Ser Met Gln Thr Val Phe
                515                 520                 525

Asn Met Asn Ala Pro Val Pro Pro Val Asn Glu Pro Glu Thr Leu Lys
        530                 535                 540

Gln Gln Asn Gln Tyr Gln Ala Ser Tyr Asn Gln Ser Phe Ser Ser Gln
545                 550                 555                 560

Pro His Gln Val Glu Gln Thr Asp Leu Gln Gln Glu Gln Leu Gln Thr
                565                 570                 575

Val Val Gly Thr Tyr His Gly Ser Gln Asp Gln Pro His Gln Val Thr
                580                 585                 590

Gly Asn His Gln Gln Pro Pro Gln Gln Asn Thr Gly Phe Pro Arg Ser
        595                 600                 605

Ser Gln Pro Tyr Tyr Asn Ser Arg Gly Val Ser Arg Gly Gly Ser Arg
        610                 615                 620

Gly Ala Arg Gly Leu Met Asn Gly Tyr Arg Gly Pro Ala Asn Gly Phe
625                 630                 635                 640

Arg Gly Gly Tyr Asp Gly Tyr Arg Pro Ser Phe Ser Asn Thr Pro Asn
                645                 650                 655

Ser Gly Tyr Thr Gln Ser Gln Phe Ser Ala Pro Arg Asp Tyr Ser Gly
                660                 665                 670

Tyr Gln Arg Gly Cys Arg Lys
        675

<210> SEQ ID NO 13
<211> LENGTH: 2281
<212> TYPE: DNA
<213> ORGANISM: Canis familiaris
<220> FEATURE:
<221> NAME/KEY: CDS
<222> LOCATION: (1)..(2154)
<223> OTHER INFORMATION:

<400> SEQUENCE: 13 atg ccg tcg gcc acc agc ctc agc gga agc ggc agc aag tcg tcg ggc    48
Met Pro Ser Ala Thr Ser Leu Ser Gly Ser Gly Ser Lys Ser Ser Gly
1               5                   10                  15 ccg ccg ccc ccg tcg ggt tcc tcc ggg agc gag gcg gcg gcg gcg gcg    96
Pro Pro Pro Pro Ser Gly Ser Ser Gly Ser Glu Ala Ala Ala Ala Ala
            20                  25                  30 ggg gcg gcg ggg gcg gcg ggg gcc ggg gcg gct gcg ccc gcc tcc cag   144
Gly Ala Ala Gly Ala Ala Gly Ala Gly Ala Ala Ala Pro Ala Ser Gln
        35                  40                  45 cac ccc gcg acc ggc acc ggc gct gtc cag acc gag gcc atg aag cag   192
His Pro Ala Thr Gly Thr Gly Ala Val Gln Thr Glu Ala Met Lys Gln
    50                  55                  60 atc ctc ggg gtg atc gac aag aaa ctc cgg aac ctg gag aag aaa aag   240
Ile Leu Gly Val Ile Asp Lys Lys Leu Arg Asn Leu Glu Lys Lys Lys
65                  70                  75                  80
```

-continued

```
ggc aag ctt gat gat tac cag gaa cga atg aac aaa ggg gaa agg ctt      288
Gly Lys Leu Asp Asp Tyr Gln Glu Arg Met Asn Lys Gly Glu Arg Leu
             85                  90                  95 aat caa gat cag ctg gat gcc gta tct aag tac cag gaa gtc aca aat      336
Asn Gln Asp Gln Leu Asp Ala Val Ser Lys Tyr Gln Glu Val Thr Asn
            100                 105                 110 aac ttg gag ttt gca aaa gaa tta cag agg agt ttc atg gca tta agt      384
Asn Leu Glu Phe Ala Lys Glu Leu Gln Arg Ser Phe Met Ala Leu Ser
        115                 120                 125 caa gat att cag aaa aca ata aag aag act gca cgt cgg gag cag ctt      432
Gln Asp Ile Gln Lys Thr Ile Lys Lys Thr Ala Arg Arg Glu Gln Leu
    130                 135                 140 atg aga gag gaa gcg gaa caa aaa cgt tta aaa act gta ctt gag ctc      480
Met Arg Glu Glu Ala Glu Gln Lys Arg Leu Lys Thr Val Leu Glu Leu
145                 150                 155                 160 cag tat gtt ttg gac aaa ttg gga gat gat gaa gtg aga act gac ctg      528
Gln Tyr Val Leu Asp Lys Leu Gly Asp Asp Glu Val Arg Thr Asp Leu
                165                 170                 175 aag caa ggt ttg aat gga gtg cca ata ttg tct gaa gaa gaa ttg tcg      576
Lys Gln Gly Leu Asn Gly Val Pro Ile Leu Ser Glu Glu Glu Leu Ser
            180                 185                 190 ttg ttg gat gaa ttc tac aaa tta gca gac cct gaa cgg gac atg agc      624
Leu Leu Asp Glu Phe Tyr Lys Leu Ala Asp Pro Glu Arg Asp Met Ser
        195                 200                 205 ttg agg ttg aat gag cag tat gaa cat gct tcc att cac ctg tgg gac      672
Leu Arg Leu Asn Glu Gln Tyr Glu His Ala Ser Ile His Leu Trp Asp
    210                 215                 220 ttg ctg gaa gga aag gaa aag tct gta tgt gga aca acc tat aaa gca      720
Leu Leu Glu Gly Lys Glu Lys Ser Val Cys Gly Thr Thr Tyr Lys Ala
225                 230                 235                 240 cta aag gaa att gtt gag cgt gtt ttc cag tca aat tac ttt gac agc      768
Leu Lys Glu Ile Val Glu Arg Val Phe Gln Ser Asn Tyr Phe Asp Ser
                245                 250                 255 act cac aac cac cag aat ggg cta tgt gag gaa gaa gag gca gcc tca      816
Thr His Asn His Gln Asn Gly Leu Cys Glu Glu Glu Glu Ala Ala Ser
            260                 265                 270 gca cct aca gtt gaa gac cag gta gct gaa gct gag cct gag cca gca      864
Ala Pro Thr Val Glu Asp Gln Val Ala Glu Ala Glu Pro Glu Pro Ala
        275                 280                 285 gaa gaa tac act gaa caa agt gaa gtt gaa tca aca gag tat gta aat      912
Glu Glu Tyr Thr Glu Gln Ser Glu Val Glu Ser Thr Glu Tyr Val Asn
    290                 295                 300 aga caa ttt atg gca gaa aca cag ttc agc agt ggt gaa aag gag cag      960
Arg Gln Phe Met Ala Glu Thr Gln Phe Ser Ser Gly Glu Lys Glu Gln
305                 310                 315                 320 gta gat gag tgg acg gtc gaa aca gtg gag gtg gtg aat tca ctc cag     1008
Val Asp Glu Trp Thr Val Glu Thr Val Glu Val Val Asn Ser Leu Gln
                325                 330                 335 cag caa cct cag gct gcg tct cct tca gta cca gag ccc cac tct ttg     1056
Gln Gln Pro Gln Ala Ala Ser Pro Ser Val Pro Glu Pro His Ser Leu
            340                 345                 350 act ccg gtg gct cag gca gat ccc ctt gtg aga aga cag cga gtc cag     1104
Thr Pro Val Ala Gln Ala Asp Pro Leu Val Arg Arg Gln Arg Val Gln
        355                 360                 365 gac ctt atg gcg cag atg cag ggg ccc tat aat ttc ata cag gat tca     1152
Asp Leu Met Ala Gln Met Gln Gly Pro Tyr Asn Phe Ile Gln Asp Ser
    370                 375                 380 atg ctg gat ttt gaa aac cag aca ctc gat cct gcc att gta tct gca     1200
Met Leu Asp Phe Glu Asn Gln Thr Leu Asp Pro Ala Ile Val Ser Ala
```

```
             385                 390                 395                 400
cag cct atg aat ccg aca caa aac atg gac atg ccc cag ctg gtt tgc        1248
Gln Pro Met Asn Pro Thr Gln Asn Met Asp Met Pro Gln Leu Val Cys
            405                 410                 415 cct cca gtt cat tct gaa tct aga ctt gct caa cct aat caa gtt cct        1296
Pro Pro Val His Ser Glu Ser Arg Leu Ala Gln Pro Asn Gln Val Pro
        420                 425                 430 gta caa cca gaa gct aca cag gtt cct ttg gtt tca tcc aca agt gag        1344
Val Gln Pro Glu Ala Thr Gln Val Pro Leu Val Ser Ser Thr Ser Glu
    435                 440                 445 ggg tat aca gca tct caa ccc ttg tac cag cct tct cat gct aca gag        1392
Gly Tyr Thr Ala Ser Gln Pro Leu Tyr Gln Pro Ser His Ala Thr Glu
450                 455                 460 caa cga cca caa aag gaa cca att gac cag att cag gca aca atc tct        1440
Gln Arg Pro Gln Lys Glu Pro Ile Asp Gln Ile Gln Ala Thr Ile Ser
465                 470                 475                 480 tta aat aca gac cag act aca gcg tca tca tcc ctt ccg gct gct tct        1488
Leu Asn Thr Asp Gln Thr Thr Ala Ser Ser Ser Leu Pro Ala Ala Ser
                485                 490                 495 cag cct cag gta ttc cag gct ggg aca agc aaa cca tta cat agc agt        1536
Gln Pro Gln Val Phe Gln Ala Gly Thr Ser Lys Pro Leu His Ser Ser
            500                 505                 510 gga atc aat gta aat gca gct cca ttc caa tcc atg caa acg gtg ttc        1584
Gly Ile Asn Val Asn Ala Ala Pro Phe Gln Ser Met Gln Thr Val Phe
        515                 520                 525 aat atg aat gcc cca gtt cct cct gtt aat gaa cca gaa act ttg aaa        1632
Asn Met Asn Ala Pro Val Pro Pro Val Asn Glu Pro Glu Thr Leu Lys
    530                 535                 540 caa caa aat cag tac cag gcc agt tat aac cag agc ttt tct agt cag        1680
Gln Gln Asn Gln Tyr Gln Ala Ser Tyr Asn Gln Ser Phe Ser Ser Gln
545                 550                 555                 560 cct cac caa gta gaa caa aca gac ctt cag caa gaa cag ctt caa aca        1728
Pro His Gln Val Glu Gln Thr Asp Leu Gln Gln Glu Gln Leu Gln Thr
                565                 570                 575 gtg gtt ggc act tac cat ggt tcc cag gac cag ccc cac caa gtg act        1776
Val Val Gly Thr Tyr His Gly Ser Gln Asp Gln Pro His Gln Val Thr
            580                 585                 590 ggt aac cat cag cag cct ccc cag cag aac act gga ttt cca cgt agc        1824
Gly Asn His Gln Gln Pro Pro Gln Gln Asn Thr Gly Phe Pro Arg Ser
        595                 600                 605 agt cag ccc tat tac aat agt cgt ggt gtg tct cgt ggt ggt tcc cgt        1872
Ser Gln Pro Tyr Tyr Asn Ser Arg Gly Val Ser Arg Gly Gly Ser Arg
    610                 615                 620 ggt gct aga ggc tta atg aat gga tac agg ggc cct gcc aat gga ttc        1920
Gly Ala Arg Gly Leu Met Asn Gly Tyr Arg Gly Pro Ala Asn Gly Phe
625                 630                 635                 640 aga gga gga tat gat ggt tac cgc cct tca ttc tct aac act cca aac        1968
Arg Gly Gly Tyr Asp Gly Tyr Arg Pro Ser Phe Ser Asn Thr Pro Asn
                645                 650                 655 agt ggt tat aca cag tct cag ttc agt gct ccc cgg gac tac tct ggc        2016
Ser Gly Tyr Thr Gln Ser Gln Phe Ser Ala Pro Arg Asp Tyr Ser Gly
            660                 665                 670 tat cag cgg gat gga tat cag cag aat ttc aag cga ggc tct ggg cag        2064
Tyr Gln Arg Asp Gly Tyr Gln Gln Asn Phe Lys Arg Gly Ser Gly Gln
        675                 680                 685 agt gga cca cgg gga gcc cca cga ggt cgt gga ggg ccc cca aga ccc        2112
Ser Gly Pro Arg Gly Ala Pro Arg Gly Arg Gly Gly Pro Pro Arg Pro
    690                 695                 700 aac aga ggg atg ccg caa atg aac act cag caa gtg aat taa              2154
```

```
Asn Arg Gly Met Pro Gln Met Asn Thr Gln Gln Val Asn
705                 710                 715
```

```
tctgattcac aggattatgt ttaaacgcca aaaacacact ggccagtgta ccataatatg   2214
ttaccagaag agttattatc tatttggact gttttcatcc cataaagaca ggactacaat   2274
tgtcagc                                                             2281
```

<210> SEQ ID NO 14
<211> LENGTH: 717
<212> TYPE: PRT
<213> ORGANISM: Canis familiaris

<400> SEQUENCE: 14

```
Met Pro Ser Ala Thr Ser Leu Ser Gly Ser Gly Ser Lys Ser Gly
1               5                   10                  15

Pro Pro Pro Ser Gly Ser Ser Gly Ser Glu Ala Ala Ala Ala
                20                  25                  30

Gly Ala Ala Gly Ala Ala Gly Ala Gly Ala Ala Pro Ala Ser Gln
                35                  40                  45

His Pro Ala Thr Gly Thr Gly Ala Val Gln Thr Glu Ala Met Lys Gln
            50                  55                  60

Ile Leu Gly Val Ile Asp Lys Lys Leu Arg Asn Leu Glu Lys Lys Lys
65                  70                  75                  80

Gly Lys Leu Asp Asp Tyr Gln Glu Arg Met Asn Lys Gly Glu Arg Leu
                85                  90                  95

Asn Gln Asp Gln Leu Asp Ala Val Ser Lys Tyr Gln Glu Val Thr Asn
                100                 105                 110

Asn Leu Glu Phe Ala Lys Glu Leu Gln Arg Ser Phe Met Ala Leu Ser
            115                 120                 125

Gln Asp Ile Gln Lys Thr Ile Lys Lys Thr Ala Arg Arg Glu Gln Leu
        130                 135                 140

Met Arg Glu Glu Ala Glu Gln Lys Arg Leu Lys Thr Val Leu Glu Leu
145                 150                 155                 160

Gln Tyr Val Leu Asp Lys Leu Gly Asp Asp Glu Val Arg Thr Asp Leu
                165                 170                 175

Lys Gln Gly Leu Asn Gly Val Pro Ile Leu Ser Glu Glu Leu Ser
                180                 185                 190

Leu Leu Asp Glu Phe Tyr Lys Leu Ala Asp Pro Glu Arg Asp Met Ser
            195                 200                 205

Leu Arg Leu Asn Glu Gln Tyr Glu His Ala Ser Ile His Leu Trp Asp
        210                 215                 220

Leu Leu Glu Gly Lys Glu Lys Ser Val Cys Gly Thr Thr Tyr Lys Ala
225                 230                 235                 240

Leu Lys Glu Ile Val Glu Arg Val Phe Gln Ser Asn Tyr Phe Asp Ser
                245                 250                 255

Thr His Asn His Gln Asn Gly Leu Cys Glu Glu Glu Ala Ala Ser
                260                 265                 270

Ala Pro Thr Val Glu Asp Gln Val Ala Glu Ala Glu Pro Glu Pro Ala
            275                 280                 285

Glu Glu Tyr Thr Glu Gln Ser Glu Val Glu Ser Thr Glu Tyr Val Asn
        290                 295                 300

Arg Gln Phe Met Ala Glu Thr Gln Phe Ser Ser Gly Glu Lys Glu Gln
305                 310                 315                 320

Val Asp Glu Trp Thr Val Glu Thr Val Glu Val Val Asn Ser Leu Gln
                325                 330                 335
```

```
Gln Gln Pro Gln Ala Ala Ser Pro Ser Val Pro Glu Pro His Ser Leu
                340                 345                 350

Thr Pro Val Ala Gln Ala Asp Pro Leu Val Arg Arg Gln Arg Val Gln
            355                 360                 365

Asp Leu Met Ala Gln Met Gln Gly Pro Tyr Asn Phe Ile Gln Asp Ser
        370                 375                 380

Met Leu Asp Phe Glu Asn Gln Thr Leu Asp Pro Ala Ile Val Ser Ala
385                 390                 395                 400

Gln Pro Met Asn Pro Thr Gln Asn Met Asp Met Pro Gln Leu Val Cys
                405                 410                 415

Pro Pro Val His Ser Glu Ser Arg Leu Ala Gln Pro Asn Gln Val Pro
            420                 425                 430

Val Gln Pro Glu Ala Thr Gln Val Pro Leu Val Ser Ser Thr Ser Glu
        435                 440                 445

Gly Tyr Thr Ala Ser Gln Pro Leu Tyr Gln Pro Ser His Ala Thr Glu
    450                 455                 460

Gln Arg Pro Gln Lys Glu Pro Ile Asp Gln Ile Gln Ala Thr Ile Ser
465                 470                 475                 480

Leu Asn Thr Asp Gln Thr Thr Ala Ser Ser Leu Pro Ala Ala Ser
                485                 490                 495

Gln Pro Gln Val Phe Gln Ala Gly Thr Ser Lys Pro Leu His Ser Ser
            500                 505                 510

Gly Ile Asn Val Asn Ala Ala Pro Phe Gln Ser Met Gln Thr Val Phe
        515                 520                 525

Asn Met Asn Ala Pro Val Pro Pro Val Asn Glu Pro Glu Thr Leu Lys
    530                 535                 540

Gln Gln Asn Gln Tyr Gln Ala Ser Tyr Asn Gln Ser Phe Ser Ser Gln
545                 550                 555                 560

Pro His Gln Val Glu Gln Thr Asp Leu Gln Gln Glu Gln Leu Gln Thr
                565                 570                 575

Val Val Gly Thr Tyr His Gly Ser Gln Asp Gln Pro His Gln Val Thr
            580                 585                 590

Gly Asn His Gln Gln Pro Pro Gln Gln Asn Thr Gly Phe Pro Arg Ser
        595                 600                 605

Ser Gln Pro Tyr Tyr Asn Ser Arg Gly Val Ser Arg Gly Gly Ser Arg
    610                 615                 620

Gly Ala Arg Gly Leu Met Asn Gly Tyr Arg Gly Pro Ala Asn Gly Phe
625                 630                 635                 640

Arg Gly Gly Tyr Asp Gly Tyr Arg Pro Ser Phe Ser Asn Thr Pro Asn
                645                 650                 655

Ser Gly Tyr Thr Gln Ser Gln Phe Ser Ala Pro Arg Asp Tyr Ser Gly
            660                 665                 670

Tyr Gln Arg Asp Gly Tyr Gln Gln Asn Phe Lys Arg Gly Ser Gly Gln
        675                 680                 685

Ser Gly Pro Arg Gly Ala Pro Arg Gly Arg Gly Pro Pro Arg Pro
    690                 695                 700

Asn Arg Gly Met Pro Gln Met Asn Thr Gln Gln Val Asn
705                 710                 715

<210> SEQ ID NO 15
<211> LENGTH: 3386
<212> TYPE: DNA
<213> ORGANISM: Bos taurus
<220> FEATURE:
```

<210> NAME/KEY: CDS
<222> LOCATION: (82)..(2208)
<223> OTHER INFORMATION:

<400> SEQUENCE: 15

```
cgcgtctcgc cccgtccacc gattgactcg ccgctcttgt ccttcctccc gctctttctt      60
ctctcccctt acggtttcaa g atg cct tcg gcc acc agc cac agc gga agc       111
                         Met Pro Ser Ala Thr Ser His Ser Gly Ser
                         1               5                      10 ggc agc aag tcg tcc gga ccg cca ccg ccg tcg ggt tcc tcc ggg aat       159
Gly Ser Lys Ser Ser Gly Pro Pro Pro Pro Ser Gly Ser Ser Gly Asn
            15                  20                  25 gag gcg ggg gcc ggg gcc gcc gcg ccg gct tcc caa cac ccc atg acc       207
Glu Ala Gly Ala Gly Ala Ala Ala Pro Ala Ser Gln His Pro Met Thr
30                  35                  40 ggc acc ggg gct gtc cag acc gag gcc atg aag cag att ctc ggg gtg       255
Gly Thr Gly Ala Val Gln Thr Glu Ala Met Lys Gln Ile Leu Gly Val
    45                  50                  55 atc gac aag aaa ctt cgg aac ctg gag aag aaa aag ggc aag ctt gat       303
Ile Asp Lys Lys Leu Arg Asn Leu Glu Lys Lys Lys Gly Lys Leu Asp
60                  65                  70 gat tat cag gaa cga atg aac aaa ggg gaa agg ctt aat caa gat cag       351
Asp Tyr Gln Glu Arg Met Asn Lys Gly Glu Arg Leu Asn Gln Asp Gln
75                  80                  85                  90 ctg gat gcc gtg tct aag tac cag gaa gtc aca aat aac ttg gag ttt       399
Leu Asp Ala Val Ser Lys Tyr Gln Glu Val Thr Asn Asn Leu Glu Phe
                95                  100                 105 gca aaa gaa tta cag agg agt ttc atg gca tta agc caa gat att cag       447
Ala Lys Glu Leu Gln Arg Ser Phe Met Ala Leu Ser Gln Asp Ile Gln
            110                 115                 120 aaa aca ata aag aag aca gca cgt cgg gag cag ctt atg aga gag gaa       495
Lys Thr Ile Lys Lys Thr Ala Arg Arg Glu Gln Leu Met Arg Glu Glu
        125                 130                 135 gct gaa cag aaa cgt tta aaa aca gta ctt gag ctg cag tat gtt ttg       543
Ala Glu Gln Lys Arg Leu Lys Thr Val Leu Glu Leu Gln Tyr Val Leu
    140                 145                 150 gac aaa cta gga gat gat gaa gtg aga act gac ctg aag caa ggt ttg       591
Asp Lys Leu Gly Asp Asp Glu Val Arg Thr Asp Leu Lys Gln Gly Leu
155                 160                 165                 170 aat gga gtg cca ata ttg tct gaa gag gag ttg tcg ttg tta gat gag       639
Asn Gly Val Pro Ile Leu Ser Glu Glu Glu Leu Ser Leu Leu Asp Glu
                175                 180                 185 ttc tac aaa tta gca gac cct gaa cga gac atg agc ttg agg ttg aat       687
Phe Tyr Lys Leu Ala Asp Pro Glu Arg Asp Met Ser Leu Arg Leu Asn
            190                 195                 200 gag cag tat gaa cat gcc tcc att cac ctg tgg gac ttg ctg gaa gga       735
Glu Gln Tyr Glu His Ala Ser Ile His Leu Trp Asp Leu Leu Glu Gly
        205                 210                 215 aag gaa aaa cct gta tgt gga aca act tat aaa gct cta aag gaa att       783
Lys Glu Lys Pro Val Cys Gly Thr Thr Tyr Lys Ala Leu Lys Glu Ile
    220                 225                 230 gtt gag cgt gtt ttc agt tca aac tac ttt gac agc acc cac aac cac       831
Val Glu Arg Val Phe Gln Ser Asn Tyr Phe Asp Ser Thr His Asn His
235                 240                 245                 250 cag aat ggt ctg tgt gag gaa gag gag gca gcc tca gca cct aca gtt       879
Gln Asn Gly Leu Cys Glu Glu Glu Glu Ala Ala Ser Ala Pro Thr Val
                255                 260                 265 gaa gac cag gca gct gaa gct gaa cct gag cca gtg gaa gaa tat act       927
Glu Asp Gln Ala Ala Glu Ala Glu Pro Glu Pro Val Glu Glu Tyr Thr
            270                 275                 280
```

| | |
|---|---|
| gaa caa aat gag gtt gaa tca aca gag tat gta aat aga caa ttt atg<br>Glu Gln Asn Glu Val Glu Ser Thr Glu Tyr Val Asn Arg Gln Phe Met<br>285                  290                295 | 975 |
| gca gaa aca cag ttc agc agt ggt gaa aag gag cag gta gat gat tgg<br>Ala Glu Thr Gln Phe Ser Ser Gly Glu Lys Glu Gln Val Asp Asp Trp<br>300                  305              310 | 1023 |
| aca gtt gaa aca gtt gag gtg gta aat tca ctc cag cag caa cct cag<br>Thr Val Glu Thr Val Glu Val Val Asn Ser Leu Gln Gln Gln Pro Gln<br>315                  320              325              330 | 1071 |
| gct gca tct cct tca gta cca gaa ccc cac tct ttg acc cca gtg gct<br>Ala Ala Ser Pro Ser Val Pro Glu Pro His Ser Leu Thr Pro Val Ala<br>                335              340              345 | 1119 |
| caa gcc gat ccc ctc gtg aga aga cag cga gta cag gac ctt atg gca<br>Gln Ala Asp Pro Leu Val Arg Arg Gln Arg Val Gln Asp Leu Met Ala<br>350                  355              360 | 1167 |
| caa atg cag ggg ccc tat aat ttc ata cag gat tca atg ttg gat ttt<br>Gln Met Gln Gly Pro Tyr Asn Phe Ile Gln Asp Ser Met Leu Asp Phe<br>                365              370              375 | 1215 |
| gaa aac cag aca ctt gat cct gcc att gta tct gca cag ccg atg aat<br>Glu Asn Gln Thr Leu Asp Pro Ala Ile Val Ser Ala Gln Pro Met Asn<br>380                  385              390 | 1263 |
| cca gca cag aac atg gac ata ccc cag ctg gtt tgc cct cca gtt cat<br>Pro Ala Gln Asn Met Asp Ile Pro Gln Leu Val Cys Pro Pro Val His<br>395                  400              405              410 | 1311 |
| tct gaa tct aga ctt gct caa cct aat caa gtt tct gta cag cca gaa<br>Ser Glu Ser Arg Leu Ala Gln Pro Asn Gln Val Ser Val Gln Pro Glu<br>                415              420              425 | 1359 |
| gct aca cag gtt cct ttg gtt tca tcc aca agt gag gga tat aca gca<br>Ala Thr Gln Val Pro Leu Val Ser Ser Thr Ser Glu Gly Tyr Thr Ala<br>                      430              435              440 | 1407 |
| tct caa ccc ttg tac caa cct tct cat gct act gac caa cga cca caa<br>Ser Gln Pro Leu Tyr Gln Pro Ser His Ala Thr Asp Gln Arg Pro Gln<br>            445              450              455 | 1455 |
| aag gaa ccg att gat cag att cag gcg acg atc tct tta aat aca gac<br>Lys Glu Pro Ile Asp Gln Ile Gln Ala Thr Ile Ser Leu Asn Thr Asp<br>460                  465              470 | 1503 |
| cag act aca gca tca tca tcc ctt cct gct gct tct cag cct caa gtg<br>Gln Thr Thr Ala Ser Ser Ser Leu Pro Ala Ala Ser Gln Pro Gln Val<br>475                  480              485              490 | 1551 |
| ttc cag gct ggg aca agc aaa cct tta cat agc agt gga atc aat gta<br>Phe Gln Ala Gly Thr Ser Lys Pro Leu His Ser Ser Gly Ile Asn Val<br>                495              500              505 | 1599 |
| aat gca gct cca ttc caa tcc atg caa acg gta ttc aat atg aat gcc<br>Asn Ala Ala Pro Phe Gln Ser Met Gln Thr Val Phe Asn Met Asn Ala<br>                      510              515              520 | 1647 |
| cca gtt cct cct gtt aat gaa cca gaa act tta aaa cag caa aat cag<br>Pro Val Pro Pro Val Asn Glu Pro Glu Thr Leu Lys Gln Gln Asn Gln<br>            525              530              535 | 1695 |
| tac cag gcc agt tac aac cag agc ttt agt cag cct cac caa gta<br>Tyr Gln Ala Ser Tyr Asn Gln Ser Phe Ser Ser Gln Pro His Gln Val<br>540                  545              550 | 1743 |
| gaa caa aca gag ctt cag caa gaa cag ctt caa aca gtg gtt ggc act<br>Glu Gln Thr Glu Leu Gln Gln Glu Gln Leu Gln Thr Val Val Gly Thr<br>555                  560              565              570 | 1791 |
| tat cat ggt tct cag gac cag ccc cat caa gtg act ggt aac cac cag<br>Tyr His Gly Ser Gln Asp Gln Pro His Gln Val Thr Gly Asn His Gln<br>                      575              580              585 | 1839 |
| cag cct cct cag cag aac act gga ttt cca cgt agc aat cag ccc tat<br>Gln Pro Pro Gln Gln Asn Thr Gly Phe Pro Arg Ser Asn Gln Pro Tyr | 1887 |

| | | | |
|---|---|---|---|
| tac aac agt cgt ggt gtg tct cgt gga ggt tcc cgt ggt gct aga ggc | | | 1935 |
| Tyr Asn Ser Arg Gly Val Ser Arg Gly Gly Ser Arg Gly Ala Arg Gly | | | |
| 605 610 615 | | | |
| ttg atg aat gga tac aga gga cct gct aat gga ttc aga gga gga tat | | | 1983 |
| Leu Met Asn Gly Tyr Arg Gly Pro Ala Asn Gly Phe Arg Gly Gly Tyr | | | |
| 620 625 630 | | | |
| gat ggt tac cgc cct tca ttc tct act aac act cca aac agt ggt tat | | | 2031 |
| Asp Gly Tyr Arg Pro Ser Phe Ser Thr Asn Thr Pro Asn Ser Gly Tyr | | | |
| 635 640 645 650 | | | |
| aca caa tct caa ttc agt gct ccc cgg gac tac tct ggc tat cag cgg | | | 2079 |
| Thr Gln Ser Gln Phe Ser Ala Pro Arg Asp Tyr Ser Gly Tyr Gln Arg | | | |
| 655 660 665 | | | |
| gat gga tat cag cag aat ttc aag cga ggc tct ggg cag agt gga cca | | | 2127 |
| Asp Gly Tyr Gln Gln Asn Phe Lys Arg Gly Ser Gly Gln Ser Gly Pro | | | |
| 670 675 680 | | | |
| cgg gga gcc cca cga ggt cgt gga ggg ccc cca aga ccc aac aga ggg | | | 2175 |
| Arg Gly Ala Pro Arg Gly Arg Gly Gly Pro Pro Arg Pro Asn Arg Gly | | | |
| 685 690 695 | | | |
| atg ccg caa atg aac act cag caa gtg aat taa tctgattcac aggattatgt | | | 2228 |
| Met Pro Gln Met Asn Thr Gln Gln Val Asn | | | |
| 700 705 | | | |
| ttaatcgcca aaacacact ggccagtgta ccataatatg ttaccagaag agttattatc | | | 2288 |
| tatttgttct ccctttcagg aaacttattg taaaggggact gttttcatcc cataaagaca | | | 2348 |
| ggactacaat tgtcagcttt atattacctg gatatggaag gaaactatttt ttactctgca | | | 2408 |
| tgttctgtcc taagcgtcat cttgagcctt gcacatgata ctcagattcc tcacccttgc | | | 2468 |
| ttaggagtaa acataatat actttaatgg ggtgatatct ccatagttat ttgaagtggc | | | 2528 |
| ttggataaag caagactgac ttctgacatt ggataaaatc tacaaatcag ccctagagtc | | | 2588 |
| attcagtggt aactgacaaa actaaaatat ttcccttgaa aggaagatgg aaggagtgga | | | 2648 |
| gtgtggtttg gcagaacaac tgcatttcac agcttttcca cttaaattgg agcactgaac | | | 2708 |
| atttagatgc ataccgaatt atgcatgggc cctaatcaca cagacaaggc tggtgccagc | | | 2768 |
| cttaggcttg acacggcagt gttcacccctc tggccagacg actgtggttc aagacacatg | | | 2828 |
| taaattgctt tttaacagct gatactgtat aagacaaagc caaaatgcaa aattaggctt | | | 2888 |
| tgattggcac ttttcgaaaa atatgcaaca attaagggat ataatctgga tggccgcttc | | | 2948 |
| tgtacttaat gtgaaatatt tagataccctt tcaaacactt aacagtttct ttgacaatga | | | 3008 |
| gttttgtaag gattggtagt aaatatcatt ccttatgacg tacattgtct gtcactaatc | | | 3068 |
| cttggatctt gctgtattgt cacctaaatt ggtacaggta ctgatgaaaa tctaatggat | | | 3128 |
| aatcataaca ctcttggtta catgtttttc ctgcagcctg aaagttttta taagaaaaag | | | 3188 |
| acatcaaatg cctgctgctg ccacccttt aaattgctat cttttgaaaa gcaccagtat | | | 3248 |
| gtgtttaga ttgatttccc tatttttaggg aaatgacagt cagtagtttc acttctgatg | | | 3308 |
| gtataagcaa acaaataaaa catgtttata aaaaaaaaa aaaaaaaaa aaaaaaaaa | | | 3368 |
| aaaaaaaaaa aaaaaaaa | | | 3386 |

<210> SEQ ID NO 16
<211> LENGTH: 708
<212> TYPE: PRT
<213> ORGANISM: Bos taurus

<400> SEQUENCE: 16

Met Pro Ser Ala Thr Ser His Ser Gly Ser Gly Ser Lys Ser Ser Gly

-continued

```
1               5                   10                  15
Pro Pro Pro Pro Ser Gly Ser Ser Gly Asn Glu Ala Gly Ala Gly Ala
                20                  25                  30

Ala Ala Pro Ala Ser Gln His Pro Met Thr Gly Thr Gly Ala Val Gln
                35                  40                  45

Thr Glu Ala Met Lys Gln Ile Leu Gly Val Ile Asp Lys Lys Leu Arg
    50                  55                  60

Asn Leu Glu Lys Lys Gly Lys Leu Asp Asp Tyr Gln Glu Arg Met
65                  70                  75                  80

Asn Lys Gly Glu Arg Leu Asn Gln Asp Gln Leu Asp Ala Val Ser Lys
                85                  90                  95

Tyr Gln Glu Val Thr Asn Asn Leu Glu Phe Ala Lys Glu Leu Gln Arg
                100                 105                 110

Ser Phe Met Ala Leu Ser Gln Asp Ile Gln Lys Thr Ile Lys Lys Thr
            115                 120                 125

Ala Arg Arg Glu Gln Leu Met Arg Glu Ala Glu Gln Lys Arg Leu
            130                 135                 140

Lys Thr Val Leu Glu Leu Gln Tyr Val Leu Asp Lys Leu Gly Asp Asp
145                 150                 155                 160

Glu Val Arg Thr Asp Leu Lys Gln Gly Leu Asn Gly Val Pro Ile Leu
                165                 170                 175

Ser Glu Glu Glu Leu Ser Leu Leu Asp Glu Phe Tyr Lys Leu Ala Asp
                180                 185                 190

Pro Glu Arg Asp Met Ser Leu Arg Leu Asn Glu Gln Tyr Glu His Ala
            195                 200                 205

Ser Ile His Leu Trp Asp Leu Leu Glu Gly Lys Glu Lys Pro Val Cys
        210                 215                 220

Gly Thr Thr Tyr Lys Ala Leu Lys Glu Ile Val Glu Arg Val Phe Gln
225                 230                 235                 240

Ser Asn Tyr Phe Asp Ser Thr His Asn His Gln Asn Gly Leu Cys Glu
                245                 250                 255

Glu Glu Glu Ala Ala Ser Ala Pro Thr Val Glu Asp Gln Ala Ala Glu
                260                 265                 270

Ala Glu Pro Glu Pro Val Glu Glu Tyr Thr Glu Gln Asn Glu Val Glu
            275                 280                 285

Ser Thr Glu Tyr Val Asn Arg Gln Phe Met Ala Glu Thr Gln Phe Ser
    290                 295                 300

Ser Gly Glu Lys Glu Gln Val Asp Asp Trp Thr Val Glu Thr Val Glu
305                 310                 315                 320

Val Val Asn Ser Leu Gln Gln Gln Pro Gln Ala Ala Ser Pro Ser Val
                325                 330                 335

Pro Glu Pro His Ser Leu Thr Pro Val Ala Gln Ala Asp Pro Leu Val
            340                 345                 350

Arg Arg Gln Arg Val Gln Asp Leu Met Ala Gln Met Gln Gly Pro Tyr
            355                 360                 365

Asn Phe Ile Gln Asp Ser Met Leu Asp Phe Glu Asn Gln Thr Leu Asp
        370                 375                 380

Pro Ala Ile Val Ser Ala Gln Pro Met Asn Pro Ala Gln Asn Met Asp
385                 390                 395                 400

Ile Pro Gln Leu Val Cys Pro Pro Val His Ser Glu Ser Arg Leu Ala
                405                 410                 415

Gln Pro Asn Gln Val Ser Val Gln Pro Glu Ala Thr Gln Val Pro Leu
                420                 425                 430
```

```
Val Ser Ser Thr Ser Glu Gly Tyr Thr Ala Ser Gln Pro Leu Tyr Gln
        435                 440                 445

Pro Ser His Ala Thr Asp Gln Arg Pro Gln Lys Glu Pro Ile Asp Gln
    450                 455                 460

Ile Gln Ala Thr Ile Ser Leu Asn Thr Asp Gln Thr Thr Ala Ser Ser
465                 470                 475                 480

Ser Leu Pro Ala Ala Ser Gln Pro Gln Val Phe Gln Ala Gly Thr Ser
                485                 490                 495

Lys Pro Leu His Ser Ser Gly Ile Asn Val Asn Ala Ala Pro Phe Gln
            500                 505                 510

Ser Met Gln Thr Val Phe Asn Met Asn Ala Pro Val Pro Pro Val Asn
        515                 520                 525

Glu Pro Glu Thr Leu Lys Gln Gln Asn Gln Tyr Gln Ala Ser Tyr Asn
    530                 535                 540

Gln Ser Phe Ser Ser Gln Pro His Gln Val Glu Gln Thr Glu Leu Gln
545                 550                 555                 560

Gln Glu Gln Leu Gln Thr Val Val Gly Thr Tyr His Gly Ser Gln Asp
                565                 570                 575

Gln Pro His Gln Val Thr Gly Asn His Gln Gln Pro Pro Gln Gln Asn
            580                 585                 590

Thr Gly Phe Pro Arg Ser Asn Gln Pro Tyr Tyr Asn Ser Arg Gly Val
        595                 600                 605

Ser Arg Gly Gly Ser Arg Gly Ala Arg Gly Leu Met Asn Gly Tyr Arg
    610                 615                 620

Gly Pro Ala Asn Gly Phe Arg Gly Gly Tyr Asp Gly Tyr Arg Pro Ser
625                 630                 635                 640

Phe Ser Thr Asn Thr Pro Asn Ser Gly Tyr Thr Gln Ser Gln Phe Ser
                645                 650                 655

Ala Pro Arg Asp Tyr Ser Gly Tyr Gln Arg Asp Gly Tyr Gln Gln Asn
            660                 665                 670

Phe Lys Arg Gly Ser Gly Gln Ser Gly Pro Arg Gly Ala Pro Arg Gly
        675                 680                 685

Arg Gly Gly Pro Pro Arg Pro Asn Arg Gly Met Pro Gln Met Asn Thr
    690                 695                 700

Gln Gln Val Asn
705

<210> SEQ ID NO 17
<211> LENGTH: 3150
<212> TYPE: DNA
<213> ORGANISM: Equus caballus
<220> FEATURE:
<221> NAME/KEY: CDS
<222> LOCATION: (1)..(1917)
<223> OTHER INFORMATION:

<400> SEQUENCE: 17 atg gag ggc aag ctc gat gat tac caa gag cga atg aac aaa gga gaa      48
Met Glu Gly Lys Leu Asp Asp Tyr Gln Glu Arg Met Asn Lys Gly Glu
1               5                   10                  15 agg ctt aat cag gat cag ctg gat gct gtg tct aag tac cag gaa gtc      96
Arg Leu Asn Gln Asp Gln Leu Asp Ala Val Ser Lys Tyr Gln Glu Val
            20                  25                  30 aca aat aac ttg gag ttt gcg aaa gaa ttg cag agg agt ttc atg gcg     144
Thr Asn Asn Leu Glu Phe Ala Lys Glu Leu Gln Arg Ser Phe Met Ala
        35                  40                  45
```

-continued

| | | |
|---|---|---|
| ttg agt cag gat att cag aaa aca ata aag aag acg gca cgt cgg gag<br>Leu Ser Gln Asp Ile Gln Lys Thr Ile Lys Lys Thr Ala Arg Arg Glu<br>50              55              60 | 192 | |
| cag ctt atg aga gaa gaa gct gaa cag aaa cgt tta aaa act gta ctt<br>Gln Leu Met Arg Glu Glu Ala Glu Gln Lys Arg Leu Lys Thr Val Leu<br>65              70              75              80 | 240 | |
| gag ctg cag tat gtt ttg gac aaa ttg gga gat gaa gaa gtg cga act<br>Glu Leu Gln Tyr Val Leu Asp Lys Leu Gly Asp Glu Glu Val Arg Thr<br>85              90              95 | 288 | |
| gac ctg aaa caa ggt ttg aat gga gtg cca ata ctc tct gaa gaa gag<br>Asp Leu Lys Gln Gly Leu Asn Gly Val Pro Ile Leu Ser Glu Glu Glu<br>100             105             110 | 336 | |
| ttg tcg ctg ttg gat gag ttc tac aag tta gca gac cct gta cgg gac<br>Leu Ser Leu Leu Asp Glu Phe Tyr Lys Leu Ala Asp Pro Val Arg Asp<br>115             120             125 | 384 | |
| atg agc ttg agg ttg aat gag cag tat gag cat gcc tcc att cac ctg<br>Met Ser Leu Arg Leu Asn Glu Gln Tyr Glu His Ala Ser Ile His Leu<br>130             135             140 | 432 | |
| tgg gac ttg ctg gaa ggg aag gaa aaa tct gtc tgt gga aca acc tat<br>Trp Asp Leu Leu Glu Gly Lys Glu Lys Ser Val Cys Gly Thr Thr Tyr<br>145             150             155             160 | 480 | |
| aaa gct ctg agg gaa att gtt gag cgt gtt ttc cag tcc aac tac ttt<br>Lys Ala Leu Arg Glu Ile Val Glu Arg Val Phe Gln Ser Asn Tyr Phe<br>165             170             175 | 528 | |
| gac agc acc cac aac cac cag aat ggg ctc tgt gag gag gaa gag gct<br>Asp Ser Thr His Asn His Gln Asn Gly Leu Cys Glu Glu Glu Glu Ala<br>180             185             190 | 576 | |
| acc tca gct cca aca gct gaa gac cag gga gct gaa gct gaa cct gag<br>Thr Ser Ala Pro Thr Ala Glu Asp Gln Gly Ala Glu Ala Glu Pro Glu<br>195             200             205 | 624 | |
| cca gca gaa gaa tac act gaa caa agt gaa gtt gaa tca aca gag tat<br>Pro Ala Glu Glu Tyr Thr Glu Gln Ser Glu Val Glu Ser Thr Glu Tyr<br>210             215             220 | 672 | |
| gta aat aga cag ttt atg gca gaa gcg cag ttc agt ggt gag aag gag<br>Val Asn Arg Gln Phe Met Ala Glu Ala Gln Phe Ser Gly Glu Lys Glu<br>225             230             235             240 | 720 | |
| cag gtg gat gag tgg aca gtc gag acg gtc gag gtg gta aat tca ctc<br>Gln Val Asp Glu Trp Thr Val Glu Thr Val Glu Val Val Asn Ser Leu<br>245             250             255 | 768 | |
| cag cag caa cct cag gct gca tct cct tca gta ccg gag ccc cac tct<br>Gln Gln Gln Pro Gln Ala Ala Ser Pro Ser Val Pro Glu Pro His Ser<br>260             265             270 | 816 | |
| ttg act cca gtg gct cag gca gat ccc ctt gtg aga aga cag cga gta<br>Leu Thr Pro Val Ala Gln Ala Asp Pro Leu Val Arg Arg Gln Arg Val<br>275             280             285 | 864 | |
| cag gac ctt atg gcg caa atg cag ggg ccc tat aat ttc ata cag gat<br>Gln Asp Leu Met Ala Gln Met Gln Gly Pro Tyr Asn Phe Ile Gln Asp<br>290             295             300 | 912 | |
| tca atg ctg gat ttt gaa aac cag aca ctt gat cct gcc att gta tct<br>Ser Met Leu Asp Phe Glu Asn Gln Thr Leu Asp Pro Ala Ile Val Ser<br>305             310             315             320 | 960 | |
| gca cag cct atg aat cca gca cag aat atg gac atg ccc cag ctg gtt<br>Ala Gln Pro Met Asn Pro Ala Gln Asn Met Asp Met Pro Gln Leu Val<br>325             330             335 | 1008 | |
| tgc cct cca gtt cat gct gaa tct aga ctt gct caa cct aat caa gtt<br>Cys Pro Pro Val His Ala Glu Ser Arg Leu Ala Gln Pro Asn Gln Val<br>340             345             350 | 1056 | |
| cct gta caa cca gaa gct aca cag gtt cct ttg gtt tca tcc aca agt<br>Pro Val Gln Pro Glu Ala Thr Gln Val Pro Leu Val Ser Ser Thr Ser<br>355             360             365 | 1104 | |

| | | | | | | | | | | | | | | | |
|---|---|---|---|---|---|---|---|---|---|---|---|---|---|---|---|
| gag | ggg | tat | aca | gca | tct | cag | ccc | ttg | tac | cag | cct | tct | cat | gct | aca | 1152 |
| Glu | Gly | Tyr | Thr | Ala | Ser | Gln | Pro | Leu | Tyr | Gln | Pro | Ser | His | Ala | Thr | |
| | 370 | | | | 375 | | | | | 380 | | | | | | |

| gag | caa | cga | ccg | caa | aag | gaa | ccg | act | gac | cag | atc | cag | gca | aca | atc | 1200 |
| Glu | Gln | Arg | Pro | Gln | Lys | Glu | Pro | Thr | Asp | Gln | Ile | Gln | Ala | Thr | Ile | |
| 385 | | | | | 390 | | | | | 395 | | | | | 400 | |

| tct | tta | aat | aca | gac | cag | act | aca | gca | tca | tca | tcc | ctt | cct | gct | gct | 1248 |
| Ser | Leu | Asn | Thr | Asp | Gln | Thr | Thr | Ala | Ser | Ser | Ser | Leu | Pro | Ala | Ala | |
| | | | | 405 | | | | | 410 | | | | | 415 | | |

| tct | cag | cct | cag | gtg | ttc | cag | gct | ggg | aca | agc | aaa | cct | tta | cac | agc | 1296 |
| Ser | Gln | Pro | Gln | Val | Phe | Gln | Ala | Gly | Thr | Ser | Lys | Pro | Leu | His | Ser | |
| | | | 420 | | | | | 425 | | | | | 430 | | | |

| agt | ggg | atc | aat | gta | aat | gca | gcg | cca | ttc | cag | tcc | atg | caa | acg | gtg | 1344 |
| Ser | Gly | Ile | Asn | Val | Asn | Ala | Ala | Pro | Phe | Gln | Ser | Met | Gln | Thr | Val | |
| | | | 435 | | | | | 440 | | | | | 445 | | | |

| ttc | aac | atg | aat | gcc | ccg | gtt | cct | cct | gtt | aat | gaa | cca | gaa | act | tta | 1392 |
| Phe | Asn | Met | Asn | Ala | Pro | Val | Pro | Pro | Val | Asn | Glu | Pro | Glu | Thr | Leu | |
| | 450 | | | | | 455 | | | | | 460 | | | | | |

| aaa | cag | caa | aat | cag | tac | cag | gcc | agc | tat | aac | cag | agc | ttt | tcc | agt | 1440 |
| Lys | Gln | Gln | Asn | Gln | Tyr | Gln | Ala | Ser | Tyr | Asn | Gln | Ser | Phe | Ser | Ser | |
| 465 | | | | | 470 | | | | | 475 | | | | | 480 | |

| ccg | cct | cac | caa | gta | gag | cag | aca | gag | ctt | ccg | caa | gag | cag | ctt | cag | 1488 |
| Pro | Pro | His | Gln | Val | Glu | Gln | Thr | Glu | Leu | Pro | Gln | Glu | Gln | Leu | Gln | |
| | | | | 485 | | | | | 490 | | | | | 495 | | |

| acg | gtg | gtt | ggt | act | tac | cat | gct | tcc | caa | gac | cag | ccc | cat | caa | gtg | 1536 |
| Thr | Val | Val | Gly | Thr | Tyr | His | Ala | Ser | Gln | Asp | Gln | Pro | His | Gln | Val | |
| | | | | 500 | | | | | 505 | | | | | 510 | | |

| acc | ggt | aac | cac | cag | cag | cct | ccc | cag | cag | aac | act | ggg | ttt | cca | cgt | 1584 |
| Thr | Gly | Asn | His | Gln | Gln | Pro | Pro | Gln | Gln | Asn | Thr | Gly | Phe | Pro | Arg | |
| | | | 515 | | | | | 520 | | | | | 525 | | | |

| agc | agt | cag | ccc | tat | tac | aac | agt | cgt | ggt | gtg | tct | cgt | gga | ggc | tcc | 1632 |
| Ser | Ser | Gln | Pro | Tyr | Tyr | Asn | Ser | Arg | Gly | Val | Ser | Arg | Gly | Gly | Ser | |
| | | | | 530 | | | | | 535 | | | | | 540 | | |

| cgt | ggt | gct | aga | ggc | ttg | atg | aat | gga | tac | agg | ggc | cct | gcc | aat | gga | 1680 |
| Arg | Gly | Ala | Arg | Gly | Leu | Met | Asn | Gly | Tyr | Arg | Gly | Pro | Ala | Asn | Gly | |
| 545 | | | | | 550 | | | | | 555 | | | | | 560 | |

| ttc | aga | gga | gga | tat | gat | ggt | tac | cgc | cct | tcg | ttc | tct | aac | act | cca | 1728 |
| Phe | Arg | Gly | Gly | Tyr | Asp | Gly | Tyr | Arg | Pro | Ser | Phe | Ser | Asn | Thr | Pro | |
| | | | | 565 | | | | | 570 | | | | | 575 | | |

| aac | agc | ggt | tac | aca | cag | tct | cag | ttc | agt | gct | ccc | cgg | gac | tac | tct | 1776 |
| Asn | Ser | Gly | Tyr | Thr | Gln | Ser | Gln | Phe | Ser | Ala | Pro | Arg | Asp | Tyr | Ser | |
| | | | 580 | | | | | 585 | | | | | 590 | | | |

| ggc | tat | cag | cgg | gat | gga | tat | cag | cag | aat | ttc | aag | cga | ggc | tct | ggg | 1824 |
| Gly | Tyr | Gln | Arg | Asp | Gly | Tyr | Gln | Gln | Asn | Phe | Lys | Arg | Gly | Ser | Gly | |
| | | 595 | | | | | 600 | | | | | 605 | | | | |

| cag | agt | gga | ccc | cgg | gga | gcc | cca | cga | ggt | cgt | gga | ggg | ccc | cca | aga | 1872 |
| Gln | Ser | Gly | Pro | Arg | Gly | Ala | Pro | Arg | Gly | Arg | Gly | Gly | Pro | Pro | Arg | |
| | | 610 | | | | | 615 | | | | | 620 | | | | |

| ccc | aac | aga | ggg | atg | ccg | caa | atg | aac | act | cag | caa | gtg | aat | taa | | 1917 |
| Pro | Asn | Arg | Gly | Met | Pro | Gln | Met | Asn | Thr | Gln | Gln | Val | Asn | | | |
| 625 | | | | 630 | | | | | 635 | | | | | | | |

| tctgattcac | aggattatct | ttaatcgcca | aaacacactg | gccagtgtac | cataatatgt | 1977 |
| taccagaaga | gttattatct | atttgttctc | cctttcagga | aacttattgt | aaagggactg | 2037 |
| ttttcatccc | ataaagacag | gactacagtt | gtcagcttta | tattacctgg | atatggaagg | 2097 |
| aaactatttt | tactctgcat | gttctgtcct | aagcgtcatc | ttgagccttg | cacatgatac | 2157 |
| tcagattcct | ttcccttgct | taggagtaaa | acataatata | ctttatgggg | tgataatatc | 2217 |

```
tccatagtta tttgaagtgg cttggaaaaa gcaagattga cttttgacat tggataaaat    2277
ctacaaatca gccctagagt ttcatggtca ttcacaaaac taaaatattt cccttgaaag    2337
gaagatggaa ggactggagt gtggtttggc agaacaactg catttcacag cttttcctat    2397
taaattggag cactgaatgt taaatgcata ccaaattatg catgggccct taatcacaca    2457
tacatggcta ccagctttga cacagcacta ttcatcctct ggccaaacga ctgtggttaa    2517
aaacacgtgt aaattgcttt ttaacagctg atactgtaaa agacaaagct aaaatgcaaa    2577
attaggcttt cattggcact tttcgaaaaa tatgcaacaa atttgggatg taatctggat    2637
ggccacttct gtacttaatg tgaagtattt agatacctttt ttgaacactt aacagtttct    2697
tcgacaatga cttttgtaag gattggtagt atatatcatt ccttatgaca tacattgtct    2757
gttgctaatc cttggatctt gctgtattgt cacctaaatt ggtacaggta ctgatgaaaa    2817
tctctcatgg ataaacctaa cactcttcgt cacatgtttt tcctgcagcc tgaaggtttt    2877
taaaaggaaa agatatcaaa tgcctgctgc taccaccctt ttaaattgct atcttttgaa    2937
aagcaccagt atgtgttttt agattgattt ccctatttta gggaaatgac agtcagtagt    2997
ttcagttctg atggtataag caaagcaaat aaaacgtgtt tataaaagtt gtatcttgaa    3057
acactggtgt tcaacagcta gcagcttctg tggttcaccc cctgccttgt tagtgttacc    3117
catttatggt tatctccagc agcaatttct cta                                 3150
```

<210> SEQ ID NO 18
<211> LENGTH: 638
<212> TYPE: PRT
<213> ORGANISM: Equus caballus

<400> SEQUENCE: 18

```
Met Glu Gly Lys Leu Asp Asp Tyr Gln Glu Arg Met Asn Lys Gly Glu
1               5                   10                  15

Arg Leu Asn Gln Asp Gln Leu Asp Ala Val Ser Lys Tyr Gln Glu Val
            20                  25                  30

Thr Asn Asn Leu Glu Phe Ala Lys Glu Leu Gln Arg Ser Phe Met Ala
        35                  40                  45

Leu Ser Gln Asp Ile Gln Lys Thr Ile Lys Lys Thr Ala Arg Arg Glu
    50                  55                  60

Gln Leu Met Arg Glu Glu Ala Glu Gln Lys Arg Leu Lys Thr Val Leu
65                  70                  75                  80

Glu Leu Gln Tyr Val Leu Asp Lys Leu Gly Asp Glu Glu Val Arg Thr
                85                  90                  95

Asp Leu Lys Gln Gly Leu Asn Gly Val Pro Ile Leu Ser Glu Glu Glu
            100                 105                 110

Leu Ser Leu Leu Asp Glu Phe Tyr Lys Leu Ala Asp Pro Val Arg Asp
        115                 120                 125

Met Ser Leu Arg Leu Asn Glu Gln Tyr Glu His Ala Ser Ile His Leu
    130                 135                 140

Trp Asp Leu Leu Glu Gly Lys Glu Lys Ser Val Cys Gly Thr Thr Tyr
145                 150                 155                 160

Lys Ala Leu Arg Glu Ile Val Glu Arg Val Phe Gln Ser Asn Tyr Phe
                165                 170                 175

Asp Ser Thr His Asn His Gln Asn Gly Leu Cys Glu Glu Glu Glu Ala
            180                 185                 190

Thr Ser Ala Pro Thr Ala Glu Asp Gln Gly Ala Glu Ala Glu Pro Glu
        195                 200                 205
```

-continued

```
Pro Ala Glu Glu Tyr Thr Glu Gln Ser Glu Val Glu Ser Thr Glu Tyr
    210                 215                 220

Val Asn Arg Gln Phe Met Ala Glu Ala Gln Phe Ser Gly Glu Lys Glu
225                 230                 235                 240

Gln Val Asp Glu Trp Thr Val Glu Thr Val Glu Val Val Asn Ser Leu
                245                 250                 255

Gln Gln Gln Pro Gln Ala Ala Ser Pro Ser Val Pro Glu Pro His Ser
            260                 265                 270

Leu Thr Pro Val Ala Gln Ala Asp Pro Leu Val Arg Arg Gln Arg Val
        275                 280                 285

Gln Asp Leu Met Ala Gln Met Gln Gly Pro Tyr Asn Phe Ile Gln Asp
    290                 295                 300

Ser Met Leu Asp Phe Glu Asn Gln Thr Leu Asp Pro Ala Ile Val Ser
305                 310                 315                 320

Ala Gln Pro Met Asn Pro Ala Gln Asn Met Asp Met Pro Gln Leu Val
                325                 330                 335

Cys Pro Pro Val His Ala Glu Ser Arg Leu Ala Gln Pro Asn Gln Val
            340                 345                 350

Pro Val Gln Pro Glu Ala Thr Gln Val Pro Leu Val Ser Ser Thr Ser
        355                 360                 365

Glu Gly Tyr Thr Ala Ser Gln Pro Leu Tyr Gln Pro Ser His Ala Thr
    370                 375                 380

Glu Gln Arg Pro Gln Lys Glu Pro Thr Asp Gln Ile Gln Ala Thr Ile
385                 390                 395                 400

Ser Leu Asn Thr Asp Gln Thr Thr Ala Ser Ser Leu Pro Ala Ala
                405                 410                 415

Ser Gln Pro Gln Val Phe Gln Ala Gly Thr Ser Lys Pro Leu His Ser
        420                 425                 430

Ser Gly Ile Asn Val Asn Ala Ala Pro Phe Gln Ser Met Gln Thr Val
    435                 440                 445

Phe Asn Met Asn Ala Pro Val Pro Pro Val Asn Glu Pro Glu Thr Leu
450                 455                 460

Lys Gln Gln Asn Gln Tyr Gln Ala Ser Tyr Asn Gln Ser Phe Ser Ser
465                 470                 475                 480

Pro Pro His Gln Val Glu Gln Thr Glu Leu Pro Gln Glu Gln Leu Gln
                485                 490                 495

Thr Val Val Gly Thr Tyr His Ala Ser Gln Asp Gln Pro His Gln Val
        500                 505                 510

Thr Gly Asn His Gln Gln Pro Pro Gln Gln Asn Thr Gly Phe Pro Arg
    515                 520                 525

Ser Ser Gln Pro Tyr Tyr Asn Ser Arg Gly Val Ser Arg Gly Gly Ser
530                 535                 540

Arg Gly Ala Arg Gly Leu Met Asn Gly Tyr Arg Gly Pro Ala Asn Gly
545                 550                 555                 560

Phe Arg Gly Gly Tyr Asp Gly Tyr Arg Pro Ser Phe Ser Asn Thr Pro
                565                 570                 575

Asn Ser Gly Tyr Thr Gln Ser Gln Phe Ser Ala Pro Arg Asp Tyr Ser
            580                 585                 590

Gly Tyr Gln Arg Asp Gly Tyr Gln Asn Phe Lys Arg Gly Ser Gly
        595                 600                 605

Gln Ser Gly Pro Arg Gly Ala Pro Arg Gly Arg Gly Pro Pro Arg
    610                 615                 620

Pro Asn Arg Gly Met Pro Gln Met Asn Thr Gln Gln Val Asn
```

<210> SEQ ID NO 19
<211> LENGTH: 6181
<212> TYPE: DNA
<213> ORGANISM: Mus musculus
<220> FEATURE:
<221> NAME/KEY: CDS
<222> LOCATION: (179)..(2302)
<223> OTHER INFORMATION:

<400> SEQUENCE: 19

```
gctggctggc taagtccctc ccgcgccggc tcttgtccca ctaggagcag ctcagagccg      60
cggggacagg gcgaagcggc ctgcgcccac ggagcgcacg tctctgttct caacgcagca     120
ccacccttgc cccctcggc tgcccactcc agacgtccag cggctccgcg cgcgcacg       178 atg ccc tcg gcc acc agc cac agc gga agc ggc agc aaa tcg tcg gga      226
Met Pro Ser Ala Thr Ser His Ser Gly Ser Gly Ser Lys Ser Ser Gly
1               5                   10                  15 ccg ccg ccg ccg tcc ggt tcc tcc ggg agt gag gcg gcg gcc ggg gca      274
Pro Pro Pro Pro Ser Gly Ser Ser Gly Ser Glu Ala Ala Ala Gly Ala
                20                  25                  30 gct gcg ccg gct tct cag cat ccg gca acc ggc acc ggc gcc gtc cag      322
Ala Ala Pro Ala Ser Gln His Pro Ala Thr Gly Thr Gly Ala Val Gln
            35                  40                  45 acc gag gcc atg aag cag att ctc ggc gta atc gac aag aaa ctt cgg      370
Thr Glu Ala Met Lys Gln Ile Leu Gly Val Ile Asp Lys Lys Leu Arg
        50                  55                  60 aac ctg gag aag aaa aag ggt aaa ctt gat gat tac cag gaa cga atg      418
Asn Leu Glu Lys Lys Lys Gly Lys Leu Asp Asp Tyr Gln Glu Arg Met
65                  70                  75                  80 aat aaa ggg gaa agg ctc aat caa gac cag ctg gat gcc gta tct aag      466
Asn Lys Gly Glu Arg Leu Asn Gln Asp Gln Leu Asp Ala Val Ser Lys
                85                  90                  95 tac cag gaa gtc aca aat aat ttg gag ttt gca aag gaa tta cag agg      514
Tyr Gln Glu Val Thr Asn Asn Leu Glu Phe Ala Lys Glu Leu Gln Arg
                100                 105                 110 agt ttc atg gca tta agt caa gat att cag aaa aca ata aag aag aca      562
Ser Phe Met Ala Leu Ser Gln Asp Ile Gln Lys Thr Ile Lys Lys Thr
            115                 120                 125 gca cgt cgg gaa cag ctt atg aga gaa gaa gca gaa cag aag cgc tta      610
Ala Arg Arg Glu Gln Leu Met Arg Glu Glu Ala Glu Gln Lys Arg Leu
        130                 135                 140 aaa act gta ctt gag tta cag tat gta ttg gat aag ctg gga gat gat      658
Lys Thr Val Leu Glu Leu Gln Tyr Val Leu Asp Lys Leu Gly Asp Asp
145                 150                 155                 160 gat gtg aga aca gat ctg aaa caa ggt ttg agt gga gtg cca ata ttg      706
Asp Val Arg Thr Asp Leu Lys Gln Gly Leu Ser Gly Val Pro Ile Leu
                165                 170                 175 tct gag gag gag ttg tca ttg ctg gat gag ttc tac aag ctc gta gat      754
Ser Glu Glu Glu Leu Ser Leu Leu Asp Glu Phe Tyr Lys Leu Val Asp
                180                 185                 190 cct gag cgt gac atg agt tta agg tta aat gag cag tat gaa cat gcc      802
Pro Glu Arg Asp Met Ser Leu Arg Leu Asn Glu Gln Tyr Glu His Ala
            195                 200                 205 tca att cac ttg tgg gat ttg ctg gaa ggg aaa gaa aag cct gtg tgt      850
Ser Ile His Leu Trp Asp Leu Leu Glu Gly Lys Glu Lys Pro Val Cys
        210                 215                 220 gga aca acc tat aaa gct cta aag gaa att gtt gag cgt gtt ttc cag      898
Gly Thr Thr Tyr Lys Ala Leu Lys Glu Ile Val Glu Arg Val Phe Gln
225                 230                 235                 240
```

```
tca aac tac ttt gat agc act cac aat cat caa aat ggg ttg tgt gag    946
Ser Asn Tyr Phe Asp Ser Thr His Asn His Gln Asn Gly Leu Cys Glu
                245                 250                 255 gag gaa gag gcg gct tca gcg ccc aca gtg gag gac cag gta gct gaa    994
Glu Glu Glu Ala Ala Ser Ala Pro Thr Val Glu Asp Gln Val Ala Glu
            260                 265                 270 gct gaa cct gag cca gcg gaa gaa tac aca gag caa agt gag gtt gaa   1042
Ala Glu Pro Glu Pro Ala Glu Glu Tyr Thr Glu Gln Ser Glu Val Glu
        275                 280                 285 tca aca gag tat gtc aat agg cag ttc atg gca gaa aca cag ttc agc   1090
Ser Thr Glu Tyr Val Asn Arg Gln Phe Met Ala Glu Thr Gln Phe Ser
    290                 295                 300 agt ggt gag aag gag caa gtg gat gag tgg aca gtt gaa aca gtt gag   1138
Ser Gly Glu Lys Glu Gln Val Asp Glu Trp Thr Val Glu Thr Val Glu
305                 310                 315                 320 gtt gta aac tca ctc cag cag caa cct cag gct gcg tcc cct tca gtc   1186
Val Val Asn Ser Leu Gln Gln Gln Pro Gln Ala Ala Ser Pro Ser Val
                325                 330                 335 cca gag ccc cac tct ttg act cca gtg gct cag tca gat cca ctt gtg   1234
Pro Glu Pro His Ser Leu Thr Pro Val Ala Gln Ser Asp Pro Leu Val
            340                 345                 350 aga agg cag cgt gta caa gat ctt atg gca caa atg caa ggg ccc tat   1282
Arg Arg Gln Arg Val Gln Asp Leu Met Ala Gln Met Gln Gly Pro Tyr
        355                 360                 365 aat ttc ata cag gat tca atg ttg gat ttt gaa aat cag acg ctt gat   1330
Asn Phe Ile Gln Asp Ser Met Leu Asp Phe Glu Asn Gln Thr Leu Asp
    370                 375                 380 cct gcc att gta tcc gca cag cct atg aac cct acc cag aac atg gat   1378
Pro Ala Ile Val Ser Ala Gln Pro Met Asn Pro Thr Gln Asn Met Asp
385                 390                 395                 400 atg cct cag ctg gtt tgc cct cag gtt cat tct gaa tct aga ctt gcc   1426
Met Pro Gln Leu Val Cys Pro Gln Val His Ser Glu Ser Arg Leu Ala
                405                 410                 415 caa tct aat caa gtt cct gta caa cca gaa gcc aca cag gtt cct ttg   1474
Gln Ser Asn Gln Val Pro Val Gln Pro Glu Ala Thr Gln Val Pro Leu
            420                 425                 430 gtt tca tcc aca agt gag ggg tat aca gca tct cag ccc ttg tac cag   1522
Val Ser Ser Thr Ser Glu Gly Tyr Thr Ala Ser Gln Pro Leu Tyr Gln
        435                 440                 445 cca tct cat gct acg gag cag cgg ccg cag aaa gag cca atg gat cag   1570
Pro Ser His Ala Thr Glu Gln Arg Pro Gln Lys Glu Pro Met Asp Gln
    450                 455                 460 att cag gca aca ata tct ttg aat aca gac cag act aca gca tcc tca   1618
Ile Gln Ala Thr Ile Ser Leu Asn Thr Asp Gln Thr Thr Ala Ser Ser
465                 470                 475                 480 tcc ctt cct gct gct tct cag cct caa gtg ttc cag gct ggg aca agt   1666
Ser Leu Pro Ala Ala Ser Gln Pro Gln Val Phe Gln Ala Gly Thr Ser
                485                 490                 495 aaa cct ttg cac agc agt gga atc aat gta aat gca gct cca ttc cag   1714
Lys Pro Leu His Ser Ser Gly Ile Asn Val Asn Ala Ala Pro Phe Gln
            500                 505                 510 tcc atg caa acg gtg ttc aat atg aat gct cca gtc cct cct gct aat   1762
Ser Met Gln Thr Val Phe Asn Met Asn Ala Pro Val Pro Pro Ala Asn
        515                 520                 525 gaa cca gaa acg tta aaa caa cag agt cag tac cag gcc act tat aac   1810
Glu Pro Glu Thr Leu Lys Gln Gln Ser Gln Tyr Gln Ala Thr Tyr Asn
    530                 535                 540 cag agt ttt tcc agt cag cct cac caa gtg gaa caa aca gag ctt caa   1858
Gln Ser Phe Ser Ser Gln Pro His Gln Val Glu Gln Thr Glu Leu Gln
```

```
                  545                  550                  555                  560
caa gac caa ctg caa acg gtg gtt ggc act tac cat gga tcc cag gac           1906
Gln Asp Gln Leu Gln Thr Val Val Gly Thr Tyr His Gly Ser Gln Asp
                565                  570                  575 cag cct cat caa gtg cct ggt aac cac cag caa ccc cca cag cag aac           1954
Gln Pro His Gln Val Pro Gly Asn His Gln Gln Pro Pro Gln Gln Asn
            580                  585                  590 act ggc ttt cca cgt agc agt cag cct tat tac aac agt cgt ggg gta           2002
Thr Gly Phe Pro Arg Ser Ser Gln Pro Tyr Tyr Asn Ser Arg Gly Val
        595                  600                  605 tct cga gga ggg tct cgt ggt gcc aga ggc ttg atg aat gga tac agg           2050
Ser Arg Gly Gly Ser Arg Gly Ala Arg Gly Leu Met Asn Gly Tyr Arg
    610                  615                  620 ggc cct gcc aat gga ttt aga gga gga tat gat ggt tac cgc cct tca           2098
Gly Pro Ala Asn Gly Phe Arg Gly Gly Tyr Asp Gly Tyr Arg Pro Ser
625                  630                  635                  640 ttc tcg aac act cca aac agt ggt tat tca cag tct cag ttc act gct           2146
Phe Ser Asn Thr Pro Asn Ser Gly Tyr Ser Gln Ser Gln Phe Thr Ala
                645                  650                  655 ccc cgg gac tac tct ggt tac cag cgg gat gga tat cag cag aat ttc           2194
Pro Arg Asp Tyr Ser Gly Tyr Gln Arg Asp Gly Tyr Gln Gln Asn Phe
            660                  665                  670 aag cga ggc tct ggg cag agt gga cca cgg gga gcc cca cga ggt cgt           2242
Lys Arg Gly Ser Gly Gln Ser Gly Pro Arg Gly Ala Pro Arg Gly Arg
        675                  680                  685 gga ggg ccc cca aga ccc aac aga ggg atg ccg caa atg aac act cag           2290
Gly Gly Pro Pro Arg Pro Asn Arg Gly Met Pro Gln Met Asn Thr Gln
    690                  695                  700 caa gtg aat taa tgtgatacac aggattatgt ttaatcgcca aaaacacact              2342
Gln Val Asn
705 ggccagtgta ccataatatg ttaccagaag agttattatc tatttgttct cccttttcagg        2402 aaacttattg taaagggact gttttcatcc cataaagaca ggactgcaat tgtcagcttt        2462 acattacctg gatatggaag gaaactattt ttattctgca tgttctgtcc taagcgtcat        2522 cttgagcctt gcacacaata caatactcag attcctcacc cttgcttagg agtaaaacat        2582 tatatactta tggggtgata atatctccat agttagttga agtggcttgg aaaaaaaatg        2642 caagattgaa ttttttgacct tggataaaat ctacaatcag ccctagaact attcagtggt      2702 aattgacaaa gttaaagcat tttctttgaa aggaagatgg aaggagtgga gtgtggttta       2762 gcaaaactgc atttcatagc tttcccatta aattggagca ccgacagatt aaaagcatac       2822 caaattatgc atgggtcctt actcacacaa gtgaggctgg ctaccagcct tgacatagca       2882 ctcactagtc ttctggccaa acgactgtga ttaaaacaca tgtaaattgc tctttagtag       2942 tggatactgt gtaagacaaa gccaaattgc aaatcaggct ttgattggct cttctggaaa       3002 atatgcatca aatatggggg ataatctgga tgggctgctg ctgtgctcaa tgtgaactat       3062 ttagatacct ttggaacact taacagtttc tctgaacaat gacttacatg gggattggtc      3122 ctgtttgtca ttcctcacca taattgcatt gtcatcacta atccttggat cttgctgtat      3182 tgttactcaa attggtaata ggtactgatg gaaatcgcta atggatggat aatcataaca      3242 cttttggtca catgttttct cctgcagcct gaaagttctt aaagaaaaag atatcaaatg       3302 cctgctgcta ccacccttt aaattgctat ctttagaaaa gcaccggtat gtgttttaga       3362 ttcatttccc tgttttaggg aaatgacagg cagtagtttc agttctgatg gcaaaacaaa       3422 taaaaacatg tttctaaaag ttgtatcttg aaacactggt gttcaacagc tagcagctaa      3482
```

```
agtaattcaa cccatgcatt gctagtgtca cagcctttgg ttatgtctag tagctgtttc    3542
tgaagtattt tcatttatct tttgtcaaat ttaaccctgt ttgaattctc tccttcctc    3602 aaggagacac ttatgttcaa agtgttgatt ctttgcctta ggtgcataga gagtagacag    3662
tttggagatg gaaaggttag cagtgactta gccatatgtt ctgtgttgga atttgtgcta    3722
gcagtttgag cactagctct gcgtgcctat gaactgaatg ctgcttgtcc cattccattt    3782
tatgtcatgg agaaataatt ccacttggta acacaaaggc taagttaatg ttattttctg    3842
tacagaaatt aaattttact tttagccttt tgtaaacttt ttttttttt ttccaagccg    3902 gtatcagcta ctcaaaacaa ttctcagata ttcatcatta gacaactgga gttttgctg    3962 gttttgtagc ctactaaaac tgctgaggct gttgaacatt ccacattcaa aagttttgta    4022
gggtggtgga taatggggaa gcttcaatgt ttattttaaa ataaataaaa taagttcttg    4082 actttctca tgtgtggtta tggtacatca tattggaagg ttatctgtt tacttttgcc    4142 aagactattt tgccagcacc tacacttgtg tgctttaaaa gacaactacc tgggatgtac    4202
cacaaccata tgttaattgt attttattgg gatggataaa atgtttgtgg tttattggat    4262
aatccctaga tggtgtgtta cgtgtgtaga atataatttt atgatagtaa gaaagcaaaa    4322
ttgaagaaaa taagtttagt attgaatttg agttctgaag tgaattcagg gaatgtctca    4382
cgtttcgggc ttctacccaa agtgtagggc agaaggtgta aaagttgttt gtagtttgac    4442
ttgtttattt tttaagttgc ttattccttt caacagcaac atatcattag ctgtcattct    4502
accattgcag ttctagtgag ttttaacgtc tgcattcaag actgttttaa aagcaacctc    4562
actggacaga gaactgctaa agtcttttcc ttaagatctg agtctttgtt actcagtatc    4622
ttctataata tgcaaatgct tgtctagagg cagaagacct tttgtttggt caagtgtgta    4682
ttttaccaga gtacagggaa ctgatggtcc tacatgtctc ttagtgtagt aagactataa    4742
aatcttttgt acatgcacaa ttcacagtat gtttagatac cacgtgtata atgccccccc    4802
ctcccccagg tagcatgcca ttgatgactt tttgcttagg gccattttat taccagggcc    4862
ttaatattcc taaaaagatg attttttttc atcctttctc ctcttttgat cattgtatct    4922
tgatattaaa aacatgacct tccaatgatt gtagtaaatt aacttctata gttcttttgt    4982
ctctatatgt attcatatat atgctattgt atagagactt caaggagaca tggagatgca    5042
tgcttattct caggttcatt cactaaggtg cttggcagac aaccagtttc taagtgcaga    5102
atgtagttaa gcagcttcat atatgtgcca ggcaatttgt tttgttaaat tttcatctac    5162
ttaaggaaat agggtattgt agcttaggct gatcataccc ttcatttcaa ccttaagctc    5222
tcaacctgca tccatccgac ttgagctatt aagtacttta gttttatcga gtataagtta    5282
acagaaaaag taaattaagc tttgccttta ctattttgaa tttatataca ttctggaaaa    5342
acttagaaac tgttgtatat ttcattagat taaattatat gaaaatgtga ttgtttatag    5402
caaagcctgt gagttgcata caccctaagg aaaactcctt aagtgctcct tgaagagaga    5462
agaaacaatt ctgggtctgg tcttttaag aacaaagcta gactactgta tgttagcact    5522
gtacattaat agtctgttgt gaagcttgag cagtttcctg catagccttg atccttcacc    5582
gttggcattg aaaatagcag tatccctgat gtacttaaaa cttaaagtca ggttttggta    5642
tatttatttg taagtcttaa tttcctctaa atactatatc tctttagcga gacaacctga    5702
aatttattag cacatttggg tatctcttgc ttggcattat ggccagtgtt aactattcag    5762
tggtgaaaaa attacccctc aagacactgg agtgacccca gatgtgtgta gtaagtggca    5822
```

-continued

```
tggttcaact gtgtggttaa tgataaatat atgacttagt cggtatgatc tggaaagact    5882
tgattgaaag ataattcagc tgacataagg atgagtgagg agtggcaaac tggataaaag    5942
agtcaagaga cctgtattcc agtgactcct gttttgttta agcattagca agatctgtct    6002
ggggaaactg atagggcag ttttcttcca tgtttagttt ttgtctcaac atttggaagc     6062
tattgaaggt tttaaaatgg tgtgtattgt ttttttttgg ggggggggtg gccagaatag    6122
tgggtcatct aataaaactg ccatttaaaa gatcaaaaaa aaaaaaaaaa aaaaaaaa      6181
```

```
<210> SEQ ID NO 20
<211> LENGTH: 707
<212> TYPE: PRT
<213> ORGANISM: Mus musculus

<400> SEQUENCE: 20

Met Pro Ser Ala Thr Ser His Ser Gly Ser Gly Ser Lys Ser Ser Gly
1               5                   10                  15

Pro Pro Pro Pro Ser Gly Ser Ser Gly Ser Glu Ala Ala Gly Ala
            20                  25                  30

Ala Ala Pro Ala Ser Gln His Pro Ala Thr Gly Thr Gly Ala Val Gln
        35                  40                  45

Thr Glu Ala Met Lys Gln Ile Leu Gly Val Ile Asp Lys Lys Leu Arg
    50                  55                  60

Asn Leu Glu Lys Lys Lys Gly Lys Leu Asp Asp Tyr Gln Glu Arg Met
65                  70                  75                  80

Asn Lys Gly Glu Arg Leu Asn Gln Asp Gln Leu Asp Ala Val Ser Lys
                85                  90                  95

Tyr Gln Glu Val Thr Asn Asn Leu Glu Phe Ala Lys Glu Leu Gln Arg
            100                 105                 110

Ser Phe Met Ala Leu Ser Gln Asp Ile Gln Lys Thr Ile Lys Lys Thr
        115                 120                 125

Ala Arg Arg Glu Gln Leu Met Arg Glu Ala Glu Gln Lys Arg Leu
    130                 135                 140

Lys Thr Val Leu Glu Leu Gln Tyr Val Leu Asp Lys Leu Gly Asp Asp
145                 150                 155                 160

Asp Val Arg Thr Asp Leu Lys Gln Gly Leu Ser Gly Val Pro Ile Leu
                165                 170                 175

Ser Glu Glu Glu Leu Ser Leu Leu Asp Glu Phe Tyr Lys Leu Val Asp
            180                 185                 190

Pro Glu Arg Asp Met Ser Leu Arg Leu Asn Glu Gln Tyr Glu His Ala
        195                 200                 205

Ser Ile His Leu Trp Asp Leu Leu Glu Gly Lys Glu Lys Pro Val Cys
    210                 215                 220

Gly Thr Thr Tyr Lys Ala Leu Lys Glu Ile Val Glu Arg Val Phe Gln
225                 230                 235                 240

Ser Asn Tyr Phe Asp Ser Thr His Asn His Gln Asn Gly Leu Cys Glu
                245                 250                 255

Glu Glu Glu Ala Ala Ser Ala Pro Thr Val Glu Asp Gln Val Ala Glu
            260                 265                 270

Ala Glu Pro Glu Pro Ala Glu Glu Tyr Thr Gln Ser Glu Val Glu
        275                 280                 285

Ser Thr Glu Tyr Val Asn Arg Gln Phe Met Ala Glu Thr Gln Phe Ser
    290                 295                 300

Ser Gly Glu Lys Glu Gln Val Asp Glu Trp Thr Val Glu Thr Val Glu
305                 310                 315                 320
```

```
Val Val Asn Ser Leu Gln Gln Pro Gln Ala Ala Ser Pro Ser Val
            325                 330                 335

Pro Glu Pro His Ser Leu Thr Pro Val Ala Gln Ser Asp Pro Leu Val
            340                 345                 350

Arg Arg Gln Arg Val Gln Asp Leu Met Ala Gln Met Gln Gly Pro Tyr
            355                 360                 365

Asn Phe Ile Gln Asp Ser Met Leu Asp Phe Glu Asn Gln Thr Leu Asp
            370                 375                 380

Pro Ala Ile Val Ser Ala Gln Pro Met Asn Pro Thr Gln Asn Met Asp
385                 390                 395                 400

Met Pro Gln Leu Val Cys Pro Gln Val His Ser Glu Ser Arg Leu Ala
            405                 410                 415

Gln Ser Asn Gln Val Pro Val Gln Pro Glu Ala Thr Gln Val Pro Leu
            420                 425                 430

Val Ser Ser Thr Ser Glu Gly Tyr Thr Ala Ser Gln Pro Leu Tyr Gln
            435                 440                 445

Pro Ser His Ala Thr Glu Gln Arg Pro Gln Lys Glu Pro Met Asp Gln
            450                 455                 460

Ile Gln Ala Thr Ile Ser Leu Asn Thr Asp Gln Thr Thr Ala Ser Ser
465                 470                 475                 480

Ser Leu Pro Ala Ala Ser Gln Pro Gln Val Phe Gln Ala Gly Thr Ser
            485                 490                 495

Lys Pro Leu His Ser Ser Gly Ile Asn Val Asn Ala Ala Pro Phe Gln
            500                 505                 510

Ser Met Gln Thr Val Phe Asn Met Asn Ala Pro Val Pro Pro Ala Asn
            515                 520                 525

Glu Pro Glu Thr Leu Lys Gln Gln Ser Gln Tyr Gln Ala Thr Tyr Asn
            530                 535                 540

Gln Ser Phe Ser Ser Gln Pro His Gln Val Glu Gln Thr Glu Leu Gln
545                 550                 555                 560

Gln Asp Gln Leu Gln Thr Val Val Gly Thr Tyr His Gly Ser Gln Asp
            565                 570                 575

Gln Pro His Gln Val Pro Gly Asn His Gln Gln Pro Gln Gln Asn
            580                 585                 590

Thr Gly Phe Pro Arg Ser Ser Gln Pro Tyr Tyr Asn Ser Arg Gly Val
            595                 600                 605

Ser Arg Gly Gly Ser Arg Gly Ala Arg Gly Leu Met Asn Gly Tyr Arg
            610                 615                 620

Gly Pro Ala Asn Gly Phe Arg Gly Gly Tyr Asp Gly Tyr Arg Pro Ser
625                 630                 635                 640

Phe Ser Asn Thr Pro Asn Ser Gly Tyr Ser Gln Ser Gln Phe Thr Ala
            645                 650                 655

Pro Arg Asp Tyr Ser Gly Tyr Gln Arg Asp Gly Tyr Gln Gln Asn Phe
            660                 665                 670

Lys Arg Gly Ser Gly Gln Ser Gly Pro Arg Gly Ala Pro Arg Gly Arg
            675                 680                 685

Gly Gly Pro Pro Arg Pro Asn Arg Gly Met Pro Gln Met Asn Thr Gln
            690                 695                 700

Gln Val Asn
705

<210> SEQ ID NO 21
<211> LENGTH: 6141
```

```
<212> TYPE: DNA
<213> ORGANISM: Mus musculus
<220> FEATURE:
<221> NAME/KEY: CDS
<222> LOCATION: (139)..(2262)
<223> OTHER INFORMATION:

<400> SEQUENCE: 21
cccaccgcgc gcgcgcgtag ccgcctgccc gcccgcccgc tgcgcgtttt gtcccgcgtc      60 tctcccgtc  cgtctcctga cttgctggtc ttgtccttcc ctcccgcttt tttcctctcc     120
tctcttctcg gtctaaag atg ccc tcg gcc acc agc cac agc gga agc ggc       171
                    Met Pro Ser Ala Thr Ser His Ser Gly Ser Gly
                     1               5                      10 agc aaa tcg tcg gga ccg ccg ccg ccg tcc ggt tcc tcc ggg agt gag      219
Ser Lys Ser Ser Gly Pro Pro Pro Pro Ser Gly Ser Ser Gly Ser Glu
            15                  20                  25 gcg gcg gcc ggg gca gct gcg ccg gct tct cag cat ccg gca acc ggc      267
Ala Ala Ala Gly Ala Ala Ala Pro Ala Ser Gln His Pro Ala Thr Gly
        30                  35                  40 acc ggc gcc gtc cag acc gag gcc atg aag cag att ctc ggc gta atc      315
Thr Gly Ala Val Gln Thr Glu Ala Met Lys Gln Ile Leu Gly Val Ile
    45                  50                  55 gac aag aaa ctt cgg aac ctg gag aag aaa aag ggt aaa ctt gat gat      363
Asp Lys Lys Leu Arg Asn Leu Glu Lys Lys Lys Gly Lys Leu Asp Asp
60              65                  70                  75 tac cag gaa cga atg aat aaa ggg gaa agg ctc aat caa gac cag ctg      411
Tyr Gln Glu Arg Met Asn Lys Gly Glu Arg Leu Asn Gln Asp Gln Leu
            80                  85                  90 gat gcc gta tct aag tac cag gaa gtc aca aat aat ttg gag ttt gca      459
Asp Ala Val Ser Lys Tyr Gln Glu Val Thr Asn Asn Leu Glu Phe Ala
        95                 100                 105 aag gaa tta cag agg agt ttc atg gca tta agt caa gat att cag aaa      507
Lys Glu Leu Gln Arg Ser Phe Met Ala Leu Ser Gln Asp Ile Gln Lys
    110                 115                 120 aca ata aag aag aca gca cgt cgg gaa cag ctt atg aga gaa gaa gca      555
Thr Ile Lys Lys Thr Ala Arg Arg Glu Gln Leu Met Arg Glu Glu Ala
125                 130                 135 gaa cag aag cgc tta aaa act gta ctt gag tta cag tat gta ttg gat      603
Glu Gln Lys Arg Leu Lys Thr Val Leu Glu Leu Gln Tyr Val Leu Asp
140                 145                 150                 155 aag ctg gga gat gat gat gtg aga aca gat ctg aaa caa ggt ttg agt      651
Lys Leu Gly Asp Asp Asp Val Arg Thr Asp Leu Lys Gln Gly Leu Ser
            160                 165                 170 gga gtg cca ata ttg tct gag gag gag ttg tca ttg ctg gat gag ttc      699
Gly Val Pro Ile Leu Ser Glu Glu Glu Leu Ser Leu Leu Asp Glu Phe
        175                 180                 185 tac aag ctc gta gat cct gag cgt gac atg agt tta agg tta aat gag      747
Tyr Lys Leu Val Asp Pro Glu Arg Asp Met Ser Leu Arg Leu Asn Glu
    190                 195                 200 cag tat gaa cat gcc tca att cac ttg tgg gat ttg ctg gaa ggg aaa      795
Gln Tyr Glu His Ala Ser Ile His Leu Trp Asp Leu Leu Glu Gly Lys
205                 210                 215 gaa aag cct gtg tgt gga aca acc tat aaa gct cta aag gaa att gtt      843
Glu Lys Pro Val Cys Gly Thr Thr Tyr Lys Ala Leu Lys Glu Ile Val
220                 225                 230                 235 gag cgt gtt ttc cag tca aac tac ttt gat agc act cac aat cat caa      891
Glu Arg Val Phe Gln Ser Asn Tyr Phe Asp Ser Thr His Asn His Gln
            240                 245                 250 aat ggg ttg tgt gag gag gaa gag gcg gct tca gcg ccc aca gtg gag      939
Asn Gly Leu Cys Glu Glu Glu Glu Ala Ala Ser Ala Pro Thr Val Glu
```

-continued

```
                255                  260                  265
gac cag gta gct gaa gct gaa cct gag cca gcg gaa gaa tac aca gag    987
Asp Gln Val Ala Glu Ala Glu Pro Glu Pro Ala Glu Glu Tyr Thr Glu
            270                  275                  280 caa agt gag gtt gaa tca aca gag tat gtc aat agg cag ttc atg gca   1035
Gln Ser Glu Val Glu Ser Thr Glu Tyr Val Asn Arg Gln Phe Met Ala
285                  290                  295 gaa aca cag ttc agc agt ggt gag aag gag caa gtg gat gag tgg aca   1083
Glu Thr Gln Phe Ser Ser Gly Glu Lys Glu Gln Val Asp Glu Trp Thr
300                  305                  310                  315 gtt gaa aca gtt gag gtt gta aac tca ctc cag cag caa cct cag gct   1131
Val Glu Thr Val Glu Val Val Asn Ser Leu Gln Gln Gln Pro Gln Ala
            320                  325                  330 gcg tcc cct tca gtc cca gag ccc cac tct ttg act cca gtg gct cag   1179
Ala Ser Pro Ser Val Pro Glu Pro His Ser Leu Thr Pro Val Ala Gln
            335                  340                  345 tca gat cca ctt gtg aga agg cag cgt gta caa gat ctt atg gca caa   1227
Ser Asp Pro Leu Val Arg Arg Gln Arg Val Gln Asp Leu Met Ala Gln
            350                  355                  360 atg caa ggg ccc tat aat ttc ata cag gat tca atg ttg gat ttt gaa   1275
Met Gln Gly Pro Tyr Asn Phe Ile Gln Asp Ser Met Leu Asp Phe Glu
365                  370                  375 aat cag acg ctt gat cct gcc att gta tcc gca cag cct atg aac cct   1323
Asn Gln Thr Leu Asp Pro Ala Ile Val Ser Ala Gln Pro Met Asn Pro
380                  385                  390                  395 acc cag aac atg gat atg cct cag ctg gtt tgc cct cag gtt cat tct   1371
Thr Gln Asn Met Asp Met Pro Gln Leu Val Cys Pro Gln Val His Ser
            400                  405                  410 gaa tct aga ctt gcc caa tct aat caa gtt cct gta caa cca gaa gcc   1419
Glu Ser Arg Leu Ala Gln Ser Asn Gln Val Pro Val Gln Pro Glu Ala
            415                  420                  425 aca cag gtt cct ttg gtt tca tcc aca agt gag ggg tat aca gca tct   1467
Thr Gln Val Pro Leu Val Ser Ser Thr Ser Glu Gly Tyr Thr Ala Ser
            430                  435                  440 cag ccc ttg tac cag cca tct cat gct acg gag cag cgg ccg cag aaa   1515
Gln Pro Leu Tyr Gln Pro Ser His Ala Thr Glu Gln Arg Pro Gln Lys
445                  450                  455 gag cca atg gat cag att cag gca aca ata tct ttg aat aca gac cag   1563
Glu Pro Met Asp Gln Ile Gln Ala Thr Ile Ser Leu Asn Thr Asp Gln
460                  465                  470                  475 act aca gca tcc tca tcc ctt cct gct gct tct cag cct caa gtg ttc   1611
Thr Thr Ala Ser Ser Ser Leu Pro Ala Ala Ser Gln Pro Gln Val Phe
            480                  485                  490 cag gct ggg aca agt aaa cct ttg cac agc agt gga atc aat gta aat   1659
Gln Ala Gly Thr Ser Lys Pro Leu His Ser Ser Gly Ile Asn Val Asn
            495                  500                  505 gca gct cca ttc cag tcc atg caa acg gtg ttc aat atg aat gct cca   1707
Ala Ala Pro Phe Gln Ser Met Gln Thr Val Phe Asn Met Asn Ala Pro
            510                  515                  520 gtc cct cct gct aat gaa cca gaa acg tta aaa caa cag agt cag tac   1755
Val Pro Pro Ala Asn Glu Pro Glu Thr Leu Lys Gln Gln Ser Gln Tyr
525                  530                  535 cag gcc act tat aac cag agt ttt tcc agt cag cct cac caa gtg gaa   1803
Gln Ala Thr Tyr Asn Gln Ser Phe Ser Ser Gln Pro His Gln Val Glu
540                  545                  550                  555 caa aca gag ctt caa caa gac caa ctg caa acg gtg gtt ggc act tac   1851
Gln Thr Glu Leu Gln Gln Asp Gln Leu Gln Thr Val Val Gly Thr Tyr
            560                  565                  570 cat gga tcc cag gac cag cct cat caa gtg cct ggt aac cac cag caa   1899
```

-continued

|  |  |
|---|---|
| His Gly Ser Gln Asp Gln Pro His Gln Val Pro Gly Asn His Gln Gln<br>    575       580       585 |  |
| ccc cca cag cag aac act ggc ttt cca cgt agc agt cag cct tat tac<br>Pro Pro Gln Gln Asn Thr Gly Phe Pro Arg Ser Ser Gln Pro Tyr Tyr<br>    590       595       600 | 1947 |
| aac agt cgt ggg gta tct cga gga ggg tct cgt ggt gcc aga ggc ttg<br>Asn Ser Arg Gly Val Ser Arg Gly Gly Ser Arg Gly Ala Arg Gly Leu<br>605       610       615 | 1995 |
| atg aat gga tac agg ggc cct gcc aat gga ttt aga gga gga tat gat<br>Met Asn Gly Tyr Arg Gly Pro Ala Asn Gly Phe Arg Gly Gly Tyr Asp<br>620       625       630      635 | 2043 |
| ggt tac cgc cct tca ttc tcg aac act cca aac agt ggt tat tca cag<br>Gly Tyr Arg Pro Ser Phe Ser Asn Thr Pro Asn Ser Gly Tyr Ser Gln<br>    640       645       650 | 2091 |
| tct cag ttc act gct ccc cgg gac tac tct ggt tac cag cgg gat gga<br>Ser Gln Phe Thr Ala Pro Arg Asp Tyr Ser Gly Tyr Gln Arg Asp Gly<br>    655       660       665 | 2139 |
| tat cag cag aat ttc aag cga ggc tct ggg cag agt gga cca cgg gga<br>Tyr Gln Gln Asn Phe Lys Arg Gly Ser Gly Gln Ser Gly Pro Arg Gly<br>670       675       680 | 2187 |
| gcc cca cga ggt cgt gga ggg ccc cca aga ccc aac aga ggg atg ccg<br>Ala Pro Arg Gly Arg Gly Gly Pro Pro Arg Pro Asn Arg Gly Met Pro<br>685       690       695 | 2235 |
| caa atg aac act cag caa gtg aat taa tgtgatacac aggattatgt<br>Gln Met Asn Thr Gln Gln Val Asn<br>700       705 | 2282 |
| ttaatcgcca aaaacacact ggccagtgta ccataatatg ttaccagaag agttattatc | 2342 |
| tatttgttct ccctttcagg aaacttattg taaagggact gttttcatcc cataaagaca | 2402 |
| ggactgcaat tgtcagcttt acattacctg gatatggaag gaaactattt ttattctgca | 2462 |
| tgttctgtcc taagcgtcat cttgagcctt gcacacaata caatactcag attcctcacc | 2522 |
| cttgcttagg agtaaaacat tatatactta tggggtgata atatctccat agttagttga | 2582 |
| agtggcttgg aaaaaaaatg caagattgaa ttttttgacct tggataaaat ctacaatcag | 2642 |
| ccctagaact attcagtggt aattgacaaa gttaaagcat tttctttgaa aggaagatgg | 2702 |
| aaggagtgga gtgtggttta gcaaaactgc atttcatagc tttcccatta aattggagca | 2762 |
| ccgacagatt aaaagcatac caaattatgc atgggtcctt actcacacaa gtgaggctgg | 2822 |
| ctaccagcct tgacatagca ctcactagtc ttctggccaa acgactgtga ttaaaacaca | 2882 |
| tgtaaattgc tctttagtag tggatactgt gtaagacaaa gccaaattgc aaatcaggct | 2942 |
| ttgattggct cttctggaaa atatgcatca aatatggggg ataatctgga tgggctgctg | 3002 |
| ctgtgctcaa tgtgaactat ttagatacct ttggaacact taacagtttc tctgaacaat | 3062 |
| gacttacatg gggattggtc ctgtttgtca ttcctcacca taattgcatt gtcatcacta | 3122 |
| atccttggat cttgctgtat tgttactcaa attggtaata ggtactgatg gaaatcgcta | 3182 |
| atggatggat aatcataaca cttttggtca catgttttct cctgcagcct gaaagttctt | 3242 |
| aaagaaaaag atatcaaatg cctgctgcta ccacccttttt aaattgctat ctttagaaaa | 3302 |
| gcaccggtat gtgttttaga ttcatttccc tgttttaggg aaatgacagg cagtagtttc | 3362 |
| agttctgatg gcaaacaaa taaaaacatg tttctaaaag ttgtatcttg aaacactggt | 3422 |
| gttcaacagc tagcagctaa agtaattcaa cccatgcatt gctagtgtca cagcctttgg | 3482 |
| ttatgtctag tagctgtttc tgaagtattt tcatttatct tttgtcaaat ttaaccctgt | 3542 |
| ttgaattctc tcctttcctc aaggagacac ttatgttcaa agtgttgatt ctttgcctta | 3602 |

```
ggtgcataga gagtagacag tttggagatg gaaaggttag cagtgactta gccatatgtt    3662
ctgtgttgga atttgtgcta gcagtttgag cactagctct gcgtgcctat gaactgaatg    3722
ctgcttgtcc cattccattt tatgtcatgg agaaataatt ccacttggta acacaaaggc    3782
taagttaatg ttattttctg tacagaaatt aaattttact tttagccttt tgtaaacttt    3842
tttttttttt ttccaagccg gtatcagcta ctcaaaacaa ttctcagata ttcatcatta    3902
gacaactgga gttttgctg gttttgtagc ctactaaaac tgctgaggct gttgaacatt    3962
ccacattcaa aagttttgta gggtggtgga taatggggaa gcttcaatgt ttattttaaa    4022
ataaataaaa taagttcttg acttttctca tgtgtggtta tggtacatca tattggaagg    4082
gttatctgtt tacttttgcc aagactattt tgccagcacc tacacttgtg tgctttaaaa    4142
gacaactacc tgggatgtac cacaaccata tgttaattgt atttattgg gatggataaa    4202
atgtttgtgg tttattggat aatccctaga tggtgtgtta cgtgtgtaga atataatttt    4262
atgatagtaa gaaagcaaaa ttgaagaaaa taagtttagt attgaatttg agttctgaag    4322
tgaattcagg gaatgtctca cgtttcgggc ttctacccaa agtgtagggc agaaggtgta    4382
aaagttgttt gtagtttgac ttgttttattt tttaagttgc ttattccttt caacagcaac    4442
atatcattag ctgtcattct accattgcag ttctagtgag ttttaacgtc tgcattcaag    4502
actgttttaa aagcaacctc actggacaga gaactgctaa agtcttttcc ttaagatctg    4562
agtctttgtt actcagtatc ttctataata tgcaaatgct tgtctagagg cagaagacct    4622
tttgtttggt caagtgtgta ttttaccaga gtacagggaa ctgatggtcc tacatgtctc    4682
ttagtgtagt aagactataa aatcttttgt acatgcacaa ttcacagtat gtttagatac    4742
cacgtgtata atgccccccc ctcccccagg tagcatgcca ttgatgactt tttgcttagg    4802
gccatttat taccagggcc ttaatattcc taaaagatg atttttttc atcctttctc    4862
ctcttttgat cattgtatct tgatattaaa aacatgacct tccaatgatt gtagtaaatt    4922
aacttctata gttctttgt ctctatatgt attcatatat atgctattgt atagagactt    4982
caaggagaca tggagatgca tgcttattct caggttcatt cactaaggtg cttggcagac    5042
aaccagtttc taagtgcaga atgtagttaa gcagcttcat atatgtgcca ggcaatttgt    5102
tttgttaaat tttcatctac ttaaggaaat agggtattgt agcttaggct gatcataccc    5162
ttcatttcaa ccttaagctc tcaacctgca tccatccgac ttgagctatt aagtacttta    5222
gttttatcga gtataagtta acagaaaaag taaattaagc tttgccttta ctattttgaa    5282
tttatataca ttctggaaaa acttagaaac tgttgtatat ttcattagat taaattatat    5342
gaaaatgtga ttgtttatag caaagcctgt gagttgcata caccctaagg aaaactcctt    5402
aagtgctcct tgaagagaga agaaacaatt ctgggtctgg tcttttttaag aacaaagcta    5462
gactactgta tgttagcact gtacattaat agtctgttgt gaagcttgag cagtttcctg    5522
catagccttg atccttcacc gttggcattg aaaatagcag tatccctgat gtacttaaaa    5582
cttaaagtca ggttttggta tatttatttg taagtcttaa tttcctctaa atactatatc    5642
tctttagcga gacaacctga aatttattag cacatttggg tatctcttgc ttggcattat    5702
ggccagtgtt aactattcag tggtgaaaaa attacccctc aagacactgg agtgaccca    5762
gatgtgtgta gtaagtggca tggttcaact gtgtggttaa tgataaatat atgacttagt    5822
cggtatgatc tggaaagact tgattgaaag ataattcagc tgacataagg atgagtgagg    5882
agtggcaaac tggataaaag agtcaagaga cctgtattcc agtgactcct gttttgttta    5942
agcattagca agatctgtct ggggaaactg gatagggcag ttttcttcca tgtttagttt    6002
```

-continued

```
ttgtctcaac atttggaagc tattgaaggt tttaaaatgg tgtgtattgt ttttttttgg    6062
ggggggggtg ccagaatag tgggtcatct aataaaactg ccatttaaaa gatcaaaaaa     6122
aaaaaaaaaa aaaaaaaaa                                                  6141

<210> SEQ ID NO 22
<211> LENGTH: 707
<212> TYPE: PRT
<213> ORGANISM: Mus musculus

<400> SEQUENCE: 22

Met Pro Ser Ala Thr Ser His Ser Gly Ser Gly Ser Lys Ser Ser Gly
1               5                   10                  15

Pro Pro Pro Ser Gly Ser Ser Gly Ser Glu Ala Ala Gly Ala
            20                  25                  30

Ala Ala Pro Ala Ser Gln His Pro Ala Thr Gly Thr Gly Ala Val Gln
        35                  40                  45

Thr Glu Ala Met Lys Gln Ile Leu Gly Val Ile Asp Lys Lys Leu Arg
    50                  55                  60

Asn Leu Glu Lys Lys Lys Gly Lys Leu Asp Asp Tyr Gln Glu Arg Met
65                  70                  75                  80

Asn Lys Gly Glu Arg Leu Asn Gln Asp Gln Leu Asp Ala Val Ser Lys
                85                  90                  95

Tyr Gln Glu Val Thr Asn Asn Leu Glu Phe Ala Lys Glu Leu Gln Arg
            100                 105                 110

Ser Phe Met Ala Leu Ser Gln Asp Ile Gln Lys Thr Ile Lys Lys Thr
        115                 120                 125

Ala Arg Arg Glu Gln Leu Met Arg Glu Glu Ala Glu Gln Lys Arg Leu
    130                 135                 140

Lys Thr Val Leu Glu Leu Gln Tyr Val Leu Asp Lys Leu Gly Asp Asp
145                 150                 155                 160

Asp Val Arg Thr Asp Leu Lys Gln Gly Leu Ser Gly Val Pro Ile Leu
                165                 170                 175

Ser Glu Glu Leu Ser Leu Leu Asp Glu Phe Tyr Lys Leu Val Asp
            180                 185                 190

Pro Glu Arg Asp Met Ser Leu Arg Leu Asn Glu Gln Tyr Glu His Ala
        195                 200                 205

Ser Ile His Leu Trp Asp Leu Leu Glu Gly Lys Glu Lys Pro Val Cys
    210                 215                 220

Gly Thr Thr Tyr Lys Ala Leu Lys Glu Ile Val Glu Arg Val Phe Gln
225                 230                 235                 240

Ser Asn Tyr Phe Asp Ser Thr His Asn His Gln Asn Gly Leu Cys Glu
                245                 250                 255

Glu Glu Glu Ala Ala Ser Ala Pro Thr Val Glu Asp Gln Val Ala Glu
            260                 265                 270

Ala Glu Pro Glu Pro Ala Glu Glu Tyr Thr Gln Ser Glu Val Glu
        275                 280                 285

Ser Thr Glu Tyr Val Asn Arg Gln Phe Met Ala Glu Thr Gln Phe Ser
    290                 295                 300

Ser Gly Glu Lys Glu Gln Val Asp Glu Trp Thr Val Glu Thr Val Glu
305                 310                 315                 320

Val Val Asn Ser Leu Gln Gln Gln Pro Gln Ala Ala Ser Pro Ser Val
                325                 330                 335

Pro Glu Pro His Ser Leu Thr Pro Val Ala Gln Ser Asp Pro Leu Val
```

```
                340                 345                 350
Arg Arg Gln Arg Val Gln Asp Leu Met Ala Gln Met Gln Gly Pro Tyr
            355                 360                 365

Asn Phe Ile Gln Asp Ser Met Leu Asp Phe Glu Asn Gln Thr Leu Asp
    370                 375                 380

Pro Ala Ile Val Ser Ala Gln Pro Met Asn Pro Thr Gln Asn Met Asp
385                 390                 395                 400

Met Pro Gln Leu Val Cys Pro Gln Val His Ser Glu Ser Arg Leu Ala
                405                 410                 415

Gln Ser Asn Gln Val Pro Val Gln Pro Glu Ala Thr Gln Val Pro Leu
            420                 425                 430

Val Ser Thr Ser Glu Gly Tyr Thr Ala Ser Gln Pro Leu Tyr Gln
        435                 440                 445

Pro Ser His Ala Thr Glu Gln Arg Pro Gln Lys Glu Pro Met Asp Gln
    450                 455                 460

Ile Gln Ala Thr Ile Ser Leu Asn Thr Asp Gln Thr Thr Ala Ser Ser
465                 470                 475                 480

Ser Leu Pro Ala Ala Ser Gln Pro Gln Val Phe Gln Ala Gly Thr Ser
                485                 490                 495

Lys Pro Leu His Ser Ser Gly Ile Asn Val Asn Ala Ala Pro Phe Gln
            500                 505                 510

Ser Met Gln Thr Val Phe Asn Met Asn Ala Pro Val Pro Pro Ala Asn
        515                 520                 525

Glu Pro Glu Thr Leu Lys Gln Gln Ser Gln Tyr Gln Ala Thr Tyr Asn
    530                 535                 540

Gln Ser Phe Ser Ser Gln Pro His Gln Val Glu Gln Thr Glu Leu Gln
545                 550                 555                 560

Gln Asp Gln Leu Gln Thr Val Val Gly Thr Tyr His Gly Ser Gln Asp
                565                 570                 575

Gln Pro His Gln Val Pro Gly Asn His Gln Gln Pro Gln Gln Asn
            580                 585                 590

Thr Gly Phe Pro Arg Ser Ser Gln Pro Tyr Tyr Asn Ser Arg Gly Val
        595                 600                 605

Ser Arg Gly Gly Ser Arg Gly Ala Arg Gly Leu Met Asn Gly Tyr Arg
    610                 615                 620

Gly Pro Ala Asn Gly Phe Arg Gly Gly Tyr Asp Gly Tyr Arg Pro Ser
625                 630                 635                 640

Phe Ser Asn Thr Pro Asn Ser Gly Tyr Ser Gln Ser Gln Phe Thr Ala
                645                 650                 655

Pro Arg Asp Tyr Ser Gly Tyr Gln Arg Asp Gly Tyr Gln Gln Asn Phe
            660                 665                 670

Lys Arg Gly Ser Gly Gln Ser Gly Pro Arg Gly Ala Pro Arg Gly Arg
        675                 680                 685

Gly Gly Pro Pro Arg Pro Asn Arg Gly Met Pro Gln Met Asn Thr Gln
    690                 695                 700

Gln Val Asn
705

<210> SEQ ID NO 23
<211> LENGTH: 6114
<212> TYPE: DNA
<213> ORGANISM: Mus musculus
<220> FEATURE:
<221> NAME/KEY: CDS
<222> LOCATION: (139)..(2235)
```

<223> OTHER INFORMATION:

<400> SEQUENCE: 23

```
cccaccgcgc gcgcgcgtag ccgcctgccc gcccgcccgc tgcgcgtttt gtcccgcgtc      60
tctccccgtc cgtctcctga cttgctggtc ttgtccttcc ctcccgcttt tttcctctcc     120
```

| | | | | | | | | | | | | | | |
|---|---|---|---|---|---|---|---|---|---|---|---|---|---|---|
| tctcttctcg gtctaaag atg ccc tcg gcc acc agc cac agc gga agc ggc | | | | | | | | | | | | | | 171 |
| | Met Pro Ser Ala Thr Ser His Ser Gly Ser Gly | | | | | | | | | | | | | |
| | 1 | | | 5 | | | | | 10 | | | | | |

```
agc aaa tcg tcg gga ccg ccg ccg tcc ggt tcc tcc ggg agt gag      219
Ser Lys Ser Ser Gly Pro Pro Pro Ser Gly Ser Ser Gly Ser Glu
         15                  20                  25 gcg gcg gcc ggg gca gct gcg ccg gct tct cag cat ccg gca acc ggc  267
Ala Ala Ala Gly Ala Ala Ala Pro Ala Ser Gln His Pro Ala Thr Gly
             30                  35                  40 acc ggc gcc gtc cag acc gag gcc atg aag cag att ctc ggc gta atc  315
Thr Gly Ala Val Gln Thr Glu Ala Met Lys Gln Ile Leu Gly Val Ile
 45                  50                  55 gac aag aaa ctt cgg aac ctg gag aag aaa aag ggt aaa ctt gat gat  363
Asp Lys Lys Leu Arg Asn Leu Glu Lys Lys Lys Gly Lys Leu Asp Asp
 60                  65                  70                  75 tac cag gaa cga atg aat aaa ggg gaa agg ctc aat caa gac cag ctg  411
Tyr Gln Glu Arg Met Asn Lys Gly Glu Arg Leu Asn Gln Asp Gln Leu
                 80                  85                  90 gat gcc gta tct aag tac cag gaa gtc aca aat aat ttg gag ttt gca  459
Asp Ala Val Ser Lys Tyr Gln Glu Val Thr Asn Asn Leu Glu Phe Ala
             95                 100                 105 aag gaa tta cag agg agt ttc atg gca tta agt caa gat att cag aaa  507
Lys Glu Leu Gln Arg Ser Phe Met Ala Leu Ser Gln Asp Ile Gln Lys
         110                 115                 120 aca ata aag aag aca gca cgt cgg gaa cag ctt atg aga gaa gaa gca  555
Thr Ile Lys Lys Thr Ala Arg Arg Glu Gln Leu Met Arg Glu Glu Ala
     125                 130                 135 gaa cag aag cgc tta aaa act gta ctt gag tta cag tat gta ttg gat  603
Glu Gln Lys Arg Leu Lys Thr Val Leu Glu Leu Gln Tyr Val Leu Asp
 140                 145                 150                 155 aag ctg gga gat gat gat gtg aga aca gat ctg aaa caa ggt ttg agt  651
Lys Leu Gly Asp Asp Asp Val Arg Thr Asp Leu Lys Gln Gly Leu Ser
                 160                 165                 170 gga gtg cca ata ttg tct gag gag gag ttg tca ttg ctg gat gag ttc  699
Gly Val Pro Ile Leu Ser Glu Glu Glu Leu Ser Leu Leu Asp Glu Phe
             175                 180                 185 tac aag ctc gta gat cct gag cgt gac atg agt tta agg tta aat gag  747
Tyr Lys Leu Val Asp Pro Glu Arg Asp Met Ser Leu Arg Leu Asn Glu
         190                 195                 200 cag tat gaa cat gcc tca att cac ttg tgg gat ttg ctg gaa ggg aaa  795
Gln Tyr Glu His Ala Ser Ile His Leu Trp Asp Leu Leu Glu Gly Lys
     205                 210                 215 gaa aag cct gtg tgt gga aca acc tat aaa gct cta aag gaa att gtt  843
Glu Lys Pro Val Cys Gly Thr Thr Tyr Lys Ala Leu Lys Glu Ile Val
 220                 225                 230                 235 gag cgt gtt ttc cag tca aac tac ttt gat agc act cac aat cat caa  891
Glu Arg Val Phe Gln Ser Asn Tyr Phe Asp Ser Thr His Asn His Gln
                 240                 245                 250 aat ggg ttg tgt gag gag gaa gag gcg gct tca gcg ccc aca gtg gag  939
Asn Gly Leu Cys Glu Glu Glu Glu Ala Ala Ser Ala Pro Thr Val Glu
             255                 260                 265 gac cag gta gct gaa gct gaa cct gag cca gcg gaa gaa tac aca gag  987
Asp Gln Val Ala Glu Ala Glu Pro Glu Pro Ala Glu Glu Tyr Thr Glu
         270                 275                 280
```

| | | |
|---|---|---|
| caa agt gag gtt gaa tca aca gag tat gtc aat agg cag ttc atg gca<br>Gln Ser Glu Val Glu Ser Thr Glu Tyr Val Asn Arg Gln Phe Met Ala<br>285                        290                        295 | | 1035 |
| gaa aca cag ttc agc agt ggt gag aag gag caa gtg gat gag tgg aca<br>Glu Thr Gln Phe Ser Ser Gly Glu Lys Glu Gln Val Asp Glu Trp Thr<br>300                        305                        310                  315 | | 1083 |
| gtt gaa aca gtt gag gtt gta aac tca ctc cag cag caa cct cag gct<br>Val Glu Thr Val Glu Val Val Asn Ser Leu Gln Gln Gln Pro Gln Ala<br>                  320                        325                        330 | | 1131 |
| gcg tcc cct tca gtc cca gag ccc cac tct ttg act cca gtg gct cag<br>Ala Ser Pro Ser Val Pro Glu Pro His Ser Leu Thr Pro Val Ala Gln<br>                335                        340                        345 | | 1179 |
| tca gat cca ctt gtg aga agg cag cgt gta caa gat ctt atg gca caa<br>Ser Asp Pro Leu Val Arg Arg Gln Arg Val Gln Asp Leu Met Ala Gln<br>350                        355                        360 | | 1227 |
| atg caa ggg ccc tat aat ttc ata cag acg ctt gat cct gcc att gta<br>Met Gln Gly Pro Tyr Asn Phe Ile Gln Thr Leu Asp Pro Ala Ile Val<br>                  365                        370                        375 | | 1275 |
| tcc gca cag cct atg aac cct acc cag aac atg gat atg cct cag ctg<br>Ser Ala Gln Pro Met Asn Pro Thr Gln Asn Met Asp Met Pro Gln Leu<br>380                        385                        390                  395 | | 1323 |
| gtt tgc cct cag gtt cat tct gaa tct aga ctt gcc caa tct aat caa<br>Val Cys Pro Gln Val His Ser Glu Ser Arg Leu Ala Gln Ser Asn Gln<br>                  400                        405                        410 | | 1371 |
| gtt cct gta caa cca gaa gcc aca cag gtt cct ttg gtt tca tcc aca<br>Val Pro Val Gln Pro Glu Ala Thr Gln Val Pro Leu Val Ser Ser Thr<br>415                        420                        425 | | 1419 |
| agt gag ggg tat aca gca tct cag ccc ttg tac cag cca tct cat gct<br>Ser Glu Gly Tyr Thr Ala Ser Gln Pro Leu Tyr Gln Pro Ser His Ala<br>                  430                        435                        440 | | 1467 |
| acg gag cag cgg ccg cag aaa gag cca atg gat cag att cag gca aca<br>Thr Glu Gln Arg Pro Gln Lys Glu Pro Met Asp Gln Ile Gln Ala Thr<br>                445                        450                        455 | | 1515 |
| ata tct ttg aat aca gac cag act aca gca tcc tca tcc ctt cct gct<br>Ile Ser Leu Asn Thr Asp Gln Thr Thr Ala Ser Ser Ser Leu Pro Ala<br>460                        465                        470                  475 | | 1563 |
| gct tct cag cct caa gtg ttc cag gct ggg aca agt aaa cct ttg cac<br>Ala Ser Gln Pro Gln Val Phe Gln Ala Gly Thr Ser Lys Pro Leu His<br>                  480                        485                        490 | | 1611 |
| agc agt gga atc aat gta aat gca gct cca ttc cag tcc atg caa acg<br>Ser Ser Gly Ile Asn Val Asn Ala Ala Pro Phe Gln Ser Met Gln Thr<br>                  495                        500                        505 | | 1659 |
| gtg ttc aat atg aat gct cca gtc cct cct gct aat gaa cca gaa acg<br>Val Phe Asn Met Asn Ala Pro Val Pro Pro Ala Asn Glu Pro Glu Thr<br>                510                        515                        520 | | 1707 |
| tta aaa caa cag agt cag tac cag gcc act tat aac cag agt ttt tcc<br>Leu Lys Gln Gln Ser Gln Tyr Gln Ala Thr Tyr Asn Gln Ser Phe Ser<br>525                        530                        535 | | 1755 |
| agt cag cct cac caa gtg gaa caa aca gag ctt caa caa gac caa ctg<br>Ser Gln Pro His Gln Val Glu Gln Thr Glu Leu Gln Gln Asp Gln Leu<br>540                        545                        550                  555 | | 1803 |
| caa acg gtg gtt ggc act tac cat gga tcc cag gac cag cct cat caa<br>Gln Thr Val Val Gly Thr Tyr His Gly Ser Gln Asp Gln Pro His Gln<br>                  560                        565                        570 | | 1851 |
| gtg cct ggt aac cac cag caa ccc cca cag cag aac act ggc ttt cca<br>Val Pro Gly Asn His Gln Gln Pro Pro Gln Gln Asn Thr Gly Phe Pro<br>575                        580                        585 | | 1899 |
| cgt agc agt cag cct tat tac aac agt cgt ggg gta tct cga gga ggg<br>Arg Ser Ser Gln Pro Tyr Tyr Asn Ser Arg Gly Val Ser Arg Gly Gly | | 1947 |

|     |     |     |     |     |     |     |     |     |     |     |     |     |     |     |      |
| --- | --- | --- | --- | --- | --- | --- | --- | --- | --- | --- | --- | --- | --- | --- | ---- |
|     | 590 |     |     |     | 595 |     |     |     | 600 |     |     |     |     |     |      |
| tct | cgt | ggt | gcc | aga | ggc | ttg | atg | aat | gga | tac | agg | ggc | cct | gcc | aat  | 1995 |
| Ser | Arg | Gly | Ala | Arg | Gly | Leu | Met | Asn | Gly | Tyr | Arg | Gly | Pro | Ala | Asn  |      |
|     | 605 |     |     |     | 610 |     |     |     | 615 |     |     |     |     |     |      |
| gga | ttt | aga | gga | gga | tat | gat | ggt | tac | cgc | cct | tca | ttc | tcg | aac | act  | 2043 |
| Gly | Phe | Arg | Gly | Gly | Tyr | Asp | Gly | Tyr | Arg | Pro | Ser | Phe | Ser | Asn | Thr  |      |
| 620 |     |     |     |     | 625 |     |     |     | 630 |     |     |     |     |     | 635  |      |
| cca | aac | agt | ggt | tat | tca | cag | tct | cag | ttc | act | gct | ccc | cgg | gac | tac  | 2091 |
| Pro | Asn | Ser | Gly | Tyr | Ser | Gln | Ser | Gln | Phe | Thr | Ala | Pro | Arg | Asp | Tyr  |      |
|     |     |     |     | 640 |     |     |     |     | 645 |     |     |     |     | 650 |      |      |
| tct | ggt | tac | cag | cgg | gat | gga | tat | cag | cag | aat | ttc | aag | cga | ggc | tct  | 2139 |
| Ser | Gly | Tyr | Gln | Arg | Asp | Gly | Tyr | Gln | Gln | Asn | Phe | Lys | Arg | Gly | Ser  |      |
|     |     |     | 655 |     |     |     |     | 660 |     |     |     |     | 665 |     |      |      |
| ggg | cag | agt | gga | cca | cgg | gga | gcc | cca | cga | ggt | cgt | gga | ggg | ccc | cca  | 2187 |
| Gly | Gln | Ser | Gly | Pro | Arg | Gly | Ala | Pro | Arg | Gly | Arg | Gly | Gly | Pro | Pro  |      |
|     |     | 670 |     |     |     |     | 675 |     |     |     |     | 680 |     |     |      |      |
| aga | ccc | aac | aga | ggg | atg | ccg | caa | atg | aac | act | cag | caa | gtg | aat | taa  | 2235 |
| Arg | Pro | Asn | Arg | Gly | Met | Pro | Gln | Met | Asn | Thr | Gln | Gln | Val | Asn |      |      |
|     | 685 |     |     |     | 690 |     |     |     |     | 695 |     |     |     |     |      |      |

| | |
|---|---|
| tgtgatacac aggattatgt ttaatcgcca aaaacacact ggccagtgta ccataatatg | 2295 |
| ttaccagaag agttattatc tatttgttct ccctttcagg aaacttattg taaagggact | 2355 |
| gttttcatcc cataaagaca ggactgcaat tgtcagcttt acattacctg gatatggaag | 2415 |
| gaaactattt ttattctgca tgttctgtcc taagcgtcat cttgagcctt gcacacaata | 2475 |
| caatactcag attcctcacc cttgcttagg agtaaaacat tatatactta tggggtgata | 2535 |
| atatctccat agttagttga agtggcttgg aaaaaaaatg caagattgaa tttttgacct | 2595 |
| tggataaaat ctacaatcag ccctagaact attcagtggt aattgacaaa gttaaagcat | 2655 |
| tttctttgaa aggaagatgg aaggagtgga gtgtggttta gcaaaactgc atttcatagc | 2715 |
| tttcccatta aattggagca ccgacagatt aaaagcatac caaattatgc atgggtcctt | 2775 |
| actcacacaa gtgaggctgg ctaccagcct tgacatagca ctcactagtc ttctggccaa | 2835 |
| acgactgtga ttaaaacaca tgtaaattgc tctttagtag tggatactgt gtaagacaaa | 2895 |
| gccaaattgc aaatcaggct ttgattggct cttctggaaa atatgcatca aatatggggg | 2955 |
| ataatctgga tgggctgctg ctgtgctcaa tgtgaactat ttagataccct ttggaacact | 3015 |
| taacagtttc tctgaacaat gacttacatg gggattggtc ctgtttgtca ttcctcacca | 3075 |
| taattgcatt gtcatcacta atccttggat cttgctgtat tgttactcaa attggtaata | 3135 |
| ggtactgatg gaaatcgcta atggatggat aatcataaca cttttggtca catgttttct | 3195 |
| cctgcagcct gaaagttctt aaagaaaaag atatcaaatg cctgctgcta ccacccttttt | 3255 |
| aaattgctat ctttagaaaa gcaccggtat gtgttttaga ttcatttccc tgttttaggg | 3315 |
| aaatgacagg cagtagtttc agttctgatg gcaaaacaaa taaaaacatg tttctaaaag | 3375 |
| ttgtatcttg aaacactggt gttcaacagc tagcagctaa agtaattcaa cccatgcatt | 3435 |
| gctagtgtca cagcctttgg ttatgtctag tagctgtttc tgaagtattt tcatttatct | 3495 |
| tttgtcaaat ttaaccctgt ttgaattctc tcctttcctc aaggagacac ttatgttcaa | 3555 |
| agtgttgatt ctttgcctta ggtgcataga gagtagacag tttggagatg gaaaggttag | 3615 |
| cagtgactta gccatatgtt ctgtgttgga atttgtgcta gcagtttgag cactagctct | 3675 |
| gcgtgcctat gaactgaatg ctgcttgtcc cattccattt tatgtcatgg agaaataatt | 3735 |
| ccacttggta acacaaaggc taagttaatg ttatttctg tacagaaatt aaattttact | 3795 |
| tttagccttt tgtaaacttt tttttttttt ttccaagccg gtatcagcta ctcaaaacaa | 3855 |

```
ttctcagata ttcatcatta gacaactgga gtttttgctg gttttgtagc ctactaaaac    3915
tgctgaggct gttgaacatt ccacattcaa aagttttgta gggtggtgga taatggggaa    3975
gcttcaatgt ttattttaaa ataaataaaa taagttcttg acttttctca tgtgtggtta    4035
tggtacatca tattggaagg gttatctgtt tacttttgcc aagactattt tgccagcacc    4095
tacacttgtg tgctttaaaa gacaactacc tgggatgtac cacaaccata tgttaattgt    4155
attttattgg gatggataaa atgtttgtgg tttattggat aatccctaga tggtgtgtta    4215
cgtgtgtaga atataatttt atgatagtaa gaaagcaaaa ttgaagaaaa taagtttagt    4275
attgaatttg agttctgaag tgaattcagg gaatgtctca cgtttcgggc ttctacccaa    4335
agtgtagggc agaaggtgta aaagttgttt gtagtttgac ttgtttattt tttaagttgc    4395
ttattccttt caacagcaac atatcattag ctgtcattct accattgcag ttctagtgag    4455
ttttaacgtc tgcattcaag actgttttaa aagcaacctc actggacaga gaactgctaa    4515
agtcttttcc ttaagatctg agtctttgtt actcagtatc ttctataata tgcaaatgct    4575
tgtctagagg cagaagacct tttgtttggt caagtgtgta ttttaccaga gtacagggaa    4635
ctgatggtcc tacatgtctc ttagtgtagt aagactataa atcttttgt acatgcacaa     4695
ttcacagtat gtttagatac cacgtgtata atgccccccc ctccccccagg tagcatgcca    4755
ttgatgactt tttgcttagg gccattttat taccagggcc ttaatattcc taaaaagatg    4815
atttttttc atcctttctc ctcttttgat cattgtatct tgatattaaa aacatgacct      4875
tccaatgatt gtagtaaatt aacttctata gttcttttgt ctctatatgt attcatatat    4935
atgctattgt atagagactt caaggagaca tggagatgca tgcttattct caggttcatt    4995
cactaaggtg cttggcagac aaccagtttc taagtgcaga atgtagttaa gcagcttcat    5055
atatgtgcca ggcaatttgt tttgttaaat tttcatctac ttaaggaaat agggtattgt    5115
agcttaggct gatcataccc ttcatttcaa ccttaagctc tcaacctgca tccatccgac    5175
ttgagctatt aagtactta gttttatcga gtataagtta acagaaaaag taaattaagc     5235
tttgccttta ctattttgaa tttatataca ttctggaaaa acttagaaac tgttgtatat    5295
ttcattagat taaattatat gaaaatgtga ttgtttatag caaagcctgt gagttgcata    5355
caccctaagg aaaactcctt aagtgctcct tgaagagaga agaaacaatt ctgggtctgg    5415
tcttttttaag aacaaagcta gactactgta tgttagcact gtacattaat agtctgttgt   5475
gaagcttgag cagtttcctg catagccttg atccttcacc gttggcattg aaaatagcag    5535
tatccctgat gtacttaaaa cttaaagtca ggttttggta tatttatttg taagtcttaa    5595
tttcctctaa atactatatc tctttagcga gacaacctga aatttattag cacatttggg    5655
tatctcttgc ttggcattat ggccagtgtt aactattcag tggtgaaaaa attacccctc    5715
aagacactgg agtgacccca gatgtgtgta gtaagtggca tggttcaact gtgtggttaa    5775
tgataaatat atgacttagt cggtatgatc tggaaagact tgattgaaag ataattcagc    5835
tgacataagg atgagtgagg agtggcaaac tggataaaag agtcaagaga cctgtattcc    5895
agtgactcct gttttgttta agcattagca agatctgtct ggggaaactg gatagggcag    5955
ttttcttcca tgtttagttt ttgtctcaac atttggaagc tattgaaggt tttaaaatgg    6015
tgtgtattgt ttttttttgg ggggggggtg gccagaatag tgggtcatct aataaaactg    6075
ccatttaaaa gatcaaaaaa aaaaaaaaaa aaaaaaaa                            6114
```

<210> SEQ ID NO 24

```
<211> LENGTH: 698
<212> TYPE: PRT
<213> ORGANISM: Mus musculus

<400> SEQUENCE: 24

Met Pro Ser Ala Thr Ser His Ser Gly Ser Gly Ser Lys Ser Gly
1               5                   10                  15

Pro Pro Pro Pro Ser Gly Ser Gly Ser Glu Ala Ala Gly Ala
            20                  25                  30

Ala Ala Pro Ala Ser Gln His Pro Ala Thr Gly Thr Gly Ala Val Gln
            35                  40                  45

Thr Glu Ala Met Lys Gln Ile Leu Gly Val Ile Asp Lys Lys Leu Arg
50                  55                  60

Asn Leu Glu Lys Lys Lys Gly Lys Leu Asp Asp Tyr Gln Glu Arg Met
65                  70                  75                  80

Asn Lys Gly Glu Arg Leu Asn Gln Asp Gln Leu Asp Ala Val Ser Lys
                85                  90                  95

Tyr Gln Glu Val Thr Asn Asn Leu Glu Phe Ala Lys Glu Leu Gln Arg
                100                 105                 110

Ser Phe Met Ala Leu Ser Gln Asp Ile Gln Lys Thr Ile Lys Lys Thr
            115                 120                 125

Ala Arg Arg Glu Gln Leu Met Arg Glu Glu Ala Glu Gln Lys Arg Leu
130                 135                 140

Lys Thr Val Leu Glu Leu Gln Tyr Val Leu Asp Lys Leu Gly Asp Asp
145                 150                 155                 160

Asp Val Arg Thr Asp Leu Lys Gln Gly Leu Ser Gly Val Pro Ile Leu
                165                 170                 175

Ser Glu Glu Glu Leu Ser Leu Leu Asp Glu Phe Tyr Lys Leu Val Asp
            180                 185                 190

Pro Glu Arg Asp Met Ser Leu Arg Leu Asn Glu Gln Tyr Glu His Ala
        195                 200                 205

Ser Ile His Leu Trp Asp Leu Leu Glu Gly Lys Glu Lys Pro Val Cys
210                 215                 220

Gly Thr Thr Tyr Lys Ala Leu Lys Glu Ile Val Glu Arg Val Phe Gln
225                 230                 235                 240

Ser Asn Tyr Phe Asp Ser Thr His Asn His Gln Asn Gly Leu Cys Glu
                245                 250                 255

Glu Glu Glu Ala Ala Ser Ala Pro Thr Val Glu Asp Gln Val Ala Glu
            260                 265                 270

Ala Glu Pro Glu Pro Ala Glu Glu Tyr Thr Glu Gln Ser Glu Val Glu
        275                 280                 285

Ser Thr Glu Tyr Val Asn Arg Gln Phe Met Ala Glu Thr Gln Phe Ser
290                 295                 300

Ser Gly Glu Lys Glu Gln Val Asp Glu Trp Thr Val Glu Thr Val Glu
305                 310                 315                 320

Val Val Asn Ser Leu Gln Gln Pro Gln Ala Ser Pro Ser Val
                325                 330                 335

Pro Glu Pro His Ser Leu Thr Pro Val Ala Gln Ser Asp Pro Leu Val
            340                 345                 350

Arg Arg Gln Arg Val Gln Asp Leu Met Ala Gln Met Gln Gly Pro Tyr
        355                 360                 365

Asn Phe Ile Gln Thr Leu Asp Pro Ala Ile Val Ser Ala Gln Pro Met
370                 375                 380

Asn Pro Thr Gln Asn Met Asp Met Pro Gln Leu Val Cys Pro Gln Val
```

```
        385                 390                 395                 400
His Ser Glu Ser Arg Leu Ala Gln Ser Asn Gln Val Pro Val Gln Pro
                        405                 410                 415
Glu Ala Thr Gln Val Pro Leu Val Ser Ser Thr Ser Glu Gly Tyr Thr
                    420                 425                 430
Ala Ser Gln Pro Leu Tyr Gln Pro Ser His Ala Thr Glu Gln Arg Pro
                435                 440                 445
Gln Lys Glu Pro Met Asp Gln Ile Gln Ala Thr Ile Ser Leu Asn Thr
            450                 455                 460
Asp Gln Thr Thr Ala Ser Ser Leu Pro Ala Ala Ser Gln Pro Gln
465                 470                 475                 480
Val Phe Gln Ala Gly Thr Ser Lys Pro Leu His Ser Ser Gly Ile Asn
                        485                 490                 495
Val Asn Ala Ala Pro Phe Gln Ser Met Gln Thr Val Phe Asn Met Asn
                    500                 505                 510
Ala Pro Val Pro Pro Ala Asn Glu Pro Glu Thr Leu Lys Gln Gln Ser
                515                 520                 525
Gln Tyr Gln Ala Thr Tyr Asn Gln Ser Phe Ser Ser Gln Pro His Gln
            530                 535                 540
Val Glu Gln Thr Glu Leu Gln Gln Asp Gln Leu Gln Thr Val Val Gly
545                 550                 555                 560
Thr Tyr His Gly Ser Gln Asp Gln Pro His Gln Val Pro Gly Asn His
                        565                 570                 575
Gln Gln Pro Pro Gln Gln Asn Thr Gly Phe Pro Arg Ser Ser Gln Pro
                    580                 585                 590
Tyr Tyr Asn Ser Arg Gly Val Ser Arg Gly Gly Ser Arg Gly Ala Arg
                595                 600                 605
Gly Leu Met Asn Gly Tyr Arg Gly Pro Ala Asn Gly Phe Arg Gly Gly
            610                 615                 620
Tyr Asp Gly Tyr Arg Pro Ser Phe Ser Asn Thr Pro Asn Ser Gly Tyr
625                 630                 635                 640
Ser Gln Ser Gln Phe Thr Ala Pro Arg Asp Tyr Ser Gly Tyr Gln Arg
                        645                 650                 655
Asp Gly Tyr Gln Gln Asn Phe Lys Arg Gly Ser Gly Gln Ser Gly Pro
                    660                 665                 670
Arg Gly Ala Pro Arg Gly Arg Gly Gly Pro Pro Arg Pro Asn Arg Gly
                675                 680                 685
Met Pro Gln Met Asn Thr Gln Gln Val Asn
690                 695

<210> SEQ ID NO 25
<211> LENGTH: 3548
<212> TYPE: DNA
<213> ORGANISM: Mus musculus
<220> FEATURE:
<221> NAME/KEY: CDS
<222> LOCATION: (179)..(2257)
<223> OTHER INFORMATION:

<400> SEQUENCE: 25
gctggctggc taagtccctc ccgcgccggc tcttgtccca ctaggagcag ctcagagccg       60
cggggacagg gcgaagcggc ctgcgcccac ggagcgcacg tctctgttct caacgcagca      120
ccacccttgc cccctcggc tgcccactcc agacgtccag cggctccgcg cgcgcacg         178 atg ccc tcg gcc acc agc cac agc gga agc ggc agc aaa tcg tcg gga       226
Met Pro Ser Ala Thr Ser His Ser Gly Ser Gly Ser Lys Ser Ser Gly
```

-continued

```
1               5                   10                  15 ccg ccg ccg ccg tcc ggt tcc tcc ggg agt gag gcg gcg gcc ggg gca       274
Pro Pro Pro Pro Ser Gly Ser Ser Gly Ser Glu Ala Ala Ala Gly Ala
            20                  25                  30 gct gcg ccg gct tct cag cat ccg gca acc ggc acc ggc gcc gtc cag       322
Ala Ala Pro Ala Ser Gln His Pro Ala Thr Gly Thr Gly Ala Val Gln
            35                  40                  45 acc gag gcc atg aag cag att ctc ggc gta atc gac aag aaa ctt cgg       370
Thr Glu Ala Met Lys Gln Ile Leu Gly Val Ile Asp Lys Lys Leu Arg
 50                  55                  60 aac ctg gag aag aaa aag ggt aaa ctt gat gat tac cag gaa cga atg       418
Asn Leu Glu Lys Lys Lys Gly Lys Leu Asp Asp Tyr Gln Glu Arg Met
 65                  70                  75                  80 aat aaa ggg gaa agg ctc aat caa gac cag ctg gat gcc gta tct aag       466
Asn Lys Gly Glu Arg Leu Asn Gln Asp Gln Leu Asp Ala Val Ser Lys
                 85                  90                  95 tac cag gaa gtc aca aat aat ttg gag ttt gca aag gaa tta cag agg       514
Tyr Gln Glu Val Thr Asn Asn Leu Glu Phe Ala Lys Glu Leu Gln Arg
                100                 105                 110 agt ttc atg gca tta agt caa gat att cag aaa aca ata aag aag aca       562
Ser Phe Met Ala Leu Ser Gln Asp Ile Gln Lys Thr Ile Lys Lys Thr
            115                 120                 125 gca cgt cgg gaa cag ctt atg aga gaa gaa gca gaa cag aag cgc tta       610
Ala Arg Arg Glu Gln Leu Met Arg Glu Glu Ala Glu Gln Lys Arg Leu
130                 135                 140 aaa act gta ctt gag tta cag tat gta ttg gat aag ctg gga gat gat       658
Lys Thr Val Leu Glu Leu Gln Tyr Val Leu Asp Lys Leu Gly Asp Asp
145                 150                 155                 160 gat gtg aga aca gat ctg aaa caa ggt ttg agt gga gtg cca ata ttg       706
Asp Val Arg Thr Asp Leu Lys Gln Gly Leu Ser Gly Val Pro Ile Leu
                165                 170                 175 tct gag gag gag ttg tca ttg ctg gat gag ttc tac aag ctc gta gat       754
Ser Glu Glu Glu Leu Ser Leu Leu Asp Glu Phe Tyr Lys Leu Val Asp
            180                 185                 190 cct gag cgt gac atg agt tta agg tta aat gag cag tat gaa cat gcc       802
Pro Glu Arg Asp Met Ser Leu Arg Leu Asn Glu Gln Tyr Glu His Ala
            195                 200                 205 tca att cac ttg tgg gat ttg ctg gaa ggg aaa gaa aag cct gtg tgt       850
Ser Ile His Leu Trp Asp Leu Leu Glu Gly Lys Glu Lys Pro Val Cys
210                 215                 220 gga aca acc tat aaa gct cta aag gaa att gtt gag cgt gtt ttc cag       898
Gly Thr Thr Tyr Lys Ala Leu Lys Glu Ile Val Glu Arg Val Phe Gln
225                 230                 235                 240 tca aac tac ttt gat agc act cac aat cat caa aat ggg ttg tgt gag       946
Ser Asn Tyr Phe Asp Ser Thr His Asn His Gln Asn Gly Leu Cys Glu
                245                 250                 255 gag gaa gag gcg gct tca gcg ccc aca gtg gag gac cag gta gct gaa       994
Glu Glu Glu Ala Ala Ser Ala Pro Thr Val Glu Asp Gln Val Ala Glu
            260                 265                 270 gct gaa cct gag cca gcg gaa gaa tac aca gag caa agt gag gtt gaa      1042
Ala Glu Pro Glu Pro Ala Glu Glu Tyr Thr Glu Gln Ser Glu Val Glu
            275                 280                 285 tca aca gag tat gtc aat agg cag ttc atg gca gaa aca cag ttc agc      1090
Ser Thr Glu Tyr Val Asn Arg Gln Phe Met Ala Glu Thr Gln Phe Ser
        290                 295                 300 agt ggt gag aag gag caa gtg gat gag tgg aca gtt gaa aca gtt gag      1138
Ser Gly Glu Lys Glu Gln Val Asp Glu Trp Thr Val Glu Thr Val Glu
305                 310                 315                 320 gtt gta aac tca ctc cag cag caa cct cag gct gcg tcc cct tca gtc      1186
```

-continued

```
                Val Val Asn Ser Leu Gln Gln Gln Pro Gln Ala Ala Ser Pro Ser Val
                                325                 330                 335 cca gag ccc cac tct ttg act cca gtg gct cag tca gat cca ctt gtg           1234
Pro Glu Pro His Ser Leu Thr Pro Val Ala Gln Ser Asp Pro Leu Val
            340                 345                 350 aga agg cag cgt gta caa gat ctt atg gca caa atg caa ggg ccc tat           1282
Arg Arg Gln Arg Val Gln Asp Leu Met Ala Gln Met Gln Gly Pro Tyr
        355                 360                 365 aat ttc ata cag gat tca atg ttg gat ttt gaa aat cag acg ctt gat           1330
Asn Phe Ile Gln Asp Ser Met Leu Asp Phe Glu Asn Gln Thr Leu Asp
    370                 375                 380 cct gcc att gta tcc gca cag cct atg aac cct acc cag aac atg gat           1378
Pro Ala Ile Val Ser Ala Gln Pro Met Asn Pro Thr Gln Asn Met Asp
385                 390                 395                 400 atg cct cag ctg gtt tgc cct cag gtt cat tct gaa tct aga ctt gcc           1426
Met Pro Gln Leu Val Cys Pro Gln Val His Ser Glu Ser Arg Leu Ala
            405                 410                 415 caa tct aat caa gtt cct gta caa cca gaa gcc aca cag gtt cct ttg           1474
Gln Ser Asn Gln Val Pro Val Gln Pro Glu Ala Thr Gln Val Pro Leu
        420                 425                 430 gtt tca tcc aca agt gag ggg tat aca gca tct cag ccc ttg tac cag           1522
Val Ser Ser Thr Ser Glu Gly Tyr Thr Ala Ser Gln Pro Leu Tyr Gln
    435                 440                 445 cca tct cat gct acg gag cag cgg ccg cag aaa gag cca atg gat cag           1570
Pro Ser His Ala Thr Glu Gln Arg Pro Gln Lys Glu Pro Met Asp Gln
450                 455                 460 att cag gca aca ata tct ttg aat aca gac cag act aca gca tcc tca           1618
Ile Gln Ala Thr Ile Ser Leu Asn Thr Asp Gln Thr Thr Ala Ser Ser
465                 470                 475                 480 tcc ctt cct gct gct tct cag cct caa gtg ttc cag gct ggg aca agt           1666
Ser Leu Pro Ala Ala Ser Gln Pro Gln Val Phe Gln Ala Gly Thr Ser
            485                 490                 495 aaa cct ttg cac agc agt gga atc aat gta aat gca gct cca ttc cag           1714
Lys Pro Leu His Ser Ser Gly Ile Asn Val Asn Ala Ala Pro Phe Gln
        500                 505                 510 tcc atg caa acg gtg ttc aat atg aat gct cca gtc cct cct gct aat           1762
Ser Met Gln Thr Val Phe Asn Met Asn Ala Pro Val Pro Pro Ala Asn
    515                 520                 525 gaa cca gaa acg tta aaa caa cag agt cag tac cag gcc act tat aac           1810
Glu Pro Glu Thr Leu Lys Gln Gln Ser Gln Tyr Gln Ala Thr Tyr Asn
530                 535                 540 cag agt ttt tcc agt cag cct cac caa gtg gaa caa aca gag ctt caa           1858
Gln Ser Phe Ser Ser Gln Pro His Gln Val Glu Gln Thr Glu Leu Gln
545                 550                 555                 560 caa gac caa ctg caa acg gtg gtt ggc act tac cat gga tcc cag gac           1906
Gln Asp Gln Leu Gln Thr Val Val Gly Thr Tyr His Gly Ser Gln Asp
            565                 570                 575 cag cct cat caa gtg cct ggt aac cac cag caa ccc cca cag cag aac           1954
Gln Pro His Gln Val Pro Gly Asn His Gln Gln Pro Pro Gln Gln Asn
        580                 585                 590 act ggc ttt cca cgt agc agt cag cct tat tac aac agt cgt ggg gta           2002
Thr Gly Phe Pro Arg Ser Ser Gln Pro Tyr Tyr Asn Ser Arg Gly Val
    595                 600                 605 tct cga gga ggg tct cgt ggt gcc aga ggc ttg atg aat gga tac agg           2050
Ser Arg Gly Gly Ser Arg Gly Ala Arg Gly Leu Met Asn Gly Tyr Arg
610                 615                 620 ggc cct gcc aat gga ttt aga gga gga tat gat ggt tac cgc cct tca           2098
Gly Pro Ala Asn Gly Phe Arg Gly Gly Tyr Asp Gly Tyr Arg Pro Ser
625                 630                 635                 640
```

| | | | | | | | | | | | | | | | | |
|---|---|---|---|---|---|---|---|---|---|---|---|---|---|---|---|---|
| ttc | tcg | aac | act | cca | aac | agt | ggt | tat | tca | cag | tct | cag | ttc | act | gct | 2146 |
| Phe | Ser | Asn | Thr | Pro | Asn | Ser | Gly | Tyr | Ser | Gln | Ser | Gln | Phe | Thr | Ala | |
| | | | | 645 | | | | | 650 | | | | | 655 | | |
| ccc | cgg | gac | tac | tct | ggt | tac | cag | cgg | gat | gga | tat | cag | cag | aat | ttc | 2194 |
| Pro | Arg | Asp | Tyr | Ser | Gly | Tyr | Gln | Arg | Asp | Gly | Tyr | Gln | Gln | Asn | Phe | |
| | | | 660 | | | | | 665 | | | | | 670 | | | |
| aag | cga | ggc | tct | ggg | cag | agt | gga | cca | cgg | gga | gcc | cca | cga | ggt | aat | 2242 |
| Lys | Arg | Gly | Ser | Gly | Gln | Ser | Gly | Pro | Arg | Gly | Ala | Pro | Arg | Gly | Asn | |
| | | 675 | | | | | 680 | | | | | 685 | | | | |
| ata | ttg | tgg | tgg | tga | cctagctcc | tatgtggagc | ttctgttctg | gccttggaag | | | | | | | | 2297 |
| Ile | Leu | Trp | Trp | | | | | | | | | | | | | |
| | | 690 | | | | | | | | | | | | | | | aactgttcat agtccgcatg taggttacat gttaggaata catttatctt ttccagactt 2357
gttgctaaag attaaatgaa atgctctgtt tctaaaattt catcttgaat ccaaattta 2417
attttgaat gactttccct gctgttgtct tcaaaatcag acattttct ctgcctcaga 2477
aaagcgtttt tccaactgga aatttatttt tcaggtctta aaacctgcta atgttttta 2537
ggaagtacct actgaaactt tttgtaagac atttttggaa cgagcttgaa catttatata 2597
aatttattac cctctttgat ttttgaaaca tgcatattat atttaggctg agaagccctt 2657
caaatggcca gataagccac agttttagct agagaaccat ttagaattga cataactaat 2717
ctaaacttga acactttag gaccaatgtt agtgttctaa ataccaacat atttctgatg 2777
tttaaacaga tctcccaaat tcttaggacc ttgatgtcat aaaatttag aatgacaagc 2837
ttaagaggct ttagtttcat tgttttttca agtaatgaaa ataatttct tacatgggca 2897
gatagttaat ttgttgaaca attacaggta gcattcatg taatctgatg ttctaaatgg 2957
ttctcttatt gaaggaggtt aaagaattag gtttcttaca gttttggct ggccatgaca 3017
tgtataaat gtatattaag gaggaattat aaagtacttt aatttgaatg ctagtggcaa 3077
ttgatcatta agaaagtact ttaaagcaaa aggttaatgg gtcatctggg aaaaatactg 3137
aagtatcaaa ggtatttgca tgtgaatgtg ggttatgttc ttctatccca ccttgtagca 3197
tattctatga agttgagtt aaatgatagc taaaatatct gtttcaacag catgtaaaaa 3257
gttatttaa ctgttacaag tcattataca atttgaatg ttctgtagtt tctttaac 3317
agtttaggta caaaggtctg ttttcattct ggtgcttttt attaatttg atagtatgat 3377
gtcacttcct attgaaatgt aagctagcgt gtaccttaga atgtgagctc catgagagca 3437
ggtaccttgt ttgtcttcac tgctgtatct attcccaacg cctcatgaca gtgcctggca 3497
catagtaggc actcaataaa tacttgttga atgaatgaaa aaaaaaaaa a 3548

<210> SEQ ID NO 26
<211> LENGTH: 692
<212> TYPE: PRT
<213> ORGANISM: Mus musculus

<400> SEQUENCE: 26

Met Pro Ser Ala Thr Ser His Ser Gly Ser Gly Ser Lys Ser Ser Gly
1               5                   10                  15

Pro Pro Pro Pro Ser Gly Ser Ser Gly Ser Glu Ala Ala Ala Gly Ala
            20                  25                  30

Ala Ala Pro Ala Ser Gln His Pro Ala Thr Gly Thr Gly Ala Val Gln
        35                  40                  45

Thr Glu Ala Met Lys Gln Ile Leu Gly Val Ile Asp Lys Lys Leu Arg
    50                  55                  60

Asn Leu Glu Lys Lys Lys Gly Lys Leu Asp Asp Tyr Gln Glu Arg Met

```
                65                  70                  75                  80
Asn Lys Gly Glu Arg Leu Asn Gln Asp Gln Leu Asp Ala Val Ser Lys
                    85                  90                  95

Tyr Gln Glu Val Thr Asn Asn Leu Glu Phe Ala Lys Glu Leu Gln Arg
            100                 105                 110

Ser Phe Met Ala Leu Ser Gln Asp Ile Gln Lys Thr Ile Lys Lys Thr
        115                 120                 125

Ala Arg Arg Glu Gln Leu Met Arg Glu Ala Glu Gln Lys Arg Leu
130                 135                 140

Lys Thr Val Leu Glu Leu Gln Tyr Val Leu Asp Lys Leu Gly Asp Asp
145                 150                 155                 160

Asp Val Arg Thr Asp Leu Lys Gln Gly Leu Ser Gly Val Pro Ile Leu
                165                 170                 175

Ser Glu Glu Glu Leu Ser Leu Leu Asp Glu Phe Tyr Lys Leu Val Asp
            180                 185                 190

Pro Glu Arg Asp Met Ser Leu Arg Leu Asn Glu Gln Tyr Glu His Ala
        195                 200                 205

Ser Ile His Leu Trp Asp Leu Leu Glu Gly Lys Glu Lys Pro Val Cys
210                 215                 220

Gly Thr Thr Tyr Lys Ala Leu Lys Glu Ile Glu Arg Val Phe Gln
225                 230                 235                 240

Ser Asn Tyr Phe Asp Ser Thr His Asn His Gln Asn Gly Leu Cys Glu
                245                 250                 255

Glu Glu Glu Ala Ala Ser Ala Pro Thr Val Glu Asp Gln Val Ala Glu
            260                 265                 270

Ala Glu Pro Glu Pro Ala Glu Glu Tyr Thr Glu Gln Ser Glu Val Glu
        275                 280                 285

Ser Thr Glu Tyr Val Asn Arg Gln Phe Met Ala Glu Thr Gln Phe Ser
290                 295                 300

Ser Gly Glu Lys Glu Gln Val Asp Glu Trp Thr Val Glu Thr Val Glu
305                 310                 315                 320

Val Val Asn Ser Leu Gln Gln Gln Pro Gln Ala Ala Ser Pro Ser Val
                325                 330                 335

Pro Glu Pro His Ser Leu Thr Pro Val Ala Gln Ser Asp Pro Leu Val
            340                 345                 350

Arg Arg Gln Arg Val Gln Asp Leu Met Ala Gln Met Gln Gly Pro Tyr
        355                 360                 365

Asn Phe Ile Gln Asp Ser Met Leu Asp Phe Glu Asn Gln Thr Leu Asp
370                 375                 380

Pro Ala Ile Val Ser Ala Gln Pro Met Asn Pro Thr Gln Asn Met Asp
385                 390                 395                 400

Met Pro Gln Leu Val Cys Pro Gln Val His Ser Glu Ser Arg Leu Ala
                405                 410                 415

Gln Ser Asn Gln Val Pro Val Gln Pro Glu Ala Thr Gln Val Pro Leu
            420                 425                 430

Val Ser Ser Thr Ser Glu Gly Tyr Thr Ala Ser Gln Pro Leu Tyr Gln
        435                 440                 445

Pro Ser His Ala Thr Glu Gln Arg Pro Gln Lys Glu Pro Met Asp Gln
450                 455                 460

Ile Gln Ala Thr Ile Ser Leu Asn Thr Asp Gln Thr Thr Ala Ser Ser
465                 470                 475                 480

Ser Leu Pro Ala Ala Ser Gln Pro Gln Val Phe Gln Ala Gly Thr Ser
                485                 490                 495
```

```
Lys Pro Leu His Ser Ser Gly Ile Asn Val Asn Ala Ala Pro Phe Gln
            500                 505                 510

Ser Met Gln Thr Val Phe Asn Met Asn Ala Pro Val Pro Pro Ala Asn
        515                 520                 525

Glu Pro Glu Thr Leu Lys Gln Gln Ser Gln Tyr Gln Ala Thr Tyr Asn
    530                 535                 540

Gln Ser Phe Ser Ser Gln Pro His Gln Val Glu Gln Thr Glu Leu Gln
545                 550                 555                 560

Gln Asp Gln Leu Gln Thr Val Val Gly Thr Tyr His Gly Ser Gln Asp
                565                 570                 575

Gln Pro His Gln Val Pro Gly Asn His Gln Gln Pro Gln Gln Asn
            580                 585                 590

Thr Gly Phe Pro Arg Ser Ser Gln Pro Tyr Tyr Asn Ser Arg Gly Val
            595                 600                 605

Ser Arg Gly Gly Ser Arg Gly Ala Arg Gly Leu Met Asn Gly Tyr Arg
        610                 615                 620

Gly Pro Ala Asn Gly Phe Arg Gly Gly Tyr Asp Gly Tyr Arg Pro Ser
625                 630                 635                 640

Phe Ser Asn Thr Pro Asn Ser Gly Tyr Ser Gln Ser Gln Phe Thr Ala
                645                 650                 655

Pro Arg Asp Tyr Ser Gly Tyr Gln Arg Asp Gly Tyr Gln Gln Asn Phe
            660                 665                 670

Lys Arg Gly Ser Gly Gln Ser Gly Pro Arg Gly Ala Pro Arg Gly Asn
        675                 680                 685

Ile Leu Trp Trp
        690

<210> SEQ ID NO 27
<211> LENGTH: 3508
<212> TYPE: DNA
<213> ORGANISM: Mus musculus
<220> FEATURE:
<221> NAME/KEY: CDS
<222> LOCATION: (139)..(2217)
<223> OTHER INFORMATION:

<400> SEQUENCE: 27
cccaccgcgc gcgcgcgtag ccgcctgccc gcccgcccgc tgcgcgtttt gtcccgcgtc      60
tctccccgtc cgtctcctga cttgctggtc ttgtccttcc ctcccgcttt tttcctctcc     120
tctcttctcg gtctaaag atg ccc tcg gcc acc agc cac agc gga agc ggc      171
                  Met Pro Ser Ala Thr Ser His Ser Gly Ser Gly
                    1               5                  10 agc aaa tcg tcg gga ccg ccg ccg ccg tcc ggt tcc tcc ggg agt gag      219
Ser Lys Ser Ser Gly Pro Pro Pro Pro Ser Gly Ser Ser Gly Ser Glu
            15                  20                  25 gcg gcg gcc ggg gca gct gcg ccg gct tct cag cat ccg gca acc ggc      267
Ala Ala Ala Gly Ala Ala Ala Pro Ala Ser Gln His Pro Ala Thr Gly
        30                  35                  40 acc ggc gcc gtc cag acc gag gcc atg aag cag att ctc ggc gta atc      315
Thr Gly Ala Val Gln Thr Glu Ala Met Lys Gln Ile Leu Gly Val Ile
    45                  50                  55 gac aag aaa ctt cgg aac ctg gag aag aaa aag ggt aaa ctt gat gat      363
Asp Lys Lys Leu Arg Asn Leu Glu Lys Lys Lys Gly Lys Leu Asp Asp
60                  65                  70                  75 tac cag gaa cga atg aat aaa ggg gaa agg ctc aat caa gac cag ctg      411
Tyr Gln Glu Arg Met Asn Lys Gly Glu Arg Leu Asn Gln Asp Gln Leu
                80                  85                  90
```

-continued

| | |
|---|---|
| gat gcc gta tct aag tac cag gaa gtc aca aat aat ttg gag ttt gca<br>Asp Ala Val Ser Lys Tyr Gln Glu Val Thr Asn Asn Leu Glu Phe Ala<br>            95                    100                  105 | 459 |
| aag gaa tta cag agg agt ttc atg gca tta agt caa gat att cag aaa<br>Lys Glu Leu Gln Arg Ser Phe Met Ala Leu Ser Gln Asp Ile Gln Lys<br>110                    115                    120 | 507 |
| aca ata aag aag aca gca cgt cgg gaa cag ctt atg aga gaa gaa gca<br>Thr Ile Lys Lys Thr Ala Arg Arg Glu Gln Leu Met Arg Glu Glu Ala<br>125                    130                    135 | 555 |
| gaa cag aag cgc tta aaa act gta ctt gag tta cag tat gta ttg gat<br>Glu Gln Lys Arg Leu Lys Thr Val Leu Glu Leu Gln Tyr Val Leu Asp<br>140                    145                    150                    155 | 603 |
| aag ctg gga gat gat gat gtg aga aca gat ctg aaa caa ggt ttg agt<br>Lys Leu Gly Asp Asp Asp Val Arg Thr Asp Leu Lys Gln Gly Leu Ser<br>                    160                    165                    170 | 651 |
| gga gtg cca ata ttg tct gag gag gag ttg tca ttg ctg gat gag ttc<br>Gly Val Pro Ile Leu Ser Glu Glu Glu Leu Ser Leu Leu Asp Glu Phe<br>                    175                    180                    185 | 699 |
| tac aag ctc gta gat cct gag cgt gac atg agt tta agg tta aat gag<br>Tyr Lys Leu Val Asp Pro Glu Arg Asp Met Ser Leu Arg Leu Asn Glu<br>                    190                    195                    200 | 747 |
| cag tat gaa cat gcc tca att cac ttg tgg gat ttg ctg gaa ggg aaa<br>Gln Tyr Glu His Ala Ser Ile His Leu Trp Asp Leu Leu Glu Gly Lys<br>205                    210                    215 | 795 |
| gaa aag cct gtg tgt gga aca acc tat aaa gct cta aag gaa att gtt<br>Glu Lys Pro Val Cys Gly Thr Thr Tyr Lys Ala Leu Lys Glu Ile Val<br>220                    225                    230                    235 | 843 |
| gag cgt gtt ttc cag tca aac tac ttt gat agc act cac aat cat caa<br>Glu Arg Val Phe Gln Ser Asn Tyr Phe Asp Ser Thr His Asn His Gln<br>                    240                    245                    250 | 891 |
| aat ggg ttg tgt gag gag gaa gag gcg gct tca gcg ccc aca gtg gag<br>Asn Gly Leu Cys Glu Glu Glu Glu Ala Ala Ser Ala Pro Thr Val Glu<br>255                    260                    265 | 939 |
| gac cag gta gct gaa gct gaa cct gag cca gcg gaa gaa tac aca gag<br>Asp Gln Val Ala Glu Ala Glu Pro Glu Pro Ala Glu Glu Tyr Thr Glu<br>                    270                    275                    280 | 987 |
| caa agt gag gtt gaa tca aca gag tat gtc aat agg cag ttc atg gca<br>Gln Ser Glu Val Glu Ser Thr Glu Tyr Val Asn Arg Gln Phe Met Ala<br>285                    290                    295 | 1035 |
| gaa aca cag ttc agc agt ggt gag aag gag caa gtg gat gag tgg aca<br>Glu Thr Gln Phe Ser Ser Gly Glu Lys Glu Gln Val Asp Glu Trp Thr<br>300                    305                    310                    315 | 1083 |
| gtt gaa aca gtt gag gtt gta aac tca ctc cag cag caa cct cag gct<br>Val Glu Thr Val Glu Val Val Asn Ser Leu Gln Gln Gln Pro Gln Ala<br>                    320                    325                    330 | 1131 |
| gcg tcc cct tca gtc cca gag ccc cac tct ttg act cca gtg gct cag<br>Ala Ser Pro Ser Val Pro Glu Pro His Ser Leu Thr Pro Val Ala Gln<br>335                    340                    345 | 1179 |
| tca gat cca ctt gtg aga agg cag cgt gta caa gat ctt atg gca caa<br>Ser Asp Pro Leu Val Arg Arg Gln Arg Val Gln Asp Leu Met Ala Gln<br>                    350                    355                    360 | 1227 |
| atg caa ggg ccc tat aat ttc ata cag gat tca atg ttg gat ttt gaa<br>Met Gln Gly Pro Tyr Asn Phe Ile Gln Asp Ser Met Leu Asp Phe Glu<br>365                    370                    375 | 1275 |
| aat cag acg ctt gat cct gcc att gta tcc gca cag cct atg aac cct<br>Asn Gln Thr Leu Asp Pro Ala Ile Val Ser Ala Gln Pro Met Asn Pro<br>380                    385                    390                    395 | 1323 |
| acc cag aac atg gat atg cct cag ctg gtt tgc cct cag gtt cat tct<br>Thr Gln Asn Met Asp Met Pro Gln Leu Val Cys Pro Gln Val His Ser | 1371 |

-continued

```
                     400                 405                 410
gaa tct aga ctt gcc caa tct aat caa gtt cct gta caa cca gaa gcc        1419
Glu Ser Arg Leu Ala Gln Ser Asn Gln Val Pro Val Gln Pro Glu Ala
            415                 420                 425 aca cag gtt cct ttg gtt tca tcc aca agt gag ggg tat aca gca tct        1467
Thr Gln Val Pro Leu Val Ser Ser Thr Ser Glu Gly Tyr Thr Ala Ser
        430                 435                 440 cag ccc ttg tac cag cca tct cat gct acg gag cag cgg ccg cag aaa        1515
Gln Pro Leu Tyr Gln Pro Ser His Ala Thr Glu Gln Arg Pro Gln Lys
    445                 450                 455 gag cca atg gat cag att cag gca aca ata tct ttg aat aca gac cag        1563
Glu Pro Met Asp Gln Ile Gln Ala Thr Ile Ser Leu Asn Thr Asp Gln
460                 465                 470                 475 act aca gca tcc tca tcc ctt cct gct gct tct cag cct caa gtg ttc        1611
Thr Thr Ala Ser Ser Ser Leu Pro Ala Ala Ser Gln Pro Gln Val Phe
                480                 485                 490 cag gct ggg aca agt aaa cct ttg cac agc agt gga atc aat gta aat        1659
Gln Ala Gly Thr Ser Lys Pro Leu His Ser Ser Gly Ile Asn Val Asn
            495                 500                 505 gca gct cca ttc cag tcc atg caa acg gtg ttc aat atg aat gct cca        1707
Ala Ala Pro Phe Gln Ser Met Gln Thr Val Phe Asn Met Asn Ala Pro
        510                 515                 520 gtc cct cct gct aat gaa cca gaa acg tta aaa caa cag agt cag tac        1755
Val Pro Pro Ala Asn Glu Pro Glu Thr Leu Lys Gln Gln Ser Gln Tyr
    525                 530                 535 cag gcc act tat aac cag agt ttt tcc agt cag cct cac caa gtg gaa        1803
Gln Ala Thr Tyr Asn Gln Ser Phe Ser Ser Gln Pro His Gln Val Glu
540                 545                 550                 555 caa aca gag ctt caa caa gac caa ctg caa acg gtg gtt ggc act tac        1851
Gln Thr Glu Leu Gln Gln Asp Gln Leu Gln Thr Val Val Gly Thr Tyr
                560                 565                 570 cat gga tcc cag gac cag cct cat caa gtg cct ggt aac cac cag caa        1899
His Gly Ser Gln Asp Gln Pro His Gln Val Pro Gly Asn His Gln Gln
            575                 580                 585 ccc cca cag cag aac act ggc ttt cca cgt agc agt cag cct tat tac        1947
Pro Pro Gln Gln Asn Thr Gly Phe Pro Arg Ser Ser Gln Pro Tyr Tyr
        590                 595                 600 aac agt cgt ggg gta tct cga gga ggg tct cgt ggt gcc aga ggc ttg        1995
Asn Ser Arg Gly Val Ser Arg Gly Gly Ser Arg Gly Ala Arg Gly Leu
    605                 610                 615 atg aat gga tac agg ggc cct gcc aat gga ttt aga gga gga tat gat        2043
Met Asn Gly Tyr Arg Gly Pro Ala Asn Gly Phe Arg Gly Gly Tyr Asp
620                 625                 630                 635 ggt tac cgc cct tca ttc tcg aac act cca aac agt ggt tat tca cag        2091
Gly Tyr Arg Pro Ser Phe Ser Asn Thr Pro Asn Ser Gly Tyr Ser Gln
                640                 645                 650 tct cag ttc act gct ccc cgg gac tac tct ggt tac cag cgg gat gga        2139
Ser Gln Phe Thr Ala Pro Arg Asp Tyr Ser Gly Tyr Gln Arg Asp Gly
            655                 660                 665 tat cag cag aat ttc aag cga ggc tct ggg cag agt gga cca cgg gga        2187
Tyr Gln Gln Asn Phe Lys Arg Gly Ser Gly Gln Ser Gly Pro Arg Gly
        670                 675                 680 gcc cca cga ggt aat ata ttg tgg tgg tga cctagctcc tatgtggagc           2237
Ala Pro Arg Gly Asn Ile Leu Trp Trp
    685                 690 ttctgttctg gccttggaag aactgttcat agtccgcatg taggttacat gttaggaata     2297
catttatctt ttccagactt gttgctaaag attaaatgaa atgctctgtt tctaaaattt     2357
catcttgaat ccaaatttta attttgaat gactttccct gctgttgtct tcaaaatcag      2417
```

-continued

```
aacattttct ctgcctcaga aaagcgtttt tccaactgga aatttatttt tcaggtctta      2477
aaacctgcta atgttttta ggaagtacct actgaaactt tttgtaagac attttttggaa     2537 cgagcttgaa catttatata aatttattac cctctttgat ttttgaaaca tgcatattat     2597
atttaggctg agaagcccctt caaatggcca gataagccac agttttagct agagaaccat    2657
ttagaattga cataactaat ctaaacttga acacttttag gaccaatgtt agtgttctaa     2717
ataccaacat atttctgatg tttaaacaga tctcccaaat tcttaggacc ttgatgtcat     2777
taaaatttag aatgacaagc ttaagaggct ttagtttcat ttgttttttca agtaatgaaa    2837 aataatttct tacatgggca gatagttaat ttgttgaaca attacaggta gcatttcatg     2897
taatctgatg ttctaaatgg ttctcttatt gaaggaggtt aaagaattag gtttcttaca     2957 gttttttggct ggccatgaca tgtataaaat gtatattaag gaggaattat aaagtacttt    3017
aatttgaatg ctagtggcaa ttgatcatta agaaagtact ttaaagcaaa aggttaatgg     3077
gtcatctggg aaaaatactg aagtatcaaa ggtatttgca tgtgaatgtg ggttatgttc     3137
ttctatccca ccttgtagca tattctatga agttgagtt aaatgatagc taaaatatct     3197
gtttcaacag catgtaaaaa gttatttttaa ctgttacaag tcattataca attttgaatg    3257
ttctgtagtt tctttttaac agtttaggta caaaggtctg ttttcattct ggtgcttttt    3317
attaattttg atagtatgat gtcacttcct attgaaatgt aagctagcgt gtaccttaga    3377
atgtgagctc catgagagca ggtaccttgt ttgtcttcac tgctgtatct attcccaacg    3437
cctcatgaca gtgcctggca catagtaggc actcaataaa tacttgttga atgaatgaaa    3497
aaaaaaaaaa a                                                         3508
```

<210> SEQ ID NO 28
<211> LENGTH: 692
<212> TYPE: PRT
<213> ORGANISM: Mus musculus

<400> SEQUENCE: 28

```
Met Pro Ser Ala Thr Ser His Ser Gly Ser Gly Ser Lys Ser Gly
1               5                   10                  15

Pro Pro Pro Pro Ser Gly Ser Ser Gly Ser Glu Ala Ala Gly Ala
                20                  25                  30

Ala Ala Pro Ala Ser Gln His Pro Ala Thr Gly Thr Gly Ala Val Gln
            35                  40                  45

Thr Glu Ala Met Lys Gln Ile Leu Gly Val Ile Asp Lys Lys Leu Arg
        50                  55                  60

Asn Leu Glu Lys Lys Lys Gly Lys Leu Asp Asp Tyr Gln Glu Arg Met
65                  70                  75                  80

Asn Lys Gly Glu Arg Leu Asn Gln Asp Gln Leu Asp Ala Val Ser Lys
                85                  90                  95

Tyr Gln Glu Val Thr Asn Asn Leu Glu Phe Ala Lys Glu Leu Gln Arg
            100                 105                 110

Ser Phe Met Ala Leu Ser Gln Asp Ile Gln Lys Thr Ile Lys Lys Thr
        115                 120                 125

Ala Arg Arg Glu Gln Leu Met Arg Glu Glu Ala Glu Gln Lys Arg Leu
    130                 135                 140

Lys Thr Val Leu Glu Leu Gln Tyr Val Leu Asp Lys Leu Gly Asp Asp
145                 150                 155                 160

Asp Val Arg Thr Asp Leu Lys Gln Gly Leu Ser Gly Val Pro Ile Leu
                165                 170                 175
```

```
Ser Glu Glu Glu Leu Ser Leu Leu Asp Glu Phe Tyr Lys Leu Val Asp
            180                 185                 190

Pro Glu Arg Asp Met Ser Leu Arg Leu Asn Glu Gln Tyr Glu His Ala
            195                 200                 205

Ser Ile His Leu Trp Asp Leu Leu Glu Gly Lys Glu Lys Pro Val Cys
            210                 215                 220

Gly Thr Thr Tyr Lys Ala Leu Lys Glu Ile Val Glu Arg Val Phe Gln
225                 230                 235                 240

Ser Asn Tyr Phe Asp Ser Thr His Asn His Gln Asn Gly Leu Cys Glu
                245                 250                 255

Glu Glu Glu Ala Ala Ser Ala Pro Thr Val Glu Asp Gln Val Ala Glu
            260                 265                 270

Ala Glu Pro Glu Pro Ala Glu Glu Tyr Thr Glu Gln Ser Glu Val Glu
            275                 280                 285

Ser Thr Glu Tyr Val Asn Arg Gln Phe Met Ala Glu Thr Gln Phe Ser
            290                 295                 300

Ser Gly Glu Lys Glu Gln Val Asp Glu Trp Thr Val Glu Thr Val Glu
305                 310                 315                 320

Val Val Asn Ser Leu Gln Gln Pro Gln Ala Ala Ser Pro Ser Val
            325                 330                 335

Pro Glu Pro His Ser Leu Thr Pro Val Ala Gln Ser Asp Pro Leu Val
            340                 345                 350

Arg Arg Gln Arg Val Gln Asp Leu Met Ala Gln Met Gln Gly Pro Tyr
            355                 360                 365

Asn Phe Ile Gln Asp Ser Met Leu Asp Phe Glu Asn Gln Thr Leu Asp
            370                 375                 380

Pro Ala Ile Val Ser Ala Gln Pro Met Asn Pro Thr Gln Asn Met Asp
385                 390                 395                 400

Met Pro Gln Leu Val Cys Pro Gln Val His Ser Glu Ser Arg Leu Ala
            405                 410                 415

Gln Ser Asn Gln Val Pro Val Gln Pro Glu Ala Thr Gln Val Pro Leu
            420                 425                 430

Val Ser Ser Thr Ser Glu Gly Tyr Thr Ala Ser Gln Pro Leu Tyr Gln
            435                 440                 445

Pro Ser His Ala Thr Glu Gln Arg Pro Gln Lys Glu Pro Met Asp Gln
            450                 455                 460

Ile Gln Ala Thr Ile Ser Leu Asn Thr Asp Gln Thr Thr Ala Ser Ser
465                 470                 475                 480

Ser Leu Pro Ala Ala Ser Gln Pro Gln Val Phe Gln Ala Gly Thr Ser
                485                 490                 495

Lys Pro Leu His Ser Ser Gly Ile Asn Val Asn Ala Ala Pro Phe Gln
            500                 505                 510

Ser Met Gln Thr Val Phe Asn Met Asn Ala Pro Val Pro Pro Ala Asn
            515                 520                 525

Glu Pro Glu Thr Leu Lys Gln Gln Ser Gln Tyr Gln Ala Thr Tyr Asn
            530                 535                 540

Gln Ser Phe Ser Ser Gln Pro His Gln Val Glu Gln Thr Glu Leu Gln
545                 550                 555                 560

Gln Asp Gln Leu Gln Thr Val Val Gly Thr Tyr His Gly Ser Gln Asp
                565                 570                 575

Gln Pro His Gln Val Pro Gly Asn His Gln Gln Pro Gln Gln Asn
            580                 585                 590
```

```
Thr Gly Phe Pro Arg Ser Ser Gln Pro Tyr Tyr Asn Ser Arg Gly Val
            595                 600                 605

Ser Arg Gly Gly Ser Arg Gly Ala Arg Gly Leu Met Asn Gly Tyr Arg
    610                 615                 620

Gly Pro Ala Asn Gly Phe Arg Gly Gly Tyr Asp Gly Tyr Arg Pro Ser
625                 630                 635                 640

Phe Ser Asn Thr Pro Asn Ser Gly Tyr Ser Gln Ser Gln Phe Thr Ala
                645                 650                 655

Pro Arg Asp Tyr Ser Gly Tyr Gln Arg Asp Gly Tyr Gln Gln Asn Phe
            660                 665                 670

Lys Arg Gly Ser Gly Gln Ser Gly Pro Arg Gly Ala Pro Arg Gly Asn
            675                 680                 685

Ile Leu Trp Trp
    690

<210> SEQ ID NO 29
<211> LENGTH: 2109
<212> TYPE: DNA
<213> ORGANISM: Gallus gallus
<220> FEATURE:
<221> NAME/KEY: CDS
<222> LOCATION: (1)..(2109)
<223> OTHER INFORMATION:

<400> SEQUENCE: 29 atg ccc tcg gct acc aac ggc acc atg gcg agc agc agc ggg aag gcg      48
Met Pro Ser Ala Thr Asn Gly Thr Met Ala Ser Ser Ser Gly Lys Ala
1               5                   10                  15 ggc ccg ggc ggc aac gag cag gcc ccg gcg gcg gca gcg gcg gcc ccg      96
Gly Pro Gly Gly Asn Glu Gln Ala Pro Ala Ala Ala Ala Ala Ala Pro
            20                  25                  30 cag gcg tcg ggc ggc agc atc acc tcg gtt cag acc gag gcc atg aag     144
Gln Ala Ser Gly Gly Ser Ile Thr Ser Val Gln Thr Glu Ala Met Lys
        35                  40                  45 cag atc ttg gga gtg atc gac aaa aag ctc cgc aac ctc gag aag aaa     192
Gln Ile Leu Gly Val Ile Asp Lys Lys Leu Arg Asn Leu Glu Lys Lys
    50                  55                  60 aag agc aaa ctt gac gat tac cag gaa cga atg aac aag ggg gaa cgt     240
Lys Ser Lys Leu Asp Asp Tyr Gln Glu Arg Met Asn Lys Gly Glu Arg
65                  70                  75                  80 cta aat caa gat caa ctg gat gca gtg tca aaa tac cag gaa gtg aca     288
Leu Asn Gln Asp Gln Leu Asp Ala Val Ser Lys Tyr Gln Glu Val Thr
                85                  90                  95 aat aac ctg gaa ttc gct aaa gaa ctg cag agg agc ttt atg gca ctg     336
Asn Asn Leu Glu Phe Ala Lys Glu Leu Gln Arg Ser Phe Met Ala Leu
            100                 105                 110 agc caa gat atc cag aaa aca ata aaa aag acg gct cgc agg gag cag     384
Ser Gln Asp Ile Gln Lys Thr Ile Lys Lys Thr Ala Arg Arg Glu Gln
        115                 120                 125 ctg atg aga gaa gag gct gag cag aag cgt tta aag act gtg cta gag     432
Leu Met Arg Glu Glu Ala Glu Gln Lys Arg Leu Lys Thr Val Leu Glu
    130                 135                 140 ctg cag ttc att ttg gac aag ttg ggt gac gat gaa gtg cgc agt gac     480
Leu Gln Phe Ile Leu Asp Lys Leu Gly Asp Asp Glu Val Arg Ser Asp
145                 150                 155                 160 ttg aaa caa gga tca aat gga gta ccg gta ctg aca gag gag gaa ctg     528
Leu Lys Gln Gly Ser Asn Gly Val Pro Val Leu Thr Glu Glu Glu Leu
                165                 170                 175 aca atg ctg gat gaa ttt tac aag cta gtt tac cct gaa agg gac atg     576
Thr Met Leu Asp Glu Phe Tyr Lys Leu Val Tyr Pro Glu Arg Asp Met
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     |     | 180 |     |     |     |     | 185 |     |     |     |     | 190 |     |     |     |      |
| aac | atg | agg | ttg | aat | gag | cag | tat | gag | caa | gca | tct | gtt | cac | ctg | tgg | 624  |
| Asn | Met | Arg | Leu | Asn | Glu | Gln | Tyr | Glu | Gln | Ala | Ser | Val | His | Leu | Trp |      |
|     |     | 195 |     |     |     |     | 200 |     |     |     |     | 205 |     |     |     |      |
| gac | tta | ctg | gaa | ggg | aag | gaa | aaa | ccc | gtt | tgt | gga | aca | acc | tat | aaa | 672  |
| Asp | Leu | Leu | Glu | Gly | Lys | Glu | Lys | Pro | Val | Cys | Gly | Thr | Thr | Tyr | Lys |      |
|     | 210 |     |     |     |     | 215 |     |     |     |     | 220 |     |     |     |     |      |
| gcc | ctg | aag | gag | gtt | gtt | gaa | cgt | att | ctt | caa | act | agt | tac | ttt | gat | 720  |
| Ala | Leu | Lys | Glu | Val | Val | Glu | Arg | Ile | Leu | Gln | Thr | Ser | Tyr | Phe | Asp |      |
| 225 |     |     |     |     | 230 |     |     |     |     | 235 |     |     |     |     | 240 |      |
| agc | acc | cat | aac | cat | cag | aac | ggg | tta | tgt | gag | gaa | gaa | gag | gca | gca | 768  |
| Ser | Thr | His | Asn | His | Gln | Asn | Gly | Leu | Cys | Glu | Glu | Glu | Glu | Ala | Ala |      |
|     |     |     |     | 245 |     |     |     |     | 250 |     |     |     |     | 255 |     |      |
| ccc | aca | cct | gca | gta | gaa | gac | act | gta | gca | gaa | gct | gag | cct | gat | cca | 816  |
| Pro | Thr | Pro | Ala | Val | Glu | Asp | Thr | Val | Ala | Glu | Ala | Glu | Pro | Asp | Pro |      |
|     |     |     | 260 |     |     |     |     | 265 |     |     |     |     | 270 |     |     |      |
| gca | gaa | gaa | ttt | act | gaa | cct | act | gaa | gtt | gaa | tcg | act | gag | tat | gta | 864  |
| Ala | Glu | Glu | Phe | Thr | Glu | Pro | Thr | Glu | Val | Glu | Ser | Thr | Glu | Tyr | Val |      |
|     |     | 275 |     |     |     |     | 280 |     |     |     |     | 285 |     |     |     |      |
| aac | aga | caa | ttc | atg | gca | gag | act | cag | ttc | agc | agt | agt | gag | aag | gaa | 912  |
| Asn | Arg | Gln | Phe | Met | Ala | Glu | Thr | Gln | Phe | Ser | Ser | Ser | Glu | Lys | Glu |      |
|     | 290 |     |     |     |     | 295 |     |     |     |     | 300 |     |     |     |     |      |
| cag | gta | gat | gag | tgg | aca | gtt | gaa | acg | gtt | gag | gtt | gta | aat | tca | ctg | 960  |
| Gln | Val | Asp | Glu | Trp | Thr | Val | Glu | Thr | Val | Glu | Val | Val | Asn | Ser | Leu |      |
| 305 |     |     |     |     | 310 |     |     |     |     | 315 |     |     |     |     | 320 |      |
| cag | caa | caa | aca | caa | gct | aca | tct | cct | cca | gtt | cct | gaa | cct | cat | aca | 1008 |
| Gln | Gln | Gln | Thr | Gln | Ala | Thr | Ser | Pro | Pro | Val | Pro | Glu | Pro | His | Thr |      |
|     |     |     |     | 325 |     |     |     |     | 330 |     |     |     |     | 335 |     |      |
| ctc | act | act | gtg | gct | caa | gca | gat | cct | ctt | gtt | aga | aga | cag | aga | gta | 1056 |
| Leu | Thr | Thr | Val | Ala | Gln | Ala | Asp | Pro | Leu | Val | Arg | Arg | Gln | Arg | Val |      |
|     |     |     | 340 |     |     |     |     | 345 |     |     |     |     | 350 |     |     |      |
| cag | gac | ctt | atg | gcc | cag | atg | cag | ggt | cca | tat | aac | ttc | atg | cag | gac | 1104 |
| Gln | Asp | Leu | Met | Ala | Gln | Met | Gln | Gly | Pro | Tyr | Asn | Phe | Met | Gln | Asp |      |
|     |     | 355 |     |     |     |     | 360 |     |     |     |     | 365 |     |     |     |      |
| tct | atg | ctg | gag | ttt | gag | aac | cag | aca | ctt | gat | cct | gcc | att | gta | tct | 1152 |
| Ser | Met | Leu | Glu | Phe | Glu | Asn | Gln | Thr | Leu | Asp | Pro | Ala | Ile | Val | Ser |      |
|     | 370 |     |     |     |     | 375 |     |     |     |     | 380 |     |     |     |     |      |
| gca | cag | ccc | atg | aat | cca | gca | cag | aat | ttg | gac | atg | ccg | caa | atg | gtc | 1200 |
| Ala | Gln | Pro | Met | Asn | Pro | Ala | Gln | Asn | Leu | Asp | Met | Pro | Gln | Met | Val |      |
| 385 |     |     |     |     | 390 |     |     |     |     | 395 |     |     |     |     | 400 |      |
| tgc | cct | cca | gtt | cat | act | gag | tca | aga | ctt | gcc | cag | cct | aat | caa | gtt | 1248 |
| Cys | Pro | Pro | Val | His | Thr | Glu | Ser | Arg | Leu | Ala | Gln | Pro | Asn | Gln | Val |      |
|     |     |     |     | 405 |     |     |     |     | 410 |     |     |     |     | 415 |     |      |
| cct | gtg | caa | cca | gaa | gct | acg | cag | gtt | ccc | ttg | gtt | tca | tct | aca | agt | 1296 |
| Pro | Val | Gln | Pro | Glu | Ala | Thr | Gln | Val | Pro | Leu | Val | Ser | Ser | Thr | Ser |      |
|     |     |     | 420 |     |     |     |     | 425 |     |     |     |     | 430 |     |     |      |
| gag | gga | tat | aca | gcc | tcc | cag | ccc | atg | tat | cag | cct | tct | cat | acc | aca | 1344 |
| Glu | Gly | Tyr | Thr | Ala | Ser | Gln | Pro | Met | Tyr | Gln | Pro | Ser | His | Thr | Thr |      |
|     |     | 435 |     |     |     |     | 440 |     |     |     |     | 445 |     |     |     |      |
| gag | caa | cgg | cca | cag | aag | gaa | tcc | att | gac | cag | att | cag | gct | tca | atg | 1392 |
| Glu | Gln | Arg | Pro | Gln | Lys | Glu | Ser | Ile | Asp | Gln | Ile | Gln | Ala | Ser | Met |      |
|     | 450 |     |     |     |     | 455 |     |     |     |     | 460 |     |     |     |     |      |
| tca | ctg | aat | gca | gac | cag | acc | ccg | tca | tca | tca | ctt | ccc | act | gca | 1440 |     |
| Ser | Leu | Asn | Ala | Asp | Gln | Thr | Pro | Ser | Ser | Ser | Leu | Pro | Thr | Ala |     |      |
| 465 |     |     |     |     | 470 |     |     |     |     | 475 |     |     |     | 480 |     |      |
| tcc | cag | ccg | caa | gtt | ttc | caa | gct | gga | tct | agc | aaa | cct | ttg | cat | agc | 1488 |
| Ser | Gln | Pro | Gln | Val | Phe | Gln | Ala | Gly | Ser | Ser | Lys | Pro | Leu | His | Ser |      |
|     |     |     |     | 485 |     |     |     |     | 490 |     |     |     |     | 495 |     |      |
| agc | gga | atc | aat | gtt | aat | gca | gct | cca | ttc | caa | tcc | atg | caa | aca | gta | 1536 |

```
Ser Gly Ile Asn Val Asn Ala Ala Pro Phe Gln Ser Met Gln Thr Val
            500                 505                 510 ttc aac atg aat gca cct gtt cct cct gtt aat gag cca gaa gcc ctt     1584
Phe Asn Met Asn Ala Pro Val Pro Pro Val Asn Glu Pro Glu Ala Leu
            515                 520                 525 aag caa caa aat cag tac cag gcc agt tac aac cag agt ttc tcc aat     1632
Lys Gln Gln Asn Gln Tyr Gln Ala Ser Tyr Asn Gln Ser Phe Ser Asn
        530                 535                 540 cag cca cac caa gta gaa caa tca gat ctt cag caa gaa cag ctc cag     1680
Gln Pro His Gln Val Glu Gln Ser Asp Leu Gln Gln Glu Gln Leu Gln
545                 550                 555                 560 aca gtg gtt ggt act tac cat ggt tct ccg gac cag acc cat caa gtg     1728
Thr Val Val Gly Thr Tyr His Gly Ser Pro Asp Gln Thr His Gln Val
                565                 570                 575 gca gga aac cac cag caa cct ccc cag cag aat act gga ttt cca cgc     1776
Ala Gly Asn His Gln Gln Pro Pro Gln Gln Asn Thr Gly Phe Pro Arg
            580                 585                 590 aac agt cag cct tat tac aac agt cgg gga gtg tct cgt ggt gga tca     1824
Asn Ser Gln Pro Tyr Tyr Asn Ser Arg Gly Val Ser Arg Gly Gly Ser
        595                 600                 605 cgt ggg act cgt gga ttg atg aat ggt tac agg gga cct gca aat gga     1872
Arg Gly Thr Arg Gly Leu Met Asn Gly Tyr Arg Gly Pro Ala Asn Gly
610                 615                 620 ttt aga gga gga tat gat ggc tac cgt cct tca ttt tcc aac act ccg     1920
Phe Arg Gly Gly Tyr Asp Gly Tyr Arg Pro Ser Phe Ser Asn Thr Pro
625                 630                 635                 640 aac agt ggt tac acg cag ccc caa ttt aat gct cct cga gat tat tca     1968
Asn Ser Gly Tyr Thr Gln Pro Gln Phe Asn Ala Pro Arg Asp Tyr Ser
                645                 650                 655 aac tac cag cgg gat gga tat cag cag aac ttc aaa cgt ggt tct gga     2016
Asn Tyr Gln Arg Asp Gly Tyr Gln Gln Asn Phe Lys Arg Gly Ser Gly
            660                 665                 670 caa agt ggg cct cgg gga gct cct cga ggt cgt gga ggg ccc cca aga     2064
Gln Ser Gly Pro Arg Gly Ala Pro Arg Gly Arg Gly Gly Pro Pro Arg
        675                 680                 685 cca aac aga ggg atg cct caa atg aac gct cag caa gtg aat taa          2109
Pro Asn Arg Gly Met Pro Gln Met Asn Ala Gln Gln Val Asn
690                 695                 700

<210> SEQ ID NO 30
<211> LENGTH: 702
<212> TYPE: PRT
<213> ORGANISM: Gallus gallus

<400> SEQUENCE: 30

Met Pro Ser Ala Thr Asn Gly Thr Met Ala Ser Ser Ser Gly Lys Ala
1               5                   10                  15

Gly Pro Gly Gly Asn Glu Gln Ala Pro Ala Ala Ala Ala Ala Ala Pro
            20                  25                  30

Gln Ala Ser Gly Gly Ser Ile Thr Ser Val Gln Thr Glu Ala Met Lys
        35                  40                  45

Gln Ile Leu Gly Val Ile Asp Lys Lys Leu Arg Asn Leu Glu Lys Lys
    50                  55                  60

Lys Ser Lys Leu Asp Asp Tyr Gln Glu Arg Met Asn Lys Gly Glu Arg
65                  70                  75                  80

Leu Asn Gln Asp Gln Leu Asp Ala Val Ser Lys Tyr Gln Glu Val Thr
                85                  90                  95

Asn Asn Leu Glu Phe Ala Lys Glu Leu Gln Arg Ser Phe Met Ala Leu
            100                 105                 110
```

```
Ser Gln Asp Ile Gln Lys Thr Ile Lys Lys Thr Ala Arg Arg Glu Gln
        115                 120                 125

Leu Met Arg Glu Glu Ala Glu Gln Lys Arg Leu Lys Thr Val Leu Glu
130                 135                 140

Leu Gln Phe Ile Leu Asp Lys Leu Gly Asp Asp Glu Val Arg Ser Asp
145                 150                 155                 160

Leu Lys Gln Gly Ser Asn Gly Val Pro Val Leu Thr Glu Glu Glu Leu
                165                 170                 175

Thr Met Leu Asp Glu Phe Tyr Lys Leu Val Tyr Pro Glu Arg Asp Met
                180                 185                 190

Asn Met Arg Leu Asn Glu Gln Tyr Glu Gln Ala Ser Val His Leu Trp
            195                 200                 205

Asp Leu Leu Glu Gly Lys Glu Lys Pro Val Cys Gly Thr Thr Tyr Lys
            210                 215                 220

Ala Leu Lys Glu Val Val Glu Arg Ile Leu Gln Thr Ser Tyr Phe Asp
225                 230                 235                 240

Ser Thr His Asn His Gln Asn Gly Leu Cys Glu Glu Glu Ala Ala
                245                 250                 255

Pro Thr Pro Ala Val Glu Asp Thr Val Ala Glu Ala Glu Pro Asp Pro
            260                 265                 270

Ala Glu Glu Phe Thr Glu Pro Thr Glu Val Glu Ser Thr Glu Tyr Val
            275                 280                 285

Asn Arg Gln Phe Met Ala Glu Thr Gln Phe Ser Ser Glu Lys Glu
            290                 295                 300

Gln Val Asp Glu Trp Thr Val Glu Thr Val Glu Val Val Asn Ser Leu
305                 310                 315                 320

Gln Gln Gln Thr Gln Ala Thr Ser Pro Pro Val Pro Glu Pro His Thr
                325                 330                 335

Leu Thr Thr Val Ala Gln Ala Asp Pro Leu Val Arg Arg Gln Arg Val
                340                 345                 350

Gln Asp Leu Met Ala Gln Met Gln Gly Pro Tyr Asn Phe Met Gln Asp
            355                 360                 365

Ser Met Leu Glu Phe Glu Asn Gln Thr Leu Asp Pro Ala Ile Val Ser
            370                 375                 380

Ala Gln Pro Met Asn Pro Ala Gln Asn Leu Asp Met Pro Gln Met Val
385                 390                 395                 400

Cys Pro Pro Val His Thr Glu Ser Arg Leu Ala Gln Pro Asn Gln Val
                405                 410                 415

Pro Val Gln Pro Glu Ala Thr Gln Val Pro Leu Val Ser Ser Thr Ser
            420                 425                 430

Glu Gly Tyr Thr Ala Ser Gln Pro Met Tyr Gln Pro Ser His Thr Thr
            435                 440                 445

Glu Gln Arg Pro Gln Lys Glu Ser Ile Asp Gln Ile Gln Ala Ser Met
450                 455                 460

Ser Leu Asn Ala Asp Gln Thr Pro Ser Ser Ser Leu Pro Thr Ala
465                 470                 475                 480

Ser Gln Pro Gln Val Phe Gln Ala Gly Ser Ser Lys Pro Leu His Ser
                485                 490                 495

Ser Gly Ile Asn Val Asn Ala Ala Pro Phe Gln Ser Met Gln Thr Val
                500                 505                 510

Phe Asn Met Asn Ala Pro Val Pro Pro Val Asn Glu Pro Glu Ala Leu
            515                 520                 525
```

```
Lys Gln Gln Asn Gln Tyr Gln Ala Ser Tyr Asn Gln Ser Phe Ser Asn
            530                 535                 540

Gln Pro His Gln Val Glu Gln Ser Asp Leu Gln Glu Gln Leu Gln
545                 550                 555                 560

Thr Val Val Gly Thr Tyr His Gly Ser Pro Asp Gln Thr His Gln Val
                565                 570                 575

Ala Gly Asn His Gln Gln Pro Pro Gln Gln Asn Thr Gly Phe Pro Arg
            580                 585                 590

Asn Ser Gln Pro Tyr Tyr Asn Ser Arg Gly Val Ser Arg Gly Gly Ser
            595                 600                 605

Arg Gly Thr Arg Gly Leu Met Asn Gly Tyr Arg Gly Pro Ala Asn Gly
610                 615                 620

Phe Arg Gly Gly Tyr Asp Gly Tyr Arg Pro Ser Phe Ser Asn Thr Pro
625                 630                 635                 640

Asn Ser Gly Tyr Thr Gln Pro Gln Phe Asn Ala Pro Arg Asp Tyr Ser
                645                 650                 655

Asn Tyr Gln Arg Asp Gly Tyr Gln Gln Asn Phe Lys Arg Gly Ser Gly
            660                 665                 670

Gln Ser Gly Pro Arg Gly Ala Pro Arg Gly Arg Gly Pro Pro Arg
            675                 680                 685

Pro Asn Arg Gly Met Pro Gln Met Asn Ala Gln Gln Val Asn
690                 695                 700

<210> SEQ ID NO 31
<211> LENGTH: 20
<212> TYPE: DNA
<213> ORGANISM: Artificial
<220> FEATURE:
<223> OTHER INFORMATION: T3 primer

<400> SEQUENCE: 31
aattaaccct cactaaaggg                                                20

<210> SEQ ID NO 32
<211> LENGTH: 19
<212> TYPE: DNA
<213> ORGANISM: Artificial
<220> FEATURE:
<223> OTHER INFORMATION: T7 primer

<400> SEQUENCE: 32
taatacgact cactatagg                                                 19

<210> SEQ ID NO 33
<211> LENGTH: 18
<212> TYPE: DNA
<213> ORGANISM: Artificial
<220> FEATURE:
<223> OTHER INFORMATION: primer

<400> SEQUENCE: 33
aaggtttgaa tggagtgc                                                  18

<210> SEQ ID NO 34
<211> LENGTH: 18
<212> TYPE: DNA
<213> ORGANISM: Artificial
<220> FEATURE:
<223> OTHER INFORMATION: primer

<400> SEQUENCE: 34
```

```
tgctcctttt caccactg                                               18

<210> SEQ ID NO 35
<211> LENGTH: 18
<212> TYPE: DNA
<213> ORGANISM: Artificial
<220> FEATURE:
<223> OTHER INFORMATION: GAPDH primer

<400> SEQUENCE: 35 gggctgctttt taactctg                                              18

<210> SEQ ID NO 36
<211> LENGTH: 18
<212> TYPE: DNA
<213> ORGANISM: Artificial
<220> FEATURE:
<223> OTHER INFORMATION: GAPDH primer

<400> SEQUENCE: 36
ccaggaaatg agcttgac                                               18

<210> SEQ ID NO 37
<211> LENGTH: 58
<212> TYPE: PRT
<213> ORGANISM: Homo sapiens

<400> SEQUENCE: 37

Val Phe Gln Ser Asn Tyr Phe Asp Ser Thr His Asn His Gln Asn Gly
1               5                   10                  15

Leu Cys Glu Glu Glu Ala Ala Ser Ala Pro Ala Val Glu Asp Gln
            20                  25                  30

Val Pro Glu Ala Glu Pro Glu Pro Ala Glu Gly Tyr Thr Glu Gln Ser
        35                  40                  45

Glu Val Glu Ser Thr Glu Tyr Val Asn Arg
    50                  55

<210> SEQ ID NO 38
<211> LENGTH: 22
<212> TYPE: DNA
<213> ORGANISM: Artificial
<220> FEATURE:
<223> OTHER INFORMATION: primer

<400> SEQUENCE: 38
aggtsharct gcagsagtcw gg                                          22

<210> SEQ ID NO 39
<211> LENGTH: 23
<212> TYPE: DNA
<213> ORGANISM: Artificial
<220> FEATURE:
<223> OTHER INFORMATION: primer

<400> SEQUENCE: 39
ctcgagttaa ttcacttgct gag                                         23

<210> SEQ ID NO 40
<211> LENGTH: 5
<212> TYPE: PRT
<213> ORGANISM: Mus musculus

<400> SEQUENCE: 40

Asp Tyr Asn Met Asp
```

<210> SEQ ID NO 41
<211> LENGTH: 17
<212> TYPE: PRT
<213> ORGANISM: Mus musculus

<400> SEQUENCE: 41

Asp Ile Asn Pro Asn Tyr Asp Ser Thr Ser Tyr Asn Gln Lys Phe Lys
1               5                   10                  15

Gly

<210> SEQ ID NO 42
<211> LENGTH: 11
<212> TYPE: PRT
<213> ORGANISM: Mus musculus

<400> SEQUENCE: 42

Ser Arg Ser Tyr Asp Tyr Glu Gly Phe Ala Tyr
1               5                   10

<210> SEQ ID NO 43
<211> LENGTH: 148
<212> TYPE: PRT
<213> ORGANISM: Mus musculus

<400> SEQUENCE: 43

Met Glu Trp Ser Gly Val Phe Ile Phe Leu Leu Ser Gly Thr Ala Gly
1               5                   10                  15

Val Leu Ser Glu Val Gln Leu His Gln Phe Gly Ala Glu Leu Val Lys
            20                  25                  30

Pro Gly Ala Ser Val Lys Ile Ser Cys Lys Ala Ser Gly Tyr Thr Phe
        35                  40                  45

Thr Asp Tyr Asn Met Asp Trp Val Lys Gln Ser His Gly Lys Ser Leu
    50                  55                  60

Glu Trp Ile Gly Asp Ile Asn Pro Asn Tyr Asp Ser Thr Ser Tyr Asn
65                  70                  75                  80

Gln Lys Phe Lys Gly Lys Ala Thr Leu Thr Val Asp Lys Ser Ser Ser
                85                  90                  95

Thr Ala Tyr Met Glu Leu Arg Ser Leu Thr Ser Glu Asp Thr Ala Val
            100                 105                 110

Tyr Tyr Cys Ala Arg Ser Arg Ser Tyr Asp Tyr Glu Gly Phe Ala Tyr
        115                 120                 125

Trp Gly Gln Gly Thr Leu Val Thr Val Ser Ala Ala Lys Thr Thr Pro
    130                 135                 140

Pro Ser Val Tyr
145

<210> SEQ ID NO 44
<211> LENGTH: 11
<212> TYPE: PRT
<213> ORGANISM: Mus musculus

<400> SEQUENCE: 44

Arg Ala Ser Gly Asn Ile His Asn Tyr Leu Ala
1               5                   10

<210> SEQ ID NO 45
<211> LENGTH: 7
<212> TYPE: PRT

<210> SEQ ID NO 45
<211> LENGTH: 6
<212> TYPE: PRT
<213> ORGANISM: Mus musculus

<400> SEQUENCE: 45

Asn Ala Lys Thr Leu Ala Asp
1               5

<210> SEQ ID NO 46
<211> LENGTH: 8
<212> TYPE: PRT
<213> ORGANISM: Mus musculus

<400> SEQUENCE: 46

Gln His Phe Trp Ser Thr Leu Thr
1               5

<210> SEQ ID NO 47
<211> LENGTH: 139
<212> TYPE: PRT
<213> ORGANISM: Mus musculus

<400> SEQUENCE: 47

Met Ser Val Leu Thr Gln Val Leu Gly Leu Leu Leu Trp Leu Thr
1               5                   10                  15

Gly Ala Arg Cys Asp Ile Gln Met Thr Gln Ser Pro Ala Ser Leu Ser
                20                  25                  30

Ala Ser Val Gly Glu Thr Val Thr Ile Thr Cys Arg Ala Ser Gly Asn
        35                  40                  45

Ile His Asn Tyr Leu Ala Trp Tyr Gln Gln Lys Gln Gly Lys Ser Pro
    50                  55                  60

Gln Leu Leu Val Tyr Asn Ala Lys Thr Leu Ala Asp Gly Val Pro Ser
65                  70                  75                  80

Arg Phe Ser Gly Ser Gly Ser Gly Thr Gln Tyr Ser Leu Lys Ile Asn
                85                  90                  95

Ser Leu Gln Pro Glu Asp Phe Gly Ser Tyr Tyr Cys Gln His Phe Trp
            100                 105                 110

Ser Thr Leu Thr Phe Gly Ala Gly Thr Lys Leu Glu Leu Lys Arg Ala
        115                 120                 125

Asp Ala Ala Pro Thr Val Ser Asn Pro Tyr Asp
        130                 135

<210> SEQ ID NO 48
<211> LENGTH: 444
<212> TYPE: DNA
<213> ORGANISM: Mus musculus

<400> SEQUENCE: 48
atggaatgga gcggggtctt tatctttctc ctgtcaggaa ctgcaggtgt cctctctgag       60
gtccagctgc atcagtttgg agctgagctg gtgaagcctg ggcttcagt gaagatatcc      120 tgcaaggctt ctggctacac attcactgac tacaacatgg actgggtgaa gcagagccat      180
ggaaagagcc ttgagtggat tggagatatt aatcctaact atgatagtac tagctacaac      240
cagaagttca aggaaaggc cacattgact gtagacaagt cctccagcac agcctacatg      300
gagctccgca gcctgacatc tgaggacact gcagtctatt actgtgcaag atcgaggagc      360
tatgattacg aaggatttgc ttactggggc caagggactc tggtcactgt ctctgcagcc      420
aaaacaacac ccccatcagt ctat                                              444

<210> SEQ ID NO 49

<211> LENGTH: 444
<212> TYPE: DNA
<213> ORGANISM: Mus musculus

<400> SEQUENCE: 49

```
atggaatgga gcggggtctt tatctttctc ctgtcaggaa ctgcaggtgt cctctctgag    60
gtccagctgc atcagtttgg agctgagctg gtgaagcctg ggcttcagt gaagatatcc   120
tgcaaggctt ctggctacac attcactgac tacaacatgg actgggtgaa gcagagccat   180
ggaaagagcc ttgagtggat tggagatatt aatcctaact atgatagtac tagctacaac   240
cagaagttca agggaaaggc cacattgact gtagacaagt cctccagcac agcctacatg   300
gagctccgca gcctgacatc tgaggacact gcagtctatt actgtgcaag atcgaggagc   360
tatgattacg aaggatttgc ttactggggc caagggactc tggtcactgt ctctgcagcc   420
aaaacaacac ccccatcagt ctat                                         444
```

<210> SEQ ID NO 50
<211> LENGTH: 11
<212> TYPE: PRT
<213> ORGANISM: Mus musculus

<400> SEQUENCE: 50

Leu Trp Ser Val Asn Gln Lys Asn Tyr Leu Ser
1               5                   10

<210> SEQ ID NO 51
<211> LENGTH: 7
<212> TYPE: PRT
<213> ORGANISM: Mus musculus

<400> SEQUENCE: 51

Gly Ala Ser Ile Arg Glu Ser
1               5

<210> SEQ ID NO 52
<211> LENGTH: 9
<212> TYPE: PRT
<213> ORGANISM: Mus musculus

<400> SEQUENCE: 52

Gln His Asn His Gly Ser Phe Leu Pro
1               5

<210> SEQ ID NO 53
<211> LENGTH: 132
<212> TYPE: PRT
<213> ORGANISM: Mus musculus

<400> SEQUENCE: 53

Ala Val Leu Arg Cys Ser Arg Gly Leu Leu Val Ile Trp Ile Ser Asp
1               5                   10                  15
Ile Gln Leu Thr Gln Ser Pro Ser Leu Ala Val Thr Ala Gly Glu
            20                  25                  30
Lys Val Thr Met Ser Cys Lys Ser Ser Gln Ser Leu Leu Trp Ser Val
        35                  40                  45
Asn Gln Lys Asn Tyr Leu Ser Trp Tyr Gln Gln Lys Gln Arg Gln Pro
    50                  55                  60
Pro Lys Leu Leu Ile Tyr Gly Ala Ser Ile Arg Glu Ser Trp Val Pro
65                  70                  75                  80
Asp Arg Phe Thr Gly Ser Gly Ser Gly Thr Asp Phe Thr Leu Thr Ile

```
                85                  90                  95
Ser Asn Val His Ala Glu Asp Leu Ala Val Tyr Tyr Cys Gln His Asn
            100                 105                 110

His Gly Ser Phe Leu Pro Ser Arg Ser Glu Gln Val Pro Ser Trp Arg
        115                 120                 125

Ser Asn Asn Arg
    130
```

```
<210> SEQ ID NO 54
<211> LENGTH: 398
<212> TYPE: DNA
<213> ORGANISM: Mus musculus

<400> SEQUENCE: 54
gcggtcctgc ggtgctctag aggactacta gtcatatgga tttccgatat ccagctgacc      60
cagtctccat cctccctggc tgtgacagca ggagagaagg tcactatgag ctgcaagtcc     120
agtcagagtc ttttgtggag tgtaaaccag aagaactact gtcctggta ccagcagaaa     180 caaaggcagc tcctaaaact gcttatctat ggggcatcca ttagagaatc ttgggtccct     240
gatcggttca caggaagtgg atctgggaca gacttcactc tcaccattag caatgtgcat     300
gctgaagacc tagcagttta ttactgtcaa cacaatcatg gcagctttct ccctcacgt     360 tcggagcagg taccaagctg agatcaaac aatcggat                              398
```

```
<210> SEQ ID NO 55
<211> LENGTH: 11
<212> TYPE: PRT
<213> ORGANISM: Mus musculus

<400> SEQUENCE: 55

Arg Ala Ser Gly Asn Ile His Asn Tyr Leu Ala
1               5                   10
```

```
<210> SEQ ID NO 56
<211> LENGTH: 7
<212> TYPE: PRT
<213> ORGANISM: Mus musculus

<400> SEQUENCE: 56

Asn Ala Lys Thr Leu Ala Asp
1               5
```

```
<210> SEQ ID NO 57
<211> LENGTH: 9
<212> TYPE: PRT
<213> ORGANISM: Mus musculus

<400> SEQUENCE: 57

Gln His Phe Trp Ser Thr Leu Thr Phe
1               5
```

```
<210> SEQ ID NO 58
<211> LENGTH: 117
<212> TYPE: PRT
<213> ORGANISM: Mus musculus

<400> SEQUENCE: 58

Arg Thr Thr Ser His Met Asp Ser Asp Ile Gln Leu Thr Gln Ser Pro
1               5                   10                  15

Ala Ser Leu Ser Ala Ser Val Gly Glu Thr Val Thr Ile Thr Cys Arg
            20                  25                  30
```

Ala Ser Gly Asn Ile His Asn Tyr Leu Ala Trp Tyr Gln Gln Lys Gln
         35                  40                  45

Gly Lys Ser Pro Gln Leu Leu Val Tyr Asn Ala Lys Thr Leu Ala Asp
     50                  55                  60

Gly Val Pro Ser Arg Phe Ser Gly Ser Gly Ser Gly Thr Gln Tyr Ser
 65                  70                  75                  80

Leu Lys Ile Asn Ser Leu Gln Pro Glu Asp Phe Gly Ser Tyr Tyr Cys
                 85                  90                  95

Gln His Phe Trp Ser Thr Leu Thr Phe Gly Gly Gly Thr Lys Leu Glu
             100                 105                 110

Ile Lys Gln Ser Asp
         115

<210> SEQ ID NO 59
<211> LENGTH: 353
<212> TYPE: DNA
<213> ORGANISM: Mus musculus

<400> SEQUENCE: 59
gaggactact agtcatatgg attccgatat ccagctgacc cagtctccag cctccctatc     60
tgcatctgtg ggagaaactg tcaccatcac atgtcgagca agtgggaata ttcacaatta    120
tttagcatgg tatcagcaga aacagggaaa atcctcag ctcctggtct ataatgcaaa     180
aaccttagca gatggtgtgc catcaaggtt cagtggcagt ggatcaggaa cacaatattc    240
tctcaagatc aacagcctgc agcctgaaga ttttggagt tattactgtc aacattttg     300 gagtacgctc acgttcggag gtggtaccaa gctggagatc aaacaatcgg atc           353

<210> SEQ ID NO 60
<211> LENGTH: 11
<212> TYPE: PRT
<213> ORGANISM: Mus musculus

<400> SEQUENCE: 60

Arg Ala Ser Gln Ser Ile Ser Asn Tyr Leu His
1               5                   10

<210> SEQ ID NO 61
<211> LENGTH: 7
<212> TYPE: PRT
<213> ORGANISM: Mus musculus

<400> SEQUENCE: 61

Tyr Ala Ser Gln Ser Ile Ser
1               5

<210> SEQ ID NO 62
<211> LENGTH: 9
<212> TYPE: PRT
<213> ORGANISM: Mus musculus

<400> SEQUENCE: 62

Gln Gln Ser Asn Ser Trp Pro Tyr Thr
1               5

<210> SEQ ID NO 63
<211> LENGTH: 94
<212> TYPE: PRT
<213> ORGANISM: Mus musculus

<400> SEQUENCE: 63

```
Ser Gly Asp Arg Val Ser Leu Ser Cys Arg Ala Ser Gln Ser Ile Ser
1               5                  10                  15

Asn Tyr Leu His Trp Tyr Gln Gln Lys Ser His Glu Ser Pro Arg Leu
            20                  25                  30

Leu Ile Lys Tyr Ala Ser Gln Ser Ile Ser Gly Ile Pro Ser Arg Phe
        35                  40                  45

Ser Gly Ser Gly Ser Gly Thr Asp Phe Thr Leu Ser Ile Asn Ser Val
    50                  55                  60

Glu Thr Glu Asp Phe Gly Met Tyr Phe Cys Gln Gln Ser Asn Ser Trp
65                  70                  75                  80

Pro Tyr Thr Phe Gly Ala Gly Thr Lys Leu Glu Ile Lys Gln
                85                  90
```

```
<210> SEQ ID NO 64
<211> LENGTH: 283
<212> TYPE: DNA
<213> ORGANISM: Mus musculus

<400> SEQUENCE: 64
tcaggagata gagtcagtct ttcctgcagg gccagtcaaa gtattagcaa ctacctacac     60
tggtatcaac aaaaatcaca tgagtctcca aggcttctca tcaagtatgc ttcccagtcc    120
atctctggga tcccctccag gttcagtggc agtggatcag ggacagattt cactctcagt    180
atcaacagtg tggagactga agattttgga atgtatttct gtcaacagag taacagctgg    240
ccgtacacgt tcggtgcagg taccaagctg gagatcaaac aga                      283
```

```
<210> SEQ ID NO 65
<211> LENGTH: 11
<212> TYPE: PRT
<213> ORGANISM: Mus musculus

<400> SEQUENCE: 65

Leu Ser Ile Val Asn Arg Tyr His Tyr Met Ser
1               5                  10
```

```
<210> SEQ ID NO 66
<211> LENGTH: 6
<212> TYPE: PRT
<213> ORGANISM: Mus musculus

<400> SEQUENCE: 66

Glu Ala Ser Ile Thr Lys
1               5
```

```
<210> SEQ ID NO 67
<211> LENGTH: 9
<212> TYPE: PRT
<213> ORGANISM: Mus musculus

<400> SEQUENCE: 67

Gln His Asn Arg Gly Ser Phe Leu Pro
1               5
```

```
<210> SEQ ID NO 68
<211> LENGTH: 105
<212> TYPE: PRT
<213> ORGANISM: Mus musculus

<400> SEQUENCE: 68

Gly Leu Phe Cys Ser Val Glu Arg Cys His Tyr Gln Leu Gln Ser Ser
```

```
  1               5                  10                 15
Gln Asn Leu Leu Ser Ile Val Asn Arg Tyr His Tyr Met Ser Gly Asn
                 20                 25                 30

Pro Pro Lys Leu Leu Val Tyr Pro Ala Leu Leu Ile Tyr Glu Ala Ser
             35                 40                 45

Ile Thr Lys Ser Cys Val Pro Asp Arg Phe Thr Arg Ser Gly Ser Gly
         50                 55                 60

Thr Asn Phe Thr Leu Thr Ile Asn Phe Val His Ala Asp Asp Leu Ile
 65                 70                 75                 80

Phe Tyr Tyr Cys Gln His Asn Arg Gly Ser Phe Leu Pro Ser Ser Ser
                 85                 90                 95

Val Gln Val Pro Arg Arg Arg Ser Asn
                100                105
```

<210> SEQ ID NO 69
<211> LENGTH: 317
<212> TYPE: DNA
<213> ORGANISM: Mus musculus

<400> SEQUENCE: 69

```
ggactcttct gctctgtgga gagatgtcac tatcaactgc aatccagtca gaatcttttg      60
agtattgtaa accggtatca ctacatgtcc ggaaaccctc ctaaactcct ggtctatcct     120
gcactgctta tctatgaggc atccattaca aaatcctgtg tccctgatcg gttcacacga     180
agtggatctg ggacaaactt cactctcacc attaattttg tgcatgctga tgacctaatt     240
ttttattact gtcaacacaa tcgtggcagc tttctcccct caagttcggt gcaggtacca     300
agaaggagat caaacaa                                                    317
```

<210> SEQ ID NO 70
<211> LENGTH: 5
<212> TYPE: PRT
<213> ORGANISM: Mus musculus

<400> SEQUENCE: 70

```
Gly Tyr Thr Met Asn
 1               5
```

<210> SEQ ID NO 71
<211> LENGTH: 16
<212> TYPE: PRT
<213> ORGANISM: Mus musculus

<400> SEQUENCE: 71

```
Asn Pro Tyr Asn Gly Gly Thr Ser Tyr Asn Gln Lys Phe Lys Gly Lys
 1               5                  10                 15
```

<210> SEQ ID NO 72
<211> LENGTH: 9
<212> TYPE: PRT
<213> ORGANISM: Mus musculus

<400> SEQUENCE: 72

```
Trp Gly Val Trp Ser Ala Met Asp Tyr
 1               5
```

<210> SEQ ID NO 73
<211> LENGTH: 100
<212> TYPE: PRT
<213> ORGANISM: Mus musculus

<400> SEQUENCE: 73

Asp Ile Leu Gln Ala Ser Gly Tyr Ser Phe Thr Gly Tyr Thr Met Asn
1               5                   10                  15

Trp Val Lys Gln Ser His Gly Lys Asn Leu Glu Trp Ile Gly Leu Ile
            20                  25                  30

Asn Pro Tyr Asn Gly Gly Thr Ser Tyr Asn Gln Lys Phe Lys Gly Lys
        35                  40                  45

Ala Thr Leu Thr Val Asp Lys Ser Ser Ser Thr Ala Tyr Met Glu Leu
    50                  55                  60

Leu Ser Leu Thr Ser Glu Asp Ser Ala Val Tyr Tyr Cys Ala Arg Trp
65                  70                  75                  80

Gly Val Trp Ser Ala Met Asp Tyr Trp Gly Gln Gly Thr Thr Val Thr
                85                  90                  95

Val Ser Ser Lys
            100

<210> SEQ ID NO 74
<211> LENGTH: 11
<212> TYPE: PRT
<213> ORGANISM: Mus musculus

<400> SEQUENCE: 74

Lys Ala Ser Gln Asn Val Arg Thr Ala Val Ala
1               5                   10

<210> SEQ ID NO 75
<211> LENGTH: 7
<212> TYPE: PRT
<213> ORGANISM: Mus musculus

<400> SEQUENCE: 75

Leu Ala Ser Asn Arg Asp Thr
1               5

<210> SEQ ID NO 76
<211> LENGTH: 9
<212> TYPE: PRT
<213> ORGANISM: Mus musculus

<400> SEQUENCE: 76

Leu Gln His Cys Asn Tyr Pro Asn Glu
1               5

<210> SEQ ID NO 77
<211> LENGTH: 90
<212> TYPE: PRT
<213> ORGANISM: Mus musculus

<400> SEQUENCE: 77

Asp Arg Val Ser Ile Thr Cys Lys Ala Ser Gln Asn Val Arg Thr Ala
1               5                   10                  15

Val Ala Trp Tyr Gln Gln Lys Pro Arg Gln Ser Pro Lys Ala Leu Ile
            20                  25                  30

Tyr Leu Ala Ser Asn Arg Asp Thr Gly Leu Pro Asp Arg Phe Pro Gly
        35                  40                  45

Arg Gly Ser Gly Thr Asp Phe Thr Leu Asn Ile Thr Asn Val Gln Ser
    50                  55                  60

Glu Asp Leu Glu Asp Tyr Phe Cys Leu Gln His Cys Asn Tyr Pro Asn
65                  70                  75                  80

Glu Phe Arg Gly Cys Thr Lys Val Pro Ile
            85                  90

<210> SEQ ID NO 78
<211> LENGTH: 301
<212> TYPE: DNA
<213> ORGANISM: Mus musculus

<400> SEQUENCE: 78
gatatcctgc aggcttctgg ttactcattc actggctaca ccatgaactg ggtgaagcag     60
agccatggaa agaaccttga gtggattgga cttattaatc cttacaatgg tggtactagc    120
tacaaccaga agttcaaggg caaggccaca ttaactgtag acaagtcatc cagcacagcc    180
tacatggagc tcctcagtct gacatctgag gactctgcag tctattactg tgcaagatgg    240
ggggtatggt cggctatgga ctactggggc caagggacca cggtcaccgt ctcctcaaaa    300
a                                                                    301

<210> SEQ ID NO 79
<211> LENGTH: 290
<212> TYPE: DNA
<213> ORGANISM: Mus musculus

<400> SEQUENCE: 79
gacagggtca gcatcacctg caaggccagt caaaatgttc gtactgctgt agcctggtat     60
caacagaaac cacggcagtc tcctaaagca ctgatttact ggcatccaa ccgggacact    120 ggactccctg atcgcttccc aggcagggga tctgggacag atttcactct caacattacc    180
aatgtgcaat ctgaagacct ggaagattat ttctgtctgc aacattgtaa ttatcctaac    240
gagttcagag gttgtaccaa ggtgccaatc taaagaacaa acaccccctg              290

<210> SEQ ID NO 80
<211> LENGTH: 5
<212> TYPE: PRT
<213> ORGANISM: Mus musculus

<400> SEQUENCE: 80

Ser Tyr Trp Met Gln
1               5

<210> SEQ ID NO 81
<211> LENGTH: 17
<212> TYPE: PRT
<213> ORGANISM: Mus musculus

<400> SEQUENCE: 81

Ala Ile Tyr Pro Gly Asp Gly Asp Thr Arg Tyr Thr Gln Lys Phe Lys
1               5                   10                  15

Gly

<210> SEQ ID NO 82
<211> LENGTH: 11
<212> TYPE: PRT
<213> ORGANISM: Mus musculus

<400> SEQUENCE: 82

Ala Arg Gly Glu Tyr Gly Asn Tyr Phe Ala Tyr
1               5                   10

<210> SEQ ID NO 83
<211> LENGTH: 116

```
<212> TYPE: PRT
<213> ORGANISM: Mus musculus

<400> SEQUENCE: 83

Leu Gln Glu Ser Gly Ala Glu Leu Ala Arg Pro Gly Ala Ser Val Lys
1               5                   10                  15

Leu Ser Cys Lys Ala Ser Gly Tyr Thr Phe Thr Ser Tyr Trp Met Gln
            20                  25                  30

Trp Val Lys Gln Arg Pro Gly Gln Gly Leu Glu Trp Ile Gly Ala Ile
        35                  40                  45

Tyr Pro Gly Asp Gly Asp Thr Arg Tyr Thr Gln Lys Phe Lys Gly Lys
    50                  55                  60

Ala Thr Leu Thr Ala Asp Lys Ser Ser Ser Thr Ala Tyr Met Gln Leu
65                  70                  75                  80

Ser Ser Leu Ala Ser Glu Asp Ser Ala Val Tyr Tyr Cys Ala Arg Gly
                85                  90                  95

Glu Tyr Gly Asn Tyr Phe Ala Tyr Trp Gly Gln Gly Thr Thr Val Thr
            100                 105                 110

Val Ser Ser Asn
        115

<210> SEQ ID NO 84
<211> LENGTH: 11
<212> TYPE: PRT
<213> ORGANISM: Mus musculus

<400> SEQUENCE: 84

Lys Ala Ser Gln Asp Ile Asn Ser Tyr Leu Ser
1               5                   10

<210> SEQ ID NO 85
<211> LENGTH: 7
<212> TYPE: PRT
<213> ORGANISM: Mus musculus

<400> SEQUENCE: 85

Arg Ala Asn Arg Leu Val Asp
1               5

<210> SEQ ID NO 86
<211> LENGTH: 9
<212> TYPE: PRT
<213> ORGANISM: Mus musculus

<400> SEQUENCE: 86

Leu Gln Tyr Asp Glu Phe Pro Leu Thr
1               5

<210> SEQ ID NO 87
<211> LENGTH: 100
<212> TYPE: PRT
<213> ORGANISM: Mus musculus

<400> SEQUENCE: 87

Thr Ser Asp Ala Ser Leu Gly Glu Arg Val Thr Ile Thr Cys Lys Ala
1               5                   10                  15

Ser Gln Asp Ile Asn Ser Tyr Leu Ser Trp Phe Gln Gln Lys Pro Gly
            20                  25                  30

Lys Ser Pro Lys Thr Leu Ile Tyr Arg Ala Asn Arg Leu Val Asp Gly
        35                  40                  45
```

Val Pro Ser Arg Phe Ser Gly Ser Gly Ser Gly Gln Asp Tyr Ser Leu
        50                  55                  60

Thr Ile Ser Ser Leu Glu Tyr Glu Asp Met Gly Ile Tyr Tyr Cys Leu
65                  70                  75                  80

Gln Tyr Asp Glu Phe Pro Leu Thr Phe Gly Gly Gly Thr Lys Leu Glu
                85                  90                  95

Ile Lys Gln Lys
            100

<210> SEQ ID NO 88
<211> LENGTH: 352
<212> TYPE: DNA
<213> ORGANISM: Mus musculus

<400> SEQUENCE: 88
aactgcagga gtctggggct gagctggcaa gacctggggc ttcagtgaag ttgtcctgca      60
aggcttctgg ctacaccttt actagctact ggatgcagtg ggtaaaacag aggcctggac     120
agggtctgga atggattggg ctatttatc ctggagatgg tgatactagg tacactcaga      180
agttcaaggg caaggccaca ttgactgcag ataaatcctc cagcacagcc tacatgcaac     240
tcagcagctt ggcatctgag gactctgcgg tctattactg tgcaagaggg gagtatggta     300
actattttgc ttactggggc caagggacca cggtcaccgt ctcctcaaat cg             352

<210> SEQ ID NO 89
<211> LENGTH: 302
<212> TYPE: DNA
<213> ORGANISM: Mus musculus

<400> SEQUENCE: 89
ggacatcgga tgcatctcta ggagagagag tcactatcac ttgcaaggcg agtcaggaca      60
ttaatagcta tttaagctgg ttccagcaga aaccagggaa atctcctaag accctgatct     120
atcgtgcaaa cagattggta gatggggtcc catcaaggtt cagtggcagt ggatctgggc     180
aagattattc tctcaccatc agcagcctgg agtatgaaga tatgggaatt tattattgtc     240
tacagtatga tgagtttccg ctcacgttcg gaggaggtac caagctggag atcaaacaaa     300
aa                                                                    302

<210> SEQ ID NO 90
<211> LENGTH: 5
<212> TYPE: PRT
<213> ORGANISM: Mus musculus

<400> SEQUENCE: 90

Asp Thr Tyr Met His
1               5

<210> SEQ ID NO 91
<211> LENGTH: 17
<212> TYPE: PRT
<213> ORGANISM: Mus musculus

<400> SEQUENCE: 91

Arg Ile Asp Pro Ala Asn Gly Asn Thr Lys Tyr Asp Pro Lys Phe Gln
1               5                   10                  15

Gly

<210> SEQ ID NO 92
<211> LENGTH: 14

```
<212> TYPE: PRT
<213> ORGANISM: Mus musculus

<400> SEQUENCE: 92

Ala Arg Pro Ile His Tyr Tyr Tyr Gly Ser Ser Leu Ala Tyr
1               5                   10

<210> SEQ ID NO 93
<211> LENGTH: 108
<212> TYPE: PRT
<213> ORGANISM: Mus musculus

<400> SEQUENCE: 93

Ala Trp Leu Ser Gln Leu Ser Cys Thr Ala Ser Gly Phe Asn Ile Lys
1               5                   10                  15

Asp Thr Tyr Met His Trp Val Lys Gln Arg Pro Glu Gln Gly Leu Glu
            20                  25                  30

Trp Ile Gly Arg Ile Asp Pro Ala Asn Gly Asn Thr Lys Tyr Asp Pro
        35                  40                  45

Lys Phe Gln Gly Lys Ala Thr Ile Thr Ala Asp Thr Ser Ser Asn Thr
    50                  55                  60

Ala Tyr Leu Gln Leu Ser Ser Leu Thr Ser Glu Asp Thr Ala Val Tyr
65                  70                  75                  80

Tyr Cys Ala Arg Pro Ile His Tyr Tyr Tyr Gly Ser Ser Leu Ala Tyr
                85                  90                  95

Trp Gly Gln Gly Thr Thr Val Thr Val Ser Ser Lys
            100                 105

<210> SEQ ID NO 94
<211> LENGTH: 11
<212> TYPE: PRT
<213> ORGANISM: Mus musculus

<400> SEQUENCE: 94

Ser Val Asp Ser Tyr Gly Asn Ser Phe Met His
1               5                   10

<210> SEQ ID NO 95
<211> LENGTH: 7
<212> TYPE: PRT
<213> ORGANISM: Mus musculus

<400> SEQUENCE: 95

Arg Ala Ser Asn Leu Glu Ser
1               5

<210> SEQ ID NO 96
<211> LENGTH: 9
<212> TYPE: PRT
<213> ORGANISM: Mus musculus

<400> SEQUENCE: 96

Gln Gln Ser Asn Glu Asp Pro Gly Arg
1               5

<210> SEQ ID NO 97
<211> LENGTH: 104
<212> TYPE: PRT
<213> ORGANISM: Mus musculus

<400> SEQUENCE: 97

Glu Phe His Ala Val Ser Leu Gly Gln Arg Ala Thr Ile Ser Cys Arg
```

```
1               5                   10                  15
Ala Ser Glu Ser Val Asp Ser Tyr Gly Asn Ser Phe Met His Trp Tyr
                20                  25                  30

Gln Gln Lys Pro Gly Gln Pro Pro Lys Leu Leu Ile Tyr Arg Ala Ser
                35                  40                  45

Asn Leu Glu Ser Gly Ile Pro Ala Arg Phe Ser Gly Ser Gly Ser Arg
                50                  55                  60

Thr Asp Phe Thr Leu Thr Ile Asn Pro Val Glu Ala Asp Asp Val Ala
65                  70                  75                  80

Thr Tyr Tyr Cys Gln Gln Ser Asn Glu Asp Pro Gly Arg Ser Glu Val
                85                  90                  95

Val Pro Ser Trp Arg Ser Asn Lys
                100
```

<210> SEQ ID NO 98
<211> LENGTH: 326
<212> TYPE: DNA
<213> ORGANISM: Mus musculus

<400> SEQUENCE: 98

| | |
|---|---|
| gcatggctca gtcagttgtc ctgcacagct tctggcttca acattaaaga cacctatatg | 60 |
| cactgggtga agcagaggcc tgaacagggc ctggagtgga ttggaaggat tgatcctgcg | 120 |
| aatggtaata ctaaatatga cccgaagttc cagggcaagg ccactataac agcagacaca | 180 |
| tcctccaaca cagcctacct gcagctcagc agcctgacat ctgaggacac tgccgtctat | 240 |
| tactgtgcta gaccgattca ttattactac ggtagtagcc ttgcttactg gggccaaggg | 300 |
| accacggtca ccgtctcctc aaaaaa | 326 |

<210> SEQ ID NO 99
<211> LENGTH: 313
<212> TYPE: DNA
<213> ORGANISM: Mus musculus

<400> SEQUENCE: 99

| | |
|---|---|
| gagtttcatg ctgtgtctct agggcagagg gccaccatat cctgcagagc cagtgaaagt | 60 |
| gttgatagtt atggcaatag ttttatgcac tggtaccagc agaaaccagg acagccaccc | 120 |
| aaactcctca tctatcgtgc atccaaccta gaatctggga tccctgccag gttcagtggc | 180 |
| agtgggtcta ggacagactt caccctcacc attaatcctg tggaggctga tgatgttgca | 240 |
| acctattact gtcagcaaag taatgaggat cctggacgtt cggaggtggt accaagctgg | 300 |
| agatcaaaca aaa | 313 |

<210> SEQ ID NO 100
<211> LENGTH: 5
<212> TYPE: PRT
<213> ORGANISM: Mus musculus

<400> SEQUENCE: 100

```
Asp Tyr Tyr Met Ser
1               5
```

<210> SEQ ID NO 101
<211> LENGTH: 17
<212> TYPE: PRT
<213> ORGANISM: Mus musculus

<400> SEQUENCE: 101

```
Arg Asn Lys Ala Asn Gly Tyr Thr Thr Glu Tyr Ser Ala Ser Val Lys
1               5                   10                  15

Gly

<210> SEQ ID NO 102
<211> LENGTH: 9
<212> TYPE: PRT
<213> ORGANISM: Mus musculus

<400> SEQUENCE: 102

Ala Arg Ala Asn Trp Ala Phe Asp Tyr
1               5

<210> SEQ ID NO 103
<211> LENGTH: 109
<212> TYPE: PRT
<213> ORGANISM: Mus musculus

<400> SEQUENCE: 103

Pro Arg Ala Ser Leu Gly Val Ser Glu Thr Leu Leu Cys Thr Ser Gly
1               5                   10                  15

Phe Thr Phe Thr Asp Tyr Tyr Met Ser Trp Val Arg Gln Pro Pro Gly
            20                  25                  30

Lys Ala Leu Glu Trp Leu Gly Phe Ile Arg Asn Lys Ala Asn Gly Tyr
        35                  40                  45

Thr Thr Glu Tyr Ser Ala Ser Val Lys Gly Arg Phe Thr Ile Ser Arg
    50                  55                  60

Asp Asn Ser Gln Ser Ile Leu Tyr Leu Gln Met Asn Thr Leu Arg Ala
65                  70                  75                  80

Glu Asp Ser Ala Thr Tyr Tyr Cys Ala Arg Ala Asn Trp Ala Phe Asp
                85                  90                  95

Tyr Trp Gly Gln Gly Thr Thr Val Thr Val Ser Ser Lys
            100                 105

<210> SEQ ID NO 104
<211> LENGTH: 11
<212> TYPE: PRT
<213> ORGANISM: Mus musculus

<400> SEQUENCE: 104

Arg Ala Ser Gln Ser Ile Ser Asn Tyr Leu His
1               5                   10

<210> SEQ ID NO 105
<211> LENGTH: 7
<212> TYPE: PRT
<213> ORGANISM: Mus musculus

<400> SEQUENCE: 105

Tyr Ala Ser Gln Ser Ile Ser
1               5

<210> SEQ ID NO 106
<211> LENGTH: 9
<212> TYPE: PRT
<213> ORGANISM: Mus musculus

<400> SEQUENCE: 106

Gln Gln Ser Asn Ser Trp Pro Tyr Thr
1               5
```

<210> SEQ ID NO 107
<211> LENGTH: 94
<212> TYPE: PRT
<213> ORGANISM: Mus musculus

<400> SEQUENCE: 107

Ser Gly Asp Arg Val Ser Leu Ser Cys Arg Ala Ser Gln Ser Ile Ser
1               5                   10                  15
Asn Tyr Leu His Trp Tyr Gln Gln Lys Ser His Glu Ser Pro Arg Leu
            20                  25                  30
Leu Ile Lys Tyr Ala Ser Gln Ser Ile Ser Gly Ile Pro Ser Arg Phe
        35                  40                  45
Ser Gly Ser Gly Ser Gly Thr Asp Phe Thr Leu Ser Ile Asn Ser Val
    50                  55                  60
Glu Thr Glu Asp Phe Gly Met Tyr Phe Cys Gln Gln Ser Asn Ser Trp
65                  70                  75                  80
Pro Tyr Thr Phe Gly Gly Gly Thr Lys Leu Glu Ile Lys Gln
                85                  90

<210> SEQ ID NO 108
<211> LENGTH: 329
<212> TYPE: DNA
<213> ORGANISM: Mus musculus

<400> SEQUENCE: 108
ggccgcgtgc tagcctgggg gtctctgaga ctctcctgtg cacttctggg ttcaccttca      60
ctgattacta catgagctgg gtccgccagc ctccaggaaa ggcacttgag tggttgggtt     120
ttattagaaa caaagctaat ggttacacaa cagagtacag tgcatctgtg aagggtcggt     180
tcaccatctc cagagataat tcccaaagca tcctctatct tcaaatgaac accctgagag     240
ctgaggacag tgccacttat tactgtgcaa gggctaactg gcctttgac tactgggggcc     300 aagggaccac ggtcaccgtc tcctcaaaa                                        329

<210> SEQ ID NO 109
<211> LENGTH: 284
<212> TYPE: DNA
<213> ORGANISM: Mus musculus

<400> SEQUENCE: 109
tcaggagata gagtcagtct ttcctgcagg gccagtcaaa gtattagcaa ctacctacac      60
tggtatcaac aaaaatcaca tgagtctcca aggcttctca tcaagtatgc ttcccagtcc     120
atctctggga tcccctccag gttcagtggc agtggatcag ggacagattt cactctcagt     180
atcaacagtg tggagactga agattttgga atgtatttct gtcaacagag taacagctgg     240
ccgtacacgt tcggaggagg taccaagctg gagatcaaac agaa                      284

<210> SEQ ID NO 110
<211> LENGTH: 5
<212> TYPE: PRT
<213> ORGANISM: Mus musculus

<400> SEQUENCE: 110

Asp Tyr Tyr Met Ser
1               5

<210> SEQ ID NO 111
<211> LENGTH: 17
<212> TYPE: PRT
<213> ORGANISM: Mus musculus

<400> SEQUENCE: 111

Arg Asn Lys Ala Asn Gly Tyr Thr Thr Glu Tyr Ser Ala Ser Val Lys
1               5                   10                  15
Gly

<210> SEQ ID NO 112
<211> LENGTH: 12
<212> TYPE: PRT
<213> ORGANISM: Mus musculus

<400> SEQUENCE: 112

Ala Arg Ala Pro Leu Leu Tyr Tyr Ala Met Asp Tyr
1               5                   10

<210> SEQ ID NO 113
<211> LENGTH: 111
<212> TYPE: PRT
<213> ORGANISM: Mus musculus

<400> SEQUENCE: 113

Pro Ala Cys Leu Pro Gly Gly Ser Leu Arg Leu Ser Cys Ala Thr Ser
1               5                   10                  15

Gly Phe Thr Phe Thr Asp Tyr Tyr Met Ser Trp Val Arg Gln Pro Pro
            20                  25                  30

Gly Lys Ala Leu Glu Trp Leu Gly Phe Ile Arg Asn Lys Ala Asn Gly
        35                  40                  45

Tyr Thr Thr Glu Tyr Ser Ala Ser Val Lys Gly Arg Phe Thr Ile Ser
    50                  55                  60

Arg Asp Asn Ser Gln Ser Ile Leu Tyr Leu Gln Met Asn Thr Leu Arg
65                  70                  75                  80

Ala Glu Asp Ser Ala Thr Tyr Tyr Cys Ala Arg Ala Pro Leu Leu Tyr
                85                  90                  95

Tyr Ala Met Asp Tyr Trp Gly Gln Gly Thr Thr Val Thr Val Ser
            100                 105                 110

<210> SEQ ID NO 114
<211> LENGTH: 11
<212> TYPE: PRT
<213> ORGANISM: Mus musculus

<400> SEQUENCE: 114

Asn Val Ser Thr Ser Gly Tyr Ser Tyr Met His
1               5                   10

<210> SEQ ID NO 115
<211> LENGTH: 7
<212> TYPE: PRT
<213> ORGANISM: Mus musculus

<400> SEQUENCE: 115

Leu Val Ser Asn Leu Glu Ser
1               5

<210> SEQ ID NO 116
<211> LENGTH: 8
<212> TYPE: PRT
<213> ORGANISM: Mus musculus

<400> SEQUENCE: 116

Gln His Ile Arg Glu Leu Thr Arg

<210> SEQ ID NO 117
<211> LENGTH: 102
<212> TYPE: PRT
<213> ORGANISM: Mus musculus

<400> SEQUENCE: 117

Arg Leu Pro Phe Tyr Ser Leu Glu Gln Arg Ala Thr Ile Ser Tyr Arg
1               5                   10                  15

Ala Ser Lys Asn Val Ser Thr Ser Gly Tyr Ser Tyr Met His Trp Asn
            20                  25                  30

Gln Gln Lys Pro Gly Gln Pro Pro Lys Leu Leu Ile Tyr Leu Val Ser
        35                  40                  45

Asn Leu Glu Ser Gly Val Pro Ala Arg Phe Ser Gly Ser Gly Ser Gly
    50                  55                  60

Thr Asp Phe Thr Leu Asn Ile His Pro Val Glu Glu Asp Ala Ala
65                  70                  75                  80

Thr Tyr Tyr Cys Gln His Ile Arg Glu Leu Thr Arg Ser Glu Leu Val
                85                  90                  95

Pro Ser Trp Lys Ser Asn
            100

<210> SEQ ID NO 118
<211> LENGTH: 340
<212> TYPE: DNA
<213> ORGANISM: Mus musculus

<400> SEQUENCE: 118
ccggcctgct tgcctggtgg ttctctgaga ctctcctgtg caacttctgg gttcaccttc      60
actgattact acatgagctg ggtccgccag cctccaggaa aggcacttga gtggttgggt     120
tttattagaa acaaagctaa tggttacaca acagagtaca gtgcatctgt gaagggtcgg     180
ttcaccatct ccagagataa tcccaaagc atcctctatc ttcaaatgaa caccctgaga     240
gctgaggaca gtgccactta ttactgtgca agagcccctc tactttacta tgctatggac     300
tactggggcc aagggaccac ggtcaccgtc tcctaaatta                            340

<210> SEQ ID NO 119
<211> LENGTH: 306
<212> TYPE: DNA
<213> ORGANISM: Mus musculus

<400> SEQUENCE: 119
cgccttcctt tctattctct ggagcagagg gccaccatct catacagggc cagcaaaaat      60
gtcagtacat ctggctatag ttatatgcac tggaaccaac agaaaccagg acagccaccc     120
aaactcctca tctatcttgt atccaaccta gaatctgggg tccctgccag gttcagtggc     180
agtgggtctg gacagactt caccctcaac atccatcctg tggaggagga ggatgctgca     240
acctattact gtcagcacat tagggagctt acacgttcgg agctggtacc aagctggaaa     300
tcaaac                                                                 306

<210> SEQ ID NO 120
<211> LENGTH: 5
<212> TYPE: PRT
<213> ORGANISM: Mus musculus

<400> SEQUENCE: 120

```
Ser Tyr Trp Met His
1               5
```

<210> SEQ ID NO 121
<211> LENGTH: 17
<212> TYPE: PRT
<213> ORGANISM: Mus musculus

<400> SEQUENCE: 121

```
Met Ile Asp Pro Ser Asn Ser Glu Thr Arg Leu Asn Gln Lys Phe Lys
1               5                   10                  15

Asp
```

<210> SEQ ID NO 122
<211> LENGTH: 12
<212> TYPE: PRT
<213> ORGANISM: Mus musculus

<400> SEQUENCE: 122

```
Ala Arg Gly Leu Arg His Tyr Trp Tyr Phe Asp Val
1               5                   10
```

<210> SEQ ID NO 123
<211> LENGTH: 101
<212> TYPE: PRT
<213> ORGANISM: Mus musculus

<400> SEQUENCE: 123

```
Val Ser Cys Lys Ala Ser Gly Tyr Thr Phe Thr Ser Tyr Trp Met His
1               5                   10                  15

Trp Val Lys Gln Arg Pro Gly Gln Gly Leu Glu Trp Ile Gly Met Ile
                20                  25                  30

Asp Pro Ser Asn Ser Glu Thr Arg Leu Asn Gln Lys Phe Lys Asp Lys
            35                  40                  45

Ala Thr Leu Asn Val Asp Lys Ser Ser Asn Thr Ala Tyr Met Gln Leu
        50                  55                  60

Ser Ser Leu Thr Ser Glu Asp Ser Ala Val Tyr Tyr Cys Ala Arg Gly
65                  70                  75                  80

Leu Arg His Tyr Trp Tyr Phe Asp Val Trp Gly Gln Gly Thr Thr Val
                85                  90                  95

Thr Val Ser Ser Lys
            100
```

<210> SEQ ID NO 124
<211> LENGTH: 11
<212> TYPE: PRT
<213> ORGANISM: Mus musculus

<400> SEQUENCE: 124

```
Ser Val Ser Thr Ser Gly Tyr Ser Tyr Met His
1               5                   10
```

<210> SEQ ID NO 125
<211> LENGTH: 7
<212> TYPE: PRT
<213> ORGANISM: Mus musculus

<400> SEQUENCE: 125

```
Leu Val Ser Asn Leu Glu Ser
1               5
```

<210> SEQ ID NO 126
<211> LENGTH: 9
<212> TYPE: PRT
<213> ORGANISM: Mus musculus

<400> SEQUENCE: 126

Gln His Ile Arg Glu Leu Thr Arg Ser
1               5

<210> SEQ ID NO 127
<211> LENGTH: 99
<212> TYPE: PRT
<213> ORGANISM: Mus musculus

<400> SEQUENCE: 127

Thr Ile Leu Trp Arg Glu Gly Pro Phe Ser Tyr Arg Ala Ser Lys Ser
1               5                   10                  15

Val Ser Thr Ser Gly Tyr Ser Tyr Met His Trp Asn Gln Gln Lys Pro
            20                  25                  30

Gly Gln Pro Pro Arg Leu Leu Ile Tyr Leu Val Ser Asn Leu Glu Ser
        35                  40                  45

Gly Val Pro Ala Arg Phe Ser Gly Ser Gly Ser Gly Thr Asp Phe Thr
    50                  55                  60

Leu Asn Ile His Pro Val Glu Glu Asp Ala Ala Thr Tyr Tyr Cys
65                  70                  75                  80

Gln His Ile Arg Glu Leu Thr Arg Ser Glu Glu Val Pro Ser Trp Arg
                85                  90                  95

Ser Asn Lys

<210> SEQ ID NO 128
<211> LENGTH: 304
<212> TYPE: DNA
<213> ORGANISM: Mus musculus

<400> SEQUENCE: 128
gtgtcctgca aggcttcagg ctataccttc accagctact ggatgcactg ggtgaaacag      60
aggcctggac aaggccttga gtggattggc atgattgatc cttccaatag tgaaactagg     120
ttaaatcaga agttcaagga caaggccaca ttgaatgtag acaaatcctc caacacagcc     180
tacatgcagc tcagcagcct gacatctgag gactctgcag tctattactg tgcaagaggg     240
ttacgccact actggtactt cgatgtctgg ggccaaggga ccacggtcac cgtctcctca     300
aaaa                                                                   304

<210> SEQ ID NO 129
<211> LENGTH: 298
<212> TYPE: DNA
<213> ORGANISM: Mus musculus

<400> SEQUENCE: 129
actattctct ggagagaggg cccttctca tacagggcca gcaaagtgt cagtacatct        60 ggctatagtt atatgcactg gaaccaacag aaaccaggac agccacccag actcctcatc     120
tatcttgtat ccaacctaga atctggggtc cctgccaggt tcagtggcag tgggtctggg     180
acagacttca ccctcaacat ccatcctgtg gaggaggagg atgctgcaac ctattactgt     240
cagcacatta gggagcttac acgttcggag gaggtaccaa gctggagatc aaacaaaa      298

<210> SEQ ID NO 130
<211> LENGTH: 22

```
<212> TYPE: DNA
<213> ORGANISM: Artificial
<220> FEATURE:
<223> OTHER INFORMATION: primer

<400> SEQUENCE: 130
aggtsharct gcagsagtcw gg                                    22

<210> SEQ ID NO 131
<211> LENGTH: 34
<212> TYPE: DNA
<213> ORGANISM: Artificial
<220> FEATURE:
<223> OTHER INFORMATION: primer

<400> SEQUENCE: 131
tgaggagacg gtgaccgtgg tcccttggcc ccag                       34

<210> SEQ ID NO 132
<211> LENGTH: 27
<212> TYPE: DNA
<213> ORGANISM: Artificial
<220> FEATURE:
<223> OTHER INFORMATION: primer

<400> SEQUENCE: 132
tccgatatcc agctgaccca gtctcca                               27

<210> SEQ ID NO 133
<211> LENGTH: 31
<212> TYPE: DNA
<213> ORGANISM: Artificial
<220> FEATURE:
<223> OTHER INFORMATION: primer

<400> SEQUENCE: 133
gtttgatctc cagcttggta cchscdccga a                          31

<210> SEQ ID NO 134
<211> LENGTH: 15
<212> TYPE: DNA
<213> ORGANISM: Artificial
<220> FEATURE:
<223> OTHER INFORMATION: primer

<400> SEQUENCE: 134
agtcacgacg ttgta                                            15

<210> SEQ ID NO 135
<211> LENGTH: 17
<212> TYPE: DNA
<213> ORGANISM: Artificial
<220> FEATURE:
<223> OTHER INFORMATION: primer

<400> SEQUENCE: 135
caggaaacag ctatgac                                          17
```